United States Patent

Müller et al.

[11] Patent Number: 5,977,146
[45] Date of Patent: Nov. 2, 1999

[54] PYRIDYLCARBAMATES, PROCESS AND INTERMEDIATES FOR THEIR PREPARATION, AND THEIR USE

[75] Inventors: Bernd Müller, Frankenthal; Hubert Sauter; Herbert Bayer, both of Mannheim; Wassilios Grammenos, Ludwigshafen; Thomas Grote, Schifferstadt; Reinhard Kirstgen, Neustadt; Klaus Oberdorf, Heidelberg; Franz Röhl, Schifferstadt; Norbert Götz, Worms; Michael Rack, Heidelberg; Ruth Müller, Friedelsheim; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 09/091,144

[22] PCT Filed: Dec. 2, 1996

[86] PCT No.: PCT/EP96/05333

§ 371 Date: Jun. 8, 1998

§ 102(e) Date: Jun. 8, 1998

[87] PCT Pub. No.: WO97/21679

PCT Pub. Date: Jun. 19, 1997

[30] Foreign Application Priority Data

Dec. 8, 1995 [DE] Germany .............................. 195 45 878

[51] Int. Cl.⁶ .......................... C07D 213/76; A01N 47/18
[52] U.S. Cl. .............................. 514/352; 546/304
[58] Field of Search .............................. 546/304; 514/357

[56] References Cited

FOREIGN PATENT DOCUMENTS 2127110  8/1993  Canada .
2170283  3/1995  Canada .
 619 301 10/1994  European Pat. Off. .
WO95/06049  3/1995  WIPO .

Primary Examiner—Zinna Northington Davis
Attorney, Agent, or Firm—Keil & Weinkauf

[57] ABSTRACT

A pyridylcarbamate compound of the formula I

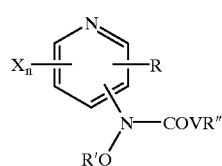

wherein

R' is hydrogen; opt. subst. alkyl, alkenyl, alkynyl, cycloalkyl, cycloalkenyl, alkylcarbonyl and alkoxycarbonyl;

R" is opt. subst. alkyl, alkenyl, alkynyl, cycloalkyl and cycloalkenyl; or is hydrogen when V is nitrogen;

V is O, S or N;

X is cyano; nitro; halogen; opt. subst. alkyl, alkenyl, alkynyl, alkoxy, alkenyloxy, alkynyloxy, or an opt. subst. bridge which is bonded to two adjacent C atoms of the pyridyl ring;

n is 0, 1, 2 or 3;

R is halogen; OH; SH; NH; CHO; $CO_2H$; $CONH_2$; opt. subst. alkyl, alkenyl, alkynyl, cycloalkyl, heterocyclyl, aryl or hetaryl, each being bonded directly or via O, S, N, $CO_2$ or CONH; or together with X and the pyridyl ring to which they are bonded an opt. subst. bicyclus, its manufacture, and pesticidal and fungicidal compositions containing I.

10 Claims, No Drawings

PYRIDYLCARBAMATES, PROCESS AND INTERMEDIATES FOR THEIR PREPARATION, AND THEIR USE

The present application is a U.S. national stage application under 35 U.S.C. §371, based on International Application PCT/EP 96/05,333, filed Feb. 12, 1996.

The present invention relates to pyridylcarbamates of the formula I

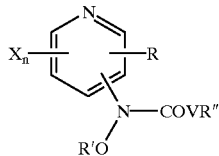

where the index and the substituents have the following meanings:

R' is hydrogen, unsubstituted or substituted alkyl, alkenyl, alkynyl, cycloalkyl, cycloalkenyl, alkylcarbonyl and alkoxycarbonyl;

R" is unsubstituted or substituted alkyl, alkenyl, alkynyl, cycloalkyl and cycloalkenyl, or in the event that V is an amino group, additionally hydrogen;

V is oxygen (—O—), sulfur (—S—) or an amino group which can have attached to it one of the following radicals: alkyl, alkenyl, alkynyl or cycloalkyl;

X is cyano, nitro, halogen, unsubstituted or substituted alkyl, alkenyl, alkynyl, alkoxy, alkenyloxy, alkynyloxy, or in the event that n>1, an unsubstituted or substituted bridge which is bonded to two adjacent C atoms of the pyridyl ring and which contains 3 to 4 members from amongst the group consisting of 3 or 4 carbon atoms, 2 to 3 carbon atoms and one or two nitrogen, oxygen and/or sulfur atoms, it being possible for this bridge together with the ring to which it is bonded to form a partially unsaturated or aromatic radical;

n is 0, 1, 2 or 3, it being possible for the radicals X to differ when n>1;

R is halogen, hydroxyl, mercapto, amino, formyl, carboxyl, carbonylamino or an organic radical which is bonded directly or via an oxy, mercapto, amino, carboxyl or carbonylamino group, or together with a group X and the pyridyl ring to which they are bonded an unsubstituted or substituted bicyclic, partially or fully unsaturated system which, in addition to carbon ring members, can contain hetero atoms from amongst the group consisting of oxygen, sulfur and nitrogen, to processes and intermediates for their preparation, and to their use.

The literature discloses phenylcarbamates for controlling harmful fungi and animal pests [WO-A 95/15,046].

It is an object of the present invention to provide novel compounds with an improved activity.

We have found that this object is achieved by the compounds I defined at the outset.

We have furthermore found processes and intermediates for their preparation, and their use for controlling animal pests or harmful fungi.

The compounds I are accessible by various routes following processes described in the literature.

When synthesizing the compounds I it is, in principle, irrelevant whether the group R or the carbamate group —N(OR')—COVR" is synthesized first.

The synthesis of the carbamate group —N(OR')—COVR" is disclosed, for example, in the literature cited at the outset. In general, a procedure is followed for this in which the conditions described in items 1.1 to 1.3 are met.

1.1 Compounds I where R' is hydrogen (Ia) are generally obtained by reducing a nitropyridine of the formula II to the corresponding hydroxylamine III and subsequently reacting III with an acylating agent of the formula IV to give Ia.

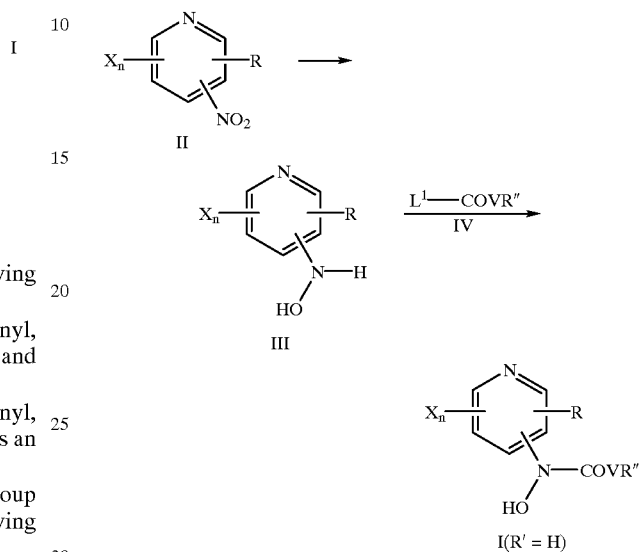

$L^1$ is a nucleophilically exchangeable leaving group, such as halogen (eg. chlorine, bromine or iodine) or alkyl- or arylsulfonate (eg. methylsulfonate, trifluoromethylsulfonate, phenylsulfonate or methylphenylsulfonate).

a) The reduction of II to the hydroxylamine III is usually carried out at from −30° C. to 80° C., preferably 0° C. to 60° C., in an inert organic solvent in the presence of a catalyst [cf. *Ann. Chem.* 316, 278 (1901); EP-A 085 890; DE Application No. 19 50 27 00.01].

b) The reaction of the hydroxylamine III with IV is usually carried out at from −20° C. to 60° C., preferably 0° C. to 30° C., in an inert organic solvent in the presence of a base [cf. WO-A 93/15, 046].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, especially preferably cyclohexane, toluene, methylene chloride, tert-butyl methyl ether and water. Mixtures of these can also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are potassium carbonate, sodium hydroxide and triethylamine.

In general, the bases are employed in catalytic amounts, but they can also be employed in equimolar amounts, in excess or, if desired, as the solvent.

A different preparation method for compounds of the formula I where R' is hydrogen is to react the hydroxylamine III with at least twice the molar amount of the acylating agent IV in an inert solvent to give compounds of the formula IIIa, which are subsequently hydrolyzed to give I.

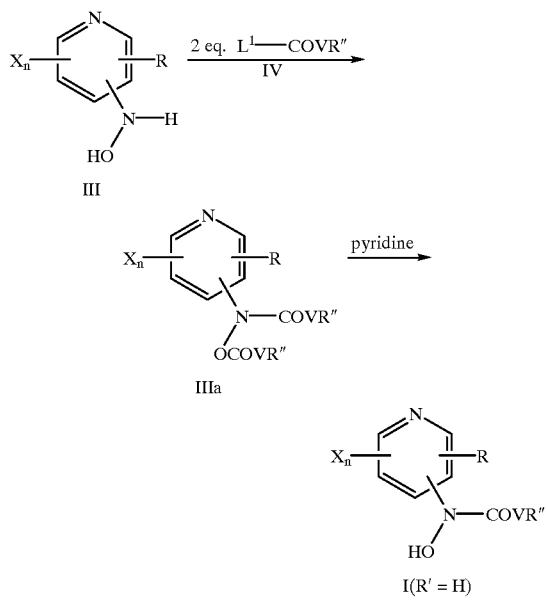

The acylation of III to IIIa is effected under the conditions mentioned above for the reaction of III with IV, except that at least two equivalents of the acylating agent IV have to be employed in this case.

The hydrolysis of IIIa to I is effected with at least equimolar amounts of a base, for example tertiary amines, in particular pyridine, in the presence of an alcohol in an inert solvent at from 30 to 150° C., in particular at 50 to 100° C. Solvents which are suitable for this reaction sequence are especially those mentioned already for the reaction of III with IV.

This preparation method is preferred for compounds I where R is the radical $L^3$.

1.2 The compounds I where R' is not hydrogen (Ib) are obtained by reacting a compound of the formula Ia with a compound of the formula V in a manner known per se.

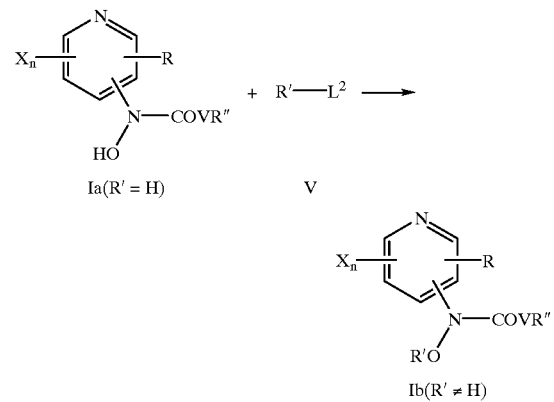

$L^2$ is a nucleophilically exchangeable leaving group, such as halogen (eg. chlorine, bromine or iodine) or alkyl- or arylsulfonate (eg. methylsulfonate, trifluoromethylsulfonate, phenylsulfonate or methylphenylsulfonate).

This reaction is usually carried out at from −20° C. to 80° C., preferably 0° C. to 60° C., in an inert organic solvent in the presence of a base [cf. WO-A 93/15,046].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, especially preferably acetone, toluene, tert-butyl methyl ether, cyclohexane and water. Mixtures of these can also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are potassium carbonate, sodium hydroxide and triethylamine.

In general, the bases are employed in catalytic amounts, but they can also be employed in equimolar amounts, in excess or, if desired, as the solvent.

1.3 Compounds I where V is an amino group (Ic) are advantageously obtained by reacting a carbamate of the formula VI with a primary or secondary amine VII

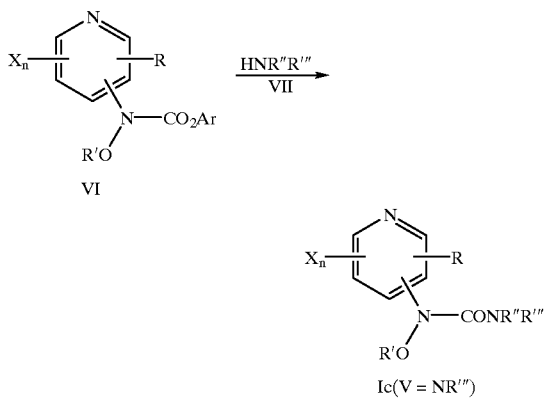

Ar in formula VI is an aromatic radical, in particular phenyl.

R" and R'" in formulae VI and Ic are hydrogen or one of the following groups: alkyl, alkenyl, alkynyl and cycloalkyl.

Similarly, compounds I where V is oxygen can be converted into compounds I where V is an amino group by reacting them with a primary or secondary amine of the formula VII.

The reaction of the compounds VI (or, analogously, compounds I where V is oxygen), with the primary or secondary amine VII is generally carried out at from 0° C. to 100° C. in an inert solvent or solvent mixture.

Particularly suitable as solvents are water, tert-butyl methyl ether and toluene or mixtures of these. To improve the solubility of the starting materials, it may be advantageous additionally to add one of the following solvents (as solubilizer): tetrahydrofuran, methanol, dimethylformamide and ethylene glycol ether.

The amines VII are usually employed in an excess of up to 100% based on the compound VI or may be used as solvents. With a view to the yield, it may be advantageous to carry out the reaction under superatmospheric pressure.

In principle, the group R may be synthesized before or after synthesis of the carbamate group. Besides, the group R may also be synthesized at the stage of suitable intermediates for the synthesis of the carbamate group. Accordingly, in the reaction equations below for the synthesis of the group R the symbol $N^\#$ will be used instead of the carbamate group to represent the following radicals: $NO_2$, NHOH, N(OR')—$CO_2$—Ar (Ar=unsubstituted or substituted aryl) or N(OR')—COVR".

Pyridyl derivatives I where the radical R is bonded to the pyridyl ring via an oxygen, sulfur or nitrogen atom are advantageously obtained starting from pyridine derivatives VIII by reacting them with the relevant alcohols, thiols or amines in the presence of a base following the equation below.

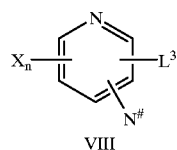

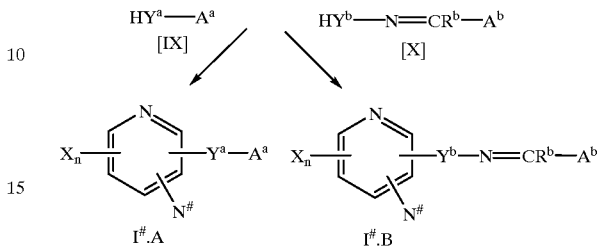

$L^3$ in formula VIII is a nucleophilic leaving group such as halogen (eg. fluorine, chlorine, bromine and iodine), alkyl- and arylsulfonate (eg. methylsulfonate, trifluoromethylsulfonate, phenylsulfonate and p-methylphenylsulfonate), especially chlorine and bromine.

This reaction with the alcohol, thiol or amine (for example of the formula IX or X) is usually carried out at from 0° C. to 200° C., preferably 20° C. to 120° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably toluene, dimethyl sulfoxide, dimethylformamide and N-methylpyrrolidone. Mixtures of these may also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are sodium methanolate, potassium tert-butanolate, sodium hydroxide, sodium hydride and potassium carbonate. The bases are generally employed in catalytic amounts, but may also be used in equimolar amounts, in excess or, if desired, as the solvent.

In general, the starting materials are reacted with each other in equimolar amounts. It may be advantageous for the yield to employ IX, or X, in an excess based on VIII.

It is especially preferred in the above-described processes to start from compounds VIII where $N^\#$ is $NO_2$, NHOH, N(OR')—$CO_2$—Ar (Ar=unsubstituted or substituted aryl) or N(OR')—COVR".

Compounds I where the radical R is bonded to the pyridine ring via a nitrogen atom are especially preferably obtained starting from the corresponding aminopyridines, for example by reaction with a ketone, following the equation below.

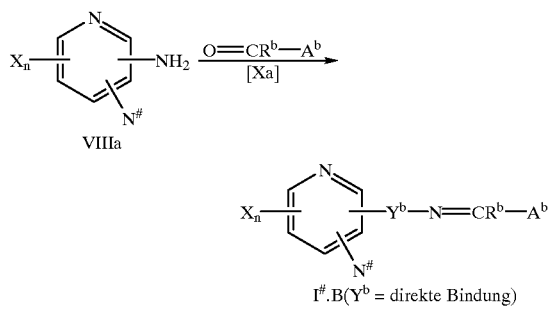

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. In general, the acids are employed in catalytic amounts, but they may also be used in equimolar amounts, in excess or, if desired, as the solvent.

In general, the starting materials are reacted with each other in equimolar amounts. It may be advantageous for the yield to employ Xa in an excess based on VIIIa.

It is especially preferred in the above-described processes to start from compounds VIIIa where $N^\#$ is $NO_2$, NHOH, N(OR')—$CO_2$—Ar (Ar=unsubstituted or substituted aryl) or N(OR')—COVR".

The resulting imino compounds can subsequently be reduced by customary methods to give the corresponding amines.

Compounds I where R is unsubstituted or substituted alkyl, alkenyl or alkynyl are obtained, for example, by reacting an alkylenepyridine XI in accordance with the following equation:

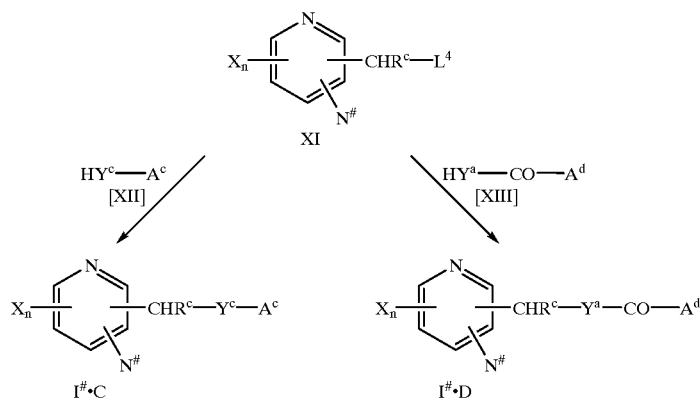

This reaction is usually carried out at from 0° C. to 100 ° C., preferably 20° C. to 60° C., in an inert organic solvent in the presence of an acidic catalyst.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably methanol, ethanol, toluene, water and dimethylformamide. Mixtures of these can also be used.

$L^4$ in formula XI is a nucleophilic leaving group such as halogen (eg. fluorine, chlorine, bromine and iodine), alkyl- and arylsulfonate (eg. methylsulfonate, trifluoromethylsulfonate, phenylsulfonate and p-methylphenylsulfonate), especially chlorine and bromine.

The reaction with an alcohol, thiol or amine, for example of the formulae XII and XIII, is usually carried out at from 0° to 100° C., preferably 20° to 60° C., in an inert organic solvent in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably toluene, dimethylformamide, water and acetone. Mixtures of these may also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are sodium methanolate, sodium ethanolate, sodium hydroxide solution, sodium hydride and potassium carbonate. In general, the bases are employed in catalytic amounts, but they may also be used in equimolar amounts, in excess or, if desired, as the solvent.

The starting materials are generally reacted with each other in equimolar amounts. It may be advantageous for the yield to employ XII, or XIII, in an excess based on XI.

It is especially preferred in the above-described processes to start from compounds XI where $N^{\#}$ is $NO_2$, NHOH, $N(OR')$—$CO_2$—Ar (Ar=unsubstituted or substituted aryl) or $N(OR')$—COVR".

Compounds I.D or $I^{\#}$.D where $Y^a$ is a direct linkage can be obtained in general and in particular by the methods described in EP-A 463 513 or in J. Org. Chem. 53, 3791 (1988) and Chem. Lett. 1982, 1135.

A further method of preparing compounds of the formula I where R is unsubstituted or substituted alkyl, alkenyl or alkynyl is shown in the equation below.

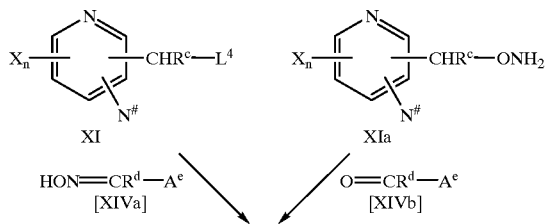

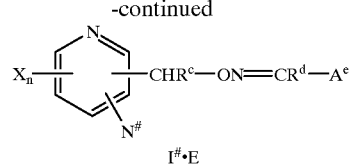
$I^{\#}\cdot E$ a) The reaction of the methylidenepyridine XI with the hydroxyimine XIVa is usually carried out at from 0° C. to 100° C., preferably 20° C. to 60° C., in an inert solvent, if desired in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylform-amide, especially preferably toluene, dimethylformamide, water and acetone. Mixtures of these may also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are sodium methanolate, sodium ethanolate, sodium hydride, sodium hydroxide solution and potassium carbonate. In general, the bases are employed in catalytic amounts, but they may also be used in equimolar amounts, in excess or, if desired, as the solvent.

The starting materials are generally reacted with each other in equimolar amounts. It may be advantageous for the yield to employ XIVa in an excess based on XI.

It is especially preferred in the above-described processes to start from compounds XI, or XIa, where $N^{\#}$ is $NO_2$, NHOH, $N(OR')$—$CO_2$—Ar (Ar=unsubstituted or substituted aryl) or $N(OR')$—COVR".

Those starting materials required for the preparation of the compounds I which are not already known from the literature (WO-A 95/21,153 or DE Application No. 44 41 674.1) can be prepared in accordance with the literature cited.

The reaction of the pyridinemethyleneoxyamine XIa with the aldehyde XIVb is usually carried out at from 0° C. to 100° C., preferably 20° C. to 60° C., in an inert solvent, if desired in the presence of an acidic catalyst.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylform-amide, especially preferably methanol, ethanol, toluene, water and dimethylformamide. Mixtures of these can also be used.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. In general, the acids are employed in catalytic amounts, but they may also be used in equimolar amounts, in excess or, if desired, as the solvent.

In general, the starting materials are reacted with each other in equimolar amounts. It may be advantageous for the yield to employ XIVb in an excess based on XIa.

It is especially preferred in the above-described processes to start from compounds XI, or XIa, where $N^\#$ is $NO_2$, NHOH, N(OR')—$CO_2$—Ar (Ar=unsubstituted or substituted aryl) or N(OR')—COVR".

Another method of preparing compounds of the formula I where R is unsubstituted or substituted alkyl, alkenyl or alkynyl is shown in the equation below:

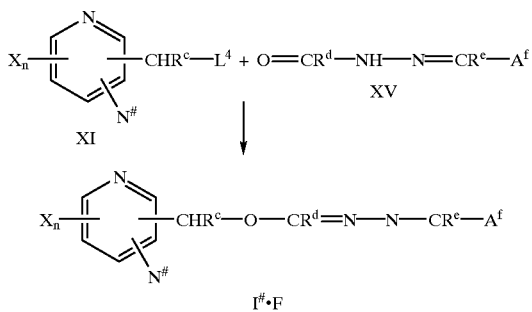

This reaction of XI with the hydrazine derivative XV is usually carried out at from 0° C. to 100° C., preferably 20° C. to 60° C., in an inert solvent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably toluene, dimethyl sulfoxide, dimethylformamide and N-methylpyrrolidone. Mixtures of these may also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are sodium methanolate, sodium ethanolate, potassium tert-butanolate, sodium hydroxide, sodium hydride and potassium carbonate. In general, the bases are employed in catalytic amounts, but they may also be used in equimolar amounts, in excess or, if desired, as the solvent.

The starting materials are generally reacted with each other in equimolar amounts. It may be advantageous for the yield to employ XV in an excess based on XI.

It is especially preferred in the above-described processes to start from compounds XI where $N^\#$ is $NO_2$, NHOH, N(OR')—$CO_2$—Ar (Ar=unsubstituted or substituted aryl) or N(OR')—COVR".

Besides, compounds I where R is unsubstituted or substituted alkyl, alkenyl or alkynyl can also be obtained by reacting an aldehyde XIb or XVIb with a phosphorus reagent in a manner known per se following the principles of a Wittig or Wittig-Horner reaction.

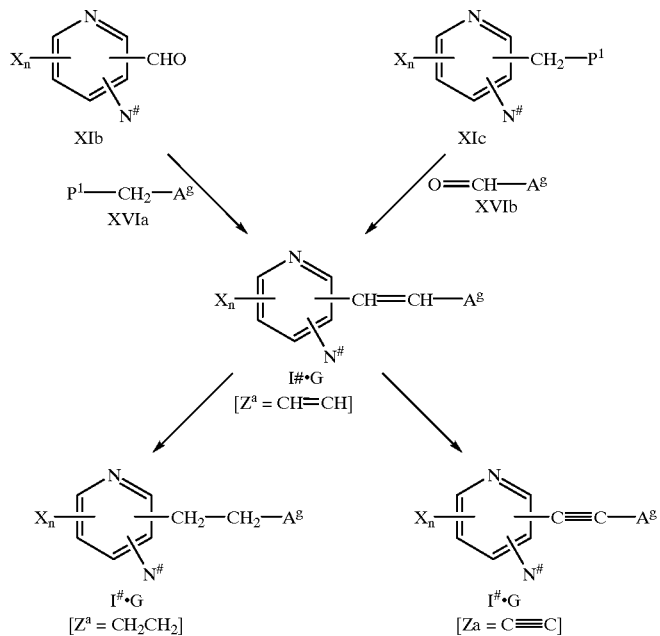

The preparation processes are known per se from the literature. The reactions proceed in general and in particular following the methods described in EP-A 534 216, EP-A 528 245 and EP-A 582 925 [cf. Tietze Eicher, Reaktionen und Synthesen (Reactions and Syntheses), Georg Thieme Verlag 1981, pp. 34–38].

It is especially preferred in the above-described processes to start from compounds XIb, or XIc, where $N^\#$ is $NO_2$, NHOH, N(OR')—$CO_2$—Ar (Ar=unsubstituted or substituted aryl) or N(OR')—COVR".

Another possibility of preparing compounds I where R is unsubstituted or substituted alkyl or unsubstituted or substituted alkenyl is, for example, to react pyridylacrylic acid derivatives of the formula XIe with an alcohol, thiol or amine of the formula IXa in a manner known per se.

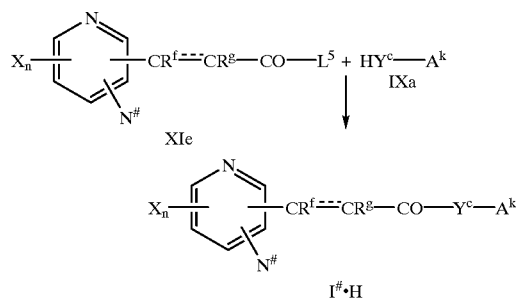

$L^5$ in formula XIa is a nucleophilic leaving group such as halogen (eg. fluorine, chlorine, bromine and iodine), alkyl- and arylsulfonate (eg. methylsulfonate, trifluoromethylsulfonate, phenylsulfonate and p-methylphenylsulfonate), especially chlorine and bromine.

This reaction is carried out by following the customary methods at from 0° C. to 80° C., preferably 20° C. to 60° C., in an inert solvent, if desired in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably toluene, tert-butyl methyl ether, cyclohexane and ethyl acetate. Mixtures of these may also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal oxides and alkaline earth metal oxides, such as lithium oxide, sodium oxide, calcium oxide and magnesium oxide, alkali metal hydrides and alkaline earth metal hydrides, such as lithium hydride, sodium hydride, potassium hydride and calcium hydride, alkali metal amides, such as lithium amide, sodium amide and potassium amide, alkali metal carbonates and alkaline earth metal carbonates, such as lithium carbonate and calcium carbonate, and also alkali metal hydrogen carbonates, such as sodium hydrogen carbonate, organometallic compounds, in particular alkali metal alkyls, such as methyllithium, butyllithium and phenyllithium, alkylmagnesium halides, such as methylmagnesium chloride, and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylamine and N-methylpiperidine, pyridine, substituted pyridines, such as collidine, lutidine and 4-dimethylaminopyridine, and also bicyclic amines. Substances which are especially preferred are pyridine, triethylamine, sodium hydroxide solution and p-N,N-dimethylaminopyridine. In general, the bases are employed in catalytic amounts, but they may also be used in equimolar amounts, in excess or, if desired, as the solvent.

The starting materials are generally reacted with each other in equimolar amounts. It may be advantageous for the yield to employ IXa in an excess based on XIe.

It is especially preferred in the above-described processes to start from compounds XIe where $N^{\#}$ is $NO_2$, NHOH, N(OR')—$CO_2$—Ar (Ar=unsubstituted or substituted aryl) or N(OR')—COVR".

In another process, compounds I where R is unsubstituted or substituted alkyl, alkenyl or alkynyl are obtained, for example, by reacting a pyridine aldehyde or ketone XId with amines of the formula XVII:

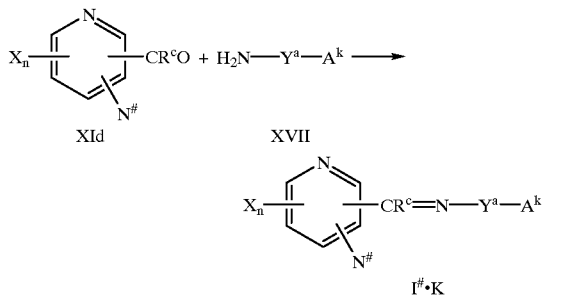

This reaction is usually carried out at from 0° C. to 100° C., preferably 20° C. to 60° C., in an inert solvent, if appropriate in the presence of an acid.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, esters such as ethyl acetate and tert-butyl acetate, and also N-methylpyrrolidone, dimethyl sulfoxide and dimethylformamide, especially preferably methanol, ethanol, toluene, water, dimethylformamide and tert-butyl methyl ether. Mixtures of these can also be used.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. In general, the acids are employed in catalytic amounts, but they may also be used in equimolar amounts, in excess or, if desired, as the solvent.

In general, the starting materials are reacted with each other in equimolar amounts. It may be advantageous for the yield to employ XVII in an excess based on XId.

It is especially preferred in the above-described processes to start from compounds XId where $N^{\#}$ is $NO_2$, NHOH, N(OR')—$CO_2$—Ar (Ar=unsubstituted or substituted aryl) or N(OR')—COVR".

The reaction mixtures are worked up in a customary manner, eg. by mixing with water, phase separation and, if desired, chromatographic purification of the crude products. Some of the intermediates and end products are obtained in the form of colorless or pale brown viscous oils which are freed from volatile components or purified under reduced pressure at moderately elevated temperatures. If the intermediates and end products are obtained as solids, they may also be purified by recrystallization or digestion.

Due to their C=C and C=N double bonds, the compounds I may be obtained from their preparation in the form of E/Z isomer mixtures, which can be separated into the individual compounds in a customary manner, eg. by crystallization or chromatography.

If isomer mixtures are obtained from the synthesis, however, a separation is generally not absolutely necessary since some of the individual isomers can be converted into each other during formulation for use or upon use (eg. when exposed to light, acids or bases). Similar conversions can also take place after use, for example in the fungi or animal pests to be controlled, or, on treatment of plants, within the treated plant.

In particular, the present invention relates to compounds of the general formula I

where R is an organic radical which is bonded directly or via an oxy, mercapto, amino, carboxyl or carbonylamino group, or where R together with a group X and the pyridyl ring to which they are bonded form an unsubstituted or substituted bicyclic, partially or fully unsaturated system which, besides carbon ring members, may contain hetero atoms from amongst the group consisting of oxygen, sulfur and nitrogen.

Moreover, preferred compounds of the general formula I are those where R is unsubstituted or substituted alkyl, unsubstituted or substituted alkenyl or unsubstituted or substituted alkynyl, these groups being bonded directly to the pyridyl ring or via an oxy, mercapto or amino group, or where R together with a group X and the pyridyl ring to which they are bonded is an unsubstituted or substituted bicyclic, partially or fully unsaturated system which, besides carbon ring members, may contain hetero atoms from amongst the group consisting of oxygen, sulfur and nitrogen.

Particularly preferred compounds of the general formula I are those where R is unsubstituted or substituted $C_1$–$C_4$-alkyl, unsubstituted or substituted $C_2$–$C_4$-alkenyl or unsubstituted or substituted $C_2$–$C_4$-alkynyl, these groups being bonded to the pyridyl ring directly or via an oxy, mercapto or amino group, or where R together with a group X and the pyridyl ring to which they are bonded is an unsubstituted or substituted bicyclic, partially or fully unsaturated system which, besides carbon ring members, may contain hetero atoms from amongst the group consisting of oxygen, sulfur and nitrogen.

Particularly preferred compounds of the general formula I are also those where R is $C_1$–$C_4$-alkyl, $C_2$–$C_4$-alkenyl or $C_2$–$C_4$-alkynyl, these groups being bonded to the pyridyl ring directly or via an oxy, mercapto, amino or imino group, it being possible for these radicals to be partially or fully halogenated, and these radicals additionally having attached to them one of the following groups: aryl, aryloxy, arylthio, arylamino, arylcarbonyl, aryloxycarbonyl, arylthiocarbonyl, arylaminocarbonyl, arylcarbonyloxy, arylcarbonylthio, arylcarbonylamino, hetaryl, hetaryloxy, hetarylthio, hetarylamino, hetarylcarbonyl, hetaryloxycarbonyl, hetarylthiocarbonyl, hetarylaminocarbonyl, hetarylcarbonyloxy, hetarylcarbonylthio, hetarylcarbonylamino, it being possible for the abovementioned aromatic or heteroaromatic radicals to be unsubstituted or additionally mono- to tetrasubstituted, or where R together with a group X and the pyridyl ring to which they are bonded is an unsubstituted or substituted bicyclic, partially or fully unsaturated system which, besides carbon ring members, may contain hetero atoms from amongst the group consisting of oxygen, sulfur and nitrogen.

Furthermore, particularly preferred compounds of the general formula I are those where R is $C_1$–$C_4$-alkyl, $C_2$–$C_4$-alkenyl or $C_2$–$C_4$-alkynyl which can be partially or fully halogenated, these groups being bonded to the pyridyl ring directly or via an oxy, mercapto or amino group, and these groups having attached to them an imino or iminooxy radical, or where R together with a group X and the pyridyl ring to which they are bonded is an unsubstituted or substituted bicyclic, partially or fully unsaturated system which, besides carbon ring members, may contain hetero atoms from amongst the group consisting of oxygen, sulfur and nitrogen.

Especially preferred compounds are those of the formula I.A

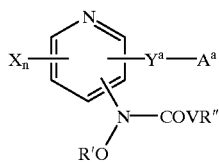

I.A where $X_n$, R', V and R" have the meanings given above and $Y^a$ and $A^a$ are the following groups:

$Y^a$ is a direct linkage, oxygen, sulfur, or an amino group which can have attached to it one of the following radicals: alkyl, alkenyl, alkynyl or cycloalkyl;

$A^a$ is unsubstituted or substituted alkyl, alkenyl, alkynyl, cycloalkyl, heterocyclyl, aryl or hetaryl.

Furthermore, preferred compounds are those of the formula I.B

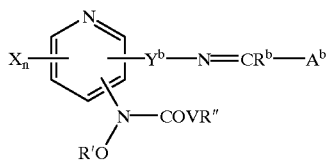

I.B where $X_n$, R', V and R" have the meanings given above and $Y^b$, $R^b$ and $A^b$ are the following groups:

$Y^b$ is a direct linkage, oxygen or an amino group which can have attached to it one of the following radicals: alkyl, alkenyl, alkynyl or cycloalkyl;

$R^b$ is hydrogen, unsubstituted or substituted alkyl, alkenyl, alkynyl or cycloalkyl;

$A^b$ is unsubstituted or substituted alkyl, alkenyl, alkynyl, cycloalkyl, heterocyclyl, aryl or hetaryl.

Other preferred compounds of the formula I.B

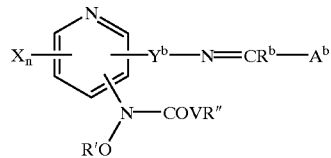

I.B are those where $X_n$, R', V, R", $Y^b$ and $R^b$ have the meanings given above and $A^b$ is one of the following groups:

$A^b$ is unsubstituted or substituted alkyl, alkenyl, alkynyl, cycloalkyl, heterocyclyl, aryl, hetaryl or $CR^\alpha$=$NOR^\beta$ where $R^\alpha$ is hydrogen, unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio or hetarylamino and $R^\beta$ is hydrogen, unsubstituted or substituted alkyl, unsubstituted or substituted alkenyl, unsubstituted or substituted alkynyl, unsubstituted or substituted cycloalkyl, unsubstituted or substituted heterocyclyl, unsubstituted or substituted aryl and unsubstituted or substituted hetaryl.

Moreover, preferred compounds are those of the formula I.C

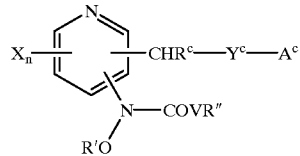

I.C where $X_n$, R', V and R" have the meanings given above and $Y^c$, $R^c$ and $A^c$ are the following groups:

$Y^c$ is oxygen, sulfur or an amino group which can have attached to it one of the following radicals: alkyl, alkenyl, alkynyl or cycloalkyl;

$R^c$ is hydrogen, unsubstituted or substituted alkyl, unsubstituted or substituted alkenyl or unsubstituted or substituted alkynyl;

$A^c$ is unsubstituted or substituted alkyl, alkenyl, alkynyl, cycloalkyl, heterocyclyl, aryl or hetaryl.

Other preferred compounds are those of the formula I.D

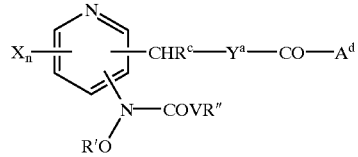

I.D where $X_n$, R', V and R" have the meanings given above and $Y^a$, $R^c$ and $A^d$ are the following groups:

$R^c$ is hydrogen, unsubstituted or substituted alkyl, unsubstituted or substituted alkenyl or unsubstituted or substituted alkynyl;

Y$^a$ is a direct linkage, oxygen, sulfur or an amino group which can have attached to it one of the following radicals: alkyl, alkenyl, alkynyl or cycloalkyl;

A$^d$ is unsubstituted or substituted alkyl, alkoxy, alkylamino, alkenyl, alkenyloxy, alkenylamino, alkynyl, alkynyloxy, alkynylamino, cycloalkyl, cycloalkoxy, cycloalkylamino, heterocyclyl, heterocyclyloxy, heterocyclylamino, aryl, aryloxy, arylamino, hetaryl, hetaryloxy and hetarylamino.

Moreover, preferred compounds are those of the formula I.E

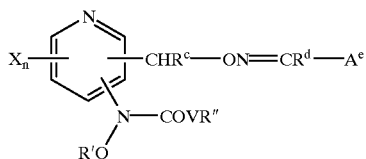

I.E where X$_n$, R', V and R" have the meanings given above and R$^c$, R$^d$ and A$^e$ are the following groups:

R$^c$ is hydrogen, unsubstituted or substituted alkyl, unsubstituted or substituted alkenyl or unsubstituted or substituted alkynyl;

R$^d$ is hydrogen, unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio, hetarylamino;

A$^e$ is hydrogen, unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio, hetarylamino or CR$^\alpha$=NO—R$^\beta$;

R$^\alpha$ is hydrogen, unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio or hetarylamino;

R$^\beta$ is hydrogen, unsubstituted or substituted alkyl, unsubstituted or substituted alkenyl, unsubstituted or substituted alkynyl, unsubstituted or substituted cycloalkyl, unsubstituted or substituted heterocyclyl, unsubstituted or substituted aryl and unsubstituted or substituted hetaryl.

Equally preferred compounds are those of the formula I.F

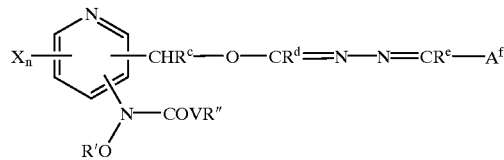

I.F where X$_n$, R', V and R" have the meanings given above and R$^c$, R$^d$, R$^e$ and A$^f$ are the following groups:

R$^c$ is hydrogen, unsubstituted or substituted alkyl, unsubstituted or substituted alkenyl or unsubstituted or substituted alkynyl;

R$^d$ is hydrogen, unsubstituted or substituted alkyl, alkenyl, alkynyl, cycloalkyl, heterocyclyl, aryl or hetaryl;

R$^e$ is hydrogen, unsubstituted or substituted alkyl, alkenyl, alkynyl, cycloalkyl, heterocyclyl, aryl or hetaryl;

A$^f$ is unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio, hetarylamino or CR$^\alpha$=NO—R$^\beta$.

Preferred compounds are also those of the formula I.G

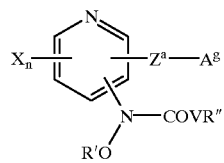

I.G where X$_n$, R', V and R" have the meanings given above and Z$^a$ and A$^g$ are the following groups:

Z$^a$ is ethylene or ethenylene, it being possible for these groups to be unhalogenated or halogenated, or is ethynylene;

A$^g$ is unsubstituted or substituted alkyl, alkenyl, alkynyl, cycloalkyl, heterocyclyl, aryl or hetaryl.

Furthermore, preferred compounds are those of the formula I.H

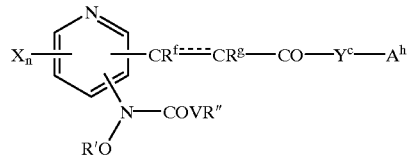

I.H where X$_n$, R', V and R" have the meanings given above and R$^f$, R$^g$, Y$^c$ and A$^h$ are the following groups:

R$^f$ is hydrogen, unsubstituted or substituted alkyl, unsubstituted or substituted alkenyl or unsubstituted or substituted alkynyl;

R$^g$ is hydrogen, unsubstituted or substituted alkyl, unsubstituted or substituted alkenyl or unsubstituted or substituted alkynyl;

$Y^c$ is oxygen, sulfur or an amino group which can have attached to it one of the following radicals: alkyl, alkenyl, alkynyl or cycloalkyl;

$A^h$ is unsubstituted or substituted alkyl, alkenyl, alkynyl, cycloalkyl, heterocyclyl, aryl or hetaryl.

Moreover, preferred compounds are those of the formula I.K

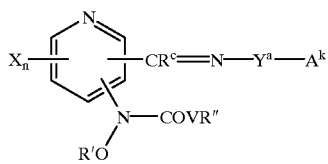

I.K where $X_n$, R', V and R'', have the meanings given above and $R^c$, $Y^a$ and $A^k$ are the following groups:

$R^c$ is hydrogen, unsubstituted or substituted alkyl, unsubstituted or substituted alkenyl or unsubstituted or substituted alkynyl;

$Y^a$ is a direct linkage, oxygen, sulfur or an amino group which can have attached to it one of the following radicals: alkyl, alkenyl, alkynyl or cycloalkyl;

$A^k$ is unsubstituted or substituted alkyl, alkenyl, alkynyl, cycloalkyl, heterocyclyl, aryl or hetaryl.

Moreover, preferred compounds are those of the formula I.L

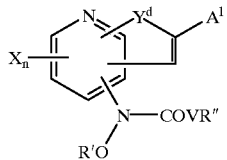

I.L where $X_n$, R', V and R'' have the meanings given above and $Y^d$ and $A^l$ are the following groups:

$Y^d$ is oxygen, sulfur or an amino group which can have attached to it one of the following radicals: unsubstituted or substituted alkyl, alkenyl, alkynyl, cycloalkyl, heterocyclyl, aryl or hetaryl;

$A^l$ is unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio or hetarylamino.

Equally preferred compounds are those of the formula I.M

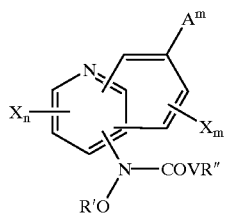

I.M where $X_n$, R', V and R'' have the meanings given above, m is 0, 1, 2 or 3 and $A^m$ is one of the following groups:

$A^m$ is unsubstituted or substituted alkyl, alkoxy, alkylthio, alkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, heterocyclyl, heterocyclyloxy, heterocyclylthio, heterocyclylamino, aryl, aryloxy, arylthio, arylamino, hetaryl, hetaryloxy, hetarylthio or hetarylamino.

Depending on the choice of the starting materials, the compounds of the general formula I may be obtained in the form of various positional isomers, eg. the preferred isomers of the formulae I.1 to I.4.

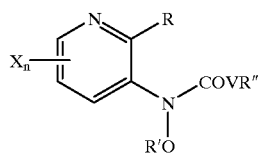

I.1

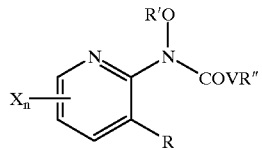

I.2

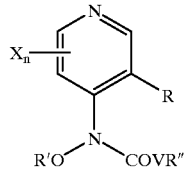

I.3

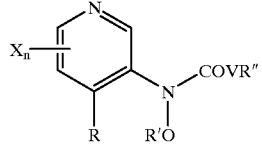

I.4

In the definitions of the symbols given in the above formulae, collective terms have been used which generally represent the following substituents:

Halogen: fluorine, chlorine, bromine and iodine;

Alkyl: saturated, straight-chain or branched hydrocarbon radicals having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1- dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), it being possible for some or all of the hydrogen atoms in these groups to be replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 10 carbon atoms (as mentioned above) which are bonded to the skeleton via an oxygen atom (—O—);

Haloalkoxy: straight-chain or branched haloalkyl groups having 1 to 10 carbon atoms (as mentioned above) which are bonded to the skeleton via an oxygen atom (—O—);

Alkylthio: straight-chain or branched alkyl groups having 1 to 10 or 1 to 4 carbon atoms (as mentioned above) which are bonded to the skeleton via an sulfur atom (—S—);

Alkylamino: a straight-chain or branched alkyl group having 1 to 10 carbon atoms (as mentioned above) which is bonded to the skeleton via an amino group (—NH—) or which is bonded to the skeleton via a group —$NY^1$— or —$NZ^a$—;

Alkenyl: unsaturated, straight-chain or branched hydrocarbon radicals having 2 to carbon atoms and one double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched hydrocarbon groups having 2 to carbon atoms and a triple bond in any position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: monocyclic alkyl groups having 3 to 12 carbon ring members, eg. $C_3$–$C_8$-cycloalkyl such as cyclopropyl, cyclobutyl, cyclopentyl, cyclohexyl, cycloheptyl and cyclooctyl;

saturated or partially unsaturated cyclic radical which, besides carbon atoms, may contain hetero atoms from amongst the group consisting of oxygen, sulfur or nitrogen as ring members: cycloalkyl having 3 to 12 carbon ring members as mentioned above or 5- or 6-membered heterocycles (heterocyclyl) containing, besides carbon ring members, one to three nitrogem atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4- dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

Aryl: a mono- to trinuclear aromatic ring system containing 6 to 14 carbon ring members, eg. phenyl, naphthyl and anthracenyl;

aromatic ring system which, besides carbon ring members, can contain hetero atoms from amongst the group consisting of oxygen, sulfur and nitrogen: aryl as mentioned above or mono- or binuclear hetaryl, eg.

5-membered hetaryl containing one to four nitrogen atoms or one to three nitrogen atoms and one sulfur or oxygen atom: 5-membered hetaryl ring groups which, besides carbon atoms, may contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl, containing one to three nitrogen atoms or one nitrogen atom and one oxygen or sulfur atom: 5-membered hetaryl ring groups which, besides carbon atoms, may contain one to four nitrogen atoms or one to three nitrogen atoms and one sulfur or oxygen atom as ring members, and in which two adjacent carbon ring members or one nitrogen and an adjacent carbon ring member may be bridged by a buta-1,3-diene-1,4-diyl group;

5-membered hetaryl bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, may contain one to four nitrogen atoms, or one to three nitrogen atoms, as ring members and in which two adjacent carbon ring members or one nitrogen and an adjacent carbon ring member may be bridged by a buta-1,3-diene-1,4-diyl group, these rings being bonded to the skeleton via one of the nitrogen ring members;

6-membered hetaryl, containing one to three, or one to four, nitrogen atoms: 6-membered hetaryl ring groups which, besides carbon atoms, may contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl nd 1,2,4-triazin-3-yl;

Alkylene: divalent unbranched chains of 3 to 5 $CH_2$ groups, eg. —$CH_2$—, —$CH_2CH_2$—, —$CH_2CH_2CH_2$—, —$CH_2CH_2CH_2CH_2$— and $CH_2CH_2CH_2CH_2CH_2$—;

Oxyalkylene: divalent unbranched chains of 2 to 4 $CH_2$ groups, one valency being bonded to the skeleton via an oxygen atom, eg. —$OCH_2CH_2$—, —$OCH_2CH_2CH_2$— and —$OCH_2CH_2CH_2CH_2$—;

Oxyalkyleneoxy: divalent unbranched chains of 1 to 3 $CH_2$ groups, both valencies being bonded to the skeleton via an oxygen atom, eg. —$OCH_2O$—, —$OCH_2CH_2O$—and —$OCH_2CH_2CH_2O$—;

Alkenylene: divalent unbranched chains of 1 to 3 $CH_2$ groups and one CH=CH group in any position, eg. —CH=$CHCH_2$—, —$CH_2$CH=$CHCH_2$—, —CH=$CHCH_2CH_2$—, —$CH_2$CH=$CHCH_2CH_2$— and —CH=$CHCH_2CH_2CH_2$—;

Oxyalkenylene: divalent unbranched chains of 0 to 2 $CH_2$ groups and one CH=CH group in any position, one valency being bonded to the skeleton via an oxygen atom, eg. —OCH=CH—, —OCH=$CHCH_2$—, —$OCH_2$CH=CH—, —$OCH_2$CH=$CHCH_2$—, —OCH=$CHCH_2CH_2$—and —$OCH_2CH_2$—CH=CH—;

Oxyalkenyleneoxy: divalent unbranched chains of 0 to 2 $CH_2$ groups and one CH=CH group in any position, both valencies being bonded to the skeleton via an oxygen atom, eg. —OCH=CHO—, —OCH=$CHCH_2O$—, —$OCH_2$CH=$CHCH_2O$— and —OCH=$CHCH_2CH_2O$—.

organic radical: unsubstituted or substituted alkyl, alkenyl, alkynyl, cycloalkyl, heterocyclyl, aryl or hetaryl.

The affix "unsubstituted or substituted" when referring to alkyl, alkenyl and alkynyl groups is intended to express the fact that these groups may be partially or fully halogenated (ie. some or all of the hydrogen atoms of these groups may be replaced by identical or different halogen atoms as mentioned above (preferably fluorine, chlorine or bromine) and/or have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, the aryl radicals preferably containing 6 to 10 ring members, in particular 6 ring members (phenyl), the hetaryl radicals containing, in particular, 5or 6 ring members and the alkyl groups in these radicals preferably containing 1 to 6 carbon atoms, in particular 1 to 4 carbon atoms.

The affix "unsubstituted or substituted" when referring to the cyclic (saturated, unsaturated or aromatic) groups is intended to express the fact that these groups may be partially or fully halogenated (ie. some or all of the hydrogen atoms of these groups may be replaced by identical or different halogen atoms as mentioned above (preferably fluorine, chlorine or bromine, in particular fluorine or chlorine) and/or have attached to them one to four (in particular one to three) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 bis 6 carbon atoms, in particular 1 to 4 carbon atoms, and the alkenyl or alkynyl groups mentioned in these radicals containing 2 to 8, preferably 2 to 6, in particular 2 to 4 carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing, in particular, 5 or 6 ring members and the alkyl groups in these radicals preferably containing 1 to 6 carbon atoms, in particular 1 to 4 carbon atoms, and/or one or two (in particular one) of the following radicals:

formyl, $CR^{iii}$=$NOR^{iv}$ [where $R^{iii}$ is hydrogen, alkyl, cycloalkyl and aryl and $R^{iv}$ is alkyl, alkenyl, haloalkenyl, alkynyl and arylalkyl (the abovementioned alkyl groups preferably containing 1 to 6 carbon atoms, in particular 1 to 4 carbon atoms, the abovementioned cycloalkyl groups, alkenyl groups and alkynyl groups preferably containing 3 to 8, in particular 3 to 6, carbon atoms) and aryl is, in particular, phenyl which is unsubstituted or may be substituted by customary groups] or $NR^{v}$—CO—D—$R^{vi}$ [where $R^{v}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl, $R^{vi}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl and D is a direct linkage, oxygen or nitrogen, it being possible for the nitrogen to have attached to it one of the groups mentioned under $R^{vi}$], or where two adjacent C atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group, it being possible for these bridges, in turn, to be partially or fully halogenated and/or to have attached to them one to three, in particular one or two, of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning, in particular, the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

With a view to their use as intermediates for the preparation of the compounds I, especially preferred compounds are those of the formula XX

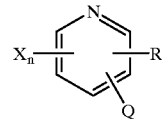

XX where X, n and R have the abovementioned meanings and Q is $NO_2$, NHOH or N(OR')—$CO_2$—Ar, Ar being an unsubstituted or substituted aromatic radical.

Moreover, preferred intermediates are those of the formula XY

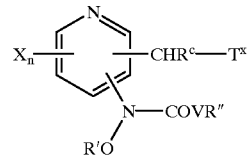

XY where X, n, R', V and R" have the abovementioned meanings, $R^c$ is hydrogen or an alkyl group and $T^x$ is hydrogen, hydroxyl, oxyamino (O—$NH_2$), halogen, alkoxy, alkylcarbonyloxy, aryloxy, triarylphosphonium halide or alkyl- or arylphosphonate, it being possible for the alkyl and aryl groups to have attached to them customary substituents.

Other preferred intermediates are those of the formula XZ

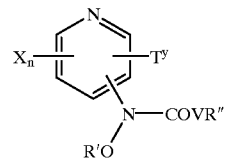

XZ where X, n, R', V and R" have the meanings given in claim 1 and $T^y$ is cyano, nitro, hydroxyl, amino, formyl, halogen, alkylcarbonyl, alkylsulfonyl, alkylsulfonyloxy, arylsulfonyl or arylsulfonyloxy, it being possible for the alkyl and aryl groups to have attached to them customary substituents.

With a view to their biological activity, preferred compounds of the formula I are those where n is 0 or 1, in particular 0.

In the event that n is not 0, preferred compounds I are those where X is fluorine, chlorine, methyl and trifluoromethyl.

Particularly preferred compounds I are those where V is oxygen.

Moreover, especially preferred compounds I are those where V is NH.

Equally especially preferred compounds I are those where V is a direct linkage.

Particularly preferred compounds I are those where R" is methyl.

Moreover, especially preferred compounds I are those where R" is ethyl.

Equally especially preferred compounds I are those where R" is cyclopropyl.

Other especially preferred compounds I are those where R" is amino ($NH_2$).

Particularly preferred compounds I are those where R' is hydrogen.

Moreover, especially preferred compounds I are those where R' is methyl.

Equally especially preferred compounds I are those where R' is ethyl.

Other especially preferred compounds I are those where R' is methoxymethyl, allyl or propargyl.

Particularly preferred compounds are those of the formula I.A

I.A $$X_n \underset{R'O}{\overset{N}{\diagdown}} \overset{}{\underset{N-COVR''}{\bigg|}} Y^a - A^a$$

where $X_n$, R', V and R" have the abovementioned meanings and $Y^a$ and $A^a$ are the following groups:

$Y^a$ is a direct linkage, oxygen, sulfur, or an amino group which may have attached to it one of the following radicals: $C_1$–$C_6$-alkyl, $C_3$–$C_6$-alkenyl, $C_3$–$C_6$-alkynyl or $C_3$–$C_8$-cycloalkyl;

$A^a$ is unsubstituted or substituted $C_1$–$C_6$-alkyl, $C_3$–$C_6$-alkenyl, $C_3$–$C_6$-alkynyl, $C_3$–$C_6$-cycloalkyl, 3- to 7-membered heterocyclyl, 5- to 10-membered aryl or hetaryl.

$A^a$ in formula I.A is, in particular, unsubstituted or substituted 5- to 10-membered aryl or hetaryl.

Other preferred compounds are those of the formula I.B

I.B $$X_n \underset{R'O}{\overset{N}{\diagdown}} \overset{}{\underset{N-COVR''}{\bigg|}} Y^b - N = CR^b - A^b$$

where $X_n$, R', V and R" have the abovementioned meanings and $Y^b$, $R^b$ and $A^b$ are the following groups:

$Y^b$ is a direct linkage, oxygen or an amino group which may have attached to it one of the following radicals: $C_1$–$C_6$-alkyl, $C_3$–$C_6$-alkenyl, $C_3$–$C_6$-alkynyl or $C_3$–$C_8$-cycloalkyl;

$R^b$ is hydrogen, unsubstituted or substituted $C_1$–$C_6$-alkyl, $C_3$–$C_6$-alkenyl, $C_3$–$C_6$-alkynyl or $C_3$–$C_8$-cycloalkyl;

$A^b$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl.

$A^b$ in formula I.B is, in particular, unsubstituted or substituted 5- to 10-membered aryl or hetaryl.

Moreover, preferred compounds of the formula I.B

I.B $$X_n \underset{R'O}{\overset{N}{\diagdown}} \overset{}{\underset{N-COVR''}{\bigg|}} Y^b - N = CR^b - A^b$$

are those where $X_n$, R', V, R", $Y^b$ and $R^b$ have the abovementioned meanings and $A^b$ is one of the following groups:

$A^b$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl, hetaryl or $CR^\alpha$=$NOR^\beta$ where $R^\alpha$ is hydrogen, halogen, unsubstituted or substituted $C_1$–$C_6$-alkyl, $C_1$–$C_6$-alkoxy, $C_1$–$C_6$-alkylthio, $C_1$–$C_6$-alkylamino, $C_1$–$C_6$-haloalkyl, $C_1$–$C_6$-haloalkyloxy, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, $C_3$–$C_8$-cycloalkyl-$C_1$–$C_4$-alkyl, 3- to 7-membered heterocyclyl, heterocyclyloxy, heterocyclylthio, heterocyclylamino, 5- to 10-membered aryl, aryloxy, arylthio, arylamino, hetaryl, aryl-$C_1$–$C_4$-alkyl, aryloxy-$C_1$–$C_4$-alkyl and aryl-$C_1$–$C_4$-alkoxy, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(CH_3)$=$N$—$A^1$—$R^1$;

$R^1$ is $C_1$–$C_6$-alkyl, $A^1$ is oxygen or nitrogen, the nitrogen atom having attached to it a hydrogen atom or a $C_1$–$C_4$-alkyl group;

hetaryl, hetaryloxy, hetarylthio or hetarylamino, $R^\beta$ is hydrogen, unsubstituted or substituted $C_1$–$C_6$-alkyl, $C_3$–$C_6$-alkenyl, $C_3$–$C_6$-alkynyl, $C_1$–$C_{10}$-alkylcarbonyl, $C_2$–$C_{10}$-alkenylcarbonyl, $C_2$–$C_{10}$-alkynylcarbonyl, $C_1$–$C_{10}$-alkylsulfonyl, $C_3$–$C_8$-cycloalkyl, 3- to 7-membered heterocyclyl, 5- to 10-membered aryl, hetaryl, arylcarbonyl, hetarylcarbonyl, arylsulfonyl or hetarylsulfonyl.

$A^b$ in formula I.B is, in particular, unsubstituted or substituted 5- to 10-membered aryl, hetaryl or $C(R^\alpha)$=$NOR^\beta$ where $R^\alpha$ and $R^\beta$ have the meanings mentioned for the formula I.E.

Moreover, preferred compounds are those of the formula I.C

I.C $$X_n \underset{R'O}{\overset{N}{\diagdown}} \overset{}{\underset{N-COVR''}{\bigg|}} CHR^c - Y^c - A^c$$

where $X_n$, R', V and R" have the abovementioned meanings and $Y^c$, $R^c$ and $A^c$ are the following groups:

$Y^c$ is oxygen, sulfur or an amino group which may have attached to it one of the following radicals: $C_1$–$C_6$-alkyl, $C_3$–$C_6$-alkenyl, $C_3$–$C_6$-alkynyl or $C_3$–$C_8$-cycloalkyl;

$R^c$ is hydrogen, unsubstituted or substituted $C_1$–$C_6$-alkyl, $C_3$–$C_6$-alkenyl or $C_3$–$C_6$-alkynyl;

$A^c$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl.

$R^c$ in formula I.C is, in particular, hydrogen and methyl.

$A^c$ in formula I.C is, in particular, unsubstituted or substituted 5- to 10-membered aryl or hetaryl.

Equally preferred compounds are those of the formula I.D

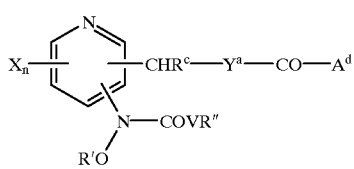
I.D where $X_n$, R', V and R'' have the abovementioned meanings and $Y^a$, $R^c$ and $A^d$ are the following groups:

$R^c$ is hydrogen, unsubstituted or substituted $C_1$–$C_6$-alkyl, $C_3$–$C_6$-alkenyl or $C_3$–$C_6$-alkynyl;

$Y^a$ is a direct linkage, oxygen, sulfur or an amino group which can have attached to it one of the following radicals: $C_1$–$C_6$-alkyl, $C_3$–$C_6$-alkenyl, $C_3$–$C_6$-alkynyl or $C_3$–$C_8$-cycloalkyl;

$A^d$ is unsubstituted or substituted $C_1$–$C_6$-alkyl, $C_1$–$C_6$-alkoxy, $C_1$–$C_6$-alkylamino, $C_3$–$C_6$-alkenyl, $C_3$–$C_6$-alkenyloxy, $C_3$–$C_6$-alkenylamino, $C_3$–$C_6$-alkynyl, $C_3$–$C_6$-alkynyloxy, $C_3$–$C_6$-alkynylamino, $C_3$–$C_8$-cycloalkyl, $C_3$-$C_8$-cycloalkoxy, $C_3$–$C_8$-cycloalkylamino, 3- to 7-membered heterocyclyl, heterocyclyloxy, heterocyclylamino, 5- to 10-membered aryl, aryloxy, arylamino, hetaryl, hetaryloxy and hetarylamino.

$R^c$ in formula I.D is, in particular, hydrogen and methyl.

$A^d$ in formula I.D is, in particular, unsubstituted or substituted 5- to 10-membered aryl or hetaryl.

Furthermore, preferred compounds are those of the formula I.E

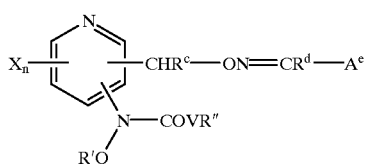
I.E where $X_n$, R', V and R'' have the abovementioned meanings and $R^c$, $R^d$ and $A^e$ are the following groups:

$R^c$ is hydrogen, unsubstituted or substituted $C_1$–$C_6$-alkyl, $C_3$–$C_6$-alkenyl or $C_3$–$C_6$-alkynyl;

$R^d$ is hydrogen, halogen, unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio or hetarylamino;

$A^e$ is unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio, hetarylamino or $CR^\alpha$=NO—$R^\beta$;

$R^\alpha$ is hydrogen, halogen, unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio or hetarylamino;

$R^\beta$ is hydrogen, unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl and hetaryl.

$R^c$ in formula I.E is, in particular, hydrogen and methyl.

$R^d$ in formula I.E is, in particular, hydrogen, methyl, ethyl, isopropyl, trifluoromethyl, methoxy, ethoxy and cyclopropyl.

$A^e$ in formula I.E is, in particular, unsubstituted or substituted 5- to 10-membered aryl, hetaryl or $CR^\alpha$=NO—$R^\beta$.

In the event that $A^e$ is $CR^\alpha$=NO—$R^\beta$, $R^\alpha$ is, in particular, unsubstituted or substituted 5- to 10-membered aryl or hetaryl.

In the event that $A^e$ is $CR^\alpha$=NO—$R^\beta$, $R^\beta$ is, in particular, unhalogenated or halogenated $C_1$–$C_6$-alkyl, $C_3$–$C_6$-alkenyl, $C_3$–$C_6$-alkynyl, $C_3$–$C_8$-cycloalkyl, unsubstituted or substituted benzyl and unsubstituted or substituted 5- to 10-membered aryl or hetaryl.

Also preferred are compounds of the formula I.F

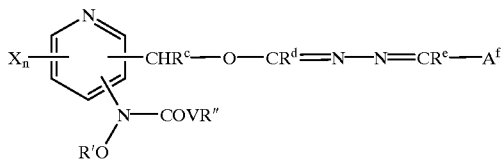
I.F where $X_n$, R', V and R'' have the abovementioned meanings and $R^c$, $R^d$, $R^e$ and $A^f$ are the following groups:

$R^c$ is hydrogen, unsubstituted or substituted $C_1$–$C_6$-alkyl, $C_3$–$C_6$-alkenyl or $C_3$–$C_6$-alkynyl;

$R^d$ is hydrogen, unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl;

$R^e$ is hydrogen, unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl;

$A^f$ is unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$- alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio, hetarylamino or $CR^\alpha$=NO—$R^\beta$.

$R^c$ in formula I.F is, in particular, hydrogen and methyl.

$R^d$ in formula I.F is, in particular, hydrogen, $C_1$–$C_4$-alkyl, especially methyl, unsubstituted or substituted cycloalkyl, especially cycloalkyl, aryl, especially unsubstituted or substituted phenyl, hetaryl, especially unsubstituted or substituted isoxazolyl, pyrazolyl and pyridinyl.

$R^e$ in formula I.F is, in particular, hydrogen, $C_1$–$C_4$-alkyl, especially methyl, unsubstituted or substituted cycloalkyl, especially cycloalkyl, aryl, especially unsubstituted or substituted phenyl, hetaryl, especially unsubstituted or substituted isoxazolyl, pyrazolyl and pyridinyl.

$A^f$ in formula I.F is, in particular, unsubstituted or substituted 5- to 10-membered aryl, hetaryl or $CR^\alpha$=NO—$R^\beta$.

In the event that $A^f$ is $CR^\alpha$=NO—$R^\beta$, $R^\alpha$ is, in particular, unsubstituted or substituted 5- to 10-membered aryl or hetaryl.

In the event that $A^e$ is $CR^\alpha$=NO—$R^\beta$, $R^\beta$ is, in particular, unhalogenated or halogenated $C_1$–$C_6$-alkyl, $C_3$–$C_6$-alkenyl, $C_3$–$C_6$-alkynyl, $C_3$–$C_8$-cycloalkyl, unsubstituted or substituted benzyl and unsubstituted or substituted 5- to 10-membered aryl or hetaryl.

Other preferred compounds are those of the formula I.G

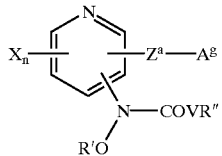

I.G where $X_n$, R', V and R" have the abovementioned meanings and $Z^a$ and $A^g$ are the following groups:

$Z^a$ is ethylene or ethenylene, it being possible for these groups to be unhalogenated or halogenated, or ethynylene;

$A^g$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl.

$A^g$ in formula I.G is, in particular, unsubstituted or substituted 5- to 10-membered aryl or hetaryl.

Moreover, preferred compounds are those of the formula I.H

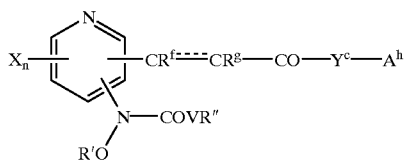

I.H where $X_n$, R', V and R" have the abovementioned meanings and $R^f$, $R^g$, $Y^c$ and $A^h$ are the following groups:

$R^f$ is hydrogen, unsubstituted or substituted $C_1$–$C_6$-alkyl, $C_3$–$C_6$-alkenyl or $C_3$–$C_6$-alkynyl;

$R^g$ is hydrogen, unsubstituted or substituted $C_1$–$C_6$-alkyl, $C_3$–$C_6$-alkenyl or $C_3$–$C_6$-alkynyl;

$Y^c$ is oxygen, sulfur or an amino group which may have attached to it one of the following radicals: $C_1$–$C_6$-alkyl, $C_3$–$C_6$-alkenyl, $C_3$–$C_6$-alkynyl or $C_3$–$C_8$-cycloalkyl;

$A^h$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl.

$R^f$ in formula I.H is, in particular, hydrogen or $C_1$–$C_4$-alkyl, especially methyl.

$R^g$ in formula I.H is, in particular, hydrogen or $C_1$–$C_4$-alkyl, especially methyl.

$A^h$ in formula I.H is, in particular, unsubstituted or substituted 5- to 10-membered aryl or hetaryl.

Equally preferred compounds are those of the formula I.K

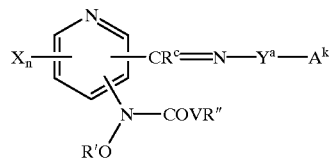

I.K where $X_n$, R', V and R" have the abovementioned meanings and $R^c$, $Y^a$ and $A^k$ are the following groups:

$R^c$ is hydrogen, substituted or unsubstituted $C_1$–$C_6$-alkyl, $C_3$–$C_6$-alkenyl or $C_3$–$C_6$-alkynyl;

$Y^a$ is a direct linkage, oxygen, sulfur or an amino group which may have attached to it one of the following radicals: $C_1$–$C_6$-alkyl, $C_3$–$C_6$-alkenyl, $C_3$–$C_6$-alkynyl or $C_3$–$C_8$-cycloalkyl;

$A^k$ is unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl.

$R^c$ in formula I.K is, in particular, hydrogen or $C_1$–$C_4$-alkyl, especially methyl.

$A^k$ in formula I.K is, in particular, unsubstituted or substituted 5- to 10-membered aryl or hetaryl.

Furthermore, preferred compounds are those of the formula I.L

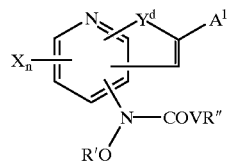

I.L where $X_n$, R', V and R" have the abovementioned meanings and $Y'^d$ and $A^l$ are the following groups:

$Y^d$ is oxygen, sulfur or an amino group which may have attached to it one of the following radicals: unsubstituted or substituted $C_1$–$C_6$-alkyl, $C_3$–$C_6$-alkenyl, $C_3$–$C_6$-alkynyl, $C_3$–$C_8$-cycloalkyl, 3- to 7-membered heterocyclyl, 5- to 10-membered aryl or hetaryl;

$A^l$ is unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio or hetarylamino.

$A^l$ in formula I.L is, in particular, unsubstituted or substituted 5- to 10-membered aryl, aryloxy, arylthio, arylamino, hetaryl, hetaryloxy, hetarylthio or hetarylamino.

Equally preferred compounds are those of the formula I.M

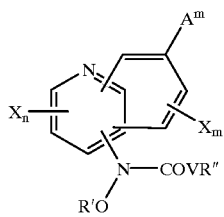

I.M where $X_n$, R', V and R" have the abovementioned meanings, m is 0, 1, 2 or 3, especially 0 or 1, and $A^m$ is one of the following groups:

$A^m$ is unsubstituted or substituted $C_1$–$C_6$-alkyl, $C_1$–$C_6$-alkoxy, $C_1$–$C_6$-alkylthio, $C_1$–$C_6$-alkylamino, $C_3$–$C_6$-alkenyl, $C_3$–$C_6$-alkenyloxy, $C_3$–$C_6$-alkenylthio, $C_3$–$C_6$-alkenylamino, $C_3$–$C_6$-alkynyl, $C_3$–$C_6$-alkynyloxy, $C_3$–$C_6$-alkynylthio, $C_3$–$C_6$-alkynylamino, $C_3$–$C_8$-cycloalkyl, $C_3$–$C_8$-cycloalkoxy, $C_3$–$C_8$-cycloalkylthio, $C_3$–$C_8$-cycloalkylamino, 3- to 7-membered heterocyclyl, heterocyclyloxy, heterocyclylthio, heterocyclylamino, 5- to 10-membered aryl, aryloxy, arylthio, arylamino, hetaryl, hetaryloxy, hetarylthio or hetarylamino.

$A^m$ in formula I.M is, in particular, unsubstituted or substituted 5- to 10-membered aryl, aryloxy, arylthio, arylamino, hetaryl, hetaryloxy, hetarylthio or hetarylamino.

Particularly preferred with a view to their use are the compounds I compiled in the tables which follow. Moreover, the groups mentioned in the tables for one substituent are, by themselves and independently of the combination in which they are mentioned, an especially preferred embodiment of the substituent in question.

Table 1

Compounds of the formula I.1C/1 where R' is hydrogen, VR" is methoxy and $R^1_x$ for each compound corresponds to one line of Table A.

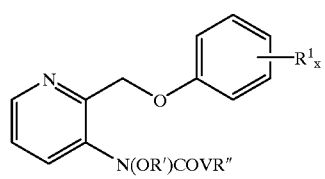

I.1C/1

Table 2

Compounds of the formula I.1C/1 where R' is methyl, VR" is methoxy and $R^1_x$ for each compound corresponds to one line of Table A.

Table 3

Compounds of the formula I.1C/1 where R' is hydrogen, VR" is methylamino and $R^1_x$ for each compound corresponds to one line of Table A.

Table 4

Compounds of the formula I.1C/1 where R' is methyl, VR" is methylamino and $R^1_x$ for each compound corresponds to one line of Table A.

Table 5

Compounds of the formula I.1C/2 where R' is hydrogen, VR" is methoxy and $R^1_x$ for each compound corresponds to one line of Table B.

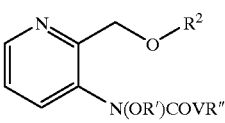

I.1C/2

Table 6

Compounds of the formula I.1C/2 where R' is methyl, VR" is methoxy and $R^2$ for each compound corresponds to one line of Table B.

Table 7

Compounds of the formula I.1C/2 where R' is hydrogen, VR" is methylamino and $R^2$ for each compound corresponds to one line of Table B.

Table 8

Compounds of the formula I.1C/2 where R' is methyl, VR" is methylamino and $R^2$ for each compound corresponds to one line of Table B.

Table 9

Compounds of the formula I.1E/1 where R' is hydrogen, VR" is methoxy and $R^2$ for each compound corresponds to one line of Table A.

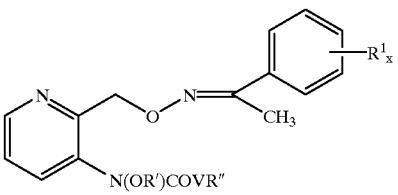

I.1E/1

Table 10

Compounds of the formula I.1E/1 where R' is methyl, VR" is methoxy and $R^1_x$ for each compound corresponds to one line of Table A.

Table 11

Compounds of the formula I.1E/1 where R' is hydrogen, VR" is methylamino and $R^1_x$ for each compound corresponds to one line of Table A.

Table 12

Compounds of the formula I.1E/1 where R' is methyl, VR" is methylamino and $R^1_x$ for each compound corresponds to one line of Table A.

Table 13

Compounds of the formula I.1E/2 where R' is hydrogen, VR" is methoxy and $R^2$ for each compound corresponds to one line of Table B.

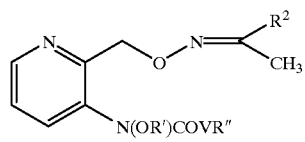

I.1E/2

Table 14

Compounds of the formula I.1E/2 where R' is methyl, VR" is methoxy and $R^2$ for each compound corresponds to one line of Table B.

Table 15

Compounds of the formula I.1E/2 where R' is hydrogen, VR" is methylamino and $R^2$ for each compound corresponds to one line of Table B.

Table 16

Compounds of the formula I.1E/2 where R' is methyl, VR" is methylamino and $R^2$ for each compound corresponds to one line of Table B.

Table 17

Compounds of the formula I.1G/1 where R' is hydrogen, VR" is methoxy and $R^1_x$ for each compound corresponds to one line of Table A.

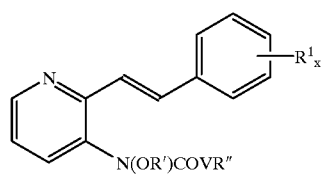

I.1G/1

Table 18

Compounds of the formula I.1G/1 where R' is methyl, VR" is methoxy and $R^1_x$ for each compound corresponds to one line of Table A.

Table 19

Compounds of the formula I.1G/1 where R' is hydrogen, VR" is methylamino and $R^1_x$ for each compound corresponds to one line of Table A.

Table 20

Compounds of the formula I.1G/1 where R' is methyl, VR" is methylamino and $R^1_x$ for each compound corresponds to one line of Table A.

Table 21

Compounds of the formula I.1G/2 where R' is hydrogen, VR" is methoxy and $R^2$ for each compound corresponds to one line of Table B.

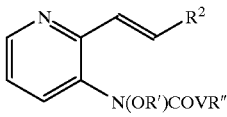

I.1G/2

Table 22

Compounds of the formula I.1G/2 where R' is methyl, VR" is methoxy and $R^2$ for each compound corresponds to one line of Table B.

Table 23

Compounds of the formula I.1G/2 where R' is hydrogen, VR" is methylamino and $R^2$ for each compound corresponds to one line of Table B.

Table 24

Compounds of the formula I.1G/2 where R' is methyl, VR" is methylamino and $R^2$ for each compound corresponds to one line of Table B.

Table 25

Compounds of the formula I.1C/3 where R' is hydrogen, VR" is methoxy and $R^1_x$ for each compound corresponds to one line of Table A.

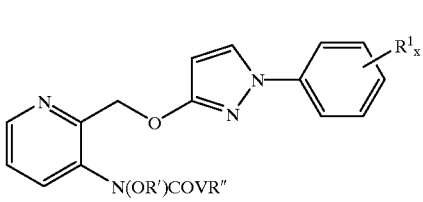

I.1C/3

Table 26

Compounds of the formula I.1C/3 where R' is methyl, VR" is methoxy and $R^1_x$ for each compound corresponds to one line of Table A.

Table 27

Compounds of the formula I.1C/3 where R' is hydrogen, VR" is methylamino and $R^1_x$ for each compound corresponds to one line of Table A.

Table 28

Compounds of the formula I.1C/3 where R' is methyl, VR" is methylamino and $R^1_x$ for each compound corresponds to one line of Table A.

Table 29

Compounds of the formula I.1C/4 where R' is hydrogen, VR" is methoxy and $R^1_x$ for each compound corresponds to one line of Table A.

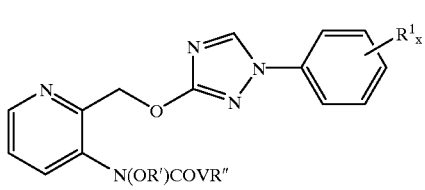

I.1C/4

Table 30
Compounds of the formula I.1C/4 where R' is methyl, VR" is methoxy and $R^1_x$ for each compound corresponds to one line of Table A.

Table 31
Compounds of the formula I.1C/4 where R' is hydrogen, VR" is methylamino and $R^1_x$ for each compound corresponds to one line of Table A.

Table 32
Compounds of the formula I.1C/4 where R' is methyl, VR" is methylamino and $R^1_x$ for each compound corresponds to one line of Table A.

Table 33
Compounds of the formula I.1C/5 where R' is hydrogen, VR" is methoxy, $R^3$ is hydrogen, $R^4_y$ is hydrogen and $R^1_x$ for each compound corresponds to one line of Table A.

I.1C/5

Table 34
Compounds of the formula I.1C/5 where R' is methyl, VR" is methoxy, $R^3$ is hydrogen, $R^4_y$ is hydrogen and $R^1_x$ for each compound corresponds to one line of Table A.

Table 35
Compounds of the formula I.1C/5 where R' is hydrogen, VR" is methylamino, $R^3$ is hydrogen, $R^4_y$ is hydrogen and $R^1_x$ for each compound corresponds to one line of Table A.

Table 36
Compounds of the formula I.1C/5 where R' is methyl, VR" is methylamino, $R^3$ is hydrogen, $R^4_y$ is hydrogen and $R^1_x$ for each compound corresponds to one line of Table A.

Table 37
Compounds of the formula I.1C/5 where R' is hydrogen, VR" is methoxy, $R^3$ is methyl, $R^4_y$ is hydrogen and $R^1_x$ for each compound corresponds to one line of Table A.

Table 38
Compounds of the formula I.1C/5 where R' is methyl, VR" is methoxy, $R^3$ is methyl, $R^4_y$ is hydrogen and $R^1_x$ for each compound corresponds to one line of Table A.

Table 39
Compounds of the formula I.1C/5 where R' is hydrogen, VR" is methylamino, $R^3$ is methyl, $R^4_y$ is hydrogen and $R^1_x$ for each compound corresponds to one line of Table A.

Table 40
Compounds of the formula I.1C/5 where R' is methyl, VR" is methylamino, $R^3$ is methyl, $R^4_y$ is hydrogen and $R^1_x$ for each compound corresponds to one line of Table A.

Table 41
Compounds of the formula I.1C/5 where R' is hydrogen, VR" is methoxy, $R^3$ is fluorine, $R^4_y$ is hydrogen and $R^1_x$ for each compound corresponds to one line of Table A.

Table 42
Compounds of the formula I.1C/5 where R' is methyl, VR" is methoxy, $R^3$ is fluorine, $R^4_y$ is hydrogen and $R^1_x$ for each compound corresponds to one line of Table A.

Table 43
Compounds of the formula I.1C/5 where R' is hydrogen, VR" is methylamino, $R^3$ is fluorine, $R^4_y$ is hydrogen and $R^1_x$ for each compound corresponds to one line of Table A.

Table 44
Compounds of the formula I.1C/5 where R' is methyl, VR" is methylamino, $R^3$ is fluorine, $R^4_y$ is hydrogen and $R^1_x$ for each compound corresponds to one line of Table A.

Table 45
Compounds of the formula I.1C/5 where R' is hydrogen, VR" is methoxy, $R^3$ is chlorine, $R^4_y$ is hydrogen and $R^1_x$ for each compound corresponds to one line of Table A.

Table 46
Compounds of the formula I.1C/5 where R' is methyl, VR" is methoxy, $R^3$ is chlorine, $R^4_y$ is hydrogen and $R^1_x$ for each compound corresponds to one line of Table A.

Table 47
Compounds of the formula I.1C/5 where R' is hydrogen, VR" is methylamino, $R^3$ is chlorine, $R^4_y$ is hydrogen and $R^1_x$ for each compound corresponds to one line of Table A.

Table 48
Compounds of the formula I.1C/5 where R' is methyl, VR" is methylamino, $R^3$ is chlorine, $R^4_y$ is hydrogen and $R^1_x$ for each compound corresponds to one line of Table A.

Table 49
Compounds of the formula I.1C/5 where R' is hydrogen, VR" is methoxy, $R^3$ is cyano, $R^4_y$ is hydrogen and $R^1_x$ for each compound corresponds to one line of Table A.

Table 50
Compounds of the formula I.1C/5 where R' is methyl, VR" is methoxy, $R^3$ is cyano, $R^4_y$ is hydrogen and $R^1_x$ for each compound corresponds to one line of Table A.

Table 51
Compounds of the formula I.1C/5 where R' is hydrogen, VR" is methylamino, $R^3$ is cyano, $R^4_y$ is hydrogen and $R^1_x$ for each compound corresponds to one line of Table A.

Table 52

Compounds of the formula I.1C/5 where R' is methyl, VR" is methylamino, $R^3$ is cyano, $R^4_y$ is hydrogen and $R^1_x$ for each compound corresponds to one line of Table A.

Table 53

Compounds of the formula I.1C/5 where R' is hydrogen, VR" is methoxy, $R^3$ is methoxy, $R^4_y$ is hydrogen and $R^1_x$ for each compound corresponds to one line of Table A.

Table 54

Compounds of the formula I.1C/5 where R' is methyl, VR" is methoxy, $R^3$ is methoxy, $R^4_y$ is hydrogen and $R^1_x$ for each compound corresponds to one line of Table A.

Table 55

Compounds of the formula I.1C/5 where R' is hydrogen, VR" is methylamino, $R^3$ is methoxy, $R^4_y$ is hydrogen and $R^1_x$ for each compound corresponds to one line of Table A.

Table 56

Compounds of the formula I.1C/5 where R' is methyl, VR" is methylamino, $R^3$ is methoxy, $R^4_y$ is hydrogen and $R^1_x$ for each compound corresponds to one line of Table A.

Table 57

Compounds of the formula I.1C/5 where R' is hydrogen, VR" is methoxy, $R^3$ is methyl, $R^4_y$ is 5-methyl and $R^1_x$ for each compound corresponds to one line of Table A.

Table 58

Compounds of the formula I.1C/5 where R' is methyl, VR" is methoxy, $R^3$ is methyl, $R^4_y$ is 5-methyl and $R^1_x$ for each compound corresponds to one line of Table A.

Table 59

Compounds of the formula I.1C/5 where R' is hydrogen, VR" is methylamino, $R^3$ is methyl, $R^4_y$ is 5-methyl and $R^1_x$ for each compound corresponds to one line of Table A.

Table 60

Compounds of the formula I.1C/5 where R' is methyl, VR" is methylamino and $R^1_x$ for each compound corresponds to one line of Table A.

Table 61

Compounds of the formula I.1E/3 where R' is hydrogen, VR" is methoxy and the combination of the substituents $R^d$ and $R^1_x$ for each compound corresponds to one line of Table C.

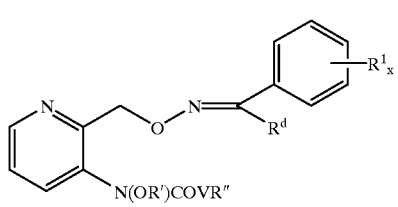

I.1E/3

Table 62

Compounds of the formula I.1E/3 where R' is methyl, VR" is methoxy and the combination of the substituents $R^d$ and $R^1_x$ for each compound corresponds to one line of Table C.

Table 63

Compounds of the formula I.1E/3 where R' is hydrogen, VR" is methylamino and the combination of the substituents $R^d$ and $R^1_x$ for each compound corresponds to one line of Table C.

Table 64

Compounds of the formula I.1E/3 where R' is methyl, VR" is methylamino and the combination of the substituents $R^d$ and $R^1_x$ for each compound corresponds to one line of Table C.

Table 65

Compounds of the formula I.1F/1 where R' is hydrogen, VR" is methoxy and $R^1_x$ for each compound corresponds to one line of Table A.

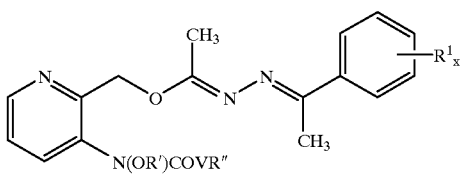

I.1F/1

Table 66

Compounds of the formula I.1F/1 where R' is methyl, VR" is methoxy and $R^1_x$ for each compound corresponds to one line of Table A.

Table 67

Compounds of the formula I.1F/1 where R' is hydrogen, VR" is methylamino and $R^1_x$ for each compound corresponds to one line of Table A.

Table 68

Compounds of the formula I.1F/1 where R' is methyl, VR" is methylamino and $R^1_x$ for each compound corresponds to one line of Table A.

Table 69

Compounds of the formula I.1F/2 where R' is hydrogen, VR" is methoxy and $R^2$ for each compound corresponds to one line of Table B.

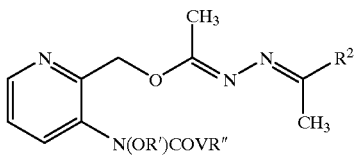

I.1F/2

Table 70

Compounds of the formula I.1F/2 where R' is methyl, VR" is methoxy and $R^2$ for each compound corresponds to one line of Table B.

Table 71

Compounds of the formula I.1F/2 where R' is hydrogen, VR" is methylamino and $R^2$ for each compound corresponds to one line of Table B.

Table 72

Compounds of the formula I.1F/2 where R' is methyl, VR" is methylamino and $R^2$ for each compound corresponds to one line of Table B.

Table 73

Compounds of the formula I.1F/3 where R' is hydrogen, VR" is methoxy and the combination of the substituents $R^d$, $R^e$ and $A^f$ for each compound corresponds to one line of Table D.

I.1F/3

Table 74

Compounds of the formula I.1F/3 where R' is methyl, VR" is methoxy and the combination of the substituents $R^d$, $R^e$ and $A^f$ for each compound corresponds to one line of Table D.

Table 75

Compounds of the formula I.1F/3 where R' is hydrogen, VR" is methylamino and the combination of the substituents $R^d$, $R^e$ and $A^f$ for each compound corresponds to one line of Table D.

Table 76

Compounds of the formula I.1F/3 where R' is methyl, VR" is methylamino and the combination of the substituents $R^d$, $R^e$ and $A^f$ for each compound corresponds to one line of Table D.

Table 77

Compounds of the formula I.1F/4 where R' is hydrogen, VR" is methoxy, $R^d$ is methyl, $R^e$ is methyl, $R^\beta$ is methyl and $R^\alpha$ is $R^1_x$-substituted phenyl, $R^1_x$ for each compound corresponding to one line of Table A.

I.1F/4

Table 78

Compounds of the formula I.1F/4 where R' is methyl, VR" is methoxy, $R^d$ is methyl, $R^e$ is methyl, $R^\beta$ is methyl and $R^\alpha$ is $R^1_x$-substituted phenyl, $R^1_x$ for each compound corresponding to one line of Table A.

Table 79

Compounds of the formula I.1F/4 where R' is hydrogen, VR" is methylamino, $R^d$ is methyl, $R^e$ is methyl, $R^\beta$ is methyl and $R^\alpha$ is $R^1_x$-substituted phenyl, $R^1_x$ for each compound corresponding to one line of Table A.

Table 80

Compounds of the formula I.1F/4 where R' is methyl, VR" is methylamino, $R^d$ is methyl, $R^e$ is methyl, $R^\beta$ is methyl and $R^\alpha$ is $R^1_x$-substituted phenyl, $R^1_x$ for each compound corresponding to one line of Table A.

Table 81

Compounds of the formula I.1F/4 where R' is hydrogen, VR" is methoxy, $R^d$ is methyl, $R^e$ is methyl, $R^\beta$ is ethyl and $R^\alpha$ is $R^1_x$-substituted phenyl, $R^1_x$ for each compound corresponding to one line of Table A.

Table 82

Compounds of the formula I.1F/4 where R' is methyl, VR" is methoxy, $R^d$ is methyl, $R^e$ is methyl, $R^\beta$ is ethyl and $R^\alpha$ is $R^1_x$-substituted phenyl, $R^1_x$ for each compound corresponding to one line of Table A.

Table 83

Compounds of the formula I.1F/4 where R' is hydrogen, VR" is methylamino, $R^d$ is methyl, $R^e$ is methyl, $R^\beta$ is ethyl and $R^\alpha$ is $R^1_x$-substituted phenyl, $R^1_x$ for each compound corresponding to one line of Table A.

Table 84

Compounds of the formula I.1F/4 where R' is methyl, VR" is methylamino, $R^d$ is methyl, $R^e$ is methyl, $R^\beta$ is ethyl and $R^\alpha$ is $R^1_x$-substituted phenyl, $R^1_x$ for each compound corresponding to one line of Table A.

Table 85

Compounds of the formula I.1F/4 where R' is hydrogen, VR" is methoxy, $R^d$ is methyl, $R^e$ is methyl, $R^\beta$ is allyl and $R^\alpha$ is $R^1_x$-substituted phenyl, $R^1_x$ for each compound corresponding to one line of Table A.

Table 86

Compounds of the formula I.1F/4 where R' is methyl, VR" is methoxy, $R^d$ is methyl, $R^e$ is methyl, $R^\beta$ is allyl and $R^\alpha$ is $R^1_x$-substituted phenyl, $R^1_x$ for each compound corresponding to one line of Table A.

Table 87

Compounds of the formula I.1F/4 where R' is hydrogen, VR" is methylamino, $R^d$ is methyl, $R^e$ is methyl, $R^\beta$ is allyl and $R^\alpha$ is $R^1_x$-substituted phenyl, $R^1_x$ for each compound corresponding to one line of Table A.

Table 88

Compounds of the formula I.1F/4 where R' is methyl, VR" is methylamino, $R^d$ is methyl, $R^e$ is methyl, $R^\beta$ is allyl and $R^\alpha$ is $R^1_x$-substituted phenyl, $R^1_x$ for each compound corresponding to one line of Table A.

Table 89

Compounds of the formula I.1F/4 where R' is hydrogen, VR" is methoxy, $R^d$ is methyl, $R^e$ is methyl, $R^\beta$ is propargyl and $R^\alpha$ is $R^1_x$-substituted phenyl, $R^1_x$ for each compound corresponding to one line of Table A.

Table 90

Compounds of the formula I.1F/4 where R' is methyl, VR" is methoxy, $R^d$ is methyl, $R^e$ is methyl, $R^\beta$ is propargyl and $R^\alpha$ is $R^1_x$-substituted phenyl, $R^1_x$ for each compound corresponding to one line of Table A.

Table 91

Compounds of the formula I.1F/4 where R' is hydrogen, VR" is methylamino, $R^d$ is methyl, $R^e$ is methyl, $R^\beta$ is propargyl and $R^\alpha$ is $R^1_x$-substituted phenyl, $R^1_x$ for each compound corresponding to one line of Table A.

Table 92

Compounds of the formula I.1F/4 where R' is methyl, VR" is methylamino, $R^d$ is methyl, $R^e$ is methyl, $R^\beta$ is propargyl and $R^\alpha$ is $R^1_x$-substituted phenyl, $R^1_x$ for each compound corresponding to one line of Table A.

Table 93

Compounds of the formula I.1F/4 where R' is hydrogen, VR" is methoxy, $R^d$ is methyl, $R^e$ is methyl, $R^\beta$ is trans-chloroallyl and $R^\alpha$ is $R^1_x$-substituted phenyl, $R^1_x$ for each compound corresponding to one line of Table A.

Table 94

Compounds of the formula I.1F/4 where R' is methyl, VR" is methoxy, $R^d$ is methyl, $R^e$ is methyl, $R^\beta$ is trans-chloroallyl and $R^\alpha$ is $R^1_x$-substituted phenyl, $R^1_x$ for each compound corresponding to one line of Table A.

Table 95

Compounds of the formula I.1F/4 where R' is hydrogen, VR" is methylamino, $R^d$ is methyl, $R^e$ is methyl, $R^\beta$ is trans-chloroallyl and $R^\alpha$ is $R^1_x$-substituted phenyl, $R^1_x$ for each compound corresponding to one line of Table A.

Table 96

Compounds of the formula I.1F/4 where R' is methyl, VR" is methylamino, $R^d$ is methyl, $R^e$ is methyl, $R^\beta$ is trans-chloroallyl and $R^\alpha$ is $R^1_x$-substituted phenyl, $R^1_x$ for each compound corresponding to one line of Table A.

Table 97

Compounds of the formula I.1F/4 where R' is hydrogen, VR" is methoxy, $R^d$ is methyl, $R^e$ is methyl, $R^\beta$ is methyl and $R^\alpha$ for each compound corresponds to one group $R^2$ of Table B.

Table 98

Compounds of the formula I.1F/4 where R' is methyl, VR" is methoxy, $R^d$ is methyl, $R^e$ is methyl, $R^{62}$ is methyl and $R^\alpha$ for each compound corresponds to one group $R^2$ of Table B.

Table 99

Compounds of the formula I.1F/4 where R' is hydrogen, VR" is methylamino, $R^d$ is methyl, $R^e$ is methyl, $R^\beta$ is methyl and $R^\alpha$ for each compound corresponds to one group $R^2$ of Table B.

Table 100

Compounds of the formula I.1F/4 where R' is methyl, VR" is methylamino, $R^d$ is methyl, $R^e$ is methyl, $R^\beta$ is methyl and $R^\alpha$ for each compound corresponds to one group $R^2$ of Table B.

Table 101

Compounds of the formula I.1F/4 where R' is hydrogen, VR" is methoxy, $R^d$ is methyl, $R^e$ is methyl, $R^\beta$ is ethyl and $R^\alpha$ for each compound corresponds to one group $R^2$ of Table B.

Table 102

Compounds of the formula I.1F/4 where R' is methyl, VR" is methoxy, $R^d$ is methyl, $R^e$ is methyl, $R^\beta$ is ethyl and $R^\alpha$ for each compound corresponds to one group $R^2$ of Table B.

Table 103

Compounds of the formula I.1F/4 where R' is hydrogen, VR" is methylamino, $R^d$ is methyl, $R^e$ is methyl, $R^\beta$ is ethyl and $R^\alpha$ for each compound corresponds to one group $R^2$ of Table B.

Table 104

Compounds of the formula I.1F/4 where R' is methyl, VR" is methylamino, $R^d$ is methyl, $R^e$ is methyl, $R^\beta$ is ethyl and $R^\alpha$ for each compound corresponds to one group $R^2$ of Table B.

Table 105

Compounds of the formula I.1F/4 where R' is hydrogen, VR" is methoxy, $R^d$ is methyl, $R^e$ is methyl, $R^\beta$ is allyl and $R^\alpha$ for each compound corresponds to one group $R^2$ of Table B.

Table 106

Compounds of the formula I.1F/4 where R' is methyl, VR" is methoxy, $R^d$ is methyl, $R^e$ is methyl, $R^\beta$ is allyl and $R^\alpha$ is $R^1_x$-substituted phenyl, $R^1_x$ for each compound corresponding to one group $R^2$ of Table B.

Table 107

Compounds of the formula I.1F/4 where R' is hydrogen, VR" is methylamino, $R^d$ is methyl, $R^e$ is methyl, $R^\beta$ is allyl and $R^\alpha$ for each compound corresponds to one group $R^2$ of Table B.

Table 108

Compounds of the formula I.1F/4 where R' is methyl, VR" is methylamino, $R^d$ is methyl, $R^e$ is methyl, $R^\beta$ is allyl and $R^\alpha$ for each compound corresponds to one group $R^2$ of Table B.

Table 109

Compounds of the formula I.1F/4 where R' is hydrogen, VR" is methoxy, $R^d$ is methyl, $R^e$ is methyl, $R^\beta$ is propargyl and $R^\alpha$ for each compound corresponds to one group $R^2$ of Table B.

Table 110

Compounds of the formula I.1F/4 where R' is methyl, VR" is methoxy, $R^d$ is methyl, $R^e$ is methyl, $R^\beta$ is propargyl and $R^\alpha$ for each compound corresponds to one group $R^2$ of Table B.

Table 111

Compounds of the formula I.1F/4 where R' is hydrogen, VR" is methylamino, $R^d$ is methyl, $R^e$ is methyl, $R^\beta$ is propargyl and $R^\alpha$ for each compound corresponds to one group $R^2$ of Table B.

Table 112

Compounds of the formula I.1F/4 where R' is methyl, VR" is methylamino, $R^d$ is methyl, $R^e$ is methyl, $R^\beta$ is propargyl and $R^\alpha$ for each compound corresponds to one group $R^2$ of Table B.

Table 113

Compounds of the formula I.1F/4 where R' is hydrogen, VR" is methoxy, $R^d$ is methyl, $R^e$ is methyl, $R^\beta$ is trans-chloroallyl and $R^\alpha$ for each compound corresponds to one group $R^2$ of Table B.

Table 114

Compounds of the formula I.1F/4 where R' is methyl, VR" is methoxy, $R^d$ is methyl, $R^e$ is methyl, $R^\beta$ is trans-chloroallyl and $R^\alpha$ for each compound corresponds to one group $R^2$ of Table B.

Table 115

Compounds of the formula I.1F/4 where R' is hydrogen, VR" is methylamino, $R^d$ is methyl, $R^e$ is methyl, $R^\beta$ is trans-chloroallyl and $R^\alpha$ for each compound corresponds to one group $R^2$ of Table B.

Table 116

Compounds of the formula I.1F/4 where R' is methyl, VR" is methylamino, $R^d$ is methyl, $R^e$ is methyl, $R^\beta$ is trans-chloroallyl and $R^\alpha$ for each compound corresponds to one group $R^2$ of Table B.

Table 117

Compounds of the formula I.1F/4 where R' is hydrogen, VR" is methoxy and the combination of the substituents $R^d$, $R^e$, $R^\alpha$ and $R^\beta$ for each compound corresponds to one line of Table E.

Table 118

Compounds of the formula I.1F/4 where R' is methyl, VR" is methoxy and the combination of the substituents $R^d$, $R^e$, $R^\alpha$ and $R^\beta$ for each compound corresponds to one line of Table E.

Table 119

Compounds of the formula I.1F/4 where R' is hydrogen, VR" is methylamino and the combination of the substituents $R^d$, $R^e$, $R^\alpha$ and $R^\beta$ for each compound corresponds to one line of Table E.

Table 120

Compounds of the formula I.1F/4 where R' is methyl, VR" is methylamino and the combination of the substituents $R^d$, $R^e$, $R^\alpha$ and $R^\beta$ for each compound corresponds to one line of Table E.

Table 121

Compounds of the formula I.1E/4 where R' is hydrogen, VR" is methoxy, $R^d$ is methyl, $R^\beta$ is methyl and $R^\alpha$ is $R^1_x$-substituted phenyl, $R^1_x$ for a compound corresponding to one line of Table A.

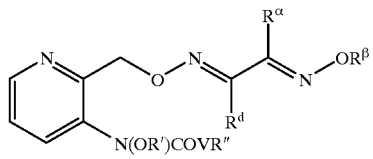

I.1E/4

Table 122

Compounds of the formula I.1E/4 where R' is methyl, VR" is methoxy, $R^d$ is methyl, $R^\beta$ is methyl and $R^\alpha$ is $R^1_x$-substituted phenyl, $R^1_x$ for a compound corresponding to one line of Table A.

Table 123

Compounds of the formula I.1E/4 where R' is hydrogen, VR" is methylamino, $R^d$ is methyl, $R^\beta$ is methyl and $R^\alpha$ is $R^1_x$-substituted phenyl, $R^1_x$ for a compound corresponding to one line of Table A.

Table 124

Compounds of the formula I.1E/4 where R' is methyl, VR" is methylamino, $R^d$ is methyl, $R^\beta$ is methyl and $R^\alpha$ is $R^1_x$-substituted phenyl, $R^1_x$ for a compound corresponding to one line of Table A.

Table 125

Compounds of the formula I.1E/4 where R' is hydrogen, VR" is methoxy, $R^d$ is ethyl, $R^\beta$ is methyl and $R^\alpha$ is $R^1_x$-substituted phenyl, $R^1_x$ for a compound corresponding to one line of Table A.

Table 126

Compounds of the formula I.1E/4 where R' is methyl, VR" is methoxy, $R^d$ is ethyl, $R^\beta$ is methyl and $R^\alpha$ is $R^1_x$-substituted phenyl, $R^1_x$ for a compound corresponding to one line of Table A.

Table 127

Compounds of the formula I.1E/4 where R' is hydrogen, VR" is methylamino, $R^d$ is ethyl, $R^\beta$ is methyl and $R^\alpha$ is $R^1_x$-substituted phenyl, $R^1_x$ for a compound corresponding to one line of Table A.

Table 128

Compounds of the formula I.1E/4 where R' is methyl, VR" is methylamino, $R^d$ is ethyl, $R^\beta$ is methyl and $R^\alpha$ is $R^1_x$-substituted phenyl, $R^1_x$ for a compound corresponding to one line of Table A.

Table 129

Compounds of the formula I.1E/4 where R' is hydrogen, VR" is methoxy, $R^d$ is methyl, $R^\beta$ is ethyl and $R^\alpha$ is $R^1_x$-substituted phenyl, $R^1_x$ for a compound corresponding to one line of Table A.

Table 130

Compounds of the formula I.1E/4 where R' is methyl, VR" is methoxy, $R^d$ is methyl, $R^\beta$ is ethyl and $R^\alpha$ is $R^1_x$-substituted phenyl, $R^1_x$ for a compound corresponding to one line of Table A.

Table 131

Compounds of the formula I.1E/4 where R' is hydrogen, VR" is methylamino, $R^d$ is methyl, $R^\beta$ is ethyl and $R^\alpha$ is $R^1_x$-substituted phenyl, $R^1_x$ for a compound corresponding to one line of Table A.

Table 132

Compounds of the formula I.1E/4 where R' is methyl, VR" is methylamino, $R^d$ is methyl, $R^\beta$ is ethyl and $R^\alpha$ is $R^1_x$-substituted phenyl, $R^1_x$ for a compound corresponding to one line of Table A.

Table 133

Compounds of the formula I.1E/4 where R' is hydrogen, VR" is methoxy, $R^d$ is ethyl, $R^\beta$ is ethyl and $R^\alpha$ is $R^1_x$-substituted phenyl, $R^1_x$ for a compound corresponding to one line of Table A.

Table 134

Compounds of the formula I.1E/4 where R' is methyl, VR" is methoxy, $R^d$ is ethyl, $R^\beta$ is ethyl and $R^\alpha$ is $R^1_x$-substituted phenyl, $R^1_x$ for a compound corresponding to one line of Table A.

Table 135

Compounds of the formula I.1E/4 where R' is hydrogen, VR" is methylamino, $R^d$ is ethyl, $R^\beta$ is ethyl and $R^\alpha$ is $R^1_x$-substituted phenyl, $R^1_x$ for a compound corresponding to one line of Table A.

Table 136

Compounds of the formula I.1E/4 where R' is methyl, VR" is methylamino, $R^d$ is ethyl, $R^\beta$ is ethyl and $R^\alpha$ is $R^1_x$-substituted phenyl, $R^1_x$ for a compound corresponding to one line of Table A.

Table 137

Compounds of the formula I.1E/4 where R' is hydrogen, VR" is methoxy, $R^d$ is methyl, $R^\beta$ is allyl and $R^\alpha$ is $R^1_x$-substituted phenyl, $R^1_x$ for a compound corresponding to one line of Table A.

Table 138

Compounds of the formula I.1E/4 where R' is methyl, VR" is methoxy, $R^d$ is methyl, $R^\beta$ is allyl and $R^\alpha$ is $R^1_x$-substituted phenyl, $R^1_x$ for a compound corresponding to one line of Table A.

Table 139

Compounds of the formula I.1E/4 where R' is hydrogen, VR" is methylamino, $R^d$ is methyl, $R^\beta$ is allyl and $R^\alpha$ is $R^1_x$-substituted phenyl, $R^1_x$ for a compound corresponding to one line of Table A.

Table 140

Compounds of the formula I.1E/4 where R' is methyl, VR" is methylamino, $R^d$ is methyl, $R^\beta$ is allyl and $R^\alpha$ is $R^1_x$-substituted phenyl, $R^1_x$ for a compound corresponding to one line of Table A.

Table 141

Compounds of the formula I.1E/4 where R' is hydrogen, VR" is methoxy, $R^d$ is ethyl, $R^\beta$ is allyl and $R^\alpha$ is $R^1_x$-substituted phenyl, $R^1_x$ for a compound corresponding to one line of Table A.

Table 142

Compounds of the formula I.1E/4 where R' is methyl, VR" is methoxy, $R^d$ is ethyl, $R^\beta$ is allyl and $R^\alpha$ is $R^1_x$-substituted phenyl, $R^1_x$ for a compound corresponding to one line of Table A.

Table 143

Compounds of the formula I.1E/4 where R' is hydrogen, VR" is methylamino, $R^d$ is ethyl, $R^\beta$ is allyl and $R^\alpha$ is $R^1_x$-substituted phenyl, $R^1_x$ for a compound corresponding to one line of Table A.

Table 144

Compounds of the formula I.1E/4 where R' is methyl, VR" is methylamino, $R^d$ is ethyl, $R^\beta$ is allyl and $R^\alpha$ is $R^1_x$-substituted phenyl, $R^1_x$ for a compound corresponding to one line of Table A.

Table 145

Compounds of the formula I.1E/4 where R' is hydrogen, VR" is methoxy, $R^d$ is methyl, $R^\beta$ is propargyl and $R^\alpha$ is $R^1_x$-substituted phenyl, $R^1_x$ for a compound corresponding to one line of Table A.

Table 146

Compounds of the formula I.1E/4 where R' is methyl, VR" is methoxy, $R^d$ is methyl, $R^\beta$ is propargyl and $R^\alpha$ is $R^1_x$-substituted phenyl, $R^1_x$ for a compound corresponding to one line of Table A.

Table 147

Compounds of the formula I.1E/4 where R' is hydrogen, VR" is methylamino, $R^d$ is methyl, $R^\beta$ is propargyl and $R^\alpha$ is $R^1_x$-substituted phenyl, $R^1_x$ for a compound corresponding to one line of Table A.

Table 148

Compounds of the formula I.1E/4 where R' is methyl, VR" is methylamino, $R^d$ is methyl, $R^\beta$ is propargyl and $R^\alpha$ is $R^1_x$-substituted phenyl, $R^1_x$ for a compound corresponding to one line of Table A.

Table 149

Compounds of the formula I.1E/4 where R' is hydrogen, VR" is methoxy, $R^d$ is ethyl, $R^\beta$ is propargyl and $R^\alpha$ is $R^1_x$-substituted phenyl, $R^1_x$ for a compound corresponding to one line of Table A.

Table 150

Compounds of the formula I.1E/4 where R' is methyl, VR" is methoxy, $R^d$ is ethyl, $R^\beta$ is propargyl and $R^\alpha$ is $R^1_x$-substituted phenyl, $R^1_x$ for a compound corresponding to one line of Table A.

Table 151

Compounds of the formula I.1E/4 where R' is hydrogen, VR" is methylamino, $R^d$ is ethyl, $R^\beta$ is propargyl and $R^\alpha$ is $R^1_x$-substituted phenyl, $R^1_x$ for a compound corresponding to one line of Table A.

Table 152

Compounds of the formula I.1E/4 where R' is methyl, VR" is methylamino, $R^d$ is ethyl, $R^\beta$ is propargyl and $R^\alpha$ is $R^1_x$-substituted phenyl, $R^1_x$ for a compound corresponding to one line of Table A.

Table 153

Compounds of the formula I.1E/4 where R' is hydrogen, VR" is methoxy, $R^d$ is methyl, $R^\beta$ is trans-chloroallyl and $R^\alpha$ is $R^1_x$-substituted phenyl, $R^1_x$ for a compound corresponding to one line of Table A.

Table 154

Compounds of the formula I.1E/4 where R' is methyl, VR" is methoxy, $R^d$ is methyl, $R^\beta$ is trans-chloroallyl and $R^\alpha$ is $R^1_x$-substituted phenyl, $R^1_x$ for a compound corresponding to one line of Table A.

Table 155

Compounds of the formula I.1E/4 where R' is hydrogen, VR" is methylamino, $R^d$ is methyl, $R^\beta$ is trans-chloroallyl and $R^\alpha$ is $R^1_x$-substituted phenyl, $R^1_x$ for a compound corresponding to one line of Table A.

Table 156

Compounds of the formula I.1E/4 where R' is methyl, VR" is methylamino, $R^d$ is methyl, $R^\beta$ is trans-chloroallyl and $R^\alpha$ is $R^1_x$-substituted phenyl, $R^1_x$ for a compound corresponding to one line of Table A.

Table 157

Compounds of the formula I.1E/4 where R' is hydrogen, VR" is methoxy, $R^d$ is ethyl, $R^\beta$ is trans-chloroallyl and $R^\alpha$ is $R^1_x$-substituted phenyl, $R^1_x$ for a compound corresponding to one line of Table A.

Table 158

Compounds of the formula I.1E/4 where R' is methyl, VR" is methoxy, $R^d$ is ethyl, $R^\beta$ is trans-chloroallyl and $R^\alpha$ is $R^1_x$-substituted phenyl, $R^1_x$ for a compound corresponding to one line of Table A.

Table 159

Compounds of the formula I.1E/4 where R' is hydrogen, VR" is methylamino, $R^d$ is ethyl, $R^\beta$ is trans-chloroallyl and $R^\alpha$ is $R^1_x$-substituted phenyl, $R^1_x$ for a compound corresponding to one line of Table A.

Table 160

Compounds of the formula I.1E/4 where R' is methyl, VR" is methylamino, $R^d$ is ethyl, $R^\beta$ is trans-chloroallyl and $R^\alpha$ is $R^1_x$-substituted phenyl, $R^1_x$ for a compound corresponding to one line of Table A.

Table 161

Compounds of the formula I.1E/4 where R' is hydrogen, VR" is methoxy, $R^d$ is methyl, $R^\beta$ is methyl and $R^\alpha$ for a compound corresponds to one group $R^2$ of Table B.

Table 162

Compounds of the formula I.1E/4 where R' is methyl, VR" is methoxy, $R^d$ is methyl, $R^\beta$ is methyl and $R^\alpha$ for a compound corresponds to one group $R^2$ of Table B.

Table 163

Compounds of the formula I.1E/4 where R' is hydrogen, VR" is methylamino, $R^d$ is methyl, $R^\beta$ is methyl and $R^\alpha$ for a compound corresponds to one group $R^2$ of Table B.

Table 164

Compounds of the formula I.1E/4 where R' is methyl, VR" is methylamino, $R^d$ is methyl, $R^\beta$ is methyl and $R^\alpha$ for a compound corresponds to one group $R^2$ of Table B.

Table 165

Compounds of the formula I.1E/4 where R' is hydrogen, VR" is methoxy, $R^d$ is ethyl, $R^\beta$ is methyl and $R^\alpha$ for a compound corresponds to one group $R^2$ of Table B.

Table 166

Compounds of the formula I.1E/4 where R' is methyl, VR" is methoxy, $R^d$ is ethyl, $R^\beta$ is methyl and $R^\alpha$ for a compound corresponds to one group $R^2$ of Table B.

Table 167

Compounds of the formula I.1E/4 where R' is hydrogen, VR" is methylamino, $R^d$ is ethyl, $R^\beta$ is methyl and $R^\alpha$ for a compound corresponds to one group $R^2$ of Table B.

Table 168

Compounds of the formula I.1E/4 where R' is methyl, VR" is methylamino, $R^d$ is ethyl, $R^\beta$ is methyl and $R^\alpha$ for a compound corresponds to one group $R^2$ of Table B.

Table 169

Compounds of the formula I.1E/4 where R' is hydrogen, VR" is methoxy, $R^d$ is methyl, $R^\beta$ is ethyl and $R^\alpha$ for a compound corresponds to one group $R^2$ of Table B.

Table 170

Compounds of the formula I.1E/4 where R' is methyl, VR" is methoxy, $R^d$ is methyl, $R^\beta$ is ethyl and $R^\alpha$ for a compound corresponds to one group $R^2$ of Table B.

Table 171

Compounds of the formula I.1E/4 where R' is hydrogen, VR" is methylamino, $R^d$ is methyl, $R^\beta$ is ethyl and $R^\alpha$ for a compound corresponds to one group $R^2$ of Table B.

Table 172

Compounds of the formula I.1E/4 where R' is methyl, VR" is methylamino, $R^d$ is methyl, $R^\beta$ is ethyl and $R^\alpha$ for a compound corresponds to one group $R^2$ of Table B.

Table 173

Compounds of the formula I.1E/4 where R' is hydrogen, VR" is methoxy, $R^d$ is ethyl, $R^\beta$ is ethyl and $R^\alpha$ for a compound corresponds to one group $R^2$ of Table B.

Table 174

Compounds of the formula I.1E/4 where R' is methyl, VR" is methoxy, $R^d$ is ethyl, $R^\beta$ is ethyl and $R^\alpha$ for a compound corresponds to one group $R^2$ of Table B.

Table 175

Compounds of the formula I.1E/4 where R' is hydrogen, VR" is methylamino, $R^d$ is ethyl, $R^\beta$ is ethyl and $R^\alpha$ for a compound corresponds to one group $R^2$ of Table B.

Table 176

Compounds of the formula I.1E/4 where R' is methyl, VR" is methylamino, $R^d$ is ethyl, $R^\beta$ is ethyl and $R^\alpha$ for a compound corresponds to one group $R^2$ of Table B.

Table 177

Compounds of the formula I.1E/4 where R' is hydrogen, VR" is methoxy, $R^d$ is methyl, $R^\beta$ is allyl and $R^\alpha$ for a compound corresponds to one group $R^2$ of Table B.

Table 178

Compounds of the formula I.1E/4 where R' is methyl, VR" is methoxy, $R^d$ is methyl, $R^\beta$ is allyl and $R^\alpha$ for a compound corresponds to one group $R^2$ of Table B.

Table 179

Compounds of the formula I.1E/4 where R' is hydrogen, VR" is methylamino, $R^d$ is methyl, $R^\beta$ is allyl and $R^\alpha$ for a compound corresponds to one group $R^2$ of Table B.

Table 180

Compounds of the formula I.1E/4 where R' is methyl, VR" is methylamino, $R^d$ is methyl, $R^\beta$ is allyl and $R^\alpha$ for a compound corresponds to one group $R^2$ of Table B.

Table 181

Compounds of the formula I.1E/4 where R' is hydrogen, VR" is methoxy, $R^d$ is ethyl, $R^\beta$ is allyl and $R^\alpha$ for a compound corresponds to one group $R^2$ of Table B

Table 182

Compounds of the formula I.1E/4 where R' is methyl, VR" is methoxy, $R^d$ is ethyl, $R^\beta$ is allyl and $R^\alpha$ for a compound corresponds to one group $R^2$ of Table B

Table 183

Compounds of the formula I.1E/4 where R' is hydrogen, VR" is methylamino, $R^d$ is ethyl, $R^\beta$ is allyl and $R^\alpha$ for a compound corresponds to one group $R^2$ of Table B

Table 184

Compounds of the formula I.1E/4 where R' is methyl, VR" is methylamino, $R^d$ is ethyl, $R^\beta$ is allyl and $R^\alpha$ for a compound corresponds to one group $R^2$ of Table B

Table 185

Compounds of the formula I.1E/4 where R' is hydrogen, VR" is methoxy, $R^d$ is methyl, $R^\beta$ is propargyl and $R^\alpha$ for a compound corresponds to one group $R^2$ of Table B.

Table 186

Compounds of the formula I.1E/4 where R' is methyl, VR" is methoxy, $R^d$ is methyl, $R^\beta$ is propargyl and $R^\alpha$ for a compound corresponds to one group $R^2$ of Table B.

Table 187

Compounds of the formula I.1E/4 where R' is hydrogen, VR" is methylamino, $R^d$ is methyl, $R^\beta$ is propargyl and $R^\alpha$ for a compound corresponds to one group $R^2$ of Table B.

Table 188

Compounds of the formula I.1E/4 where R' is methyl, VR" is methylamino, $R^d$ is methyl, $R^\beta$ is propargyl and $R^\alpha$ for a compound corresponds to one group $R^2$ of Table B.

Table 189

Compounds of the formula I.1E/4 where R' is hydrogen, VR" is methoxy, $R^d$ is ethyl, $R^\beta$ is propargyl and $R^\alpha$ for a compound corresponds to one group $R^2$ of Table B.

Table 190

Compounds of the formula I.1E/4 where R' is methyl, VR" is methoxy, $R^d$ is ethyl, $R^\beta$ is propargyl and $R^\alpha$ for a compound corresponds to one group $R^2$ of Table B.

Table 191

Compounds of the formula I.1E/4 where R' is hydrogen, VR" is methylamino, $R^d$ is ethyl, $R^\beta$ is propargyl and $R^\alpha$ for a compound corresponds to one group $R^2$ of Table B.

Table 192

Compounds of the formula I.1E/4 where R' is methyl, VR" is methylamino, $R^d$ is ethyl, $R^\beta$ is propargyl and $R^\alpha$ for a compound corresponds to one group $R^2$ of Table B.

Table 193

Compounds of the formula I.1E/4 where R' is hydrogen, VR" is methoxy, $R^d$ is methyl, $R^\beta$ is trans-chloroallyl and $R^\alpha$ for a compound corresponds to one group $R^2$ of Table B.

Table 194

Compounds of the formula I.1E/4 where R' is methyl, VR" is methoxy, $R^d$ is methyl, $R^\beta$ is trans-chloroallyl and $R^\alpha$ for a compound corresponds to one group $R^2$ of Table B.

Table 195

Compounds of the formula I.1E/4 where R' is hydrogen, VR" is methylamino, $R^d$ is methyl, $R^\beta$ is trans-chloroallyl and $R^\alpha$ for a compound corresponds to one group $R^2$ of Table B.

Table 196

Compounds of the formula I.1E/4 where R' is methyl, VR" is methylamino, $R^d$ is methyl, $R^\beta$ is trans-chloroallyl and $R^\alpha$ for a compound corresponds to one group $R^2$ of Table B.

Table 197

Compounds of the formula I.1E/4 where R' is hydrogen, VR" is methoxy, $R^d$ is ethyl, $R^\beta$ is trans-chloroallyl and $R^\alpha$ for a compound corresponds to one group $R^2$ of Table B.

Table 198

Compounds of the formula I.1E/4 where R' is methyl, VR" is methoxy, $R^d$ is ethyl, $R^\beta$ is trans-chloroallyl and $R^\alpha$ for a compound corresponds to one group $R^2$ of Table B.

Table 199

Compounds of the formula I.1E/4 where R' is hydrogen, VR" is methylamino, $R^d$ is ethyl, $R^\beta$ is trans-chloroallyl and $R^\alpha$ for a compound corresponds to one group $R^2$ of Table B.

Table 200

Compounds of the formula I.1E/4 where R' is methyl, VR" is methylamino, $R^d$ is ethyl, $R^\beta$ is trans-chloroallyl and $R^\alpha$ for a compound corresponds to one group $R^2$ of Table B.

Table 201

Compounds of the formula I.1E/4 where R' is hydrogen, VR" is methoxy and the combination of the substituents $R^d$, $R^\alpha$ and $R^\beta$ for a compound corresponds to one line of Table F.

Table 202

Compounds of the formula I.1E/4 where R' is methyl, VR" is methoxy and the combination of the substituents $R^d$, $R^\alpha$ and $R^\beta$ for a compound corresponds to one line of Table F.

Table 203

Compounds of the formula I.1E/4 where R' is hydrogen, VR" is methylamino and the combination of the substituents $R^d$, $R^\alpha$ and $R^\beta$ for a compound corresponds to one line of Table F.

Table 204

Compounds of the formula I.1E/4 where R' is methyl, VR" is methylamino and the combination of the substituents $R^d$, $R^\alpha$ and $R^\beta$ for a compound corresponds to one line of Table F.

Table 205

Compounds of the formula I (n=0) where the combination and position of the substituents R, R' and VR" for a compound corresponds to one line of Table G.

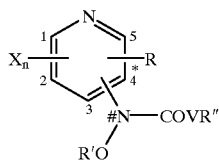

I

Table 206

Compounds of the formula I.1B where R' is hydrogen, VR" is methoxy and $R^b$, $R^\alpha$ and $R^\beta$ for a compound corresponds to one line of Table H.

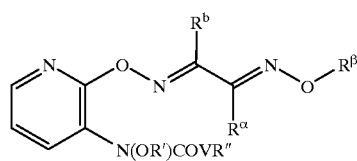

I.1B

Table 207

Compounds of the formula I.1B where R' is methyl, VR" is methoxy and $R^b$, $R^\alpha$ and $R^\beta$ for a compound corresponds to one line of Table H.

Table 208

Compounds of the formula I.1B where R' is hydrogen, VR" is methylamino and $R^b$, $R^\alpha$ and $R^\beta$ for a compound corresponds to one line of Table H.

Table 209

Compounds of the formula I.1B where R' is methyl, VR" is methylamino and $R^b$, $R^\alpha$ and $R^\beta$ for a compound corresponds to one line of Table H.

Table 210

Compounds of the formula I.2B where R' is hydrogen, VR" is methoxy and $R^b$, $R^\alpha$ and $R^\beta$ for a compound corresponds to one line of Table H.

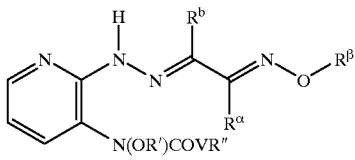

I.2B

Table 211

Compounds of the formula I.2B where R' is methyl, VR" is methoxy and $R^b$, $R^\alpha$ and $R^\beta$ for a compound corresponds to one line of Table H.

Table 212

Compounds of the formula I.2B where R' is hydrogen, VR" is methylamino and $R^b$, $R^\alpha$ and $R^\beta$ for a compound corresponds to one line of Table H.

Table 213

Compounds of the formula I.2B where R' is methyl, VR" is methylamino and $R^b$, $R^\alpha$ and $R^\beta$ for a compound corresponds to one line of Table H.

Table 214

Compounds of the formula I.3B where R' is hydrogen, VR" is methoxy and $R^b$, $R^\alpha$ and $R^\beta$ for a compound corresponds to one line of Table H.

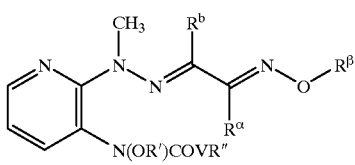

I.3B

Table 215

Compounds of the formula I.3B where R' is methyl, VR" is methoxy and $R^b$, $R^\alpha$ and $R^\beta$ for a compound corresponds to one line of Table H.

Table 216

Compounds of the formula I.3B where R' is hydrogen, VR" is methylamino and $R^b$, $R^\alpha$ and $R^\beta$ for a compound corresponds to one line of Table H.

Table 217

Compounds of the formula I.3B where R' is methyl, VR" is methylamino and $R^b$, $R^\alpha$ and $R^\beta$ for a compound corresponds to one line of Table H.

TABLE A

| No. | $R^1_x$ |
|---|---|
| A.1 | H |
| A.2 | 2-F |
| A.3 | 3-F |
| A.4 | 4-F |
| A.5 | 2,4-$F_2$ |
| A.6 | 2,4,6-$F_3$ |
| A.7 | 2,3,4,5,6-$F_5$ |
| A.8 | 2,3-$F_2$ |
| A.9 | 2-Cl |
| A.10 | 3-Cl |
| A.11 | 4-Cl |
| A.12 | 2,3-$Cl_2$ |
| A.13 | 2,4-$Cl_2$ |
| A.14 | 2,5-$Cl_2$ |
| A.15 | 2,6-$Cl_2$ |
| A.16 | 3,4-$Cl_2$ |
| A.17 | 3,5-$Cl_2$ |
| A.18 | 2,3,4-$Cl_3$ |
| A.19 | 2,3,5-$Cl_3$ |
| A.20 | 2,3,6-$Cl_3$ |
| A.21 | 2,4,5-$Cl_3$ |
| A.22 | 2,4,6-$Cl_3$ |
| A.23 | 3,4,5-$Cl_3$ |
| A.24 | 2,3,4,6-$Cl_4$ |
| A.25 | 2,3,5,6-$Cl_4$ |
| A.26 | 2,3,4,5,6-$Cl_5$ |
| A.27 | 2-Br |
| A.28 | 3-Br |
| A.29 | 4-Br |
| A.30 | 2,4-$Br_2$ |
| A.31 | 2,5-$Br_2$ |
| A.32 | 2,6-$Br_2$ |
| A.33 | 2,4,6-$Br_3$ |
| A.34 | 2,3,4,5,6-$Br_5$ |
| A.35 | 2-I |
| A.36 | 3-I |
| A.37 | 4-I |
| A.38 | 2,4-$I_2$ |
| A.39 | 2-Cl, 3-F |
| A.40 | 2-Cl, 4-F |
| A.41 | 2-Cl, 5-F |
| A.42 | 2-Cl, 6-F |
| A.43 | 2-Cl, 3-Br |
| A.44 | 2-Cl, 4-Br |
| A.45 | 2-Cl, 5-Br |
| A.46 | 2-Cl, 6-Br |
| A.47 | 2-Br, 3-Cl |
| A.48 | 2-Br, 4-Cl |
| A.49 | 2-Br, 5-Cl |
| A.50 | 2-Br, 3-F |
| A.51 | 2-Br, 4-F |
| A.52 | 2-Br, 5-F |
| A.53 | 2-Br, 6-F |
| A.54 | 2-F, 3-Cl |
| A.55 | 2-F, 4-Cl |
| A.56 | 2-F, 5-Cl |
| A.57 | 3-Cl, 4-F |
| A.58 | 3-Cl, 5-F |
| A.59 | 3-Cl, 4-Br |
| A.60 | 3-Cl, 5-Br |
| A.61 | 3-F, 4-Cl |
| A.62 | 3-F, 4-Br |
| A.63 | 3-Br, 4-Cl |
| A.64 | 3-Br, 4-F |
| A.65 | 2,6-$Cl_2$, 4-Br |
| A.66 | 2-$CH_3$ |
| A.67 | 3-$CH_3$ |
| A.68 | 4-$CH_3$ |
| A.69 | 2,3-$(CH_3)_2$ |
| A.70 | 2,4-$(CH_3)_2$ |
| A.71 | 2,5-$(CH_3)_2$ |
| A.72 | 2,6-$(CH_3)_2$ |
| A.73 | 3,4-$(CH_3)_2$ |
| A.74 | 3,5-$(CH_3)_2$ |
| A.75 | 2,3,5-$(CH_3)_3$ |
| A.76 | 2,3,4-$(CH_3)_3$ |
| A.77 | 2,3,6-$(CH_3)_3$ |
| A.78 | 2,4,5-$(CH_3)_3$ |
| A.79 | 2,4,6-$(CH_3)_3$ |
| A.80 | 3,4,5-$(CH_3)_3$ |
| A.81 | 2,3,4,6-$(CH_3)_4$ |
| A.82 | 2,3,5,6-$(CH_3)_4$ |
| A.83 | 2,3,4,5,6-$(CH_3)_5$ |
| A.84 | 2-$C_2H_5$ |
| A.85 | 3-$C_2H_5$ |
| A.86 | 4-$C_2H_5$ |
| A.87 | 2,4-$(C_2H_5)_2$ |
| A.88 | 2,6-$(C_2H_5)_2$ |
| A.89 | 3,5-$(C_2H_5)_2$ |
| A.90 | 2,4,6-$(C_2H_5)_2$3 |
| A.91 | 2-n-$C_3H_7$ |
| A.92 | 3-n-$C_3H_7$ |
| A.93 | 4-n-$C_3H_7$ |
| A.94 | 2-i-$C_3H_7$ |
| A.95 | 3-i-$C_3H_7$ |
| A.96 | 4-i-$C_3H_7$ |
| A.97 | 2,4-$(i-C_3H_7)_2$ |
| A.98 | 2,6-$(i-C_3H_7)_2$ |
| A.99 | 3,5-$(i-C_3H_7)_2$ |
| A.100 | 2,4,6-$(i-C_3H_7)_3$ |
| A.101 | 2-s-$C_4H_9$ |
| A.102 | 3-s-$C_4H_9$ |
| A.103 | 4-s-$C_4H_9$ |
| A.104 | 2-t-$C_4H_9$ |
| A.105 | 3-t-$C_4H_9$ |
| A.106 | 4-t-$C_4H_9$ |
| A.107 | 2,3-$(t-C_4H_9)_2$ |
| A.108 | 2,4-$(t-C_4H_9)_2$ |
| A.109 | 2,5-$(t-C_4H_9)_2$ |
| A.110 | 2,6-$(t-C_4H_9)_2$ |
| A.111 | 3,4-$(t-C_4H_9)_2$ |
| A.112 | 2,4,6-$(t-C_4H_9)_3$ |
| A.113 | 4-n-$C_9H_{19}$ |
| A.114 | 4-n-$C_{12}H_{25}$ |
| A.115 | 4-n-$C_{15}H_{31}$ |
| A.116 | 4-(1,1,3,3-tetramethylbutyl) |
| A.117 | 4-(2,4,4-trimethylpropyl) |
| A.118 | 2-t-$C_4H_9$, 4-$CH_3$ |
| A.119 | 2-t-$C_4H_9$, 5-$CH_3$ |
| A.120 | 2,6-$(t-C_4H_9)_2$, 4-$CH_3$ |
| A.121 | 2-$CH_3$, 4-t-$C_4H_9$ |
| A.122 | 2-$CH_3$, 6-t-$C_4H_9$ |
| A.123 | 2-$CH_3$, 4-i-$C_3H_7$ |
| A.124 | 2-$CH_3$, 5-i-$C_3H_7$ |
| A.125 | 3-$CH_3$, 4-i-$C_3H_7$ |
| A.126 | 2-i-$C_3H_7$, 5-$CH_3$ |
| A.127 | 2,4-$(t-C_4H_9)_2$, 6-i-$C_3H_7$ |
| A.128 | 2-allyl |
| A.129 | 3-allyl |
| A.130 | 4-allyl |
| A.131 | 2-allyl, 6-$CH_3$ |
| A.132 | 2-cyclo-$C_6H_{11}$ |
| A.133 | 3-cyclo-$C_6H_{11}$ |
| A.134 | 4-cyclo-$C_6H_{11}$ |
| A.135 | 2,4-$(cyclo-C_6H_{11})_2$, 6-$CH_3$ |
| A.136 | 2-$CH_3$, 4-cyclo-$C_6H_{11}$ |
| A.137 | 2-$CH_2$—$C_6H_5$ |
| A.138 | 3-$CH_2$—$C_6H_5$ |
| A.139 | 4-$CH_2$—$C_6H_5$ |
| A.140 | 2-$CH_2$—$C_6H_5$, 4-$CH_3$ |
| A.141 | 2-$CH_3$, 4-$CH_2$—$C_6H_5$ |
| A.142 | 2-$C_6H_5$ |
| A.143 | 3-$C_6H_5$ |
| A.144 | 4-$C_6H_5$ |
| A.145 | 4-(2-i-$C_3H_7$—$C_6H_4$) |
| A.146 | 4-$C_6H_5$, 2,6-$(CH_3)_2$ |
| A.147 | 2-Cl, 4-$C_6H_5$ |
| A.148 | 2-Br, 4-$C_6H_5$ |
| A.149 | 2-$C_6H_5$, 4-Cl |
| A.150 | 2-$C_6H_5$, 4-Br |
| A.151 | 2-$CH_2C_6H_5$, 4-Cl |
| A.152 | 2-$CH_2C_6H_5$, 4-Br |
| A.153 | 2-Cl, 4-$CH_2C_6H_5$ |
| A.154 | 2-Br, 4-$CH_2C_6H_5$ |

TABLE A-continued

| No. | $R^1_x$ |
|---|---|
| A.155 | 2-cyclo-$C_6H_{11}$, 4-Cl |
| A.156 | 2-cyclo-$C_6H_{11}$, 4-Br |
| A.157 | 2-Cl, 4-cyclo-$C_6H_{11}$ |
| A.158 | 2-Br, 4-cyclo-$C_6H_{11}$ |
| A.159 | 2-$OCH_3$ |
| A.160 | 3-$OCH_3$ |
| A.161 | 4-$OCH_3$ |
| A.162 | 2-$OC_2H_5$ |
| A.163 | 3-O—$C_2H_5$ |
| A.164 | 4-O—$C_2H_5$ |
| A.165 | 2-O-n-$C_3H_7$ |
| A.166 | 3-O-n-$C_3H_7$ |
| A.167 | 4-O-n-$C_3H_7$ |
| A.168 | 2-O-i-$C_3H_7$ |
| A.169 | 3-O-i-$C_3H_7$ |
| A.170 | 4-O-i-$C_3H_7$ |
| A.171 | 2-O-n-$C_6H_{13}$ |
| A.172 | 3-O-n-$C_6H_{13}$ |
| A.173 | 4-O-n-$C_6H_{13}$ |
| A.174 | 2-O-n-$C_8H_{17}$ |
| A.175 | 3-O-n-$C_8H_{17}$ |
| A.176 | 4-O-n-$C_8H_{17}$ |
| A.177 | 2-O—$CH_2C_6H_5$ |
| A.178 | 3-O—$CH_2C_6H_5$ |
| A.179 | 4-O—$CH_2C_6H_5$ |
| A.180 | 2-O—$(CH_2)_3C_6H_5$ |
| A.181 | 3-O—$(CH_2)_3C_6H_5$ |
| A.182 | 4-O—$(CH_2)_3C_6H_5$ |
| A.183 | 2,4-$(OCH_3)_2$ |
| A.184 | 2-$CF_3$ |
| A.185 | 3-$CF_3$ |
| A.186 | 4-$CF_3$ |
| A.187 | 2-$OCF_3$ |
| A.188 | 3-$OCF_3$ |
| A.189 | 4-$OCF_3$ |
| A.190 | 3-$OCH_2CHF_2$ |
| A.191 | 2-$NO_2$ |
| A.192 | 3-$NO_2$ |
| A.193 | 4-$NO_2$ |
| A.194 | 2-CN |
| A.195 | 3-CN |
| A.196 | 4-CN |
| A.197 | 2-$CH_3$, 3-Cl |
| A.198 | 2-$CH_3$, 4-Cl |
| A.199 | 2-$CH_3$, 5-Cl |
| A.200 | 2-$CH_3$, 6-Cl |
| A.201 | 2-$CH_3$, 3-F |
| A.202 | 2-$CH_3$, 4-F |
| A.203 | 2-$CH_3$, 5-F |
| A.204 | 2-$CH_3$, 6-F |
| A.205 | 2-$CH_3$, 3-Br |
| A.206 | 2-$CH_3$, 4-Br |
| A.207 | 2-$CH_3$, 5-Br |
| A.208 | 2-$CH_3$, 6-Br |
| A.209 | 2-Cl, 3-$CH_3$ |
| A.210 | 2-Cl, 4-$CH_3$ |
| A.211 | 2-Cl, 5-$CH_3$ |
| A.212 | 2-F, 3-$CH_3$ |
| A.213 | 2-F, 4-$CH_3$ |
| A.214 | 2-F, 5-$CH_3$ |
| A.215 | 2-Br, 3-$CH_3$ |
| A.216 | 2-Br, 4-$CH_3$ |
| A.217 | 2-Br, 5-$CH_3$ |
| A.218 | 3-$CH_3$, 4-Cl |
| A.219 | 3-$CH_3$, 5-Cl |
| A.220 | 3-$CH_3$, 4-F |
| A.221 | 3-$CH_3$, 5-F |
| A.222 | 3-$CH_3$, 4-Br |
| A.223 | 3-$CH_3$, 5-Br |
| A.224 | 3-F, 4-$CH_3$ |
| A.225 | 3-Cl, 4-$CH_3$ |
| A.226 | 3-Br, 4-$CH_3$ |
| A.227 | 2-Cl, 4,5-$(CH_3)_2$ |
| A.228 | 2-Br, 4,5-$(CH_3)_2$ |
| A.229 | 2-Cl, 3,5-$(CH_3)_2$ |
| A.230 | 2-Br, 3,5-$(CH_3)_2$ |
| A.231 | 2,6-$Cl_2$, 4-$CH_3$ |
| A.232 | 2,6-$F_2$, 4-$CH_3$ |
| A.233 | 2,6-$Br_2$, 4-$CH_3$ |
| A.234 | 2,4-$Br_2$, 6-$CH_3$ |
| A.235 | 2,4-$F_2$, 6-$CH_3$ |
| A.236 | 2,4-$Br_2$, 6-$CH_3$ |
| A.237 | 2,6-$(CH_3)_2$, 4-F |
| A.238 | 2,6-$(CH_3)_2$, 4-Cl |
| A.239 | 2,6-$(CH_3)_2$, 4-Br |
| A.240 | 3,5-$(CH_3)_2$, 4-F |
| A.241 | 3,5-$(CH_3)_2$, 4-Cl |
| A.242 | 3,5-$(CH_3)_2$, 4-Br |
| A.243 | 2,3,6-$(CH_3)_3$, 4-F |
| A.244 | 2,3,6-$(CH_3)_3$, 4-Cl |
| A.245 | 2,3,6-$(CH_3)_3$, 4-Br |
| A.246 | 2,4-$(CH_3)_2$, 6-F |
| A.247 | 2,4-$(CH_3)_2$, 6-Cl |
| A.248 | 2,4-$(CH_3)_2$, 6-Br |
| A.249 | 2-i-$C_3H_7$, 4-Cl, 5-$CH_3$ |
| A.250 | 2-Cl, 4-$NO_2$ |
| A.251 | 2-$NO_2$, 4-Cl |
| A.252 | 2-$OCH_3$, 5-$NO_2$ |
| A.253 | 2,4-$Cl_2$, 5-$NO_2$ |
| A.254 | 2,4-$Cl_2$, 6-$NO_2$ |
| A.255 | 2,6-$Cl_2$, 4-$NO_2$ |
| A.256 | 2,6-$Br_2$, 4-$NO_2$ |
| A.257 | 2,6-$I_2$, 4-$NO_2$ |
| A.258 | 2-$CH_3$, 5-i-$C_3H_7$, 4-Cl |
| A.259 | 2-$CO_2CH_3$ |
| A.260 | 3-$CO_2CH_3$ |
| A.261 | 4-$CO_2CH_3$ |
| A.262 | 2-$CO_2(C_2H_5)$ |
| A.263 | 3-$CO_2(C_2H_5)$ |
| A.264 | 4-$CO_2(C_2H_5)$ |
| A.265 | 2-$CO_2$(n-$C_3H_7$) |
| A.266 | 3-$CO_2$(n-$C_3H_7$) |
| A.267 | 4-$CO_2$(n-$C_3H_7$) |
| A.268 | 2-$CO_2$(i-$C_3H_7$) |
| A.269 | 3-$CO_2$(i-$C_3H_7$) |
| A.270 | 4-$CO_2$(i-$C_3H_7$) |
| A.271 | 2-$CO_2$(n-$C_6H_{13}$) |
| A.272 | 3-$CO_2$(n-$C_6H_{13}$) |
| A.273 | 4-$CO_2$(n-$C_6H_{13}$) |
| A.274 | 2-$CH_2$—$OCH_3$ |
| A.275 | 3-$CH_2$—$OCH_3$ |
| A.276 | 4-$CH_2$—$OCH_3$ |
| A.277 | 2-$CH_2O(C_2H_5)$ |
| A.278 | 3-$CH_2O(C_2H_5)$ |
| A.279 | 4-$CH_2O(C_2H_5)$ |
| A.280 | 2-$CH_2O$(n-$C_3H_7$) |
| A.281 | 3-$CH_2O$(n-$C_3H_7$) |
| A.282 | 4-$CH_2O$(n-$C_3H_7$) |
| A.283 | 2-$CH_2O$(i-$C_3H_7$) |
| A.284 | 3-$CH_2O$(i-$C_3H_7$) |
| A.285 | 4-$CH_2O$(i-$C_3H_7$) |
| A.286 | 2-CHO |
| A.287 | 3-CHO |
| A.288 | 4-CHO |
| A.289 | 2-CO—$CH_3$ |
| A.290 | 3-CO—$CH_3$ |
| A.291 | 4-CO—$CH_3$ |
| A.292 | 2-CO—$CH_2$—$CH_3$ |
| A.293 | 3-CO—$CH_2$—$CH_3$ |
| A.294 | 4-CO—$CH_2$—$CH_3$ |
| A.295 | 2-CO—$CH_2$—$CH_2$—$CH_3$ |
| A.296 | 3-CO—$CH_2$—$CH_2$—$CH_3$ |
| A.297 | 4-CO—$CH_2$—$CH_2$—$CH_3$ |
| A.298 | 2-CO—$CH(CH_3)$—$CH_3$ |
| A.299 | 3-CO—$CH(CH_3)$—$CH_3$ |
| A.300 | 4-CO—$CH(CH_3)$—$CH_3$ |
| A.301 | 2-Me-4-CHO |
| A.302 | 2-Me-4-$CH_3$—CO |
| A.303 | 2-Me-4-$CH_3$—$CH_2$—CO |
| A.304 | 2-Me-4-$CH_3$—$CH_2$—$CH_2$—CO |
| A.305 | 2-Me-4-$CH_3$—$CH(CH_3)$—CO |
| A.306 | 2,5-$Me_2$-4-CHO |
| A.307 | 2,5-$Me_2$-4-$CH_3$—CO |
| A.308 | 2,5-$Me_2$-4-$CH_3$—$CH_2$—CO |

TABLE A-continued

| No. | $R^1_x$ |
|---|---|
| A.309 | 2,5-Me$_2$-4-CH$_3$—CH$_2$—CH$_2$—CO |
| A.310 | 2,5-Me$_2$-4-CH$_3$—CH(CH$_3$)—CO |
| A.311 | 2-Cl-4-CHO |
| A.312 | 2-Cl-4-CH$_3$—CO |
| A.313 | 2-Cl-4-CH$_3$—CH$_2$—CO |
| A.314 | 2-Cl-4-CH$_3$—CH(CH$_3$)—CO |
| A.315 | 2,5-Cl$_2$-4-CHO |
| A.316 | 2,5-Cl$_2$-4-CH$_3$—CO |
| A.317 | 2,5-Cl$_2$-4-CH$_3$—CH$_2$—CO |
| A.318 | 2,5-Cl$_2$-4-CH$_3$—CH$_2$—CH$_2$—CO |
| A.319 | 2,5-Cl$_2$-4-CH$_3$—CH(CH$_3$)—CO |
| A.320 | 2-C(=NOCH$_3$)—CH$_3$ |
| A.321 | 3-C(=NOCH$_3$)—CH$_3$ |
| A.322 | 4-C(=NOCH$_3$)—CH$_3$ |
| A.323 | 2-C(=NOC$_2$H$_5$)—CH$_3$ |
| A.324 | 3-C(=NOC$_2$H$_5$)—CH$_3$ |
| A.325 | 4-C(=NOC$_2$H$_5$)—CH$_3$ |
| A.326 | 2-C(=NO-n-C$_3$H$_7$)—CH$_3$ |
| A.327 | 3-C(=NO-n-C$_3$H$_7$)—CH$_3$ |
| A.328 | 4-C(=NO-n-C$_3$H$_7$)—CH$_3$ |
| A.329 | 2-C(=NO-i-C$_3$H$_7$)—CH$_3$ |
| A.330 | 3-C(=NO-i-C$_3$H$_7$)—CH$_3$ |
| A.331 | 4-C(=NO-i-C$_3$H$_7$)—CH$_3$ |
| A.332 | 2-C(=NO-allyl)-CH$_3$ |
| A.333 | 3-C(=NO-allyl)-CH$_3$ |
| A.334 | 4-C(=NO-allyl)-CH$_3$ |
| A.335 | 2-C(=NO-trans-chloroallyl)-CH$_3$ |
| A.336 | 3-C(=NO-trans-chloroallyl)-CH$_3$ |
| A.337 | 4-C(=NO-trans-chloroallyl)-CH$_3$ |
| A.338 | 2-C(=NO-propargyl)-CH$_3$ |
| A.339 | 3-C(=NO-propargyl)-CH$_3$ |
| A.340 | 4-C(=NO-propargyl)-CH$_3$ |
| A.341 | 2-C(=NO-n-C$_4$H$_9$)—CH$_3$ |
| A.342 | 3-C(=NO-n-C$_4$H$_9$)—CH$_3$ |
| A.343 | 4-C(=NO-n-C$_4$H$_9$)—CH$_3$ |
| A.344 | 2-C(=NO—CH$_2$—C$_6$H$_5$)—CH$_3$ |
| A.345 | 3-C(=NO—CH$_2$—C$_6$H$_5$)—CH$_3$ |
| A.346 | 4-C(=NO—CH$_2$—C$_6$H$_5$)—CH$_3$ |
| A.347 | 2-CH$_3$-4-CH=NOCH$_3$ |
| A.348 | 2-CH$_3$-4-CH=NOC$_2$H$_5$ |
| A.349 | 2-CH$_3$-4-CH=NO-n-C$_3$H$_7$ |
| A.350 | 2-CH$_3$-4-CH=NO-i-C$_3$H$_7$ |
| A.351 | 2-CH$_3$-4-CH=NO-allyl |
| A.352 | 2-CH$_3$-4-CH=NO-(trans-chloroallyl) |
| A.353 | 2-CH$_3$-4-CH=NO-propargyl |
| A.354 | 2-CH$_3$-4-CH=NO-n-C$_4$H$_9$ |
| A.355 | 2-CH$_3$-4-CH=NO—CH$_2$—C$_6$H$_5$ |
| A.356 | 2-CH$_3$-4-(CH$_3$—C=NOCH$_3$) |
| A.357 | 2-CH$_3$-4-(CH$_3$—C=NOC$_2$H$_5$) |
| A.358 | 2-CH$_3$-4-(CH$_3$—C=NO-n-C$_3$H$_7$) |
| A.359 | 2-CH$_3$-4-(CH$_3$—C=NO-i-C$_3$H$_7$) |
| A.360 | 2-CH$_3$-4-(CH$_3$—C=NO-allyl) |
| A.361 | 2-CH$_3$-4-(CH$_3$—C=NO-trans-chloroallyl) |
| A.362 | 2-CH$_3$-4-(CH$_3$—C=NO-propargyl) |
| A.363 | 2-CH$_3$-4-(CH$_3$—C=NO-n-C$_4$H$_9$) |
| A.364 | 2-CH$_3$-4-(CH$_3$—C=NO—CH$_2$—C$_6$H$_5$) |
| A.365 | 2-CH$_3$-4-(C$_2$H$_5$—C=NO—CH$_3$) |
| A.366 | 2-CH$_3$-4-(C$_2$H$_5$—C=NO—C$_2$H$_5$) |
| A.367 | 2-CH$_3$-4-(C$_2$H$_5$—C=NO-n-C$_3$H$_7$) |
| A.368 | 2-CH$_3$-4-(C$_2$H$_5$—C=NO-i-C$_3$H$_7$) |
| A.369 | 2-CH$_3$-4-(C$_2$H$_5$—C=NO-allyl) |
| A.370 | 2-CH$_3$-4-(C$_2$H$_5$—C=NO-trans-chloroallyl) |
| A.371 | 2-CH$_3$-4-(C$_2$H$_5$—C=NO-propargyl) |
| A.372 | 2-CH$_3$-4-(C$_2$H$_5$—C=NO-n-C$_4$H$_9$) |
| A.373 | 2-CH$_3$-4-(C$_2$H$_5$—C=NO—CH$_2$—C$_6$H$_5$) |
| A.374 | 2,5-(CH$_3$)$_2$-4-(CH$_3$—C=NOCH$_3$) |
| A.375 | 2,5-(CH$_3$)$_2$-4-(CH$_3$—C=NOC$_2$H$_5$) |
| A.376 | 2,5-(CH$_3$)$_2$-4-(CH$_3$—C=NO-n-C$_3$H$_7$) |
| A.377 | 2,5-(CH$_3$)$_2$-4-(CH$_3$—C=NO-i-C$_3$H$_7$) |
| A.378 | 2,5-(CH$_3$)$_2$-4-(CH$_3$—C=NO-allyl) |
| A.379 | 2,5-(CH$_3$)$_2$-4-(CH$_3$—C=NO-trans-chloroallyl) |
| A.380 | 2,5-(CH$_3$)$_2$-4-(CH$_3$—C=NO-propargyl) |
| A.381 | 2,5-(CH$_3$)$_2$-4-(CH$_3$—C=NO-n-C$_4$H$_9$) |
| A.382 | 2,5-(CH$_3$)$_2$-4-(CH$_3$—C=NO—CH$_2$—C$_6$H$_5$) |
| A.383 | 2-C$_6$H$_5$ |
| A.384 | 3-C$_6$H$_5$ |
| A.385 | 4-C$_6$H$_5$ |
| A.386 | 2-(2'-F—C$_6$H$_4$) |
| A.387 | 2-(3'-F—C$_6$H$_4$) |
| A.388 | 2-(4'-F—C$_6$H$_4$) |
| A.389 | 3-(2'-F—C$_6$H$_4$) |
| A.390 | 3-(3'-F—C$_6$H$_4$) |
| A.391 | 3-(4'-F—C$_6$H$_4$) |
| A.392 | 4-(2'-F—C$_6$H$_4$) |
| A.393 | 4-(3'-F—C$_6$H$_4$) |
| A.394 | 4-(4'-F—C$_6$H$_4$) |
| A.395 | 2-(2'-Cl—C$_6$H$_4$) |
| A.396 | 2-(3'-Cl—C$_6$H$_4$) |
| A.397 | 2-(4'-Cl—C$_6$H$_4$) |
| A.398 | 3-(2'-Cl—C$_6$H$_4$) |
| A.399 | 3-(3'-Cl—C$_6$H$_4$) |
| A.400 | 3-(4'-Cl—C$_6$H$_4$) |
| A.401 | 4-(2'-Cl—C$_6$H$_4$) |
| A.402 | 4-(3'-Cl—C$_6$H$_4$) |
| A.403 | 4-(4'-Cl—C$_6$H$_4$) |
| A.404 | 2-(2'-CH$_3$—C$_6$H$_4$) |
| A.405 | 2-(3'-CH$_3$—C$_6$H$_4$) |
| A.406 | 2-(4'-CH$_3$—C$_6$H$_4$) |
| A.407 | 3-(2'-CH$_3$—C$_6$H$_4$) |
| A.408 | 3-(3'-CH$_3$—C$_6$H$_4$) |
| A.409 | 3-(4'-CH$_3$—C$_6$H$_4$) |
| A.410 | 4-(2'-CH$_3$—C$_6$H$_4$) |
| A.411 | 4-(3'-CH$_3$—C$_6$H$_4$) |
| A.412 | 4-(4'-CH$_3$—C$_6$H$_4$) |
| A.413 | 2-(2'-CH$_3$—CO—C$_6$H$_4$) |
| A.414 | 2-(3'-CH$_3$—CO—C$_6$H$_4$) |
| A.415 | 2-(4'-CH$_3$—CO—C$_6$H$_4$) |
| A.416 | 3-(2'-CH$_3$—CO—C$_6$H$_4$) |
| A.417 | 3-(3'-CH$_3$—CO—C$_6$H$_4$) |
| A.418 | 3-(4'-CH$_3$—CO—C$_6$H$_4$) |
| A.419 | 4-(2'-CH$_3$—CO—C$_6$H$_4$) |
| A.420 | 4-(3'-CH$_3$—CO—C$_6$H$_4$) |
| A.421 | 4-(4'-CH$_3$—CO—C$_6$H$_4$) |
| A.422 | 2-(2'-(CH$_3$—C(=NOallyl))-C$_6$H$_4$) |
| A.423 | 2-(3'-(CH$_3$—C(=NOallyl))-C$_6$H$_4$) |
| A.424 | 2-(4'-(CH$_3$—C(=NOallyl))-C$_6$H$_4$) |
| A.425 | 3-(2'-(CH$_3$—C(=NOallyl))-C$_6$H$_4$) |
| A.426 | 3-(3'-(CH$_3$—C(=Noallyl))-C$_6$H$_4$) |
| A.427 | 3-(4'-(CH$_3$—C(=NOallyl))-C$_6$H$_4$) |
| A.428 | 4-(2'-(CH$_3$—C(=NOallyl))-C$_6$H$_4$) |
| A.429 | 4-(3'-(CH$_3$—C(=NOallyl))-C$_6$H$_4$) |
| A.430 | 4-(4'-(CH$_3$—C(=NOallyl))-C$_6$H$_4$) |
| A.431 | 2-(2'-CH$_3$O$_2$C—C$_6$H$_4$) |
| A.432 | 2-(3'-CH$_3$O$_2$C—C$_6$H$_4$) |
| A.433 | 2-(4'-CH$_3$O$_2$C—C$_6$H$_4$) |
| A.434 | 3-(2'-CH$_3$O$_2$C—C$_6$H$_4$) |
| A.435 | 3-(3'-CH3O2C—C$_6$H$_4$) |
| A.436 | 3-(4'-CH$_3$O$_2$C—C$_6$H$_4$) |
| A.437 | 4-(2'-CH$_3$O$_2$C—C$_6$H$_4$) |
| A.438 | 4-(3'-CH$_3$O$_2$C—C$_6$H$_4$) |
| A.439 | 4-(4'-CH$_3$O$_2$C—C$_6$H$_4$) |
| A.440 | 2-(2'-CH$_3$O—C$_6$H$_4$) |
| A.441 | 2-(3'-CH$_3$O—C$_6$H$_4$) |
| A.442 | 2-(4'-CH$_3$O—C$_6$H$_4$) |
| A.443 | 3-(2'-CH$_3$O—C$_6$H$_4$) |
| A.444 | 3-(3'-CH$_3$O—C$_6$H$_4$) |
| A.445 | 3-(4'-CH$_3$O—C$_6$H$_4$) |
| A.446 | 4-(2'-CH$_3$O—C$_6$H$_4$) |
| A.447 | 4-(3'-CH$_3$O—C$_6$H$_4$) |
| A.448 | 4-(4'-CH$_3$O—C$_6$H$_4$) |
| A.449 | 2-(2'-O$_2$N—C$_6$H$_4$) |
| A.450 | 2-(3'-O$_2$N—C$_6$H$_4$) |
| A.451 | 2-(4'-O$_2$N—C$_6$H$_4$) |
| A.452 | 3-(2'-O$_2$N—C$_6$H$_4$) |
| A.453 | 3-(3'-O$_2$N—C$_6$H$_4$) |
| A.454 | 3-(4'-O$_2$N—C$_6$H$_4$) |
| A.455 | 4-(2'-O$_2$N—C$_6$H$_4$) |
| A.456 | 4-(3'-O$_2$N—C$_6$H$_4$) |
| A.457 | 4-(4'-O$_2$N—C$_6$H$_4$) |
| A.458 | 2-(2'-NC—C$_6$H$_4$) |
| A.459 | 2-(3'-NC—C$_6$H$_4$) |
| A.460 | 2-(4'-NC—C$_6$H$_4$) |
| A.461 | 3-(2'-NC—C$_6$H$_4$) |
| A.462 | 3-(3'-NC—C$_6$H$_4$) |

TABLE A-continued

| No. | $R^1_x$ |
|---|---|
| A.463 | 3-(4'-NC—$C_6H_4$) |
| A.464 | 4-(2'-NC—$C_6H_4$) |
| A.465 | 4-(3'-NC—$C_6H_4$) |
| A.466 | 4-(4'-NC—$C_6H_4$) |
| A.467 | 2-(2'-$CF_3$—$C_6H_4$) |
| A.468 | 2-(3'-$CF_3$—$C_6H_4$) |
| A.469 | 2-(4'-$CF_3$—$C_6H_4$) |
| A.470 | 3-(2'-$CF_3$—$C_6H_4$) |
| A.471 | 3-(3'-$CF_3$—$C_6H_4$) |
| A.472 | 3-(4'-CF3—$C_6H_4$) |
| A.473 | 4-(2'-$CF_3$—$C_6H_4$) |
| A.474 | 4-(3'-$CF_3$—$C_6H_4$) |
| A.475 | 4-(4'-$CF_3$—$C_6H_4$) |
| A.476 | 2-O—$C_6H_5$ |
| A.477 | 3-O—$C_6H_5$ |
| A.478 | 4-O—$C_6H_5$ |
| A.479 | 2-O-(2'-F—$C_6H_4$) |
| A.480 | 2-O-(3'-F—$C_6H_4$) |
| A.481 | 2-O-(4'-F—$C_6H_4$) |
| A.482 | 3-O-(2'-F—$C_6H_4$) |
| A.483 | 3-O-(3'-F—$C_6H_4$) |
| A.484 | 3-O-(4'-F—$C_6H_4$) |
| A.485 | 4-O-(2'-F—$C_6H_4$) |
| A.486 | 4-O-(3'-F—$C_6H_4$) |
| A.487 | 4-O-(4'-F—$C_6H_4$) |
| A.488 | 2-O-(2'-Cl—$C_6H_4$) |
| A.489 | 2-O-(3'-Cl—$C_6H_4$) |
| A.490 | 2-O-(4'-Cl—$C_6H_4$) |
| A.491 | 3-O-(2'-Cl—$C_6H_4$) |
| A.492 | 3-O-(3'-Cl—$C_6H_4$) |
| A.493 | 3-O-(4'-Cl—$C_6H_4$) |
| A.494 | 3-O-(4'-Cl—$C_6H_4$) |
| A.495 | 4-O-(2'-Cl—$C_6H_4$) |
| A.496 | 4-O-(3'-Cl—$C_6H_4$) |
| A.497 | 4-O-(4'-Cl—$C_6H_4$) |
| A.498 | 2-O-(2'-$CH_3$—$C_6H_4$) |
| A.499 | 2-O-(3'-$CH_3$—$C_6H_4$) |
| A.500 | 2-O-(4'-$CH_3$—$C_6H_4$) |
| A.501 | 3-O-(2'-$CH_3$—$C_6H_4$) |
| A.502 | 3-O-(3'-$CH_3$—$C_6H_4$) |
| A.503 | 3-O-(4'-$CH_3$—$C_6H_4$) |
| A.504 | 4-O-(2'-$CH_3$—$C_6H_4$) |
| A.505 | 4-O-(3'-$CH_3$—$C_6H_4$) |
| A.506 | 4-O-(4'-$CH_3$—$C_6H_4$) |
| A.507 | 2-O-(2'-$CH_3$—CO—$C_6H_4$) |
| A.508 | 2-O-(3'-$CH_3$—CO—$C_6H_4$) |
| A.509 | 2-O-(4'-$CH_3$—CO—$C_6H_4$) |
| A.510 | 3-O-(2'-$CH_3$—CO—$C_6H_4$) |
| A.511 | 3-O-(3'-$CH_3$—CO—$C_6H_4$) |
| A.512 | 3-O-(4'-$CH_3$—CO—$C_6H_4$) |
| A.513 | 4-O-(2'-$CH_3$—CO—$C_6H_4$) |
| A.514 | 4-O-(3'-$CH_3$—CO—$C_6H_4$) |
| A.515 | 4-O-(4'-$CH_3$—CO—$C_6H_4$) |
| A.516 | 2-O-(2'-($CH_3$—C(=NOallyl))-$C_6H_4$) |
| A.517 | 2-O-(3'-($CH_3$—C(=NOallyl))-$C_6H_4$) |
| A.518 | 2-O-(4'-($CH_3$—C(=NOallyl))-$C_6H_4$) |
| A.519 | 3-O-(2'-($CH_3$—C(=NOallyl))-$C_6H_4$) |
| A.520 | 3-O-(3'-($CH_3$—C(=NOallyl))-$C_6H_4$) |
| A.521 | 3-O-(4'-($CH_3$—C(=NOallyl))-$C_6H_4$) |
| A.522 | 4-O-(2'-($CH_3$—C(=NOallyl))-$C_6H_4$) |
| A.523 | 4-O-(3'-($CH_3$—C(=NOallyl))-$C_6H_4$) |
| A.524 | 4-O-(4'-($CH_3$—C(=NOallyl))-$C_6H_4$) |
| A.525 | 2-O-(2'-$CH_3O_2$C—$C_6H_4$) |
| A.526 | 2-O-(3'-$CH_3O_2$C—$C_6H_4$) |
| A.527 | 2-O-(4'-$CH_3O_2$C—$C_6H_4$) |
| A.528 | 3-O-(2'-$CH_3O_2$C—$C_6H_4$) |
| A.529 | 3-O-(3'-$CH_3O_2$C—$C_6H_4$) |
| A.530 | 3-O-(4'-$CH_3O_2$C—$C_6H_4$) |
| A.531 | 4-O-(2'-$CH_3O_2$C—$C_6H_4$) |
| A.532 | 4-O-(3'-$CH_3O_2$C—$C_6H_4$) |
| A.533 | 4-O-(4'-$CH_3O_2$C—$C_6H_4$) |
| A.534 | 2-O-(2'-$CH_3$O—$C_6H_4$) |
| A.535 | 2-O-(3'-$CH_3$O—$C_6H_4$) |
| A.536 | 2-O-(4'-$CH_3$O—$C_6H_4$) |
| A.537 | 3-O-(2'-$CH_3$O—$C_6H_4$) |
| A.538 | 3-O-(3'-$CH_3$O—$C_6H_4$) |
| A.539 | 3-O-(4'-$CH_3$O—$C_6H_4$) |
| A.540 | 4-O-(2'-$CH_3$O—$C_6H_4$) |
| A.541 | 4-O-(3'-$CH_3$O—$C_6H_4$) |
| A.542 | 4-O-(4'-$CH_3$O—$C_6H_4$) |
| A.543 | 2-O-(2'-$O_2$N—$C_6H_4$) |
| A.544 | 2-O-(3'-$O_2$N—$C_6H_4$) |
| A.545 | 2-O-(4'-$O_2$N—$C_6H_4$) |
| A.546 | 3-O-(2'-$O_2$N—$C_6H_4$) |
| A.547 | 3-O-(3'-$O_2$N—$C_6H_4$) |
| A.548 | 3-O-(4'-$O_2$N—$C_6H_4$) |
| A.549 | 4-O-(2'-$O_2$N—$C_6H_4$) |
| A.550 | 4-O-(3'-$O_2$N—$C_6H_4$) |
| A.551 | 4-O-(4'-$O_2$N—$C_6H_4$) |
| A.552 | 2-O-(2'-NC—$C_6H_4$) |
| A.553 | 2-O-(3'-NC—$C_6H_4$) |
| A.554 | 2-O-(4'-NC—$C_6H_4$) |
| A.555 | 3-O-(2'-NC—$C_6H_4$) |
| A.556 | 3-O-(3'-NC—$C_6H_4$) |
| A.557 | 3-O-(4'-NC—$C_6H_4$) |
| A.558 | 4-O-(2'-NC—$C_6H_4$) |
| A.559 | 4-O-(3'-NC—$C_6H_4$) |
| A.560 | 4-O-(4'-NC—$C_6H_4$) |
| A.561 | 2-O-(2'-$CF_3$—$C_6H_4$) |
| A.562 | 2-O-(3'-$CF_3$—$C_6H_4$) |
| A.563 | 2-O-(4'-$CF_3$—$C_6H_4$) |
| A.564 | 3-O-(2'-$CF_3$—$C_6H_4$) |
| A.565 | 3-O-(3'-$CF_3$—$C_6H_4$) |
| A.566 | 3-O-(4'-$CF_3$—$C_6H_4$) |
| A.567 | 4-O-(2'-$CF_3$—$C_6H_4$) |
| A.568 | 4-O-(3'-$CF_3$—$C_6H_4$) |
| A.569 | 4-O-(4'-$CF_3$—$C_6H_4$) |
| A.570 | 2-pyridin-2'-yl |
| A.571 | 2-pyridin-3'-yl |
| A.572 | 2-pyridin-4'-yl |
| A.573 | 3-pyridin-2'-yl |
| A.574 | 3-pyridin-3'-yl |
| A.575 | 3-pyridin-4'-yl |
| A.576 | 4-pyridin-2'-yl |
| A.577 | 4-pyridin-3'-yl |
| A.578 | 4-pyridin-4'-yl |
| A.579 | 2-pyrimidin-2'-yl |
| A.580 | 2-pyrimidin-3'-yl |
| A.581 | 2-pyrimidin-4'-yl |
| A.582 | 3-pyrimidin-2'-yl |
| A.583 | 3-pyrimidin-3'-yl |
| A.584 | 3-pyrimidin-4'-yl |
| A.585 | 4-pyrimidin-2'-yl |
| A.586 | 4-pyrimidin-3'-yl |
| A.587 | 4-pyrimidin-4'-yl |
| A.588 | 2-pyrazol-1'-yl |
| A.589 | 2-pyrazol-3'-yl |
| A.590 | 2-pyrazol-4'-yl |
| A.591 | 3-pyrazol-1'-yl |
| A.592 | 3-pyrazol-3'-yl |
| A.593 | 3-pyrazol-4'-yl |
| A.594 | 4-pyrazol-1'-yl |
| A.595 | 4-pyrazol-3'-yl |
| A.596 | 4-pyrazol-4'-yl |
| A.597 | 2-isoxazol-3'-yl |
| A.598 | 2-isoxazol-4'-yl |
| A.599 | 2-isoxazol-5'-yl |
| A.600 | 3-isoxazol-3'-yl |
| A.601 | 3-isoxazol-4'-yl |
| A.602 | 3-isoxazol-5'-yl |
| A.603 | 4-isoxazol-3'-yl |
| A.604 | 4-isoxazol-4'-yl |
| A.605 | 4-isoxazol-5'-yl |
| A.606 | 2-isothiazol-3'-yl |
| A.607 | 2-isothiazol-4'-yl |
| A.608 | 2-isothiazol-5'-yl |
| A.609 | 3-isothiazol-3'-yl |
| A.610 | 3-isothiazol-4'-yl |
| A.611 | 3-isothiazol-5'-yl |
| A.612 | 4-isothiazol-3'-yl |
| A.613 | 4-isothiazol-4'-yl |
| A.614 | 4-isothiazol-5'-yl |
| A.615 | 2-imidazol-1'-yl |
| A.616 | 2-imidazol-2'-yl |

TABLE A-continued

| No. | $R^1_x$ |
|---|---|
| A.617 | 2-imidazol-4'-yl |
| A.618 | 3-imidazol-1'-yl |
| A.619 | 3-imidazol-2'-yl |
| A.620 | 3-imidazol-4'-yl |
| A.621 | 4-imidazol-1'-yl |
| A.622 | 4-imidazol-2'-yl |
| A.623 | 4-imidazol-4'-yl |
| A.624 | 2-oxazol-2'-yl |
| A.625 | 2-oxazol-4'-yl |
| A.626 | 2-oxazol-5'-yl |
| A.627 | 3-oxazol-2'-yl |
| A.628 | 3-oxazol-4'-yl |
| A.629 | 3-oxazol-5'-yl |
| A.630 | 4-oxazol-2'-yl |
| A.631 | 4-oxazol-4'-yl |
| A.632 | 4-oxazol-5'-yl |
| A.633 | 2-thiazol-2'-yl |
| A.634 | 2-thiazol-4'-yl |
| A.635 | 2-thiazol-5'-yl |
| A.636 | 3-thiazol-2'-yl |
| A.637 | 3-thiazol-4'-yl |
| A.638 | 3-thiazol-5'-yl |
| A.639 | 4-thiazol-2'-yl |
| A.640 | 4-thiazol-4'-yl |
| A.641 | 4-thiazol-5'-yl |

TABLE B

| No. | $R^2$ |
|---|---|
| B. 1 | pyrrol-3-yl |
| B. 2 | N-$CH_3$-pyrrol-3-yl |
| B. 3 | N-$C_6H_5$-pyrrol-3-yl |
| B. 4 | N-(4'-$CH_3$-$C_6H_4$)-pyrrol-3-yl |
| B. 5 | N-(3'-$CH_3$-$C_6H_4$)-pyrrol-3-yl |
| B. 6 | N-(2'-$CH_3$-$C_6H_4$)-pyrrol-3-yl |
| B. 7 | N-(4'-$CH_3O$-$C_6H_4$)-pyrrol-3-yl |
| B. 8 | N-(3'-$CH_3O$-$C_6H_4$)-pyrrol-3-yl |
| B. 9 | N-(2'-$CH_3O$-$C_6H_4$)-pyrrol-3-yl |
| B. 10 | N-(4'-$NO_2$-$C_6H_4$)-pyrrol-3-yl |
| B. 11 | N-(3'-$NO_2$-$C_6H_4$)-pyrrol-3-yl |
| B. 12 | N-(2'-$NO_2$-$C_6H_4$)-pyrrol-3-yl |
| B. 13 | N-(4'-CN-$C_6H_4$)-pyrrol-3-yl |
| B. 14 | N-(3'-CN-$C_6H_4$)-pyrrol-3-yl |
| B. 15 | N-(2'-CN-$C_6H_4$)-pyrrol-3-yl |
| B. 16 | N-(4'-Cl-$C_6H_4$)-pyrrol-3-yl |
| B. 17 | N-(3'-Cl-$C_6H_4$)-pyrrol-3-yl |
| B. 18 | N-(2'-Cl-$C_6H_4$)-pyrrol-3-yl |
| B. 19 | pyrrol-2-yl |
| B. 20 | N-$CH_3$-pyrrol-2-yl |
| B. 21 | N-$C_6H_5$-pyrrol-2-yl |
| B. 22 | N-(4'-$CH_3$-$C_6H_4$)-pyrrol-2-yl |
| B. 23 | N-(3'-$CH_3$-$C_6H_4$)-pyrrol-2-yl |
| B. 24 | N-(2'-$CH_3$-$C_6H_4$)-pyrrol-2-yl |
| B. 25 | N-(4'-$CH_3O$-$C_6H_4$)-pyrrol-2-yl |
| B. 26 | N-(3'-$CH_3O$-$C_6H_4$)-pyrrol-2-yl |
| B. 27 | N-(2'-$CH_3O$-$C_6H_4$)-pyrrol-2-yl |
| B. 28 | N-(4'-$NO_2$-$C_6H_4$)-pyrrol-2-yl |
| B. 29 | N-(3'-$NO_2$-$C_6H_4$)-pyrrol-2-yl |
| B. 30 | N-(2'-$NO_2$-$C_6H_4$)-pyrrol-2-yl |
| B. 31 | N-(4'-CN-$C_6H_4$)-pyrrol-2-yl |
| B. 32 | N-(3'-CN-$C_6H_4$)-pyrrol-2-yl |
| B. 33 | N-(2'-CN-$C_6H_4$)-pyrrol-2-yl |
| B. 34 | N-(4'-Cl-$C_6H_4$)-pyrrol-2-yl |
| B. 35 | N-(3'-Cl-$C_6H_4$)-pyrrol-2-yl |
| B. 36 | N-(2'-Cl-$C_6H_4$)-pyrrol-2-yl |
| B. 37 | fur-2-yl |
| B. 38 | 5-$CH_3$-fur-2-yl |
| B. 39 | 5-$C_6H_5$-fur-2-yl |
| B. 40 | 5-(4'-$CH_3$-$C_6H_4$)-fur-2-yl |
| B. 41 | 5-(3'-$CH_3$-$C_6H_4$)-fur-2-yl |
| B. 42 | 5-(2'-$CH_3$-$C_6H_4$)-fur-2-yl |
| B. 43 | 5-(4'-$CH_3O$-$C_6H_4$)-fur-2-yl |
| B. 44 | 5-(3'-$CH_3O$-$C_6H_4$)-fur-2-yl |
| B. 45 | 5-(2'-$CH_3O$-$C_6H_4$)-fur-2-yl |
| B. 46 | 5-(4'-$NO_2$-$C_6H_4$)-fur-2-yl |
| B. 47 | 5-(3'-$NO_2$-$C_6H_4$)-fur-2-yl |
| B. 48 | 5-(2'-$NO_2$-$C_6H_4$)-fur-2-yl |
| B. 49 | 5-(4'-CN-$C_6H_4$)-fur-2-yl |
| B. 50 | 5-(3'-CN-$C_6H_4$)-fur-2-yl |
| B. 51 | 5-(2'-CN-$C_6H_4$)-fur-2-yl |
| B. 52 | 5-(4'-Cl-$C_6H_4$)-fur-2-yl |
| B. 53 | 5-(3'-Cl-$C_6H_4$)-fur-2-yl |
| B. 54 | 5-(2'-Cl-$C_6H_4$)-fur-2-yl |
| B. 55 | 4-$CH_3$-fur-2-yl |
| B. 56 | 4-$C_6H_5$-fur-2-yl |
| B. 57 | 4-(4'-$CH_3$-$C_6H_4$)-fur-2-yl |
| B. 58 | 4-(3'-$CH_3$-$C_6H_4$)-fur-2-yl |
| B. 59 | 4-(2'-$CH_3$-$C_6H_4$)-fur-2-yl |
| B. 60 | 4-(4'-$CH_3O$-$C_6H_4$)-fur-2-yl |
| B. 61 | 4-(3'-$CH_3O$-$C_6H_4$)-fur-2-yl |
| B. 62 | 4-(2'-$CH_3O$-$C_6H_4$)-fur-2-yl |
| B. 63 | 4-(4'-$NO_2$-$C_6H_4$)-fur-2-yl |
| B. 64 | 4-(3'-$NO_2$-$C_6H_4$)-fur-2-yl |
| B. 65 | 4-(2'-$NO_2$-$C_6H_4$)-fur-2-yl |
| B. 66 | 4-(4'-CN-$C_6H_4$)-fur-2-yl |
| B. 67 | 4-(3'-CN-$C_6H_4$)-fur-2-yl |
| B. 68 | 4-(2'-CN-$C_6H_4$)-fur-2-yl |
| B. 69 | 4-(4'-Cl-$C_6H_4$)-fur-2-yl |
| B. 70 | 4-(3'-Cl-$C_6H_4$)-fur-2-yl |
| B. 71 | 4-(2'-Cl-$C_6H_4$)-fur-2-yl |
| B. 72 | thien-2-yl |
| B. 73 | 5-$CH_3$-thien-2-yl |
| B. 74 | 5-$C_6H_5$-thien-2-yl |
| B. 75 | 5-(4'-$CH_3$-$C_6H_4$)-thien-2-yl |
| B. 76 | 5-(3'-$CH_3$-$C_6H_4$)-thien-2-yl |
| B. 77 | 5-(2'-$CH_3$-$C_6H_4$)-thien-2-yl |
| B. 78 | 5-(4'-$CH_3O$-$C_6H_4$)-thien-2-yl |
| B. 79 | 5-(3'-$CH_3O$-$C_6H_4$)-thien-2-yl |
| B. 80 | 5-(2'-$CH_3O$-$C_6H_4$)-thien-2-yl |
| B. 81 | 5-(4'-$NO_2$-$C_6H_4$)-thien-2-yl |
| B. 82 | 5-(3'-$NO_2$-$C_6H_4$)-thien-2-yl |
| B. 83 | 5-(2'-$NO_2$-$C_6H_4$)-thien-2-yl |
| B. 84 | 5-(4'-CN-$C_6H_4$)-thien-2-yl |
| B. 85 | 5-(3'-CN-$C_6H_4$)-thien-2-yl |
| B. 86 | 5-(2'-CN-$C_6H_4$)-thien-2-yl |
| B. 87 | 5-(4'-Cl-$C_6H_4$)-thien-2-yl |
| B. 88 | 5-(3'-Cl-$C_6H_4$)-thien-2-yl |
| B. 89 | 5-(2'-Cl-$C_6H_4$)-thien-2-yl |
| B. 90 | 4-$CH_3$-thien-2-yl |
| B. 91 | 4-$C_6H_5$-thien-2-yl |
| B. 92 | 4-(4'-$CH_3$-$C_6H_4$)-thien-2-yl |
| B. 93 | 4-(3'-$CH_3$-$C_6H_4$)-thien-2-yl |
| B. 94 | 4-(2'-$CH_3$-$C_6H_4$)-thien-2-yl |
| B. 95 | 4-(4'-$CH_3O$-$C_6H_4$)-thien-2-yl |
| B. 96 | 4-(3'-$CH_3O$-$C_6H_4$)-thien-2-yl |
| B. 97 | 4-(2'-$CH_3O$-$C_6H_4$)-thien-2-yl |
| B. 98 | 4-(4'-$NO_2$-$C_6H_4$)-thien-2-yl |
| B. 99 | 4-(3'-$NO_2$-$C_6H_4$)-thien-2-yl |
| B. 100 | 4-(2'-$NO_2$-$C_6H_4$)-thien-2-yl |
| B. 101 | 4-(4'-CN-$C_6H_4$)-thien-2-yl |
| B. 102 | 4-(3'-CN-$C_6H_4$)-thien-2-yl |
| B. 103 | 4-(2'-CN-$C_6H_4$)-thien-2-yl |
| B. 104 | 4-(4'-Cl-$C_6H_4$)-thien-2-yl |
| B. 105 | 4-(3'-Cl-$C_6H_4$)-thien-2-yl |
| B. 106 | 4-(2'-Cl-$C_6H_4$)-thien-2-yl |
| B. 107 | thien-3-yl |
| B. 108 | 5-$CH_3$-thien-3-yl |
| B. 109 | 5-$C_6H_5$-thien-3-yl |
| B. 110 | 5-(4'-$CH_3$-$C_6H_4$)-thien-3-yl |
| B. 111 | 5-(3'-$CH_3$-$C_6H_4$)-thien-3-yl |
| B. 112 | 5-(2'-$CH_3$-$C_6H_4$)-thien-3-yl |
| B. 113 | 5-(4'-$CH_3O$-$C_6H_4$)-thien-3-yl |
| B. 114 | 5-(3'-$CH_3O$-$C_6H_4$)-thien-3-yl |
| B. 115 | 5-(2'-$CH_3O$-$C_6H_4$)-thien-3-yl |
| B. 116 | 5-(4'-$NO_2$-$C_6H_4$)-thien-3-yl |
| B. 117 | 5-(3'-$NO_2$-$C_6H_4$)-thien-3-yl |
| B. 118 | 5-(2'-$NO_2$-$C_6H_4$)-thien-3-yl |
| B. 119 | 5-(4'-CN-$C_6H_4$)-thien-3-yl |
| B. 120 | 5-(3'-CN-$C_6H_4$)-thien-3-yl |
| B. 121 | 5-(2'-CN-$C_6H_4$)-thien-3-yl |

TABLE B-continued

| No. | R² |
|---|---|
| B. 122 | 5-(4'-Cl-C₆H₄)-thien-3-yl |
| B. 123 | 5-(3'-Cl-C₆H₄)-thien-3-yl |
| B. 124 | 5-(2'-Cl-C₆H₄)-thien-3-yl |
| B. 125 | pyrazol-4-yl |
| B. 126 | N-CH₃-pyrazol-4-yl |
| B. 127 | N-C₆H₅-pyrazol-4-yl |
| B. 128 | N-(4'-CH₃-C₆H₄)-pyrazol-4-yl |
| B. 129 | N-(3'-CH₃-C₆H₄)-pyrazol-4-yl |
| B. 130 | N-(2'-CH₃-C₆H₄)-pyrazol-4-yl |
| B. 131 | N-(4'-CH₃O-C₆H₄)-pyrazol-4-yl |
| B. 132 | N-(3'-CH₃O-C₆H₄)-pyrazol-4-yl |
| B. 133 | N-(2'-CH₃O-C₆H₄)-pyrazol-4-yl |
| B. 134 | N-(4'-NO₂-C₆H₄)-pyrazol-4-yl |
| B. 135 | N-(3'-NO₂-C₆H₄)-pyrazol-4-yl |
| B. 136 | N-(2'-NO₂-C₆H₄)-pyrazol-4-yl |
| B. 137 | N-(4'-CN-C₆H₄)-pyrazol-4-yl |
| B. 138 | N-(3'-CN-C₆H₄)-pyrazol-4-yl |
| B. 139 | N-(2'-CN-C₆H₄)-pyrazol-4-yl |
| B. 140 | N-(4'-Cl-C₆H₄)-pyrazol-4-yl |
| B. 141 | N-(3'-Cl-C₆H₄)-pyrazol-4-yl |
| B. 142 | N-(2'-Cl-C₆H₄)-pyrazol-4-yl |
| B. 143 | 3-CH₃-N-methylpyrazol-4-yl |
| B. 144 | 3-C₆H₅-N-methylpyrazol-4-yl |
| B. 145 | 3-(4'-CH₃-C₆H₄)-N-methylpyrazol-4-yl |
| B. 146 | 3-(3'-CH₃-C₆H₄)-N-methylpyrazol-4-yl |
| B. 147 | 3-(2'-CH₃-C₆H₄)-N-methylpyrazol-4-yl |
| B. 148 | 3-(4'-CH₃O-C₆H₄)-N-methylpyrazol-4-yl |
| B. 149 | 3-(3'-CH₃O-C₆H₄)-N-methylpyrazol-4-yl |
| B. 150 | 3-(2'-CH₃O-C₆H₄)-N-methylpyrazol-4-yl |
| B. 151 | 3-(4'-NO₂-C₆H₄)-N-methylpyrazol-4-yl |
| B. 152 | 3-(3'-NO₂-C₆H₄)-N-methylpyrazol-4-yl |
| B. 153 | 3-(2'-NO₂-C₆H₄)-N-methylpyrazol-4-yl |
| B. 154 | 3-(4'-CN-C₆H₄)-N-methylpyrazol-4-yl |
| B. 155 | 3-(3'-CN-C₆H₄)-N-methylpyrazol-4-yl |
| B. 156 | 3-(2'-CN-C₆H₄)-N-methylpyrazol-4-yl |
| B. 157 | 3-(4'-Cl-C₆H₄)-N-methylpyrazol-4-yl |
| B. 158 | 3-(3'-Cl-C₆H₄)-N-methylpyrazol-4-yl |
| B. 159 | 3-(2'-Cl-C)-N-methylpyrazol-4-yl |
| B. 160 | isoxazol-5-yl |
| B. 161 | 3-CH₃-isoxazol-5-yl |
| B. 162 | 3-C₆H₅-isoxazol-5-yl |
| B. 163 | 3-(4'-CH₃-C₆H₄)-isoxazol-5-yl |
| B. 164 | 3-(3'-CH₃-C₆H₄)-isoxazol-5-yl |
| B. 165 | 3-(2'-CH₃-C₆H₄)-isoxazol-5-yl |
| B. 166 | 3-(4'-CH₃O-C₆H₄)-isoxazol-5-yl |
| B. 167 | 3-(3'-CH₃O-C₆H₄)-isoxazol-5-yl |
| B. 168 | 3-(2'-CH₃O-C₆H₄)-isoxazol-5-yl |
| B. 169 | 3-(4'-NO₂-C₆H₄)-isoxazol-5-yl |
| B. 170 | 3-(3'-NO₂-C₆H₄)-isoxazol-5-yl |
| B. 171 | 3-(2'-NO₂-C₆H₄)-isdxazol-5-y1 |
| B. 172 | 3-(4'-CN-C₆H₄)-isoxazol-5-yl |
| B. 173 | 3-(3'-CN-C₆H₄)-isoxazol-5-yl |
| B. 174 | 3-(2'-CN-C₆H₄)-isoxazol-5-yl |
| B. 175 | 3-(4'-Cl-C₆H₄)-isoxazol-5-yl |
| B. 176 | 3-(3'-Cl-C₆H₄)-isoxazol-5-yl |
| B. 177 | 3-(2'-Cl-C₆H₄)-isoxazol-5-yl |
| B. 178 | 4-chloroisoxazol-5-yl |
| B. 179 | 3-CH₃-4-chloroisoxazol-5-yl |
| B. 180 | 3-C₆H₅-4-chloroisoxazol-5-yl |
| B. 181 | 3-(4'-CH₃-C₆H₄)-4-chloroisoxazol-5-yl |
| B. 182 | 3-(3'-CH₃-C₆H₄)-4-chloroisoxazol-5-yl |
| B. 183 | 3-(2'-CH₃-C₆H₄)-4-chloroisoxazol-5-yl |
| B. 184 | 3-(4'-CH₃O-C₆H₄)-4-chloroisoxazol-5-yl |
| B. 185 | 3-(3'-CH₃O-C₆H₄)-4-chloroisoxazol-5-yl |
| B. 186 | 3-(2'-CH₃O-C₆H₄)-4-chloroisoxazol-5-yl |
| B. 187 | 3-(4'-NO₂-C₆H₄)-4-chloroisoxazol-5-yl |
| B. 188 | 3-(3'-NO₂-C₆H₄)-4-chloroisoxazol-5-yl |
| B. 189 | 3-(2'-NO₂-C₆H₄)-4-chloroisoxazol-5-yl |
| B. 190 | 3-(4'-CN-C₆H₄)-4-chloroisoxazol-5-yl |
| B. 191 | 3-(3'-CN-C₆H₄)-4-chloroisoxazol-5-yl |
| B. 192 | 3-(2'-CN-C₆H₄)-4-chloroisoxazol-5-yl |
| B. 193 | 3-(4'-Cl-C₆H₄)-4-chloroisoxazol-5-yl |
| B. 194 | 3-(3'-Cl-C₆H₄)-4-chloroisoxazol-5-yl |
| B. 195 | 3-(2'-Cl-C₆H₄)-4-chloroisoxazol-5-yl |
| B. 196 | isoxazol-3-yl |
| B. 197 | 5-CH₃-isoxazol-3-yl |
| B. 198 | 5-C₆H₅-isoxazol-3-yl |
| B. 199 | 5-(4'-CH₃-C₆H₄)-isoxazol-3-yl |
| B. 200 | 5-(3'-CH₃-C₆H₄)-isoxazol-3-yl |
| B. 201 | 5-(2'-CH₃-C₆H₄)-isoxazol-3-yl |
| B. 202 | 5-(4'-CH₃O-C₆H₄)-isoxazol-3-yl |
| B. 203 | 5-(3'-CH₃O-C₆H₄)-isoxazol-3-yl |
| B. 204 | 5-(2'-CH₃O-C₆H₄)-isoxazol-3-yl |
| B. 205 | 5-(4'-NO₂-C₆H₄)-isoxazol-3-yl |
| B. 206 | 5-(3'-NO₂-C₆H₄)-isoxazol-3-yl |
| B. 207 | 5-(2'-NO₂-C₆H₄)-isoxazol-3-yl |
| B. 208 | 5-(4'-CN-C₆H₄)-isoxazol-3-yl |
| B. 209 | 5-(3'-CN-C₆H₄)-isoxazol-3-yl |
| B. 210 | 5-(2'-CN-C₆H₄)-isoxazol-3-yl |
| B. 211 | 5-(4'-Cl-C₆H₄)-isoxazol-3-yl |
| B. 212 | 5-(3'-Cl-C₆H₄)-isoxazol-3-yl |
| B. 213 | 5-(2'-Cl-C₆H₄)-isoxazol-3-yl |
| B. 214 | isothiazol-5-l |
| B. 215 | 3-CH₃-isothiazol-5-yl |
| B. 216 | 3-C₆H₅-isothiazol-5-yl |
| B. 217 | 3-(4'-CH₃-C₆H₄)-isothiazol-5-yl |
| B. 218 | 3-(3'-CH₃-C₆H₄)-isothiazol-5-yl |
| B. 229 | 3-(2'-CH₃-C₆H₄)-isothiazol-5-yl |
| B. 220 | 3-(4'-CH₃O-C₆H₄)-isothiazol-5-yl |
| B. 221 | 3-(3'-CH₃O-C₆H₄)-isothiazol-5-yl |
| B. 222 | 3-(2'-CH₃O-C₆H₄)-isothiazol-5-yl |
| B. 223 | 3-(4'-NO₂-C₆H₄)-isothiazol-5-yl |
| B. 224 | 3-(3'-NO₂-C₆H₄)-isothiazol-5-yl |
| B. 225 | 3-(2'-NO₂-C₆H₄)-isothiazol-5-yl |
| B. 226 | 3-(4'-CN-C₆H₄)-isothiazol-5-yl |
| B. 227 | 3-(3'-CN-C₆H₄)-isothiazol-5-yl |
| B. 228 | 3-(2'-CN-C₆H₄)-isothiazol-5-yl |
| B. 229 | 3-(4'-Cl-C₆H₄)-isothiazol-5-yl |
| B. 230 | 3-(3'-Cl-C₆H₄)-isothiazol-5-yl |
| B. 231 | 3-(2'-Cl-C₆H₄)-isothiazol-5-yl |
| B. 232 | oxazol-4-yl |
| B. 233 | 2-CH₃-oxazol-4-yl |
| B. 234 | 2-C₆H₅-oxazol-4-yl |
| B. 235 | 2-(4'-CH₃-C₆H₄)-oxazol-4-yl |
| B. 236 | 2-(3'-CH₃-C₆H₄)-oxazol-4-yl |
| B. 237 | 2-(2'-CH₃-C₆H₄)-oxazol-4-yl |
| B. 238 | 2-(4'-CH₃O-C₆H₄)-oxazol-4-yl |
| B. 239 | 2-(3'-CH₃O-C₆H₄)-oxazol-4-yl |
| B. 240 | 2-(2'-CH₃O-C₆H₄)-oxazol-4-yl |
| B. 241 | 2-(4'-NO₂-C₆H₄)-oxazol-4-yl |
| B. 242 | 2-(3'-NO₂-C₆H₄)-oxazol-4-yl |
| B. 243 | 2-(2'-NO₂-C₆H₄)-oxazol-4-yl |
| B. 244 | 2-(4'-CN-C₆H₄)-oxazol-4-yl |
| B. 245 | 2-(3'-CN-C₆H₄)-oxazol-4-yl |
| B. 246 | 2-(2'-CN-C₆H₄)-oxazol-4-yl |
| B. 247 | 2-(4'-Cl-C₆H₄)-oxazol-4-yl |
| B. 248 | 2-(3'-Cl-C₆H₄)-oxazol-4-yl |
| B. 249 | 2-(2'-Cl-C₆H₄)-oxazol-4-yl |
| B. 250 | thiazol-4-yl |
| B. 251 | 2-CH₃-thiazol-4-yl |
| B. 252 | 2-C₆H₅-thiazol-4-yl |
| B. 253 | 2-(4'-CH₃-C₆H₄)-thiazol-4-yl |
| B. 254 | 2-(3'-CH₃-C₆H₄)-thiazol-4-yl |
| B. 255 | 2-(2'-CH₃-C₆H₄)-thiazol-4-yl |
| B. 256 | 2-(4'-CH₃O-C₆H₄)-thiazol-4-yl |
| B. 257 | 2-(3'-CH₃O-C₆H₄)-thiazol-4-yl |
| B. 258 | 2-(2'-CH₃O-C₆H₄)-thiazol-4-yl |
| B. 259 | 2-(4'-NO₂-C₆H₄)-thiazol-4-yl |
| B. 260 | 2-(3'-NO₂-C₆H₄)-thiazol-4-yl |
| B. 261 | 2-(2'-NO₂-C₆H₄)-thiazol-4-yl |
| B. 262 | 2-(4'-CN-C₆H₄)-thiazol-4-yl |
| B. 263 | 2-(3'-CN-C₆H₄)-thiazol-4-yl |
| B. 264 | 2-(2'-CN-C₆H₄)-thiazol-4-yl |
| B. 265 | 2-(4'-Cl-C₆H₄)-thiazol-4-yl |
| B. 266 | 2-(3'-Cl-C₆H₄)-thiazol-4-yl |
| B. 267 | 2-(2'-Cl-C₆H₄)-thiazol-4-yl |
| B. 268 | N-CH₃-1,2,4-triazol-5-yl |
| B. 269 | 3-CH₃-N-CH₃-1,2,4-triazol-5-yl |
| B. 270 | 3-C₆H₅-N-CH₃-1,2,4-triazol-5-yl |
| B. 271 | 3-(4'-CH₃-C₆H₄)-N-CH₃-1,2,4-triazol-5-yl |
| B. 272 | 3-(3'-CH₃-C₆H₄)-N-CH₃-1,2,4-triazol-5-yl |
| B. 273 | 3-(2'-CH₃-C₆H₄)-N-CH₃-1,2,4-triazol-5-yl |
| B. 274 | 3-(4'-CH₃O-C₆H₄)-N-CH₃-1,2,4-triazol-5-yl |
| B. 275 | 3-(3'-CH₃O-C₆H₄)-N-CH₃-1,2,4-triazol-5-yl |

TABLE B-continued

| No. | R² |
|---|---|
| B. 276 | 3-(2'-CH₃O-C₆H₄)-N-CH₃-1,2,4-triazol-5-yl |
| B. 277 | 3-(4'-NO₂-C₆H₄)-N-CH₃-1,2,4-triazol-5-yl |
| B. 278 | 3-(3'-NO₂-C₆H₄)-N-CH₃-1,2,4-triazol-5-yl |
| B. 279 | 3-(2'-NO₂-C₆H₄)-N-CH₃-1,2,4-triazol-5-yl |
| B. 280 | 3-(4'-CN-C₆H₄)-N-CH₃-1,2,4-triazol-5-yl |
| B. 281 | 3-(3'-CN-C₆H₄)-N-CH₃-1,2,4-triazol-5-yl |
| B. 282 | 3-(2'-CN-C₆H₄)-N-CH₃-1,2,4-triazol-5-yl |
| B. 283 | 3-(4'-Cl-C₆H₄)-N-CH₃-1,2,4-triazol-5-yl |
| B. 284 | 3-(3'-Cl-C₆H₄)-N-CH₃-1,2,4-triazol-5-yl |
| B. 285 | 3-(2'-Cl-C₆H₄)-N-CH₃-1,2,4-triazol-5-yl |
| B. 286 | 1,3,4-oxadiazol-2-yl |
| B. 287 | 5-CH₃-1,3,4-oxadiazol-2-yl |
| B. 288 | 5-C₆H₅-1,2,3-oxadiazol-2-yl |
| B. 289 | 5-(4'-CH₃-C₆H₄)-1,3,4-oxadiazol-2-yl |
| B. 290 | 5-(3'-CH₃-C₆H₄)-1,3,4-oxadiazol-2-yl |
| B. 291 | 5-(2'-CH3-C₆H₄)-1,3,4-oxadiazol-2-yl |
| B. 292 | 5-(4'-CH₃O-C₆H₄)-1,3,4-oxadiazol-2-yl |
| B. 293 | 5-(3'-CH₃O-C₆H₄)-1,3,4-oxadiazol-2-yl |
| B. 294 | 5-(2'-CH₃O-C₆H₄)-1,3,4-oxadiazol-2-yl |
| B. 295 | 5-(4'-NO₂-C₆H₄)-1,3,4-oxadiazol-2-yl |
| B. 296 | 5-(3'-NO₂-C₆H₄)-1,3,4-oxadiazol-2-yl |
| B. 297 | 5-(2'-NO₂-C₆H₄)-1,3,4-oxadiazol-2-yl |
| B. 298 | 5-(4'-CN-C₆H₄)-1,3,4-oxadiazol-2-yl |
| B. 299 | 5-(3'-CN-C₆H₄)-1,3,4-oxadiazol-2-yl |
| B. 300 | 5-(2'-CN-C₆H₄)-1,3,4-oxadiazol-2-yl |
| B. 301 | 5-(4'-Cl-C₆H₄)-1,3,4-oxadiazol-2-yl |
| B. 302 | 5-(3'-Cl-C₆H₄)-1,3,4-oxadiazol-2-yl |
| B. 303 | 5-(2'-Cl-C₆H₄)-1,3,4-oxadiazol-2-yl |
| B. 304 | 1,2,4-oxadiazol-3-yl |
| B. 305 | 5-CH₃-1,2,4-oxadiazol-3-yl |
| B. 306 | 5-C₆H₅-1,2,4-oxadiazol-3-yl |
| B. 307 | 5-(4'-CH₃-C₆H₄)-1,2,4-oxadiazol-3-yl |
| B. 308 | 5-(3'-CH₃-C₆H₄)-1,2,4-oxadiazol-3-yl |
| B. 309 | 5-(2'-CH₃-C₆H₄)-1,2,4-oxadiazol-3-yl |
| B. 310 | 5-(4'-CH₃O-C₆H₄)-1,2,4-oxadiazol-3-yl |
| B. 311 | 5-(3'-CH₃O-C₆H₄)-1,2,4-oxadiazol-3-yl |
| B. 312 | 5-(2'-CH₃O-C₆H₄)-1,2,4-oxadiazol-3-yl |
| B. 313 | 5-(4'-NO₂-C₆H₄)-1,2,4-oxadiazol-3-yl |
| B. 314 | 5-(3'-NO₂-C₆H₄)-1,2,4-oxadiazol-3-yl |
| B. 315 | 5-(2'-NO₂-C₆H₄)-1,2,4-oxadiazol-3-yl |
| B. 316 | 5-(4'-CN-C₆H₄)-1,2,4-oxadiazol-3-yl |
| B. 317 | 5-(3'-CN-C₆H₄)-1,2,4-oxadiazol-3-yl |
| B. 318 | 5-(2'-CN-C₆H₄)-1,2,4-oxadiazol-3-yl |
| B. 319 | 5-(4'-Cl-C₆H₄)-1,2,4-oxadiazol-3-yl |
| B. 320 | 5-(3'-Cl-C₆H₄)-1,2,4-oxadiazol-3-yl |
| B. 321 | 5-(2'-Cl-C₆H₄)-1,2,4-oxadiazol-3-yl |
| B. 322 | 1,2,4-oxadiazol-5-yl |
| B. 323 | 3-CH₃-1,2,4-oxadiazol-5-yl |
| B. 324 | 3-C₆H₅-1,2,4-oxadiazol-5-yl |
| B. 325 | 3-(4'-CH₃-C₆H₄)-1,2,4-oxadiazol-5-yl |
| B. 326 | 3-(3'-CH₃-C₆H₄)-1,2,4-oxadiazol-5-yl |
| B. 327 | 3-(2'-CH₃-C₆H₄)-1,2,4-oxadiazol-5-yl |
| B. 328 | 3-(4'-CH₃O-C₆H₄)-1,2,4-oxadiazol-5-yl |
| B. 329 | 3-(3'-CH₃O-C₆H₄)-1,2,4-oxadiazol-5-yl |
| B. 330 | 3-(2'-CH3O-C₆H₄)-1,2,4-oxadiazol-5-yl |
| B. 331 | 3-(4'-NO₂-C₆H₄)-1,2,4-oxadiazol-5-yl |
| B. 332 | 3-(3'-NO₂-C₆H₄)-1,2,4-oxadiazol-5-yl |
| B. 333 | 3-(2'-NO₂-C₆H₄)-1,2,4-oxadiazol-5-yl |
| B. 334 | 3-(4'-CN-C₆H₄)-1,2,4-oxadiazol-5-yl |
| B. 335 | 3-(3'-CN-C₆H₄)-1,2,4-oxadiazol-5-yl |
| B. 336 | 3-(2'-CN-C₆H₄)-1,2,4-oxadiazol-5-yl |
| B. 337 | 3-(4'-Cl-C₆H₄)-1,2,4-oxadiazol-5-yl |
| B. 338 | 3-(3'-Cl-C₆H₄)-1,2,4-oxadiazol-5-yl |
| B. 339 | 3-(2'-Cl-C₆H₄)-1,2,4-oxadiazol-5-yl |
| B. 340 | 1,2,4-thiadiazol-3-yl |
| B. 341 | 5-CH₃-1,2,4-thiadiazol-3-yl |
| B. 342 | 5-C₆H₅-1,2,4-thiadiazol-3-yl |
| B. 343 | 5-(4'-CH₃-C₆H₄)-1,2,4-thiadiazol-3-yl |
| B. 344 | 5-(3'-CH₃-C₆H₄)-1,2,4-thiadiazol-3-yl |
| B. 345 | 5-(2'-CH₃-C₆H₄)-1,2,4-thiadiazol-3-yl |
| B. 346 | 5-(4'-CH₃O-C₆H₄)-1,2,4-thiadiazol-3-yl |
| B. 347 | 5-(3'-CH₃O-C₆H₄)-1,2,4-thiadiazol-3-yl |
| B. 348 | 5-(2'-CH₃O-C₆H₄)-1,2,4-thiadiazol-3-yl |
| B. 349 | 5-(4'-NO₂-C₆H₄)-1,2,4-thiadiazol-3-yl |
| B. 350 | 5-(3'-NO₂-C₆H₄)-1,2,4-thiadiazol-3-yl |
| B. 351 | 5-(2'-NO₂-C₆H₄)-1,2,4-thiadiazol-3-yl |
| B. 352 | 5-(4'-CN-C₆H₄)-1,2,4-thiadiazol-3-yl |
| B. 353 | 5-(3'-CN-C₆H₄)-1,2,4-thiadiazol-3-yl |
| B. 354 | 5-(2'-CN-C₆H₄)-1,2,4-thiadiazol-3-yl |
| B. 355 | 5-(4'-Cl-C₆H₄)-1,2,4-thiadiazol-3-yl |
| B. 356 | 5-(3'-Cl-C₆H₄)-1,2,4-thiadiazol-3-yl |
| B. 357 | 5-(2'-Cl-C₆H₄)-1,2,4-thiadiazoi-3-yl |
| B. 358 | 1,3,4-thiadiazol-2-yl |
| B. 359 | 5-CH₃-1,3,4-thiadiazol-2-yl |
| B. 360 | 5-C₆H₅-1,3,4-thiadiazol-2-yl |
| B. 361 | 5-(4'-CH₃-C₆H₄)-1,3,4-thiadiazol-2-yl |
| B. 362 | 5-(3'-CH₃-C₆H₄)-1,3,4-thiadiazol-2-yl |
| B. 363 | 5-(2'-CH₃-C₆H₄)-1,3,4-thiadiazol-2-yl |
| B. 364 | 5-(4'-CH₃O-C₆H₄)-1,3,4-thiadiazol-2-yl |
| B. 365 | 5-(3'-CH₃O-C₆H₄)-1,3,4-thiadiazol-2-yl |
| B. 366 | 5-(2'-CH₃O-C₆H₄)-1,3,4-thiadiazol-2-yl |
| B. 367 | 5-(4'-NO₂-C₆H₄)-1,3,4-thiadiazol-2-yl |
| B. 368 | 5-(3'-NO₂-C₆H₄)-1,3,4-thiadiazol-2-yl |
| B. 369 | 5-(2'-NO₂-C₆H₄)-1,3,4-thiadiazol-2-yl |
| B. 370 | 5-(4'-CN-C₆H₄)-1,3,4-thiadiazol-2-yl |
| B. 371 | 5-(3'-CN-C₆H₄)-1,3,4-thiadiazol-2-yl |
| B. 372 | 5-(2'-CN-C₆H₄)-1,3,4-thiadiazol-2-yl |
| B. 373 | 5-(4'-Cl-C₆H₄)-1,3,4-thiadiazol-2-yl |
| B. 374 | 5-(3'-Cl-C₆H₄)-1,3,4-thiadiazol-2-yl |
| B. 375 | 5-(2'-Cl-C₆H₄)-1,3,4-thiadiazol-2-yl |
| B. 376 | pyridin-2-yl |
| B. 377 | pyridin-4-yl |
| B. 378 | pyridazin-3-yl |
| B. 379 | pyridazin-4-yl |
| B. 380 | pyridazin-2-yl |
| B. 381 | pyrimidin-4-yl |
| B. 382 | pyrimidin-5-yl |
| B. 383 | pyrimidin-2-yl |
| B. 384 | pyridin-3-yl |

TABLE C

| No. | $R^d$ | $R^1_x$ |
|---|---|---|
| C. 1 | CH₂CH₃ | H |
| C. 2 | CH₂CH₃ | 3-CF₃ |
| C. 3 | CH₂CH₃ | 4-CF₃ |
| C. 4 | CH₂CH₃ | 3-Cl |
| C. 5 | CH₂CH₃ | 4-Cl |
| C. 6 | CH₂CH₃ | 3,5-Cl₂ |
| C. 7 | CH₂CH₂CH₃ | H |
| C. 8 | CH₂CH₂CH₃ | 3-CF₃ |
| C. 9 | CH₂CH₂CH₃ | 4-CF₃ |
| C. 10 | CH₂CH₂CH₃ | 3-Cl |
| C. 11 | CH₂CH₂CH₃ | 4-Cl |
| C. 12 | CH₂CH₂CH₃ | 3,5-Cl₂ |
| C. 13 | CH(CH₃)₂ | H |
| C. 14 | CH(CH₃)₂ | 3-CF₃ |
| C. 15 | CH(CH₃)₂ | 4-CF₃ |
| C. 16 | CH(CH₃)₂ | 3-Cl |
| C. 17 | CH(CH₃)₂ | 4-Cl |
| C. 18 | CH(CH₃)₂ | 3,5-Cl₂ |
| C. 19 | cyclopropyl | H |
| C. 20 | cyclopropyl | 3-CF₃ |
| C. 21 | cyclopropyl | 4-CF₃ |
| C. 22 | cyclopropyl | 3-Cl |
| C. 23 | cyclopropyl | 4-Cl |
| C. 24 | cyclopropyl | 3,5-Cl₂ |
| C. 25 | CF₃ | H |
| C. 26 | CF₃ | 3-CF₃ |
| C. 27 | CF₃ | 4-CF₃ |
| C. 28 | CF₃ | 3-Cl |
| C. 29 | CF₃ | 4-Cl |
| C. 30 | CF₃ | 3,5-Cl₂ |
| C. 31 | CN | H |
| C. 32 | CN | 3-CF₃ |
| C. 33 | CN | 4-CF₃ |
| C. 34 | CN | 3-Cl |
| C. 35 | CN | 4-Cl |
| C. 36 | CN | 3,5-Cl₂ |
| C. 37 | OCH₃ | H |

TABLE C-continued

| No. | $R^d$ | $R^1_x$ |
|---|---|---|
| C. 38 | OCH$_3$ | 3-CF$_3$ |
| C. 39 | OCH$_3$ | 4-CF$_3$ |
| C. 40 | OCH$_3$ | 3-Cl |
| C. 41 | OCH$_3$ | 4-Cl |
| C. 42 | OCH$_3$ | 3,5-Cl$_2$ |
| C. 43 | OCH$_2$CH$_3$ | H |
| C. 44 | OCH$_2$CH$_3$ | 3-CF$_3$ |
| C. 45 | OCH$_2$CH$_3$ | 4-CF$_3$ |
| C. 46 | OCH$_2$CH$_3$ | 3-Cl |
| C. 47 | OCH$_2$CH$_3$ | 4-Cl |
| C. 48 | OCH$_2$CH$_3$ | 3,5-Cl$_2$ |
| C. 49 | OH | H |
| C. 50 | OH | 3-CF$_3$ |
| C. 51 | OH | 4-CF$_3$ |
| C. 52 | OH | 3-Cl |
| C. 53 | OH | 4-Cl |
| C. 54 | OH | 3,5-Cl$_2$ |
| C. 55 | Cl | H |
| C. 56 | Cl | 3-CF$_3$ |
| C. 57 | Cl | 4-CF$_3$ |
| C. 58 | Cl | 3-Cl |
| C. 59 | Cl | 4-Cl |
| C. 60 | Cl | 3,5-Cl$_2$ |
| C. 61 | Br | H |
| C. 62 | Br | 3-CF$_3$ |
| C. 63 | Br | 4-CF$_3$ |
| C. 64 | Br | 3-Cl |
| C. 65 | Br | 4-Cl |
| C. 66 | Br | 3,5-Cl$_2$ |
| C. 67 | SCH$_3$ | H |
| C. 68 | SCH$_3$ | 3-CF$_3$ |
| C. 69 | SCH$_3$ | 4-CF$_3$ |
| C. 70 | SCH$_3$ | 3-Cl |
| C. 71 | SCH$_3$ | 4-Cl |
| C. 72 | SCH$_3$ | 3,5-Cl$_2$ | table d

| No. | $R^d$ | $R^e$ | $A^f$ |
|---|---|---|---|
| D. 1 | H | CH$_3$ | C$_6$H$_5$ |
| D. 2 | CH$_3$ | CH$_3$ | C$_6$H$_5$ |
| D. 3 | CH$_2$CH$_3$ | CH$_3$ | C$_6$H$_5$ |
| D. 4 | CH$_2$CH$_2$CH$_3$ | CH$_3$ | C$_6$H$_5$ |
| D. 5 | CH(CH$_3$)$_2$ | CH$_3$ | C$_6$H$_5$ |
| D. 6 | cyclopropyl | CH$_3$ | C$_6$H$_5$ |
| D. 7 | pyridin-2-yl | CH$_3$ | C$_6$H$_5$ |
| D. 8 | pyridin-3-yl | CH$_3$ | C$_6$H$_5$ |
| D. 9 | pyridin-4-yl | CH$_3$ | C$_6$H$_5$ |
| D. 10 | 5-CH$_3$-isoxazol-3-yl | CH$_3$ | C$_6$H$_5$ |
| D. 11 | C$_6$H$_5$ | CH$_3$ | C$_6$H$_5$ |
| D. 12 | CH$_3$ | H | C$_6$H$_5$ |
| D. 13 | CH$_3$ | CH$_2$CH$_3$ | C$_6$H$_5$ |
| D. 14 | CH$_3$ | CH$_2$CH$_2$CH$_3$ | C$_6$H$_5$ |
| D. 15 | CH$_3$ | CH(CH$_3$)$_2$ | C$_6$H$_5$ |
| D. 16 | CH$_3$ | cyclopropyl | C$_6$H$_5$ |
| D. 17 | CH$_3$ | pyridin-2-yl | C$_6$H$_5$ |
| D. 18 | CH$_3$ | pyridin-3-yl | C$_6$H$_5$ |
| D. 19 | CH$_3$ | pyridin-4-yl | C$_6$H$_5$ |
| D. 20 | CH$_3$ | 5-CH$_3$-isoxazol-3-yl | C$_6$H$_5$ |
| D. 21 | CH$_3$ | C$_6$H$_5$ | C$_6$H$_5$ |
| D. 22 | H | CH$_3$ | CH$_3$ |
| D. 23 | CH$_3$ | CH$_3$ | CH$_3$ |
| D. 24 | CH$_2$CH$_3$ | CH$_3$ | CH$_3$ |
| D. 25 | CH$_2$CH$_2$CH$_3$ | CH$_3$ | CH$_3$ |
| D. 26 | CH(CH$_3$)$_2$ | CH$_3$ | CH$_3$ |
| D. 27 | cyclopropyl | CH$_3$ | CH$_3$ |
| D. 28 | pyridin-2-yl | CH$_3$ | CH$_3$ |
| D. 29 | pyridin-3-yl | CH$_3$ | CH$_3$ |
| D. 30 | pyridin-4-yl | CH$_3$ | CH$_3$ |
| D. 31 | 5-CH$_3$-isoxazol-3-yl | CH$_3$ | CH$_3$ |
| D. 32 | C$_6$H$_5$ | CH$_3$ | CH$_3$ |
| D. 33 | CH$_3$ | H | CH$_3$ |
| D. 34 | CH$_3$ | CH$_2$CH$_3$ | CH$_3$ | table d-continued

| No. | $R^d$ | $R^e$ | $A^f$ |
|---|---|---|---|
| D. 35 | CH$_3$ | CH$_2$CH$_2$CH$_3$ | CH$_3$ |
| D. 36 | CH$_3$ | CH(CH$_3$)2 | CH$_3$ |
| D. 37 | CH$_3$ | cyclopropyl | CH$_3$ |
| D. 38 | CH$_3$ | pyridin-2-yl | CH$_3$ |
| D. 39 | CH$_3$ | pyridin-3-yl | CH$_3$ |
| D. 40 | CH$_3$ | pyridin-4-yl | CH$_3$ |
| D. 41 | CH$_3$ | 5-CH$_3$-isoxazol-3-yl | CH$_3$ |
| D. 42 | CH$_3$ | C$_6$H$_5$ | CH$_3$ |

TABLE E

| No. | $R^d$ | $R^e$ | $R^\alpha$ | $R^\beta$ |
|---|---|---|---|---|
| E. 1 | H | CH$_3$ | CH$_3$ | CH$_3$ |
| E. 2 | CH$_3$ | CH$_3$ | CH$_3$ | CH$_3$ |
| E. 3 | CH$_2$CH$_3$ | CH$_3$ | CH$_3$ | CH$_3$ |
| E. 4 | CH$_2$CH$_2$CH$_3$ | CH$_3$ | CH$_3$ | CH$_3$ |
| E. 5 | CH(CH$_3$)$_2$ | CH$_3$ | CH$_3$ | CH$_3$ |
| E. 6 | cyclopropyl | CH$_3$ | CH$_3$ | CH$_3$ |
| E. 7 | pyridin-2-yl | CH$_3$ | CH$_3$ | CH$_3$ |
| E. 8 | pyridin-3-yl | CH$_3$ | CH$_3$ | CH$_3$ |
| E. 9 | pyridin-4-yl | CH$_3$ | CH$_3$ | CH$_3$ |
| E. 10 | 5-CH$_3$-isoxazol-3-yl | CH$_3$ | CH$_3$ | CH$_3$ |
| E. 11 | C$_6$H$_5$ | CH$_3$ | CH$_3$ | CH$_3$ |
| E. 12 | CH$_3$ | H | CH$_3$ | CH$_3$ |
| E. 13 | CH$_3$ | CH$_2$CH$_3$ | CH$_3$ | CH$_3$ |
| E. 14 | CH$_3$ | CH$_2$CH$_2$CH$_3$ | CH$_3$ | CH$_3$ |
| E. 15 | CH$_3$ | CH(CH$_3$)$_2$ | CH$_3$ | CH$_3$ |
| E. 16 | CH$_3$ | cyclopropyl | CH$_3$ | CH$_3$ |
| E. 17 | CH$_3$ | pyridin-2-yl | CH$_3$ | CH$_3$ |
| E. 18 | CH$_3$ | pyridin-3-yl | CH$_3$ | CH$_3$ |
| E. 19 | CH$_3$ | pyridin-4-yl | CH$_3$ | CH$_3$ |
| E. 20 | CH$_3$ | 5-CH$_3$-isoxazol-3-yl | CH$_3$ | CH$_3$ |
| E. 21 | CH$_3$ | C$_6$H$_5$ | CH$_3$ | CH$_3$ |
| E. 22 | CH$_3$ | CH$_3$ | H | CH$_3$ |
| E. 23 | CH$_3$ | CH$_3$ | CH$_2$CH$_3$ | CH$_3$ |
| E. 24 | CH$_3$ | CH$_3$ | CH$_2$CH$_2$CH$_3$ | CH$_3$ |
| E. 25 | CH$_3$ | CH$_3$ | CH(CH$_3$)$_2$ | CH$_3$ |
| E. 26 | CH$_3$ | CH$_3$ | cyclopropyl | CH$_3$ |
| E. 27 | CH$_3$ | CH$_3$ | pyridin-2-yl | CH$_3$ |
| E. 28 | CH$_3$ | CH$_3$ | pyridin-3-yl | CH$_3$ |
| E. 29 | CH$_3$ | CH$_3$ | pyridin-4-yl | CH$_3$ |
| E. 30 | CH$_3$ | CH$_3$ | 5-CH$_3$-isoxazol-3-yl | CH$_3$ |
| E. 31 | CH$_3$ | CH$_3$ | C$_6$H$_5$ | CH$_3$ |
| E. 32 | CH$_3$ | CH$_3$ | CH$_3$ | CH$_2$CH$_2$ |
| E. 33 | CH$_3$ | CH$_3$ | CH$_3$ | CH$_2$CH$_2$CH$_2$ |
| E. 34 | CH$_3$ | CH$_3$ | CH$_3$ | CH(CH$_2$)$_2$ |
| E. 35 | CH$_3$ | CH$_3$ | CH$_3$ | C(CH$_2$)$_3$ |
| E. 36 | CH$_3$ | CH$_3$ | CH$_3$ | benzyl |
| E. 37 | CH$_3$ | CH$_3$ | CH$_3$ | propargyl |
| E. 38 | CH$_3$ | CH$_3$ | CH$_3$ | bromo-propargyl |
| E. 39 | CH$_3$ | CH$_3$ | CH$_3$ | iodo-propargyl |
| E. 40 | CH$_3$ | CH$_3$ | CH$_3$ | allyl |
| E. 41 | CH$_3$ | CH$_3$ | CH$_3$ | trans-chloroallyl |
| E. 42 | CH$_3$ | CH$_3$ | CH$_3$ | CH$_2$CH$_2$OCH$_3$ |

TABLE F

| No. | R$^d$ | R$^\alpha$ | R$^\beta$ |
|---|---|---|---|
| F.1 | CH$_3$ | CH$_3$ | H |
| F.2 | CH$_3$ | CH$_3$ | CH$_3$ |
| F.3 | CH$_3$ | CH$_3$ | C$_2$H$_5$ |
| F.4 | CH$_3$ | CH$_3$ | n-C$_3$H$_7$ |
| F.5 | CH$_3$ | CH$_3$ | i-C$_3$H$_7$ |
| F.6 | CH$_3$ | CH$_3$ | cyclopropyl |
| F.7 | CH$_3$ | CH$_3$ | n-C$_4$H$_9$ |
| F.8 | CH$_3$ | CH$_3$ | s-C$_4$H$_9$ |
| F.9 | CH$_3$ | CH$_3$ | i-C$_4$H$_9$ |
| F.10 | CH$_3$ | CH$_3$ | t-C$_4$H$_9$ |
| F.11 | CH$_3$ | CH$_3$ | n-C$_5$H$_{11}$ |
| F.12 | CH$_3$ | CH$_3$ | i-C$_5$H$_{11}$ |
| F.13 | CH$_3$ | CH$_3$ | neo-C$_5$H$_{11}$ |
| F.14 | CH$_3$ | CH$_3$ | cyclopentyl |
| F.15 | CH$_3$ | CH$_3$ | n-C$_6$H$_{13}$ |
| F.16 | CH$_3$ | CH$_3$ | cyclohexyl |
| F.17 | CH$_3$ | CH$_3$ | n-C$_8$H$_{17}$ |
| F.18 | CH$_3$ | CH$_3$ | CH$_2$CH$_2$Cl |
| F.19 | CH$_3$ | CH$_3$ | (CH$_2$)$_4$Cl |
| F.20 | CH$_3$ | CH$_3$ | CH$_2$CN |
| F.21 | CH$_3$ | CH$_3$ | CH$_2$CH$_2$CN |
| F.22 | CH$_3$ | CH$_3$ | (CH$_2$)$_3$CN |
| F.23 | CH$_3$ | CH$_3$ | (CH$_2$)$_4$CN |
| F.24 | CH$_3$ | CH$_3$ | (CH$_2$)$_6$CN |
| F.25 | CH$_3$ | CH$_3$ | cyclohexylmethyl |
| F.26 | CH$_3$ | CH$_3$ | 2-cyclohexyleth-1-yl |
| F.27 | CH$_3$ | CH$_3$ | cyclopropylmethyl |
| F.28 | CH$_3$ | CH$_3$ | 2-cyclopropyleth-1-yl |
| F.29 | CH$_3$ | CH$_3$ | 2-methoxyeth-1-yl |
| F.30 | CH$_3$ | CH$_3$ | 2-ethoxyeth-1-yl |
| F.31 | CH$_3$ | CH$_3$ | 2-isopropoxyeth-1-yl |
| F.32 | CH$_3$ | CH$_3$ | 3-methoxyprop-1-yl |
| F.33 | CH$_3$ | CH$_3$ | 3-ethoxyprop-1-yl |
| F.34 | CH$_3$ | CH$_3$ | 3-isopropoxyprop-1-yl |
| F.35 | CH$_3$ | CH$_3$ | 4-methoxybut-1-yl |
| F.36 | CH$_3$ | CH$_3$ | 4-isopropoxybut-1-yl |
| F.37 | CH$_3$ | CH$_3$ | propen-3-yl |
| F.38 | CH$_3$ | CH$_3$ | but-2-en-1-yl |
| F.39 | CH$_3$ | CH$_3$ | 3-methylbut-2-en-1-yl |
| F.40 | CH$_3$ | CH$_3$ | 2-vinyloxyeth-1-yl |
| F.41 | CH$_3$ | CH$_3$ | allyloxyeth-1-yl |
| F.42 | CH$_3$ | CH$_3$ | 2-trifluoromethoxyeth-1-yl |
| F.43 | CH$_3$ | CH$_3$ | 3-trifluoromethoxyprop-1-yl |
| F.44 | CH$_3$ | CH$_3$ | 4-difluoromethoxybut-1-yl |
| F.45 | CH$_3$ | CH$_3$ | hydroxycarbonylmethyl |
| F.46 | CH$_3$ | CH$_3$ | methoxycarbonylmethyl |
| F.47 | CH$_3$ | CH$_3$ | aminocarbonylmethyl |
| F.48 | CH$_3$ | CH$_3$ | N-methylaminocarbonylmethyl |
| F.49 | CH$_3$ | CH$_3$ | N,N-dimethylaminocarbonylmethyl |
| F.50 | CH$_3$ | CH$_3$ | 2-hydroxycarbonyleth-1-yl |
| F.51 | CH$_3$ | CH$_3$ | 2-methoxycarbonyleth-1-yl |
| F.52 | CH$_3$ | CH$_3$ | 2-aminocarbonyleth-1-yl |
| F.53 | CH$_3$ | CH$_3$ | 2-N-methylaminocarbonyleth-1-yl |
| F.54 | CH$_3$ | CH$_3$ | 2-dimethylaminocarbonyleth-1-yl |
| F.55 | CH$_3$ | CH$_3$ | 2-aminoeth-1-yl |
| F.56 | CH$_3$ | CH$_3$ | 2-aminoprop-1-yl |
| F.57 | CH$_3$ | CH$_3$ | 4-aminobut-1-yl |
| F.58 | CH$_3$ | CH$_3$ | 3-dimethylaminoprop-1-yl |
| F.59 | CH$_3$ | CH$_3$ | 4-aminothiocarbonylbut-1-yl |
| F.60 | CH$_3$ | CH$_3$ | 2-oxopropyl |
| F.61 | CH$_3$ | CH$_3$ | cyclohexyl |
| F.62 | CH$_3$ | CH$_3$ | cyclopropyl |
| F.63 | CH$_3$ | CH$_3$ | cyclopentyl |
| F.64 | CH$_3$ | CH$_3$ | 2-methoxyiminoprop-1-yl |
| F.65 | CH$_3$ | CH$_3$ | 2-methoxyiminoeth-1-yl |
| F.66 | CH$_3$ | CH$_3$ | 6-aminocarbonylhex-1-yl |
| F.67 | CH$_3$ | CH$_3$ | 3-aminothiocarbonylprop-1-yl |
| F.68 | CH$_3$ | CH$_3$ | 2-aminothiocarbonyleth-1-yl |
| F.69 | CH$_3$ | CH$_3$ | aminothiocarbonylmethyl |
| F.70 | CH$_3$ | CH$_3$ | 4-(N,N-dimethylamino)but-1-yl |
| F.71 | CH$_3$ | CH$_3$ | 2-(methylthio)eth-1-yl |
| F.72 | CH$_3$ | CH$_3$ | 2-(methylsulfonyl)eth-1-yl |
| F.73 | CH$_3$ | CH$_3$ | 4-(methylthio)prop-1-yl |
| F.74 | CH$_3$ | CH$_3$ | 4-(methylsulfonyl)prop-1-yl |
| F.75 | CH$_3$ | CH$_3$ | benzyl |
| F.76 | CH$_3$ | CH$_3$ | 2-F—C$_6$H$_4$—CH$_2$ |
| F.77 | CH$_3$ | CH$_3$ | 3-F—C$_6$H$_4$—CH$_2$ |

TABLE F-continued

| No. | $R^d$ | $R^\alpha$ | $R^\beta$ |
|---|---|---|---|
| F.78 | $CH_3$ | $CH_3$ | 4-F—$C_6H_4$—$CH_2$ |
| F.79 | $CH_3$ | $CH_3$ | 2,3-$F_2$—$C_6H_3$—$CH_2$ |
| F.80 | $CH_3$ | $CH_3$ | 2,4-$F_2$—$C_6H_3$—$CH_2$ |
| F.81 | $CH_3$ | $CH_3$ | 2,5-$F_2$—$C_6H_3$—$CH_2$ |
| F.82 | $CH_3$ | $CH_3$ | 2,6-$F_2$—$C_6H_3$—$CH_2$ |
| F.83 | $CH_3$ | $CH_3$ | 3,4-$F_2$—$C_6H_3$—$CH_2$ |
| F.84 | $CH_3$ | $CH_3$ | 3,5-$F_2$—$C_6H_3$—$CH_2$ |
| F.85 | $CH_3$ | $CH_3$ | 2-Cl—$C_6H_4$—$CH_2$ |
| F.86 | $CH_3$ | $CH_3$ | 3-Cl—$C_6H_4$—$CH_2$ |
| F.87 | $CH_3$ | $CH_3$ | 4-Cl—$C_6H_4$—$CH_2$ |
| F.88 | $CH_3$ | $CH_3$ | 2,3-$Cl_2$—$C_6H_3$—$CH_2$ |
| F.89 | $CH_3$ | $CH_3$ | 2,4-$Cl_2$—$C_6H_3$—$CH_2$ |
| F.90 | $CH_3$ | $CH_3$ | 2,5-$Cl_2$—$C_6H_3$—$CH_2$ |
| F.91 | $CH_3$ | $CH_3$ | 2,6-$Cl_2$—$C_6H_3$—$CH_2$ |
| F.92 | $CH_3$ | $CH_3$ | 3,4-$Cl_2$—$C_6H_3$—$CH_2$ |
| F.93 | $CH_3$ | $CH_3$ | 3,5-$Cl_2$—$C_6H_3$—$CH_2$ |
| F.94 | $CH_3$ | $CH_3$ | 2,3,4-$Cl_3$—$C_6H_2$—$CH_2$ |
| F.95 | $CH_3$ | $CH_3$ | 2,3,5-$Cl_3$—$C_6H_2$—$CH_2$ |
| F.96 | $CH_3$ | $CH_3$ | 2,3,6-$Cl_3$—$C_6H_2$—$CH_2$ |
| F.97 | $CH_3$ | $CH_3$ | 2,4,5-$Cl_3$—$C_6H_2$—$CH_2$ |
| F.98 | $CH_3$ | $CH_3$ | 2,4,6-$Cl_3$—$C_6H_2$—$CH_2$ |
| F.99 | $CH_3$ | $CH_3$ | 3,4,5-$Cl_3$—$C_6H_2$—$CH_2$ |
| F.100 | $CH_3$ | $CH_3$ | 2-Br—$C_6H_4$—$CH_2$ |
| F.101 | $CH_3$ | $CH_3$ | 3-Br—$C_6H_4$—$CH_2$ |
| F.102 | $CH_3$ | $CH_3$ | 4-Br—$C_6H_4$—$CH_2$ |
| F.103 | $CH_3$ | $CH_3$ | 2,3-$Br_2$—$C_6H_3$—$CH_2$ |
| F.104 | $CH_3$ | $CH_3$ | 2,4-$Br_2$—$C_6H_3$—$CH_2$ |
| F.105 | $CH_3$ | $CH_3$ | 2,5-$Br_2$—$C_6H_3$—$CH_2$ |
| F.106 | $CH_3$ | $CH_3$ | 2,6-$Br_2$—$C_6H_3$—$CH_2$ |
| F.107 | $CH_3$ | $CH_3$ | 3,4-$Br_2$—$C_6H_3$—$CH_2$ |
| F.108 | $CH_3$ | $CH_3$ | 3,5-$Br_2$—$C_6H_3$—$CH_2$ |
| F.109 | $CH_3$ | $CH_3$ | 2-F, 3-Cl—$C_6H_3$—$CH_2$ |
| F.110 | $CH_3$ | $CH_3$ | 2-F, 4-Cl—$C_6H_3$—$CH_2$ |
| F.111 | $CH_3$ | $CH_3$ | 2-F, 5-Cl—$C_6H_3$—$CH_2$ |
| F.112 | $CH_3$ | $CH_3$ | 2-F, 3-Br—$C_6H_3$—$CH_2$ |
| F.113 | $CH_3$ | $CH_3$ | 2-F, 4-Br—$C_6H_3$—$CH_2$ |
| F.114 | $CH_3$ | $CH_3$ | 2-F, 5-Br—$C_6H_3$—$CH_2$ |
| F.115 | $CH_3$ | $CH_3$ | 2-Cl, 3-Br—$C_6H_3$—$CH_2$ |
| F.116 | $CH_3$ | $CH_3$ | 2-Cl, 4-Br—$C_6H_3$—$CH_2$ |
| F.117 | $CH_3$ | $CH_3$ | 2-Cl, 5-Br—$C_6H_3$—$CH_2$ |
| F.118 | $CH_3$ | $CH_3$ | 3-F, 4-Cl—$C_6H_3$—$CH_2$ |
| F.119 | $CH_3$ | $CH_3$ | 3-F, 5-Cl—$C_6H_3$—$CH_2$ |
| F.120 | $CH_3$ | $CH_3$ | 3-F, 6-Cl—$C_6H_3$—$CH_2$ |
| F.121 | $CH_3$ | $CH_3$ | 3-F, 4-Br—$C_6H_3$—$CH_2$ |
| F.122 | $CH_3$ | $CH_3$ | 3-F, 5-Br—$C_6H_3$—$CH_2$ |
| F.123 | $CH_3$ | $CH_3$ | 3-F, 6-Br—$C_6H_3$—$CH_2$ |
| F.124 | $CH_3$ | $CH_3$ | 3-Cl, 4-Br—$C_6H_3$—$CH_2$ |
| F.125 | $CH_3$ | $CH_3$ | 3-Cl, 5-Br—$C_6H_3$—$CH_2$ |
| F.126 | $CH_3$ | $CH_3$ | 3-Cl, 6-Br—$C_6H_3$—$CH_2$ |
| F.127 | $CH_3$ | $CH_3$ | 4-F, 5-Cl—$C_6H_3$—$CH_2$ |
| F.128 | $CH_3$ | $CH_3$ | 4-F, 6-Cl—$C_6H_3$—$CH_2$ |
| F.129 | $CH_3$ | $CH_3$ | 4-F, 5-Br—$C_6H_3$—$CH_2$ |
| F.130 | $CH_3$ | $CH_3$ | 4-F, 6-Br—$C_6H_3$—$CH_2$ |
| F.131 | $CH_3$ | $CH_3$ | 4-Cl, 5-Br—$C_6H_3$—$CH_2$ |
| F.132 | $CH_3$ | $CH_3$ | 5-F, 6-Cl—$C_6H_3$—$CH_2$ |
| F.133 | $CH_3$ | $CH_3$ | 5-F, 6-Br—$C_6H_3$—$CH_2$ |
| F.134 | $CH_3$ | $CH_3$ | 5-Cl, 6-Br—$C_6H_3$—$CH_2$ |
| F.135 | $CH_3$ | $CH_3$ | 3-Br, 4-Cl, 5-Br—$C_6H_2$—$CH_2$ |
| F.136 | $CH_3$ | $CH_3$ | 2-CN—$C_6H_4$—$CH_2$ |
| F.137 | $CH_3$ | $CH_3$ | 3-CN—$C_6H_4$—$CH_2$ |
| F.138 | $CH_3$ | $CH_3$ | 4-CN—$C_6H_4$—$CH_2$ |
| F.139 | $CH_3$ | $CH_3$ | 2-$NO_2$—$C_6H_4$—$CH_2$ |
| F.140 | $CH_3$ | $CH_3$ | 3-$NO_2$—$C_6H_4$—$CH_2$ |
| F.141 | $CH_3$ | $CH_3$ | 4-$NO_2$—$C_6H_4$—$CH_2$ |
| F.142 | $CH_3$ | $CH_3$ | 2-$CH_3$—$C_6H_4$—$CH_2$ |
| F.143 | $CH_3$ | $CH_3$ | 3-$CH_3$—$C_6H_4$—$CH_2$ |
| F.144 | $CH_3$ | $CH_3$ | 4-$CH_3$—$C_6H_4$—$CH_2$ |
| F.145 | $CH_3$ | $CH_3$ | 2,3-$(CH_3)_2$—$C_6H_3$—$CH_2$ |
| F.146 | $CH_3$ | $CH_3$ | 2,4-$(CH_3)_2$—$C_6H_3$—$CH_2$ |
| F.147 | $CH_3$ | $CH_3$ | 2,5-$(CH_3)_2$—$C_6H_3$—$CH_2$ |
| F.148 | $CH_3$ | $CH_3$ | 2,6-$(CH_3)_2$—$C_6H_3$—$CH_2$ |
| F.149 | $CH_3$ | $CH_3$ | 3,4-$(CH_3)_2$—$C_6H_3$—$CH_2$ |
| F.150 | $CH_3$ | $CH_3$ | 3,5-$(CH_3)_2$—$C_6H_3$—$CH_2$ |
| F.151 | $CH_3$ | $CH_3$ | 2-$C_2H_5$—$C_6H_4$—$CH_2$ |
| F.152 | $CH_3$ | $CH_3$ | 3-$C_2H_5$—$C_6H_4$—$CH_2$ |
| F.153 | $CH_3$ | $CH_3$ | 4-$C_2H_5$—$C_6H_4$—$CH_2$ |
| F.154 | $CH_3$ | $CH_3$ | 2-1-$C_3H_7$—$C_6H_4$—$CH_2$ |

TABLE F-continued

| No. | $R^d$ | $R^\alpha$ | $R^\beta$ |
|---|---|---|---|
| F.155 | $CH_3$ | $CH_3$ | 3-1-$C_3H_7$—$C_6H_4$—$CH_2$ |
| F.156 | $CH_3$ | $CH_3$ | 4-1-$C_3H_7$—$C_6H_4$—$CH_2$ |
| F.157 | $CH_3$ | $CH_3$ | 2-cyclohexyl-$C_6H_4$—$CH_2$ |
| F.158 | $CH_3$ | $CH_3$ | 3-cyclohexyl-$C_6H_4$—$CH_2$ |
| F.159 | $CH_3$ | $CH_3$ | 4-cyclohexyl-$C_6H_4$—$CH_2$ |
| F.160 | $CH_3$ | $CH_3$ | 2-vinyl-$C_6H_4$—$CH_2$ |
| F.161 | $CH_3$ | $CH_3$ | 3-vinyl-$C_6H_4$—$CH_2$ |
| F.162 | $CH_3$ | $CH_3$ | 4-vinyl-$C_6H_4$—$CH_2$ |
| F.163 | $CH_3$ | $CH_3$ | 2-allyl-$C_6H_4$—$CH_2$ |
| F.164 | $CH_3$ | $CH_3$ | 3-allyl-$C_6H_4$—$CH_2$ |
| F.165 | $CH_3$ | $CH_3$ | 4-allyl-$C_6H_4$—$CH_2$ |
| F.166 | $CH_3$ | $CH_3$ | 2-$C_6H_5$—$C_6H_4$—$CH_2$ |
| F.167 | $CH_3$ | $CH_3$ | 3-$C_6H_5$—$C_6H_4$—$CH_2$ |
| F.168 | $CH_3$ | $CH_3$ | 4-$C_6H_5$—$C_6H_4$—$CH_2$ |
| F.169 | $CH_3$ | $CH_3$ | 3-$CH_3$, 5-t-$C_4H_9$—$C_6H_3$—$CH_2$ |
| F.170 | $CH_3$ | $CH_3$ | 2-OH—$C_6H_4$—$CH_2$ |
| F.171 | $CH_3$ | $CH_3$ | 3-OH—$C_6H_4$—$CH_2$ |
| F.172 | $CH_3$ | $CH_3$ | 4-OH—$C_6H_4$—$CH_2$ |
| F.173 | $CH_3$ | $CH_3$ | 2-$OCH_3$—$C_6H_4$—$CH_2$ |
| F.174 | $CH_3$ | $CH_3$ | 3-$OCH_3$—$C_6H_4$—$CH_2$ |
| F.175 | $CH_3$ | $CH_3$ | 4-$OCH_3$—$C_6H_4$—$CH_2$ |
| F.176 | $CH_3$ | $CH_3$ | 2,3-$(OCH_3)_2$—$C_6H_3$—$CH_2$ |
| F.177 | $CH_3$ | $CH_3$ | 2,4-$(OCH_3)_2$—$C_6H_3$—$CH_2$ |
| F.178 | $CH_3$ | $CH_3$ | 2,5-$(OCH_3)_2$—$C_6H_3$—$CH_2$ |
| F.179 | $CH_3$ | $CH_3$ | 3,4-$(OCH_3)_2$—$C_6H_3$—$CH_2$ |
| F.180 | $CH_3$ | $CH_3$ | 3,5-$(OCH_3)_2$—$C_6H_3$—$CH_2$ |
| F.181 | $CH_3$ | $CH_3$ | 3,4,5-$(OCH_3)_3$—$C_6H_2$—$CH_2$ |
| F.182 | $CH_3$ | $CH_3$ | 2-$OC_2H_5$—$C_6H_4$—$CH_2$ |
| F.183 | $CH_3$ | $CH_3$ | 3-$OC_2H_5$—$C_6H_4$—$CH_2$ |
| F.184 | $CH_3$ | $CH_3$ | 4-$OC_2H_5$—$C_6H_4$—$CH_2$ |
| F.185 | $CH_3$ | $CH_3$ | 2-O-(n-$C_3H_7$)—$C_6H_4$—$CH_2$ |
| F.186 | $CH_3$ | $CH_3$ | 3-O-(n-$C_3H_7$)—$C_6H_4$—$CH_2$ |
| F.187 | $CH_3$ | $CH_3$ | 4-O-(n-$C_3H_7$)—$C_6H_4$—$CH_2$ |
| F.188 | $CH_3$ | $CH_3$ | 2-O-(i-$C_3H_7$)—$C_6H_4$—$CH_2$ |
| F.189 | $CH_3$ | $CH_3$ | 3-O-(i-$C_3H_7$)—$C_6H_4$—$CH_2$ |
| F.190 | $CH_3$ | $CH_3$ | 4-O-(i-$C_3H_7$)—$C_6H_4$—$CH_2$ |
| F.191 | $CH_3$ | $CH_3$ | 4-O-(n-$C_4H_9$)—$C_6H_4$—$CH_2$ |
| F.192 | $CH_3$ | $CH_3$ | 3-O-(t-$C_4H_9$)—$C_6H_4$—$CH_2$ |
| F.193 | $CH_3$ | $CH_3$ | 4-O-(n-$C_6H_{13}$)—$C_6H_4$—$CH_2$ |
| F.194 | $CH_3$ | $CH_3$ | 2-O-allyl-$C_6H_4$—$CH_2$ |
| F.195 | $CH_3$ | $CH_3$ | 3-O-allyl-$C_6H_4$—$CH_2$ |
| F.196 | $CH_3$ | $CH_3$ | 4-O-allyl-$C_6H_4$—$CH_2$ |
| F.197 | $CH_3$ | $CH_3$ | 2-$CF_3$—$C_6H_4$—$CH_2$ |
| F.198 | $CH_3$ | $CH_3$ | 3-$CF_3$—$C_6H_4$—$CH_2$ |
| F.199 | $CH_3$ | $CH_3$ | 4-$CF_3$—$C_6H_4$—$CH_2$ |
| F.200 | $CH_3$ | $CH_3$ | 2-acetyl-$C_6H_4$—$CH_2$ |
| F.201 | $CH_3$ | $CH_3$ | 3-acetyl-$C_6H_4$—$CH_2$ |
| F.202 | $CH_3$ | $CH_3$ | 4-acetyl-$C_6H_4$—$CH_2$ |
| F.203 | $CH_3$ | $CH_3$ | 2-methoxycarbonyl-$C_6H_4$—$CH_2$ |
| F.204 | $CH_3$ | $CH_3$ | 3-methoxycarbonyl-$C_6H_4$—$CH_2$ |
| F.205 | $CH_3$ | $CH_3$ | 4-methoxycarbonyl-$C_6H_4$—$CH_2$ |
| F.206 | $CH_3$ | $CH_3$ | 2-aminocarbonyl-$C_6H_4$—$CH_2$ |
| F.207 | $CH_3$ | $CH_3$ | 3-aminocarbonyl-$C_6H_4$—$CH_2$ |
| F.208 | $CH_3$ | $CH_3$ | 4-aminocarbonyl-$C_6H_4$—$CH_2$ |
| F.209 | $CH_3$ | $CH_3$ | 2-dimethylaminocarbonyl-$C_6H_4$—$CH_2$ |
| F.210 | $CH_3$ | $CH_3$ | 3-dimethylaminocarbonyl-$C_6H_4$—$CH_2$ |
| F.211 | $CH_3$ | $CH_3$ | 4-dimethylaminocarbonyl-$C_6H_4$—$CH_2$ |
| F.212 | $CH_3$ | $CH_3$ | 2-(N-methylaminocarbonyl)-$C_6H_4$—$CH_2$ |
| F.213 | $CH_3$ | $CH_3$ | 3-(N-methylaminocarbonyl)-$C_6H_4$—$CH_2$ |
| F.214 | $CH_3$ | $CH_3$ | 4-(N-methylaminocarbonyl)-$C_6H_4$—$CH_2$ |
| F.215 | $CH_3$ | $CH_3$ | 2-$H_2N$—$C_6H_4$—$CH_2$ |
| F.216 | $CH_3$ | $CH_3$ | 3-$H_2N$—$C_6H_4$—$CH_2$ |
| F.217 | $CH_3$ | $CH_3$ | 4-$H_2N$—$C_6H_4$—$CH_2$ |
| F.218 | $CH_3$ | $CH_3$ | 2-aminothiocarbonyl-$C_6H_4$—$CH_2$ |
| F.219 | $CH_3$ | $CH_3$ | 3-aminothiocarbonyl-$C_6H_4$—$CH_2$ |
| F.220 | $CH_3$ | $CH_3$ | 4-aminothiocarbonyl-$C_6H_4$—$CH_2$ |
| F.221 | $CH_3$ | $CH_3$ | 2-methoxyiminomethyl-$C_6H_4$—$CH_2$ |
| F.222 | $CH_3$ | $CH_3$ | 3-methoxyiminomethyl-$C_6H_4$—$CH_2$ |
| F.223 | $CH_3$ | $CH_3$ | 4-methoxyiminomethyl-$C_6H_4$—$CH_2$ |
| F.224 | $CH_3$ | $CH_3$ | 2-formyl-$C_6H_4$—$CH_2$ |
| F.225 | $CH_3$ | $CH_3$ | 3-formyl-$C_6H_4$—$CH_2$ |
| F.226 | $CH_3$ | $CH_3$ | 4-formyl-$C_6H_4$—$CH_2$ |
| F.227 | $CH_3$ | $CH_3$ | 2-(1'-methoxyiminoeth-1'-yl)-$C_6H_4$—$CH_2$ |
| F.228 | $CH_3$ | $CH_3$ | 3-(1'-methoxyiminoeth-1'-yl)-$C_6H_4$—$CH_2$ |
| F.229 | $CH_3$ | $CH_3$ | 4-(1'-methoxyiminoeth-1'-yl)-$C_6H_4$—$CH_2$ |
| F.230 | $CH_3$ | $CH_3$ | 2-$SCH_3$—$C_6H_4$—$CH_2$ |
| F.231 | $CH_3$ | $CH_3$ | 3-$SCH_3$—$C_6H_4$—$CH_2$ |

TABLE F-continued

| No. | $R^d$ | $R^\alpha$ | $R^\beta$ |
|---|---|---|---|
| F.232 | CH₃ | CH₃ | 4-SCH₃—C₆H₄—CH₂ |
| F.233 | CH₃ | CH₃ | 2-SO₂CH₃—C₆H₄—CH₂ |
| F.234 | CH₃ | CH₃ | 3-SO₂CH₃—C₆H₄—CH₂ |
| F.235 | CH₃ | CH₃ | 4-SO₂CH₃—C₆H₄—CH₂ |
| F.236 | CH₃ | CH₃ | 2-OCF₃—C₆H₄—CH₂ |
| F.237 | CH₃ | CH₃ | 3-OCF₃—C₆H₄—CH₂ |
| F.238 | CH₃ | CH₃ | 4-OCF₃—C₆H₄—CH₂ |
| F.239 | CH₃ | CH₃ | 2-OCHF₂—C₆H₄—CH₂ |
| F.240 | CH₃ | CH₃ | 3-OCHF₂—C₆H₄—CH₂ |
| F.241 | CH₃ | CH₃ | 4-OCHF₂—C₆H₄—CH₂ |
| F.242 | CH₃ | CH₃ | 3-CF₃, 4-OCF₃—C₆H₃—CH₂ |
| F.243 | CH₃ | CH₃ | 1-naphthyl-CH₂ |
| F.244 | CH₃ | CH₃ | 2-naphthyl-CH₂ |
| F.245 | CH₃ | CH₃ | 2-phenoxyeth-1-yl |
| F.246 | CH₃ | CH₃ | 2-(2'-chlorophenoxy)eth-1-yl |
| F.247 | CH₃ | CH₃ | 2-(3'-chlorophenoxy)eth-1-yl |
| F.248 | CH₃ | CH₃ | 2-(4'-chlorophenoxy)eth-1-yl |
| F.249 | CH₃ | CH₃ | 2-(3',5'-dichlorophenoxy)eth-1-yl |
| F.250 | CH₃ | CH₃ | 2-(2'-cyanophenoxy)eth-1-yl |
| F.251 | CH₃ | CH₃ | 2-(3'-cyanophenoxy)eth-1-yl |
| F.252 | CH₃ | CH₃ | 2-(4'-cyanophenoxy)eth-1-yl |
| F.253 | CH₃ | CH₃ | 2-(2'-methylphenoxy)eth-1-yl |
| F.254 | CH₃ | CH₃ | 2-(3'-methylphenoxy)eth-1-yl |
| F.255 | CH₃ | CH₃ | 2-(4'-methylphenoxy)eth-1-yl |
| F.256 | CH₃ | CH₃ | 2-(3'-t-butylphenoxy)eth-1-yl |
| F.257 | CH₃ | CH₃ | 2-(4'-t-butylphenoxy)eth-1-yl |
| F.258 | CH₃ | CH₃ | 2-(2'-nitrophenoxy)eth-1-yl |
| F.259 | CH₃ | CH₃ | 2-(3'-nitrophenoxy)eth-1-yl |
| F.260 | CH₃ | CH₃ | 2-(4'-nitrophenoxy)eth-1-yl |
| F.261 | CH₃ | CH₃ | 2-(2'-methoxyphenoxy)eth-1-yl |
| F.262 | CH₃ | CH₃ | 2-(3'-methoxyphenoxy)eth-1-yl |
| F.263 | CH₃ | CH₃ | 2-(4'-methoxyphenoxy)eth-1-yl |
| F.264 | CH₃ | CH₃ | 2-(2'-trifluoromethylphenoxy)eth-1-yl |
| F.265 | CH₃ | CH₃ | 2-(3'-trifluoromethylphenoxy)eth-1-yl |
| F.266 | CH₃ | CH₃ | 2-(4'-trifluoromethylphenoxy)eth-1-yl |
| F.267 | CH₃ | CH₃ | 2-(2'-acetylphenoxy)eth-1-yl |
| F.268 | CH₃ | CH₃ | 2-(3'-acetylphenoxy)eth-1-yl |
| F.269 | CH₃ | CH₃ | 2-(4'-acetylphenoxy)eth-1-yl |
| F.270 | CH₃ | CH₃ | 2-(2'-methoxycarbonyl)eth-1-yl |
| F.271 | CH₃ | CH₃ | 2-(3'-methoxycarbonyl)eth-1-yl |
| F.272 | CH₃ | CH₃ | 2-(4'-methoxycarbonyl)eth-1-yl |
| F.273 | CH₃ | CH₃ | 2-(2'-dimethylaminocarbonyl)eth-1-yl |
| F.274 | CH₃ | CH₃ | 2-(3'-dimethylaminocarbonyl)eth-1-yl |
| F.275 | CH₃ | CH₃ | 2-(4'-dimethylaminocarbonyl)eth-1-yl |
| F.276 | CH₃ | CH₃ | 2-(2'-aminothiocarbonyl)eth-1-yl |
| F.277 | CH₃ | CH₃ | 2-(3'-aminothiocarbonyl)eth-1-yl |
| F.278 | CH₃ | CH₃ | 2-(4'-aminothiocarbonyl)eth-1-yl |
| F.279 | CH₃ | CH₃ | 2-(2'-methylsulfonyl)eth-1-yl |
| F.280 | CH₃ | CH₃ | 2-(3'-methylsulfonyl)eth-1-yl |
| F.281 | CH₃ | CH₃ | 2-(4'-methylsulfonyl)eth-1-yl |
| F.282 | CH₃ | CH₃ | 3-phenoxyprop-1-yl |
| F.283 | CH₃ | CH₃ | 3-(2'-chlorophenoxy)prop-1-yl |
| F.284 | CH₃ | CH₃ | 3-(3'-chlorophenoxy)prop-1-yl |
| F.285 | CH₃ | CH₃ | 3-(4'-chlorophenoxy)prop-1-yl |
| F.286 | CH₃ | CH₃ | 3-(3',5'-dichlorophenoxy)prop-1-yl |
| F.287 | CH₃ | CH₃ | 3-(2'-cyanophenoxy)prop-1-yl |
| F.288 | CH₃ | CH₃ | 3-(3'-cyanophenoxy)prop-1-yl |
| F.289 | CH₃ | CH₃ | 3-(4'-cyanophenoxy)prop-1-yl |
| F.290 | CH₃ | CH₃ | 3-(2'-methylphenoxy)prop-1-yl |
| F.291 | CH₃ | CH₃ | 3-(3'-methylphenoxy)prop-1-yl |
| F.292 | CH₃ | CH₃ | 3-(4'-methylphenoxy)prop-1-yl |
| F.293 | CH₃ | CH₃ | 3-(2'-methoxyphenoxy)prop-1-yl |
| F.294 | CH₃ | CH₃ | 3-(3'-methoxyphenoxy)prop-1-yl |
| F.295 | CH₃ | CH₃ | 3-(4'-methoxyphenoxy)prop-1-yl |
| F.296 | CH₃ | CH₃ | 3-(2'-trifluoromethylphenoxy)prop-1-yl |
| F.297 | CH₃ | CH₃ | 3-(3'-trifluoromethylphenoxy)prop-1-yl |
| F.298 | CH₃ | CH₃ | 3-(4'-trifluoromethylphenoxy)prop-1-yl |
| F.299 | CH₃ | CH₃ | 4-phenoxybut-1-yl |
| F.300 | CH₃ | CH₃ | 2-phenyleth-1-yl |
| F.301 | CH₃ | CH₃ | 2-(2'-chlorophenyl)eth-1-yl |
| F.302 | CH₃ | CH₃ | 2-(3'-chlorophenyl)eth-l-yl |
| F.303 | CH₃ | CH₃ | 2-(4'-chlorophenyl)eth-l-yl |
| F.304 | CH₃ | CH₃ | 2-(3',5'-dichlorophenyl)eth-l-yl |
| F.305 | CH₃ | CH₃ | 2-(2'-cyanophenyl)eth-1-yl |
| F.306 | CH₃ | CH₃ | 2-(3'-cyanophenyl)eth-1-yl |
| F.307 | CH₃ | CH₃ | 2-(4'-cyanophenyl)eth-l-yl |
| F.308 | CH₃ | CH₃ | 2-(2'-methylphenyl)eth-l-yl |

TABLE F-continued

| No. | R^d | R^α | R^β |
|---|---|---|---|
| F.309 | CH₃ | CH₃ | 2-(3'-methylphenyl)eth-1-yl |
| F.310 | CH₃ | CH₃ | 2-(4'-methylphenyl)eth-1-yl |
| F.311 | CH₃ | CH₃ | 2-(2'-methoxyphenyl)eth-1-yl |
| F.312 | CH₃ | CH₃ | 2-(3'-methoxyphenyl)eth-1-yl |
| F.313 | CH₃ | CH₃ | 2-(4'-methoxyphenyl)eth-1-yl |
| F.314 | CH₃ | CH₃ | 2-(2'-trifluoromethylphenyl)eth-1-yl |
| F.315 | CH₃ | CH₃ | 2-(3'-trifluoromethylphenyl)eth-1-yl |
| F.316 | CH₃ | CH₃ | 2-(4'-trifluoromethylphenyl)eth-1-yl |
| F.317 | CH₃ | CH₃ | 3-phenylprop-1-yl |
| F.318 | CH₃ | CH₃ | 3-(2'-chlorophenyl)prop-1-yl |
| F.319 | CH₃ | CH₃ | 3-(3'-chlorophenyl)prop-1-yl |
| F.320 | CH₃ | CH₃ | 3-(4'-chlorophenyl)prop-1-yl |
| F.321 | CH₃ | CH₃ | 3-(2'-cyanophenyl)prop-1-yl |
| F.322 | CH₃ | CH₃ | 3-(3'-cyanophenyl)prop-1-yl |
| F.323 | CH₃ | CH₃ | 3-(4'-cyanophenyl)prop-1-yl |
| F.324 | CH₃ | CH₃ | 3-(2'-trifluoromethylphenyl)prop-1-yl |
| F.325 | CH₃ | CH₃ | 4-phenylbut-1-yl |
| F.326 | CH₃ | CH₃ | 4-(4'-chlorophenyl)but-1-yl |
| F.327 | CH₃ | CH₃ | 6-(4'-chlorophenyl)hex-1-yl |
| F.328 | CH₃ | CH₃ | 2-pyridylmethyl |
| F.329 | CH₃ | CH₃ | 3-pyridylmethyl |
| F.330 | CH₃ | CH₃ | 4-pyridylmethyl |
| F.331 | CH₃ | CH₃ | 4-chloropyridin-2-ylmethyl |
| F.332 | CH₃ | CH₃ | 5-chloropyridin-2-ylmethyl |
| F.333 | CH₃ | CH₃ | 6-chloropyridin-2-ylmethyl |
| F.334 | CH₃ | CH₃ | 5-chloropyridin-3-ylmethyl |
| F.335 | CH₃ | CH₃ | 6-chloropyridin-3-ylmethyl |
| F.336 | CH₃ | CH₃ | 2-chloropyridin-4-ylmethyl |
| F.337 | CH₃ | CH₃ | 2-pyrimidinylmethyl |
| F.338 | CH₃ | CH₃ | 4-chloropyrimidin-2-ylmethyl |
| F.339 | CH₃ | CH₃ | 5-chloropyrimidin-2-ylmethyl |
| F.340 | CH₃ | CH₃ | 2-chloropyrimidin-4-ylmethyl |
| F.341 | CH₃ | CH₃ | 6-chloropyrimidin-4-ylmethyl |
| F.342 | CH₃ | CH₃ | 2-chloropyrimidin-5-ylmethyl |
| F.343 | CH₃ | CH₃ | 4-pyridazinylmethyl |
| F.344 | CH₃ | CH₃ | 2-pyrazinylmethyl |
| F.345 | CH₃ | CH₃ | 5-chloropyrazin-2-ylmethyl |
| F.346 | CH₃ | CH₃ | 6-chloropyrazin-2-ylmethyl |
| F.347 | CH₃ | CH₃ | 3-pyridazinylmethyl |
| F.348 | CH₃ | CH₃ | 6-chloropyridazin-3-ylmethyl |
| F.349 | CH₃ | CH₃ | 1,3,5-triazinylmethyl |
| F.350 | CH₃ | CH₃ | 2-furylmethyl |
| F.351 | CH₃ | CH₃ | 3-furylmethyl |
| F.352 | CH₃ | CH₃ | 4-bromofur-2-ylmethyl |
| F.353 | CH₃ | CH₃ | 5-chlorofur-2-ylmethyl |
| F.354 | CH₃ | CH₃ | 2-thienylmethyl |
| F.355 | CH₃ | CH₃ | 3-thienylmethyl |
| F.356 | CH₃ | CH₃ | 5-methylthien-3-ylmethyl |
| F.357 | CH₃ | CH₃ | 5-chlorothien-2-ylmethyl |
| F.358 | CH₃ | CH₃ | 2-chlorothien-4-ylmethyl |
| F.359 | CH₃ | CH₃ | 2-pyrrolylmethyl |
| F.360 | CR3 | CH₃ | 3-pyrrolylmethyl |
| F.361 | CH₃ | CH₃ | 2-oxazolylmethyl |
| F.362 | CH₃ | CH₃ | 4-methyloxazol-2-ylmethyl |
| F.363 | CH₃ | CH₃ | 5-methyloxazol-2-ylmethyl |
| F.364 | CH₃ | CH₃ | 4-chloro-oxazol-2-ylmethyl |
| F.365 | CH₃ | CH₃ | 5-chloro-oxazol-2-ylmethyl |
| F.366 | CH₃ | CH₃ | 4-oxazolylmethyl |
| F.367 | CH₃ | CH₃ | 2-methyloxazol-4-ylmethyl |
| F.368 | CH₃ | CH₃ | 5-methyloxazol-4-ylmethyl |
| F.369 | CH₃ | CH₃ | 2-chloro-oxazol-4-ylmethyl |
| F.370 | CH₃ | CH₃ | 5-chloro-oxazol-4-ylmethyl |
| F.371 | CH₃ | CH₃ | 5-oxazolylmethyl |
| F.372 | CH₃ | CH₃ | 2-methyloxazol-5-ylmethyl |
| F.373 | CH₃ | CH₃ | 4-methyloxazol-5-ylmethyl |
| F.374 | CH₃ | CH₃ | 2-chloro-oxazol-5-ylmethyl |
| F.375 | CH₃ | CH₃ | 4-chloro-oxazol-5-ylmethyl |
| F.376 | CH₃ | CH₃ | 2-thiazolylmethyl |
| F.377 | CH₃ | CH₃ | 4-methylthiazol-2-ylmethyl |
| F.378 | CH₃ | CH₃ | 5-methylthiazol-2-ylmethyl |
| F.379 | CH₃ | CH₃ | 4-chlorothiazol 2-ylmethyl |
| F.380 | CH₃ | CH₃ | 5-chlorothiazol-2-ylmethyl |
| F.381 | CH₃ | CH₃ | 4-thiazolylmethyl |
| F.382 | CH₃ | CH₃ | 2-methylthiazol-4-ylmethyl |
| F.383 | CH₃ | CH₃ | 5-methylthiazol-4-ylmethyl |
| F.384 | CH₃ | CH₃ | 2-chlorothiazol-4-ylmethyl |
| F.385 | CH₃ | CH₃ | 5-chlorothiazol-4-ylmethyl |

TABLE F-continued

| No. | R$^d$ | R$^\alpha$ | R$^\beta$ |
|---|---|---|---|
| F.386 | CH$_3$ | CH$_3$ | 5-thiazolylmethyl |
| F.387 | CH$_3$ | CH$_3$ | 2-methylthiazol-5-ylmethyl |
| F.388 | CH$_3$ | CH$_3$ | 4-methylthiazol-5-ylmethyl |
| F.389 | CH$_3$ | CH$_3$ | 2-chlorothiazol-5-ylmethyl |
| F.390 | CH$_3$ | CH$_3$ | 4-chlorothiazol-5-ylmethyl |
| F.391 | CH$_3$ | CH$_3$ | 3-isoxazolylmethyl |
| F.392 | CH$_3$ | CH$_3$ | 4-methylisoxazol-3-ylmethyl |
| F.393 | CH$_3$ | CH$_3$ | 5-methylisoxazol-3-ylmethyl |
| F.394 | CH$_3$ | CH$_3$ | 4-chloroisoxazol-3-ylmethyl |
| F.395 | CH$_3$ | CH$_3$ | 5-chloroisoxazol-3-ylmethyl |
| F.396 | CH$_3$ | CH$_3$ | 4-isoxazolylmethyl |
| F.397 | CH$_3$ | CH$_3$ | 3-methylisoxazol-4-ylmethyl |
| F.398 | CH$_3$ | CH$_3$ | 5-methylisoxazoi-4-ylmethyl |
| F.399 | CH$_3$ | CH$_3$ | 3-chloroisoxazol-4-ylmethyl |
| F.400 | CH$_3$ | CH$_3$ | 5-chloroisoxazol-4-ylmethyl |
| F.401 | CH$_3$ | CH$_3$ | 5-isoxazolylmethyl |
| F.402 | CH$_3$ | CH$_3$ | 3-methylisoxazol-5-ylmethyl |
| F.403 | CH$_3$ | CH$_3$ | 4-methylisoxazol-5-ylmethyl |
| F.404 | CH$_3$ | CH$_3$ | 3-chloroisoxazol-5-ylmethyl |
| F.405 | CH$_3$ | CH$_3$ | 4-chloroisoxazol-5-ylmethyl |
| F.406 | CH$_3$ | CH$_3$ | 3-isothiazolylmethyl |
| F.407 | CH$_3$ | CH$_3$ | 4-methylisothiazol-3-ylmethyl |
| F.408 | CH$_3$ | CH$_3$ | 5-methylisothiazol-3-ylmethyl |
| F.409 | CH$_3$ | CH$_3$ | 4-chloroisothiazol-3-ylmethyl |
| F.410 | CH$_3$ | CH$_3$ | 5-chloroisothiazol-3-ylmethyl |
| F.411 | CH$_3$ | CH$_3$ | 4-isothiazolylmethyl |
| F.412 | CH$_3$ | CH$_3$ | 3-methylisothiazol-4-ylmethyl |
| F.413 | CH$_3$ | CH$_3$ | 5-methylisothiazol-4-ylmethyl |
| F.414 | CH$_3$ | CH$_3$ | 3-chloroisothiazol-4-ylmethyl |
| F.415 | CH$_3$ | CH$_3$ | 5-chloroisothiazol-4-ylmethyl |
| F.416 | CH$_3$ | CH$_3$ | 5-isothiazolylmethyl |
| F.417 | CH$_3$ | CH$_3$ | 3-methylisothiazol-5-ylmethyl |
| F.418 | CH$_3$ | CH$_3$ | 4-methylisothiazol-5-ylmethyl |
| F.419 | CH$_3$ | CH$_3$ | 3-chloroisothiazol-5-ylmethyl |
| F.420 | CH$_3$ | CH$_3$ | 4-chloroisothiazol-5-ylmethyl |
| F.421 | CH$_3$ | CH$_3$ | 4-imidazolylmethyl |
| F.422 | CH$_3$ | CH$_3$ | 1-phenylpyrazol-3-ylmethyl |
| F.423 | CH$_3$ | CH$_3$ | 1-methylimidazol-4-ylmethyl |
| F.424 | CH$_3$ | CH$_3$ | 1-phenyl-1,2,4-triazol-3-ylmethyl |
| F.425 | CH$_3$ | CH$_3$ | 1,2,4-oxadiazol-3-ylmethyl |
| F.426 | CH$_3$ | CH$_3$ | 5-chloro-1,2,4-oxadiazol-3-ylmethyl |
| F.427 | CH$_3$ | CH$_3$ | 5-methyl-1,2,4-oxadiazol-3-ylmethyl |
| F.428 | CH$_3$ | CH$_3$ | 5-trifluoromethyl-1,2,4-oxadiazol-3-ylmethyl |
| F.429 | CH$_3$ | CH$_3$ | 1,3,4-oxadiazol-2-ylmethyl |
| F.430 | CH$_3$ | CH$_3$ | 5-chloro-1,3,4-oxadiazol-2-ylmethyl |
| F.431 | CH$_3$ | CH$_3$ | 5-methyl-1,3,4-oxadiazol-2-ylmethyl |
| F.432 | CH$_3$ | CH$_3$ | 5-methoxy-1,3,4-oxadiazol-2-ylmethyl |
| F.433 | CH$_3$ | CH$_3$ | 1,2,4-thiadiazol-3-ylmethyl |
| F.434 | CH$_3$ | CH$_3$ | 5-chloro-1,2,4-thiadiazol-3-ylmethyl |
| F.435 | CH$_3$ | CH$_3$ | 5-methyl-1,2,4-thiadiazol-3-ylmethyl |
| F.436 | CH$_3$ | CH$_3$ | 1,3,4-thiadiazol-2-ylmethyl |
| F.437 | CH$_3$ | CH$_3$ | 5-chloro-1,3,4-thiadiazol-2-ylmethyl |
| F.438 | CH$_3$ | CH$_3$ | 5-methyl-1,3,4-thiadiazol-2-ylmethyl |
| F.439 | CH$_3$ | CH$_3$ | 5-cyano-1,3,4-thiadiazol-2-ylmethyl |
| F.440 | CH$_3$ | CH$_3$ | 2-(2'-pyridinyloxy)eth-1-yl |
| F.441 | CH$_3$ | CH$_3$ | 2-(3'-pyridinyloxy)eth-1-yl |
| F.442 | CH$_3$ | CH$_3$ | 2-(4'-pyridinyloxy)eth-1-yl |
| F.443 | CH$_3$ | CH$_3$ | 2-(2'-pyrimidinyloxy)eth-1-yl |
| F.444 | CH$_3$ | CH$_3$ | 2-(4'-pyrimidinyloxy)eth-1-yl |
| F.445 | CH$_3$ | CH$_3$ | 2-(5'-pyrimidinyloxy)eth-1-yl |
| F.446 | CH$_3$ | CH$_3$ | 2-(2'-pyrazinyloxy)eth-1-yl |
| F.447 | CH$_3$ | CH$_3$ | 2-(2'-pyridazinyloxy)eth-1-yl |
| F.448 | CH$_3$ | CH$_3$ | 2-(3'-pyridazinyloxy)eth-1-yl |
| F.449 | CH$_3$ | CH$_3$ | 2-(1',3',5'-triazinyloxy)eth-1-yl |
| F.450 | CH$_3$ | CH$_3$ | 2-(5'-methylisoxazol-3'-yloxy)eth-1-yl |
| F.451 | CH$_3$ | CH$_3$ | 2-(5'-chloroisoxazol-3'-yloxy)eth-1-yl |
| F.452 | CH$_3$ | CH$_3$ | 2-(2'-methoxythiazol-4'-yloxy)eth-1-yl |
| F.453 | CH$_3$ | CH$_3$ | 2-(4'-chlorooxazol-2'-yloxy)eth-1-yl |
| F.454 | CH$_3$ | CH$_3$ | 2-(1'-phenyl-1'H-1',2',4'-triazol-3'-yl-oxy)eth-1-yl |
| F.455 | CH$_3$ | CH$_3$ | 2-(1'-phenylpyrazol-3'-yloxy)eth-1-yl |
| F.456 | CH$_3$ | CH$_3$ | C$_6$H$_5$ |
| F.457 | CH$_3$ | CH$_3$ | 2-Cl—C$_6$H$_4$ |
| F.458 | CH$_3$ | CH$_3$ | 3-Cl—C$_6$H$_4$ |
| F.459 | CH$_3$ | CH$_3$ | 4-Cl—C$_6$H$_4$ |
| F.460 | CH$_3$ | CH$_3$ | 2,3-Cl$_2$—C$_6$H$_3$ |
| F.461 | CH$_3$ | CH$_3$ | 2,4-Cl$_2$—C$_6$H$_3$ |
| F.462 | CH$_3$ | CH$_3$ | 2,5-Cl$_2$—C$_6$H$_3$ |

TABLE F-continued

| No. | $R^d$ | $R^\alpha$ | $R^\beta$ |
|---|---|---|---|
| F.463 | CH$_3$ | CH$_3$ | 3,4-Cl$_2$—C$_6$H$_3$ |
| F.464 | CH$_3$ | CH$_3$ | 3,5-Cl$_2$—C$_6$H$_3$ |
| F.465 | CH$_3$ | CH$_3$ | 4-CN—C$_6$H$_4$ |
| F.466 | CH$_3$ | CH$_3$ | 2-NO$_2$—C$_6$H$_4$ |
| F.467 | CH$_3$ | CH$_3$ | 3-NO$_2$—C$_6$H$_4$ |
| F.468 | CH$_3$ | CH$_3$ | 4-NO$_2$—C$_6$H$_4$ |
| F.469 | CH$_3$ | CH$_3$ | 2,4-(NO$_2$)$_2$—C$_6$H$_3$ |
| F.470 | CH$_3$ | CH$_3$ | 2-CH$_3$—C$_6$H$_4$ |
| F.471 | CH$_3$ | CH$_3$ | 3-CH$_3$—C$_6$H$_4$ |
| F.472 | CH$_3$ | CH$_3$ | 4-CH$_3$—C$_6$H$_4$ |
| F.473 | CH$_3$ | CH$_3$ | 2,3-(CH$_3$)$_2$—C$_6$H$_3$ |
| F.474 | CH$_3$ | CH$_3$ | 2,4-(CH$_3$)$_2$—C$_6$H$_3$ |
| F.475 | CH$_3$ | CH$_3$ | 2,5-(CH$_3$)$_2$—C$_6$H$_3$ |
| F.476 | CH$_3$ | CH$_3$ | 2,6-(CH$_3$)$_2$—C$_6$H$_3$ |
| F.477 | CH$_3$ | CH$_3$ | 2-C$_6$H$_5$—C$_6$H$_4$ |
| F.478 | CH$_3$ | CH$_3$ | 3-C$_6$H$_5$—C$_6$H$_4$ |
| F.479 | CH$_3$ | CH$_3$ | 4-C$_6$H$_5$—C$_6$H$_4$ |
| F.480 | CH$_3$ | CH$_3$ | 3-OCH$_3$—C$_6$H$_4$ |
| F.481 | CH$_3$ | CH$_3$ | 4-OCH$_3$—C$_6$H$_4$ |
| F.482 | CH$_3$ | CH$_3$ | 3-acetyl-C$_6$H$_4$ |
| F.483 | CH$_3$ | CH$_3$ | 4-acetyl-C$_6$H$_4$ |
| F.484 | CH$_3$ | CH$_3$ | 3-methoxycarbonyl-C$_6$H$_4$ |
| F.485 | CH$_3$ | CH$_3$ | 4-methoxycarbonyl-C$_6$H$_4$ |
| F.486 | CH$_3$ | CH$_3$ | 3-CF$_3$—C$_6$H$_4$ |
| F.487 | CH$_3$ | CH$_3$ | 4-CF$_3$—C$_6$H$_4$ |
| F.488 | CH$_3$ | CH$_3$ | 2-naphthyl |
| F.489 | CH$_3$ | CH$_3$ | 6-chloropyridazin-3-yl |
| F.490 | CH$_3$ | CH$_3$ | 5-chloropyrazin-2-yl |
| F.491 | CH$_3$ | CH$_3$ | quinolin-2-yl |
| F.492 | CH$_3$ | CH$_3$ | 2,5-dimethylpyrazin-3-yl |
| F.493 | CH$_3$ | CH$_3$ | pyrazin-2-yl |
| F.494 | CH$_3$ | CH$_3$ | 3-chloropyrid-2-yl |
| F.495 | CH$_3$ | CH$_3$ | 6-chloropyrid-2-yl |
| F.496 | CH$_3$ | CH$_3$ | 4-trifluoromethyl, 6-chloropyrid-2-yl |
| F.497 | CH$_3$ | CH$_3$ | 4-trifluoromethylpyrid-2-yl |
| F.498 | CH$_3$ | CH$_3$ | 6-trifluoromethylpyrid-2-yl |
| F.499 | CH$_3$ | CH$_3$ | 6-methoxypyrid-2-yl |
| F.500 | CH$_3$ | CH$_3$ | 5-chloropyrid-2-yl |
| F.501 | CH$_3$ | CH$_3$ | pyrid-2-yl |
| F.502 | CH$_3$ | CH$_3$ | benzothiazol-2-yl |
| F.503 | CH$_3$ | CH$_3$ | 7-chloroquinolin-4-yl |
| F.504 | CH$_3$ | CH$_3$ | 3-nitropyrid-2-yl |
| F.505 | CH$_3$ | CH$_3$ | pyrrol-3-yl |
| F.506 | CH$_3$ | CH$_3$ | pyrrol-2-yl |
| F.507 | CH$_3$ | CH$_3$ | 2,6-dioctylpyrid-4-yl |
| F.508 | CH$_3$ | CH$_3$ | 5-nitropyrid-2-yl |
| F.509 | CH$_3$ | CH$_3$ | pyrid-4-yl |
| F.510 | CH$_3$ | CH$_3$ | pyrid-3-yl |
| F.511 | CH$_3$ | CH$_3$ | pyrimidin-2-yl |
| F.512 | CH$_3$ | CH$_3$ | pyrimidin-4-yl |
| F.513 | CH$_3$ | CH$_3$ | quinazolin-4-yl |
| F.514 | CH$_3$ | CH$_3$ | 6-chloropyrimidin-4-yl |
| F.515 | CH$_3$ | CH$_3$ | 6-methoxypyrimidin-4-yl |
| F.516 | CH$_3$ | CH$_3$ | 2,5,6-trichloropyrimidin-4-yl |
| F.517 | CH$_3$ | CH$_3$ | 2,6-dimethylpyrimidin-4-yl |
| F.518 | CH$_3$ | CH$_3$ | 2-methyl, 6-chloropyrimidin-4-yl |
| F.519 | CH$_3$ | CH$_3$ | 2-methyl, 6-ethoxypyrimidin-4-yl |
| F.520 | CH$_3$ | CH$_3$ | 4,5,6-trichloropyrimidin-2-yl |
| F.521 | CH$_3$ | CH$_3$ | 4,6-dimethoxypyrimidin-2-yl |
| F.522 | CH$_3$ | CH$_3$ | 4,6-dimethylpyrimidin-2-yl |
| F.523 | CH$_3$ | CH$_3$ | 4,6-dichloropyrimidin-2-yl |
| F.524 | CH$_3$ | CH$_3$ | 4-methyl, 6-methoxypyrimidin-2-yl |
| F.525 | CH$_3$ | CH$_3$ | 4-chloro, 6-methoxypyrimidin-2-yl |
| F.526 | CH$_3$ | CH$_3$ | 6-chloroquinoxalin-2-yl |
| F.527 | CH$_3$ | CH$_3$ | 3,6-dichloro-1,2,4-triazin-5-yl |
| F.528 | CH$_3$ | CH$_3$ | 4-methoxy-1,3,5-triazin-2-yl |
| F.529 | CH$_3$ | CH$_3$ | 4-ethoxy-1,3,5-triazin-2-yl |
| F.530 | CH$_3$ | CH$_3$ | 4,6-dichloro-1,3,5-triazin-2-yl |
| F.531 | CH$_3$ | CH$_3$ | 4-ethoxy, 6-chloro-1,3,5-triazin-2-yl |
| F.532 | CH$_3$ | CH$_3$ | isoxazol-3-yl |
| F.533 | CH$_3$ | CH$_3$ | thien-2-yl |
| F.534 | CH$_3$ | CH$_3$ | fur-2-yl |
| F.535 | CH$_3$ | CH$_3$ | thiatriazol-5-yl |
| F.536 | CH$_3$ | CH$_3$ | (E)-1-chloropropen-3-yl |
| F.537 | CH$_3$ | CH$_3$ | (E)-4-(4'-chlorophenyl)but-2-en-1-yl |
| F.538 | CH$_3$ | CH$_3$ | propyn-3-yl |
| F.539 | CH$_3$ | CH$_3$ | methylcarbonyl |

TABLE F-continued

| No. | $R^d$ | $R^\alpha$ | $R^\beta$ |
|---|---|---|---|
| F.540 | CH₃ | CH₃ | ethylcarbonyl |
| F.541 | CH₃ | CH₃ | n-propylcarbonyl |
| F.542 | CH₃ | CH₃ | i-propylcarbonyl |
| F.543 | CH₃ | CH₃ | n-butylcarbonyl |
| F.544 | CH₃ | CH₃ | s-butylcarbonyl |
| F.545 | CH₃ | CH₃ | i-butylcarbonyl |
| F.546 | CH₃ | CH₃ | t-butylcarbonyl |
| F.547 | CH₃ | CH₃ | n-pentylcarbonyl |
| F.548 | CH₃ | CH₃ | i-pentylcarbonyl |
| F.549 | CH₃ | CH₃ | neo-pentylcarbonyl |
| F.550 | CH₃ | CH₃ | n-hexylcarbonyl |
| F.551 | CH₃ | CH₃ | n-octylcarbonyl |
| F.552 | CH₃ | CH₃ | 1-propenylcarbonyl |
| F.553 | CH₃ | CH₃ | 2-penten-1-yl-carbonyl |
| F.554 | CH₃ | CH₃ | 2,5-heptadien-1-yl-carbonyl |
| F.555 | CH₃ | CH₃ | benzoyl |
| F.556 | CH₃ | CH₃ | 2-chlorobenzoyl |
| F.557 | CH₃ | CH₃ | 3-chlorobenzoyl |
| F.558 | CH₃ | CH₃ | 4-chlorobenzoyl |
| F.559 | CH₃ | CH₃ | 2-cyanobenzoyl |
| F.560 | CH₃ | CH₃ | 3-cyanobenzoyl |
| F.561 | CH₃ | CH₃ | 4-cyanobenzoyl |
| F.562 | CH₃ | CH₃ | 4-methoxybenzoyl |
| F.563 | CH₃ | CH₃ | 2-pyridylcarbonyl |
| F.564 | CH₃ | CH₃ | 3-pyridylcarbonyl |
| F.565 | CH₃ | CH₃ | 4-pyridylcarbonyl |
| F.566 | CH₃ | CH₃ | 2-pyrimidinylcarbonyl |
| F.567 | CH₃ | CH₃ | 2-oxazolylcarbonyl |
| F.568 | CH₃ | CH₃ | 4-methylisoxazol-5-ylcarbonyl |
| F.569 | CH₃ | CH₃ | methylsulfonyl |
| F.570 | CH₃ | CH₃ | ethylsulfonyl |
| F.571 | CH₃ | CH₃ | n-propylsulfonyl |
| F.572 | CH₃ | CH₃ | i-propylsulfonyl |
| F.573 | CH₃ | CH₃ | n-butylsulfonyl |
| F.574 | CH₃ | CH₃ | t-butylsulfonyl |
| F.575 | CH₃ | CH₃ | n-pentylsulfonyl |
| F.576 | CH₃ | CH₃ | neo-pentylsulfonyl |
| F.577 | CH₃ | CH₃ | n-hexylsulfonyl |
| F.578 | CH₃ | CH₃ | n-octylsulfonyl |
| F.579 | CH₃ | CH₃ | phenylsulfonyl |
| F.580 | CH₃ | CH₃ | 2-chlorophenylsulfonyl |
| F.581 | CH₃ | CH₃ | 3-chlorophenylsulfonyl |
| F.582 | CH₃ | CH₃ | 4-chlorophenylsulfonyl |
| F.583 | CH₃ | CH₃ | 2-cyanophenylsulfonyl |
| F.584 | CH₃ | CH₃ | 3-cyanophenylsulfonyl |
| F.585 | CH₃ | CH₃ | 4-cyanophenylsulfonyl |
| F.586 | CH₃ | CH₃ | 2-pyridylsulfonyl |
| F.587 | CH₃ | CH₃ | 3-pyridylsulfonyl |
| F.588 | CH₃ | CH₃ | 4-pyridylsulfonyl |
| F.589 | CH₃ | CH₃ | 2-pyrimidinylsulfonyl |
| F.590 | CH₃ | CH₃ | 4-oxazolylsulfonyl |
| F.591 | CH₃ | CH₃ | 5-chlorothiazol-2-ylsulfonyl |
| F.592 | CH₃ | CH₃ | 2-t-C₄H₉—C₆H₄—CH₂ |
| F.593 | CH₃ | CH₃ | 3-t-C₄H₉—C₆H₄—CH₂ |
| F.594 | CH₃ | CH₃ | 4-t-C₄H₉—C₆H₄—CH₂ |
| F.595 | CH₃ | CH₃ | 2-(4'-chlorothiazol-2'-yloxy)eth-1-yl |
| F.596 | CH₃ | CH₃ | 2-(1'-methylpyrazol-4'-yloxy)eth-1-yl |
| F.597 | CH₃ | CH₃ | 4-Br—C₆H₄ |
| F.598 | CH₃ | CH₃ | 3,5-(CH₃)₂—C₆H₃ |
| F.599 | CH₃ | CH₃ | 4-C₂H₅—C₆H₄ |
| F.600 | CH₃ | CH₃ | 3-dimethylaminocarbonyl-C₆H₄ |
| F.601 | CH₃ | CH₃ | 4-dimethylaminocarbonyl-C₆H₄ |
| F.602 | CH₃ | CH₃ | 2-hydroxyprop-1-yl |
| F.603 | CH₃ | CH₃ | 6-hydroxy-2-methylpyrimidin-4-ylmethyl |
| F.604 | CH₃ | CH₃ | [6-OH, 2-CH(CH₃)₂-pyrimidin-4-yl]-CH₂ |
| F.605 | CH₃ | CH₃ | [6-OH, 2-CH(CH₂)₂-pyrimidin-4-yl]-CH₂ |
| F.606 | CH₃ | CH₃ | 5-(2'-furan)-pent-1-yl |
| F.607 | CH₃ | CH₃ | 5-(2'-N-methylpyrrolyl)-pent-1-yl |
| F.608 | CH₃ | CH₃ | [2-(4-Cl—C₆H₄)-oxazol-4-yl]-CH₂ |
| F.609 | CH₃ | CH₃ | 3-CF₃-pyridin-2-yl |
| F.610 | CH₃ | CH₃ | 5-CF₃-pyridin-2-yl |
| F.611 | CH₃ | CH₃ | 6-(2'-thienyl)hex-1-yl |
| F.612 | CH₃ | C₂H₅ | H |
| F.613 | CH₃ | C₂H₅ | CH₃ |
| F.614 | CH₃ | C₂H₅ | C₂H₅ |
| F.615 | CH₃ | C₂H₅ | n-C₃H₇ |
| F.616 | CH₃ | C₂H₅ | i-C₃H₇ |

TABLE F-continued

| No. | $R^d$ | $R^\alpha$ | $R^\beta$ |
|---|---|---|---|
| F.617 | $CH_3$ | $C_2H_5$ | cyclopropyl |
| F.618 | $CH_3$ | $C_2H_5$ | n-$C_4H_9$ |
| F.619 | $CH_3$ | $C_2H_5$ | t-$C_4H_9$ |
| F.620 | $CH_3$ | $C_2H_5$ | n-$C_6H_{13}$ |
| F.621 | $CH_3$ | $C_2H_5$ | (E)-1-chloropropen-3-yl |
| F.622 | $CH_3$ | $C_2H_5$ | propyn-3-yl |
| F.623 | $CH_3$ | $C_2H_5$ | 3-methylbut-2-en-1-yl |
| F.624 | $CH_3$ | $C_2H_5$ | 2-naphthyl-$CH_2$ |
| F.625 | $CH_3$ | $C_2H_5$ | 4-Cl—$C_6H_4$—$CH_2$ |
| F.626 | $CH_3$ | $C_2H_5$ | (E)-4-(4'-chlorophenyl)but-2-en-1-yl |
| F.627 | $CH_3$ | $C_2H_5$ | 6-(4'-chlorophenyl)hex-1-yl |
| F.628 | $CH_3$ | $C_2H_5$ | 3-$CF_3$—$C_6H_4$ |
| F.629 | $CH_3$ | n-$C_3H_7$ | H |
| F.630 | $CH_3$ | n-$C_3H_7$ | $CH_3$ |
| F.631 | $CH_3$ | n-$C_3H_7$ | $C_2H_5$ |
| F.632 | $CH_3$ | n-$C_3H_7$ | n-$C_3H_7$ |
| F.633 | $CH_3$ | n-$C_3H_7$ | i-$C_3H_7$ |
| F.634 | $CH_3$ | n-$C_3H_7$ | cyclopropyl |
| F.635 | $CH_3$ | n-$C_3H_7$ | n-$C_4H_9$ |
| F.636 | $CH_3$ | n-$C_3H_7$ | t-$C_4H_9$ |
| F.637 | $CH_3$ | n-$C_3H_7$ | n-$C_6H_{13}$ |
| F.638 | $CH_3$ | n-$C_3H_7$ | (E)-1-chloropropen-3-yl |
| F.639 | $CH_3$ | n-$C_3H_7$ | propyn-3-yl |
| F.640 | $CH_3$ | n-$C_3H_7$ | 3-methylbut-2-en-1-yl |
| F.641 | $CH_3$ | n-$C_3H_7$ | 2-naphthyl-$CH_2$ |
| F.642 | $CH_3$ | n-$C_3H_7$ | 4-Cl—$C_6H_4$—$CH_2$ |
| F.643 | $CH_3$ | n-$C_3H_7$ | (E)-4-(4'-chlorophenyl)but-2-en-1-yl |
| F.644 | $CH_3$ | n-$C_3H_7$ | 6-(4'-chlorophenyl)hex-1-yl |
| F.645 | $CH_3$ | n-$C_3H_7$ | 3-$CF_3$—$C_6H_4$ |
| F.646 | $CH_3$ | i-$C_3H_7$ | H |
| F.647 | $CH_3$ | i-$C_3H_7$ | $CH_3$ |
| F.648 | $CH_3$ | i-$C_3H_7$ | $C_2H_5$ |
| F.649 | $CH_3$ | i-$C_3H_7$ | n-$C_3H_7$ |
| F.650 | $CH_3$ | i-$C_3H_7$ | i-$C_3H_7$ |
| F.651 | $CH_3$ | i-$C_3H_7$ | cyclopropyl |
| F.652 | $CH_3$ | i-$C_3H_7$ | n-$C_4H_9$ |
| F.653 | $CH_3$ | i-$C_3H_7$ | t-$C_4H_9$ |
| F.654 | $CH_3$ | i-$C_3H_7$ | n-$C_6H_{13}$ |
| F.655 | $CH_3$ | i-$C_3H_7$ | (E)-1-chloropropen-3-yl |
| F.656 | $CH_3$ | i-$C_3H_7$ | propyn-3-yl |
| F.657 | $CH_3$ | i-$C_3H_7$ | 3-methylbut-2-en-1-yl |
| F.658 | $CH_3$ | i-$C_3H_7$ | 2-naphthyl-$CH_2$ |
| F.659 | $CH_3$ | i-$C_3H_7$ | 4-Cl—$C_6H_4$—$CH_2$ |
| F.660 | $CH_3$ | i-$C_3H_7$ | (E)-4-(4'-chlorophenyl)but-2-en-1-yl |
| F.661 | $CH_3$ | i-$C_3H_7$ | 6-(4'-chlorophenyl)hex-1-yl |
| F.662 | $CH_3$ | i-$C_3H_7$ | 3-$CF_3$—$C_6H_4$ |
| F.663 | $CH_3$ | n-$C_4H_9$ | H |
| F.664 | $CH_3$ | n-$C_4H_9$ | $CH_3$ |
| F.665 | $CH_3$ | n-$C_4H_9$ | $C_2H_5$ |
| F.666 | $CH_3$ | n-$C_4H_9$ | n-$C_3H_7$ |
| F.667 | $CH_3$ | n-$C_4H_9$ | i-$C_3H_7$ |
| F.668 | $CH_3$ | n-$C_4H_9$ | cyclopropyl |
| F.669 | $CH_3$ | n-$C_4H_9$ | n-$C_4H_9$ |
| F.670 | $CH_3$ | n-$C_4H_9$ | t-$C_4H_9$ |
| F.671 | $CH_3$ | n-$C_4H_9$ | n-$C_6H_{13}$ |
| F.672 | $CH_3$ | n-$C_4H_9$ | (E)-1-chloropropen-3-yl |
| F.673 | $CH_3$ | n-$C_4H_9$ | propyn-3-yl |
| F.674 | $CH_3$ | n-$C_4H_9$ | 3-methylbut-2-en-1-yl |
| F.675 | $CH_3$ | n-$C_4H_9$ | 2-naphthyl-$CH_2$ |
| F.676 | $CH_3$ | n-$C_4H_9$ | 4-Cl—$C_6H_4$—$CH_2$ |
| F.677 | $CH_3$ | n-$C_4H_9$ | (E)-4-(4'-chlorophenyl)but-2-en-1-yl |
| F.678 | $CH_3$ | n-$C_4H_9$ | 6-(4'-chlorophenyl)hex-1-yl |
| F.679 | $CH_3$ | n-$C_4H_9$ | 3-$CF_3$—$C_6H_4$ |
| F.680 | $CH_3$ | $CH_3$—$CH(CH_3)$—$CH_2$ | H |
| F.681 | $CH_3$ | $CH_3$—$CH(CH_3)$—$CH_2$ | $CH_3$ |
| F.682 | $CH_3$ | $CH_3$—$CH(CH_3)$—$CH_2$ | $C_2H_5$ |
| F.683 | $CH_3$ | $CH_3$—$CH(CH_3)$—$CH_2$ | n-$C_3H_7$ |
| F.684 | $CH_3$ | $CH_3$—$CH(CH_3)$—$CH_2$ | i-$C_3H_7$ |
| F.685 | $CH_3$ | $CH_3$—$CH(CH_3)$—$CH_2$ | cyclopropyl |
| F.686 | $CH_3$ | $CH_3$—$CH(CH_3)$—$CH_2$ | n-$C_4H_9$ |
| F.687 | $CH_3$ | $CH_3$—$CH(CH_3)$—$CH_2$ | t-$C_4H_9$ |
| F.688 | $CH_3$ | $CH_3$—$CH(CH_3)$—$CH_2$ | n-$C_6H_{13}$ |
| F.689 | $CH_3$ | $CH_3$—$CH(CH_3)$—$CH_2$ | (E)-1-chloropropen-3-yl |
| F.690 | $CH_3$ | $CH_3$—$CH(CH_3)$—$CH_2$ | propyn-3-yl |
| F.691 | $CH_3$ | $CH_3$—$CH(CH_3)$—$CH_2$ | 3-methylbut-2-en-1-yl |
| F.692 | $CH_3$ | $CH_3$—$CH(CH_3)$—$CH_2$ | 2-naphthyl-$CH_2$ |
| F.693 | $CH_3$ | $CH_3$—$CH(CH_3)$—$CH_2$ | 4-Cl—$C_6H_4$—$CH_2$ |

TABLE F-continued

| No. | $R^d$ | $R^\alpha$ | $R^\beta$ |
|---|---|---|---|
| F.694 | CH$_3$ | CH$_3$—CH(CH$_3$)—CH$_2$ | (E)-4-(4'-chlorophenyl)but-2-en-1-yl |
| F.695 | CH$_3$ | CH$_3$—CH(CH$_3$)—CH$_2$ | 6-(4'-chlorophenyl)hex-1-yl |
| F.696 | CH$_3$ | CH$_3$—CH(CH$_3$)—CH$_2$ | 3-CF$_3$—C$_6$H$_4$ |
| F.697 | CH$_3$ | CH$_3$—CH$_2$—CH(CH$_3$) | H |
| F.698 | CH$_3$ | CH$_3$—CH$_2$—CH(CH$_3$) | CH$_3$ |
| F.699 | CH$_3$ | CH$_3$—CH$_2$—CH(CH$_3$) | C$_2$H$_5$ |
| F.700 | CH$_3$ | CH$_3$—CH$_2$—CH(CH$_3$) | n-C$_3$H$_7$ |
| F.701 | CH$_3$ | CH$_3$—CH$_2$—CH(CH$_3$) | i-C$_3$H$_7$ |
| F.702 | CH$_3$ | CH$_3$—CH$_2$—CH(CH$_3$) | cyclopropyl |
| F.703 | CH$_3$ | CH$_3$—CH$_2$—CH(CH$_3$) | n-C$_4$H$_9$ |
| F.704 | CH$_3$ | CH$_3$—CH$_2$—CH(CH$_3$) | t-C$_4$H$_9$ |
| F.705 | CH$_3$ | CH$_3$—CH$_2$—CH(CH$_3$) | n-C$_6$H$_{13}$ |
| F.706 | CH$_3$ | CH$_3$—CH$_2$—CH(CH$_3$) | (E)-1-chloropropen-3-yl |
| F.707 | CH$_3$ | CH$_3$—CH$_2$—CH(CH$_3$) | propyn-3-yl |
| F.708 | CH$_3$ | CH$_3$—CH$_2$—CH(CH$_3$) | 3-methylbut-2-en-1-yl |
| F.709 | CH$_3$ | CH$_3$—CH$_2$—CH(CH$_3$) | 2-naphthyl-CH$_2$ |
| F.710 | CH$_3$ | CH$_3$—CH$_2$—CH(CH$_3$) | 4-Cl—C$_6$H$_4$—CH$_2$ |
| F.711 | CH$_3$ | CH$_3$—CH$_2$—CH(CH$_3$) | (E)-4-(4'-chlorophenyl)but-2-en-1-yl |
| F.712 | CH$_3$ | CH$_3$—CH$_2$—CH(CH$_3$) | 6-(4'-chlorophenyl)hex-1-yl |
| F.713 | CH$_3$ | CH$_3$—CH$_2$—CH(CH$_3$) | 3-CF$_3$—C$_6$H$_4$ |
| F.714 | CH$_3$ | CF$_3$ | H |
| F.715 | CH$_3$ | CF$_3$ | CH$_3$ |
| F.716 | CH$_3$ | CF$_3$ | C$_2$H$_5$ |
| F.717 | CH$_3$ | CF$_3$ | n-C$_3$H$_7$ |
| F.718 | CH$_3$ | CF$_3$ | i-C$_3$H$_7$ |
| F.719 | CH$_3$ | CF$_3$ | cyclopropyl |
| F.720 | CH$_3$ | CF$_3$ | n-C$_4$H$_9$ |
| F.721 | CH$_3$ | CF$_3$ | t-C$_4$H$_9$ |
| F.722 | CH$_3$ | CF$_3$ | n-C$_6$H$_{13}$ |
| F.723 | CH$_3$ | CF$_3$ | (E)-1-chloropropen-3-yl |
| F.724 | CH$_3$ | CF$_3$ | propyn-3-yl |
| F.725 | CH$_3$ | CF$_3$ | 3-methylbut-2-en-1-yl |
| F.726 | CH$_3$ | CF$_3$ | 2-naphthyl-CH$_2$ |
| F.727 | CH$_3$ | CF$_3$ | 4-Cl—C$_6$H$_4$—CH$_2$ |
| F.728 | CH$_3$ | CF$_3$ | (E)-4-(4'-chlorophenyl)but-2-en-1-yl |
| F.729 | CH$_3$ | CF$_3$ | 6-(4'-chlorophenyl)hex-1-yl |
| F.730 | CH$_3$ | CF$_3$ | 3-CF$_3$—C$_6$H$_4$ |
| F.731 | CH$_3$ | N-pyrrolyl | H |
| F.732 | CH$_3$ | N-pyrrolyl | CH$_3$ |
| F.733 | CH$_3$ | N-pyrrolyl | C$_2$H$_5$ |
| F.734 | CH$_3$ | N-pyrrolyl | n-C$_3$H$_7$ |
| F.735 | CH$_3$ | N-pyrrolyl | i-C$_3$H$_7$ |
| F.736 | CH$_3$ | N-pyrazolyl | H |
| F.737 | CH$_3$ | N-pyrazolyl | CH$_3$ |
| F.738 | CH$_3$ | N-pyrazolyl | C$_2$H$_5$ |
| F.739 | CH$_3$ | N-pyrazolyl | n-C$_3$H$_7$ |
| F.740 | CH$_3$ | N-pyrazolyl | i-C$_3$H$_7$ |
| F.741 | CH$_3$ | N-imidazolyl | H |
| F.742 | CH$_3$ | N-imidazolyl | CH$_3$ |
| F.743 | CH$_3$ | N-imidazolyl | C$_2$H$_5$ |
| F.744 | CH$_3$ | N-imidazolyl | n-C$_3$H$_7$ |
| F.745 | CH$_3$ | N-imidazolyl | i-C$_3$H$_7$ |
| F.746 | CH$_3$ | (N-1)-1,2,4-triazolyl | H |
| F.747 | CH$_3$ | (N-1)-1,2,4-triazolyl | CH$_3$ |
| F.748 | CH$_3$ | (N-1)-1,2,4-triazolyl | C$_2$H$_5$ |
| F.749 | CH$_3$ | (N-1)-1,2,4-triazolyl | n-C$_3$H$_7$ |
| F.750 | CH$_3$ | (N-1)-1,2,4-triazolyl | i-C$_3$H$_7$ |
| F.751 | CH$_3$ | N-indolyl | H |
| F.752 | CH$_3$ | N-indolyl | CH$_3$ |
| F.753 | CH$_3$ | N-indolyl | C$_2$H$_5$ |
| F.754 | CH$_3$ | N-indolyl | n-C$_3$H$_7$ |
| F.755 | CH$_3$ | N-indolyl | i-C$_3$H$_7$ |
| F.756 | CH$_3$ | N-morpholinyl | H |
| F.757 | CH$_3$ | N-morpholinyl | CH$_3$ |
| F.758 | CH$_3$ | N-morpholinyl | C$_2$H$_5$ |
| F.759 | CH$_3$ | N-morpholinyl | n-C$_3$H$_7$ |
| F.760 | CH$_3$ | N-morpholinyl | i-C$_3$H$_7$ |
| F.761 | CH$_3$ | N-(2,6-dimethyl)-morpholinyl | H |
| F.762 | CH$_3$ | N-(2,6-dimethyl)-morpholinyl | CH$_3$ |
| F.763 | CH$_3$ | N-(2,6-dimethyl)-morpholinyl | C$_2$H$_5$ |
| F.764 | CH$_3$ | N-(2,6-dimethyl)-morpholinyl | n-C$_3$H$_7$ |
| F.765 | CH$_3$ | N-(2,6-dimethyl)-morpholinyl | i-C$_3$H$_7$ |
| F.766 | CH$_3$ | N-pyrrolidinyl | H |
| F.767 | CH$_3$ | N-pyrrolidinyl | CH$_3$ |
| F.768 | CH$_3$ | N-pyrrolidinyl | C$_2$H$_5$ |
| F.769 | CH$_3$ | N-pyrrolidinyl | n-C$_3$H$_7$ |
| F.770 | CH$_3$ | N-pyrrolidinyl | i-C$_3$H$_7$ |

TABLE F-continued

| No. | $R^d$ | $R^\alpha$ | $R^\beta$ |
|---|---|---|---|
| F.771 | CH$_3$ | N-pyridinyl | H |
| F.772 | CH$_3$ | N-pyridinyl | CH$_3$ |
| F.773 | CH$_3$ | N-pyridinyl | C$_2$H$_5$ |
| F.774 | CH$_3$ | N-pyridinyl | n-C$_3$H$_7$ |
| F.775 | CH$_3$ | N-pyridinyl | i-C$_3$H$_7$ |
| F.776 | CH$_3$ | N-piperazinyl | H |
| F.777 | CH$_3$ | N-piperazinyl | CH$_3$ |
| F.778 | CH$_3$ | N-piperazinyl | C$_2$H$_5$ |
| F.779 | CH$_3$ | N-piperazinyl | n-C$_3$H$_7$ |
| F.780 | CH$_3$ | N-piperazinyl | i-C$_3$H$_7$ |
| F.781 | H | CH$_3$ | CH$_3$ |
| F.782 | CH$_3$ | CH$_3$ | CH$_3$ |
| F.783 | C$_2$H$_5$ | CH$_3$ | CH$_3$ |
| F.784 | CH$_2$CH$_2$CH$_3$ | CH$_3$ | CH$_3$ |
| F.785 | CH(CH$_3$)$_2$ | CH$_3$ | CH$_3$ |
| F.786 | cyclopropyl | CH$_3$ | CH$_3$ |
| F.787 | CF$_3$ | CH$_3$ | CH$_3$ |
| F.788 | CN | CH$_3$ | CH$_3$ |
| F.789 | OH | CH$_3$ | CH$_3$ |
| F.790 | OCH$_3$ | CH$_3$ | CH$_3$ |
| F.791 | OCH$_2$CH$_3$ | CH$_3$ | CH$_3$ |
| F.792 | Cl | CH$_3$ | CH$_3$ |
| F.793 | Br | CH$_3$ | CH$_3$ |
| F.794 | SCH$_3$ | CH$_3$ | CH$_3$ |
| F.795 | CH$_3$ | H | CH$_3$ |
| F.796 | CH$_3$ | C$_2$H$_5$ | CH$_3$ |
| F.797 | CH$_3$ | CH$_2$CH$_2$CH$_3$ | CH$_3$ |
| F.798 | CH$_3$ | CH(CH$_3$)$_2$ | CH$_3$ |
| F.799 | CH$_3$ | cyclopropyl | CH$_3$ |
| F.800 | CH$_3$ | CF$_3$ | CH$_3$ |
| F.801 | CH$_3$ | CN | CH$_3$ |
| F.802 | CH$_3$ | OH | CH$_3$ |
| F.803 | CH$_3$ | OCH$_3$ | CH$_3$ |
| F.804 | CH$_3$ | OCH$_2$CH$_3$ | CH$_3$ |
| F.805 | CH$_3$ | Cl | CH$_3$ |
| F.806 | CH$_3$ | Br | CH$_3$ |
| F.807 | CH$_3$ | SCH$_3$ | CH$_3$ |

TABLE G

| No. | R | * | R' | VR" | # |
|---|---|---|---|---|---|
| G.1 | O—C$_6$H$_5$ | 3 | CH$_3$ | OCH$_3$ | 2 |
| G.2 | S—C$_6$H$_5$ | 3 | CH$_3$ | OCH$_3$ | 2 |
| G.3 | CH=CH—C$_6$H$_5$ | 3 | CH$_3$ | OCH$_3$ | 2 |
| G.4 | C≡C—C$_6$H$_5$ | 3 | CH$_3$ | OCH$_3$ | 2 |
| G.5 | CH$_2$CH$_2$—C$_6$H$_5$ | 3 | CH$_3$ | OCH$_3$ | 2 |
| G.6 | OCH$_2$—C$_6$H$_5$ | 3 | CH$_3$ | OCH$_3$ | 2 |
| G.7 | SCH$_2$—C$_6$H$_5$ | 3 | CH$_3$ | OCH$_3$ | 2 |
| G.8 | CH$_2$O—C$_6$H$_5$ | 3 | CH$_3$ | OCH$_3$ | 2 |
| G.9 | CH$_2$S—C$_6$H$_5$ | 3 | CH$_3$ | OCH$_3$ | 2 |
| G.10 | CH$_2$O—CO—C$_6$H$_5$ | 3 | CH$_3$ | OCH$_3$ | 2 |
| G.11 | CH=NO—CH$_2$—C$_6$H$_5$ | 3 | CH$_3$ | OCH$_3$ | 2 |
| G.12 | ON=C(CH$_3$)—C$_6$H$_5$ | 3 | CH$_3$ | OCH$_3$ | 2 |
| G.13 | CH$_2$—ON=C(CH$_3$)—C$_6$H$_5$ | 3 | CH$_3$ | OCH$_3$ | 2 |
| G.14 | CH$_2$—ON=C(CH$_3$)—C(C$_6$H$_5$)=NOCH$_3$ | 3 | CH$_3$ | OCH$_3$ | 2 |
| G.15 | CH$_2$O—C(CH$_3$)=N—N=C(CH$_3$)—C$_6$H$_5$ | 3 | CH$_3$ | OCH$_3$ | 2 |
| G.16 | CH$_2$OC(CH$_3$)=NN=C(CH$_3$)—C(C$_6$H$_5$)=NOCH$_3$ | 3 | CH$_3$ | OCH$_3$ | 2 |
| G.17 | O—C$_6$H$_5$ | 3 | CH$_3$ | OCH$_3$ | 4 |
| G.18 | S—C$_6$H$_5$ | 3 | CH$_3$ | OCH$_3$ | 4 |
| G.19 | CH=CH—C$_6$H$_5$ | 3 | CH$_3$ | OCH$_3$ | 4 |
| G.20 | C≡C—C$_6$H$_5$ | 3 | CH$_3$ | OCH$_3$ | 4 |
| G.21 | CH$_2$CH$_2$—C$_6$H$_5$ | 3 | CH$_3$ | OCH$_3$ | 4 |
| G.22 | OCH$_2$—C$_6$H$_5$ | 3 | CH$_3$ | OCH$_3$ | 4 |
| G.23 | SCH$_2$—C$_6$H$_5$ | 3 | CH$_3$ | OCH$_3$ | 4 |
| G.24 | CH$_2$O—C$_6$H$_5$ | 3 | CH$_3$ | OCH$_3$ | 4 |
| G.25 | CH$_2$S—C$_6$H$_5$ | 3 | CH$_3$ | OCH$_3$ | 4 |
| G.26 | CH$_2$O—CO—C$_6$H$_5$ | 3 | CH$_3$ | OCH$_3$ | 4 |
| G.27 | CH=NO—CH$_2$—C$_6$H$_5$ | 3 | CH$_3$ | OCH$_3$ | 4 |
| G.28 | ON=C(CH$_3$)—C$_6$H$_5$ | 3 | CH$_3$ | OCH$_3$ | 4 |
| G.29 | CH$_2$—ON=C(CH$_3$)—C$_6$H$_5$ | 3 | CH$_3$ | OCH$_3$ | 4 |
| G.30 | CH$_2$—ON=C(CH$_3$)—C(C$_6$H$_5$)=NOCH$_3$ | 3 | CH$_3$ | OCH$_3$ | 4 |
| G.31 | CH$_2$O—C(CH$_3$)=N—N=C(CH$_3$)—C$_6$H$_5$ | 3 | CH$_3$ | OCH$_3$ | 4 |
| G.32 | CH$_2$OC(CH$_3$)=NN=C(CH$_3$)—C(C$_6$H$_5$)=NOCH$_3$ | 3 | CH$_3$ | OCH$_3$ | 4 |

TABLE G-continued

| No. | R | * | R' | VR" | # |
|---|---|---|---|---|---|
| G.33 | O—C$_6$H$_5$ | 4 | CH$_3$ | OCH$_3$ | 3 |
| G.34 | S—C$_6$H$_5$ | 4 | CH$_3$ | OCH$_3$ | 3 |
| G.35 | CH=CH—C$_6$H$_5$ | 4 | CH$_3$ | OCH$_3$ | 3 |
| G.36 | C≡C—C$_6$H$_5$ | 4 | CH$_3$ | OCH$_3$ | 3 |
| G.37 | CH$_2$CH$_2$—C$_6$H$_5$ | 4 | CH$_3$ | OCH$_3$ | 3 |
| G.38 | OCH$_2$—C$_6$H$_5$ | 4 | CH$_3$ | OCH$_3$ | 3 |
| G.39 | SCH$_2$—C$_6$H$_5$ | 4 | CH$_3$ | OCH$_3$ | 3 |
| G.40 | CH$_2$O—C$_6$H$_5$ | 4 | CH$_3$ | OCH$_3$ | 3 |
| G.41 | CH$_2$S—C$_6$H$_5$ | 4 | CH$_3$ | OCH$_3$ | 3 |
| G.42 | CH$_2$O—CO—C$_6$H$_5$ | 4 | CH$_3$ | OCH$_3$ | 3 |
| G.43 | CH=NO—CH$_2$—C$_6$H$_5$ | 4 | CH$_3$ | OCH$_3$ | 3 |
| G.44 | ON=C(CH$_3$)—C$_6$H$_5$ | 4 | CH$_3$ | OCH$_3$ | 3 |
| G.45 | CH$_2$—ON=C(CH$_3$)—C$_6$H$_5$ | 4 | CH$_3$ | OCH$_3$ | 3 |
| G.46 | CH$_2$—ON=C(CH$_3$)—C(C$_6$H$_5$)=NOCH$_3$ | 4 | CH$_3$ | OCH$_3$ | 3 |
| G.47 | CH$_2$O—C(CH$_3$)=N—N=C(CH$_3$)—C$_6$H$_5$ | 4 | CH$_3$ | OCH$_3$ | 3 |
| G.48 | CH$_2$OC(CH$_3$)=NN=C(CH$_3$)—C(C$_6$H$_5$)=NOCH$_3$ | 4 | CH$_3$ | OCH$_3$ | 3 |
| G.49 | CH$_2$O-[2-CH$_3$—C$_6$H$_4$] | 3 | CH$_3$ | OCH$_2$CH$_3$ | 2 |
| G.50 | CH$_2$O—C$_6$H$_5$ | 3 | CH$_3$ | OCH$_2$CH$_3$ | 4 |
| G.51 | CH$_2$O-[2,5-(CH$_3$)$_2$—C$_6$H$_3$] | 4 | CH$_3$ | OCH$_2$CH$_3$ | 3 |
| G.52 | CH$_2$O-[2-CH$_3$—C$_6$H$_4$] | 3 | CH$_3$ | OCHCH$_2$CH$_3$ | 2 |
| G.53 | CH$_2$O—C$_6$H$_5$ | 3 | CH$_3$ | OCHCH$_2$CH$_3$ | 4 |
| G.54 | CH$_2$O-[2,5-(CH$_3$)$_2$—C$_6$H$_3$] | 4 | CH$_3$ | OCHCH$_2$CH$_3$ | 3 |
| G.55 | CH$_2$O-[2-CH$_3$—C$_6$H$_4$] | 3 | CH$_3$ | OCH(CH$_3$)$_2$ | 2 |
| G.56 | CH$_2$O—C$_6$H$_5$ | 3 | CH$_3$ | OCH(CH$_3$)$_2$ | 4 |
| G.57 | CH$_2$O-[2,5-(CH$_3$)$_2$—C$_6$H$_3$] | 4 | CH$_3$ | OCH(CH$_3$)$_2$ | 3 |
| G.58 | CH$_2$O-[2-CH$_3$—C$_6$H$_4$] | 3 | CH$_3$ | O-cyclopropyl | 2 |
| G.59 | CH$_2$O—C$_6$H$_5$ | 3 | CH$_3$ | O-cyclopropyl | 4 |
| G.60 | CH$_2$O-[2,5-(CH$_3$)$_2$—C$_6$H$_3$] | 4 | CH$_3$ | O-cyclopropyl | 3 |
| G.61 | CH$_2$O-[2-CH$_3$—C$_6$H$_4$] | 3 | CH$_3$ | O-allyl | 2 |
| G.62 | CH$_2$O—C$_6$H$_5$ | 3 | CH$_3$ | O-allyl | 4 |
| G.63 | CH$_2$O-[2,5-(CH$_3$)$_2$—C$_6$H$_3$] | 4 | CH$_3$ | O-allyl | 3 |
| G.64 | CH$_2$O-[2-CH$_3$—C$_6$H$_4$] | 3 | CH$_3$ | O-propargyl | 2 |
| G.65 | CH$_2$O—C$_6$H$_5$ | 3 | CH$_3$ | O-propargyl | 4 |
| G.66 | CH$_2$O-[2,5-(CH$_3$)$_2$—C$_6$H$_3$] | 4 | CH$_3$ | O-propargyl | 3 |
| G.67 | CH$_2$O-[2-CH$_3$—C$_6$H$_4$] | 3 | CH$_3$ | CH$_3$ | 2 |
| G.68 | CH$_2$O—C$_6$H$_5$ | 3 | CH$_3$ | CH$_3$ | 4 |
| G.69 | CH$_2$O-[2,5-(CH$_3$)$_2$—C$_6$H$_3$] | 4 | CH$_3$ | CH$_3$ | 3 |
| G.70 | CH$_2$O-[2-CH$_3$—C$_6$H$_4$] | 3 | CH$_3$ | CH$_2$CH$_3$ | 2 |
| G.71 | CH$_2$O—C$_6$H$_5$ | 3 | CH$_3$ | CH$_2$CH$_3$ | 4 |
| G.72 | CH$_2$O-[2,5-(CH$_3$)$_2$—C$_6$H$_3$] | 4 | CH$_3$ | CH$_2$CH$_3$ | 3 |
| G.73 | CH$_2$O-[2-CH$_3$—C$_6$H$_4$] | 3 | CH$_3$ | CH$_2$CH$_2$CH$_3$ | 2 |
| G.74 | CH$_2$O—C$_6$H$_5$ | 3 | CH$_3$ | CH$_2$CH$_2$CH$_3$ | 4 |
| G.75 | CH$_2$O-[2,5-(CH$_3$)$_2$—C$_6$H$_3$] | 4 | CH$_3$ | CH$_2$CH$_2$CH$_3$ | 3 |
| G.76 | CH$_2$O-[2-CH$_3$—C$_6$H$_4$] | 3 | CH$_3$ | CH(CH$_3$)$_2$ | 2 |
| G.77 | CH$_2$O—C$_6$H$_5$ | 3 | CH$_3$ | CH(CH$_3$)$_2$ | 4 |
| G.78 | CH$_2$O-[2,5-(CH$_3$)$_2$—C$_6$H$_3$] | 4 | CH$_3$ | CH(CH$_3$)$_2$ | 3 |
| G.79 | CH$_2$O-[2-CH$_3$—C$_6$H$_4$] | 3 | CH$_3$ | cyclopropyl | 2 |
| G.80 | CH$_2$O—C$_6$H$_5$ | 3 | CH$_3$ | cyclopropyl | 4 |
| G.81 | CH$_2$O-[2,5-(CH$_3$)$_2$—C$_6$H$_3$] | 4 | CH$_3$ | cyclopropyl | 3 |
| G.82 | CH$_2$O-[2-CH$_3$—C$_6$H$_4$] | 3 | CH$_3$ | NH$_2$ | 2 |
| G.83 | CH$_2$O—C$_6$H$_5$ | 3 | CH$_3$ | NH$_2$ | 4 |
| G.84 | CH$_2$O-[2,5-(CH$_3$)$_2$—C$_6$H$_3$] | 4 | CH$_3$ | NH$_2$ | 3 |
| G.85 | CH$_2$O-[2-CH$_3$—C$_6$H$_4$] | 3 | CH$_3$ | NHCH$_3$ | 2 |
| G.86 | CH$_2$O—C$_6$H$_5$ | 3 | CH$_3$ | NHCH$_3$ | 4 |
| G.87 | CH$_2$O-[2,5-(CH$_3$)$_2$—C$_6$H$_3$] | 4 | CH$_3$ | NHCH$_3$ | 3 |
| G.88 | CH$_2$O-[2-CH$_3$—C$_6$H$_4$] | 3 | CH$_3$ | N(CH$_2$)$_2$ | 2 |
| G.89 | CH$_2$O—C$_6$H$_5$ | 3 | CH$_3$ | N(CH$_2$)$_2$ | 4 |
| G.90 | CH$_2$O-[2,5-(CH$_3$)$_2$—C$_6$H$_3$] | 4 | CH$_3$ | N(CH$_2$)$_2$ | 3 |
| G.91 | CH$_2$O-[2-CH$_3$—C$_6$H$_4$] | 3 | CH$_3$ | NHCH$_2$CH$_3$ | 2 |
| G.92 | CH$_2$O—C$_6$H$_5$ | 3 | CH$_3$ | NHCH$_2$CH$_3$ | 4 |
| G.93 | CH$_2$O-[2,5-(CH$_3$)$_2$—C$_6$H$_3$] | 4 | CH$_3$ | NHCH$_2$CH$_3$ | 3 |
| G.94 | O—C$_6$H$_5$ | 2 | CH$_3$ | OCH$_3$ | 3 |
| G.95 | S—C$_6$H$_5$ | 2 | CH$_3$ | OCH$_3$ | 3 |
| G.96 | C≡C—C$_6$H$_5$ | 2 | CH$_3$ | OCH$_3$ | 3 |
| G.97 | CH$_2$CH$_2$—C$_6$H$_5$ | 2 | CH$_3$ | OCH$_3$ | 3 |
| G.98 | OCH$_2$—C$_6$H$_5$ | 2 | CH$_3$ | OCH$_3$ | 3 |
| G.99 | SCH$_2$—C$_6$H$_5$ | 2 | CH$_3$ | OCH$_3$ | 3 |
| G.100 | CH$_2$S—C$_6$H$_5$ | 2 | CH$_3$ | OCH$_3$ | 3 |
| G.101 | CH$_2$O—CO—C$_6$H$_5$ | 2 | CH$_3$ | OCH$_3$ | 3 |
| G.102 | CH=NO—CH$_2$—C$_6$H$_5$ | 2 | CH$_3$ | OCH$_3$ | 3 |
| G.103 | ON=C(CH$_3$)—C$_6$H$_5$ | 2 | CH$_3$ | OCH$_3$ | 3 |

TABLE H

| No. | R^b | R^α | R^β |
|---|---|---|---|
| H.1 | Cl | H | H |
| H.2 | Cl | CH_3 | H |
| H.3 | Cl | CH_2CH_3 | H |
| H.4 | Cl | CF_3 | H |
| H.5 | Cl | CHF_2 | H |
| H.6 | Cl | CH_2F | H |
| H.7 | Cl | Cl | H |
| H.8 | Cl | OCH_3 | H |
| H.9 | Cl | OCH_2CH_3 | H |
| H.10 | Cl | CN | H |
| H.11 | CH_3 | H | H |
| H.12 | CH_3 | CH_3 | H |
| H.13 | CH_3 | CH_2CH_3 | H |
| H.14 | CH_3 | CF_3 | H |
| H.15 | CH_3 | CHF_2 | H |
| H.16 | CH_3 | CH_2F | H |
| H.17 | CH_3 | Cl | H |
| H.18 | CH_3 | OCH_3 | H |
| H.19 | CH_3 | OCH_2CH_3 | H |
| H.20 | CH_3 | CN | H |
| H.21 | CF_3 | H | H |
| H.22 | CF_3 | CH_3 | H |
| H.23 | CF_3 | CH_2CH_3 | H |
| H.24 | CF_3 | CF_3 | H |
| H.25 | CF_3 | CHF_2 | H |
| H.26 | CF_3 | CH_2F | H |
| H.27 | CF_3 | Cl | H |
| H.28 | CF_3 | OCH_3 | H |
| H.29 | CF_3 | OCH_2CH_3 | H |
| H.30 | CF_3 | CN | H |
| H.31 | Cl | H | CH_3 |
| H.32 | Cl | CH_3 | CH_3 |
| H.33 | Cl | CH_2CH_3 | CH_3 |
| H.34 | Cl | CF_3 | CH_3 |
| H.35 | Cl | CHF_2 | CH_3 |
| H.36 | Cl | CH_2F | CH_3 |
| H.37 | Cl | Cl | CH_3 |
| H.38 | Cl | OCH_3 | CH_3 |
| H.39 | Cl | OCH_2CH_3 | CH_3 |
| H.40 | Cl | CN | CH_3 |
| H.41 | CH_3 | H | CH_3 |
| H.42 | CH_3 | CH_3 | CH_3 |
| H.43 | CH_3 | CH_2CH_3 | CH_3 |
| H.44 | CH_3 | CF_3 | CH_3 |
| H.45 | CH_3 | CHF_2 | CH_3 |
| H.46 | CH_3 | CH_2F | CH_3 |
| H.47 | CH_3 | Cl | CH_3 |
| H.48 | CH_3 | OCH_3 | CH_3 |
| H.49 | CH_3 | OCH_2CH_3 | CH_3 |
| H.50 | CH_3 | CN | CH_3 |
| H.51 | CF_3 | H | CH_3 |
| H.52 | CF_3 | CH_3 | CH_3 |
| H.53 | CF_3 | CH_2CH_3 | CH_3 |
| H.54 | CF_3 | CF_3 | CH_3 |
| H.55 | CF_3 | CHF_2 | CH_3 |
| H.56 | CF_3 | CH_2F | CH_3 |
| H.57 | CF_3 | Cl | CH_3 |
| H.58 | CF_3 | OCH_3 | CH_3 |
| H.59 | CF_3 | OCH_2CH_3 | CH_3 |
| H.60 | CF_3 | CN | CH_3 |
| H.61 | Cl | H | CH_2CH_3 |
| H.62 | Cl | CH_3 | CH_2CH_3 |
| H.63 | Cl | CH_2CH_3 | CH_2CH_3 |
| H.64 | Cl | CF_3 | CH_2CH_3 |
| H.65 | Cl | CHF_2 | CH_2CH_3 |
| H.66 | Cl | CH_2F | CH_2CH_3 |
| H.67 | Cl | Cl | CH_2CH_3 |
| H.68 | Cl | OCH_3 | CH_2CH_3 |
| H.69 | Cl | OCH_2CH_3 | CH_2CH_3 |
| H.70 | Cl | CN | CH_2CH_3 |
| H.71 | CH_3 | H | CH_2CH_3 |
| H.72 | CH_3 | CH_3 | CH_2CH_3 |
| H.73 | CH_3 | CH_2CH_3 | CH_2CH_3 |
| H.74 | CH_3 | CF_3 | CH_2CH_3 |
| H.75 | CH_3 | CHF_2 | CH_2CH_3 |
| H.76 | CH_3 | CH_2F | CH_2CH_3 |
| H.77 | CH_3 | Cl | CH_2CH_3 |
| H.78 | CH_3 | OCH_3 | CH_2CH_3 |
| H.79 | CH_3 | OCH_2CH_3 | CH_2CH_3 |
| H.80 | CH_3 | CN | CH_2CH_3 |
| H.81 | CF_3 | H | CH_2CH_3 |
| H.82 | CF_3 | CH_3 | CH_2CH_3 |
| H.83 | CF_3 | CH_2CH_3 | CH_2CH_3 |
| H.84 | CF_3 | CF_3 | CH_2CH_3 |
| H.85 | CF_3 | CHF_2 | CH_2CH_3 |
| H.86 | CF_3 | CH_2F | CH_2CH_3 |
| H.87 | CF_3 | Cl | CH_2CH_3 |
| H.88 | CF_3 | OCH_3 | CH_2CH_3 |
| H.89 | CF_3 | OCH_2CH_3 | CH_2CH_3 |
| H.90 | CF_3 | CN | CH_2CH_3 |
| H.91 | Cl | H | CH_2CH_2CH_3 |
| H.92 | Cl | CH_3 | CH_2CH_2CH_3 |
| H.93 | Cl | CH_2CH_3 | CH_2CH_2CH_3 |
| H.94 | Cl | CF_3 | CH_2CH_2CH_3 |
| H.95 | Cl | CHF_2 | CH_2CH_2CH_3 |
| H.96 | Cl | CH_2F | CH_2CH_2CH_3 |
| H.97 | Cl | Cl | CH_2CH_2CH_3 |
| H.98 | Cl | OCH_3 | CH_2CH_2CH_3 |
| H.99 | Cl | OCH_2CH_3 | CH_2CH_2CH_3 |
| H.100 | Cl | CN | CH_2CH_2CH_3 |
| H.101 | CH_3 | H | CH_2CH_2CH_3 |
| H.102 | CH_3 | CH_3 | CH_2CH_2CH_3 |
| H.103 | CH_3 | CH_2CH_3 | CH_2CH_2CH_3 |
| H.104 | CH_3 | CF_3 | CH_2CH_2CH_3 |
| H.105 | CH_3 | CHF_2 | CH_2CH_2CH_3 |
| H.106 | CH_3 | CH_2F | CH_2CH_2CH_3 |
| H.107 | CH_3 | Cl | CH_2CH_2CH_3 |
| H.108 | CH_3 | OCH_3 | CH_2CH_2CH_3 |
| H.109 | CH_3 | OCH_2CH_3 | CH_2CH_2CH_3 |
| H.110 | CH_3 | CN | CH_2CH_2CH_3 |
| H.111 | CF_3 | H | CH_2CH_2CH_3 |
| H.112 | CF_3 | CH_3 | CH_2CH_2CH_3 |
| H.113 | CF_3 | CH_2CH_3 | CH_2CH_2CH_3 |
| H.114 | CF_3 | CF_3 | CH_2CH_2CH_3 |
| H.115 | CF_3 | CHF_2 | CH_2CH_2CH_3 |
| H.116 | CF_3 | CH_2F | CH_2CH_2CH_3 |
| H.117 | CF_3 | Cl | CH_2CH_2CH_3 |
| H.118 | CF_3 | OCH_3 | CH_2CH_2CH_3 |
| H.119 | CF_3 | OCH_2CH_3 | CH_2CH_2CH_3 |
| H.120 | CF_3 | CN | CH_2CH_2CH_3 |
| H.121 | Cl | H | CH(CH_3)_2 |
| H.122 | Cl | CH_3 | CH(CH_3)_2 |
| H.123 | Cl | CH_2CH_3 | CH(CH_3)_2 |
| H.124 | Cl | CF_3 | CH(CH_3)_2 |
| H.125 | Cl | CHF_2 | CH(CH_3)_2 |
| H.126 | Cl | CH_2F | CH(CH_3)_2 |
| H.127 | Cl | Cl | CH(CH_3)_2 |
| H.128 | Cl | OCH_3 | CH(CH_3)_2 |
| H.129 | Cl | OCH_2CH_3 | CH(CH_3)_2 |
| H.130 | Cl | CN | CH(CH_3)_2 |
| H.131 | CH_3 | H | CH(CH_3)_2 |
| H.132 | CH_3 | CH_3 | CH(CH_3)_2 |
| H.133 | CH_3 | CH_2CH_3 | CH(CH_3)_2 |
| H.134 | CH_3 | CF_3 | CH(CH_3)_2 |
| H.135 | CH_3 | CHF_2 | CH(CH_3)_2 |
| H.136 | CH_3 | CH_2F | CH(CH_3)_2 |
| H.137 | CH_3 | Cl | CH(CH_3)_2 |
| H.138 | CH_3 | OCH_3 | CH(CH_3)_2 |
| H.139 | CH_3 | OCH_2CH_3 | CH(CH_3)_2 |
| H.140 | CH_3 | CN | CH(CH_3)_2 |
| H.141 | CF_3 | H | CH(CH_3)_2 |
| H.142 | CF_3 | CH_3 | CH(CH_3)_2 |
| H.143 | CF_3 | CH_2CH_3 | CH(CH_3)_2 |
| H.144 | CF_3 | CF_3 | CH(CH_3)_2 |
| H.145 | CF_3 | CHF_2 | CH(CH_3)_2 |
| H.146 | CF_3 | CH_2F | CH(CH_3)_2 |
| H.147 | CF_3 | Cl | CH(CH_3)_2 |
| H.148 | CF_3 | OCH_3 | CH(CH_3)_2 |
| H.149 | CF_3 | OCH_2CH_3 | CH(CH_3)_2 |
| H.150 | CF_3 | CN | CH(CH_3)_2 |
| H.151 | Cl | H | CH_2CH=CH_2 |
| H.152 | Cl | CH_3 | CH_2CH=CH_2 |
| H.153 | Cl | CH_2CH_3 | CH_2CH=CH_2 |
| H.154 | Cl | CF_3 | CH_2CH=CH_2 |

TABLE H-continued

| No. | $R^b$ | $R^\alpha$ | $R^\beta$ |
|---|---|---|---|
| H.155 | Cl | $CHF_2$ | $CH_2CH=CH_2$ |
| H.156 | Cl | $CH_2F$ | $CH_2CH=CH_2$ |
| H.157 | Cl | Cl | $CH_2CH=CH_2$ |
| H.158 | Cl | $OCH_3$ | $CH_2CH=CH_2$ |
| H.159 | Cl | $OCH_2CH_3$ | $CH_2CH=CH_2$ |
| H.160 | Cl | CN | $CH_2CH=CH_2$ |
| H.161 | $CH_3$ | H | $CH_2CH=CH_2$ |
| H.162 | $CH_3$ | $CH_3$ | $CH_2CH=CH_2$ |
| H.163 | $CH_3$ | $CH_2CH_3$ | $CH_2CH=CH_2$ |
| H.164 | $CH_3$ | $CF_3$ | $CH_2CH=CH_2$ |
| H.165 | $CH_3$ | $CHF_2$ | $CH_2CH=CH_2$ |
| H.166 | $CH_3$ | $CH_2F$ | $CH_2CH=CH_2$ |
| H.167 | $CH_3$ | Cl | $CH_2CH=CH_2$ |
| H.168 | $CH_3$ | $OCH_3$ | $CH_2CH=CH_2$ |
| H.169 | $CH_3$ | $OCH_2CH_3$ | $CH_2CH=CH_2$ |
| H.170 | $CH_3$ | CN | $CH_2CH=CH_2$ |
| H.171 | $CF_3$ | H | $CH_2CH=CH_2$ |
| H.172 | $CF_3$ | $CH_3$ | $CH_2CH=CH_2$ |
| H.173 | $CF_3$ | $CH_2CH_3$ | $CH_2CH=CH_2$ |
| H.174 | $CF_3$ | $CF_3$ | $CH_2CH=CH_2$ |
| H.175 | $CF_3$ | $CHF_2$ | $CH_2CH=CH_2$ |
| H.176 | $CF_3$ | $CH_2F$ | $CH_2CH=CH_2$ |
| H.177 | $CF_3$ | Cl | $CH_2CH=CH_2$ |
| H.178 | $CF_3$ | $OCH_3$ | $CH_2CH=CH_2$ |
| H.179 | $CF_3$ | $OCH_2CH_3$ | $CH_2CH=CH_2$ |
| H.180 | $CF_3$ | CN | $CH_2CH=CH_2$ |
| H.181 | Cl | H | $CH_2CH=CH-Cl$ (trans) |
| H.182 | Cl | $CH_3$ | $CH_2CH=CH-Cl$ (trans) |
| H.183 | Cl | $CH_2CH_3$ | $CH_2CH=CH-Cl$ (trans) |
| H.184 | Cl | $CF_3$ | $CH_2CH=CH-Cl$ (trans) |
| H.185 | Cl | $CHF_2$ | $CH_2CH=CH-Cl$ (trans) |
| H.186 | Cl | $CH_2F$ | $CH_2CH=CH-Cl$ (trans) |
| H.187 | Cl | Cl | $CH_2CH=CH-Cl$ (trans) |
| H.188 | Cl | $OCH_3$ | $CH_2CH=CH-Cl$ (trans) |
| H.189 | Cl | $OCH_2CH_3$ | $CH_2CH=CH-Cl$ (trans) |
| H.190 | Cl | CN | $CH_2CH=CH-Cl$ (trans) |
| H.191 | $CH_3$ | H | $CH_2CH=CH-Cl$ (trans) |
| H.192 | $CH_3$ | $CH_3$ | $CH_2CH=CH-Cl$ (trans) |
| H.193 | $CH_3$ | $CH_2CH_3$ | $CH_2CH=CH-Cl$ (trans) |
| H.194 | $CH_3$ | $CF_3$ | $CH_2CH=CH-Cl$ (trans) |
| H.195 | $CH_3$ | $CHF_2$ | $CH_2CH=CH-Cl$ (trans) |
| H.196 | $CH_3$ | $CH_2F$ | $CH_2CH=CH-Cl$ (trans) |
| H.197 | $CH_3$ | Cl | $CH_2CH=CH-Cl$ (trans) |
| H.198 | $CH_3$ | $OCH_3$ | $CH_2CH=CH-Cl$ (trans) |
| H.199 | $CH_3$ | $OCH_2CH_3$ | $CH_2CH=CH-Cl$ (trans) |
| H.200 | $CH_3$ | CN | $CH_2CH=CH-Cl$ (trans) |
| H.201 | $CF_3$ | H | $CH_2CH=CH-Cl$ (trans) |
| H.202 | $CF_3$ | $CH_3$ | $CH_2CH=CH-Cl$ (trans) |
| H.203 | $CF_3$ | $CH_2CH_3$ | $CH_2CH=CH-Cl$ (trans) |
| H.204 | $CF_3$ | $CF_3$ | $CH_2CH=CH-Cl$ (trans) |
| H.205 | $CF_3$ | $CHF_2$ | $CH_2CH=CH-Cl$ (trans) |
| H.206 | $CF_3$ | $CH_2F$ | $CH_2CH=CH-Cl$ (trans) |
| H.207 | $CF_3$ | Cl | $CH_2CH=CH-Cl$ (trans) |
| H.208 | $CF_3$ | $OCH_3$ | $CH_2CH=CH-Cl$ (trans) |
| H.209 | $CF_3$ | $OCH_2CH_3$ | $CH_2CH=CH-Cl$ (trans) |
| H.210 | $CF_3$ | CN | $CH_2CH=CH-Cl$ (trans) |
| H.211 | Cl | H | $CH_2CCl=CH_2$ |
| H.212 | Cl | $CH_3$ | $CH_2CCl=CH_2$ |
| H.213 | Cl | $CH_2CH_3$ | $CH_2CCl=CH_2$ |
| H.214 | Cl | $CF_3$ | $CH_2CCl=CH_2$ |
| H.215 | Cl | $CHF_2$ | $CH_2CCl=CH_2$ |
| H.216 | Cl | $CH_2F$ | $CH_2CCl=CH_2$ |
| H.217 | Cl | Cl | $CH_2CCl=CH_2$ |
| H.218 | Cl | $OCH_3$ | $CH_2CCl=CH_2$ |
| H.219 | Cl | $OCH_2CH_3$ | $CH_2CCl=CH_2$ |
| H.220 | Cl | CN | $CH_2CCl=CH_2$ |
| H.221 | $CH_3$ | H | $CH_2CCl=CH_2$ |
| H.222 | $CH_3$ | $CH_3$ | $CH_2CCl=CH_2$ |
| H.223 | $CH_3$ | $CH_2CH_3$ | $CH_2CCl=CH_2$ |
| H.224 | $CH_3$ | $CF_3$ | $CH_2CCl=CH_2$ |
| H.225 | $CH_3$ | $CHF_2$ | $CH_2CCl=CH_2$ |
| H.226 | $CH_3$ | $CH_2F$ | $CH_2CCl=CH_2$ |
| H.227 | $CH_3$ | Cl | $CH_2CCl=CH_2$ |
| H.228 | $CH_3$ | $OCH_3$ | $CH_2CCl=CH_2$ |
| H.229 | $CH_3$ | $OCH_2CH_3$ | $CH_2CCl=CH_2$ |
| H.230 | $CH_3$ | CN | $CH_2CCl=CH_2$ |
| H.231 | $CF_3$ | H | $CH_2CCl=CH_2$ |
| H.232 | $CF_3$ | $CH_3$ | $CH_2CCl=CH_2$ |
| H.233 | $CF_3$ | $CH_2CH_3$ | $CH_2CCl=CH_2$ |
| H.234 | $CF_3$ | $CF_3$ | $CH_2CCl=CH_2$ |
| H.235 | $CF_3$ | $CHF_2$ | $CH_2CCl=CH_2$ |
| H.236 | $CF_3$ | $CH_2F$ | $CH_2CCl=CH_2$ |
| H.237 | $CF_3$ | Cl | $CH_2CCl=CH_2$ |
| H.238 | $CF_3$ | $OCH_3$ | $CH_2CCl=CH_2$ |
| H.239 | $CF_3$ | $OCH_2CH_3$ | $CH_2CCl=CH_2$ |
| H.240 | $CF_3$ | CN | $CH_2CCl=CH_2$ |
| H.241 | Cl | H | $CH_2C\equiv CH$ |
| H.242 | Cl | $CH_3$ | $CH_2C\equiv CH$ |
| H.243 | Cl | $CH_2CH_3$ | $CH_2C\equiv CH$ |
| H.244 | Cl | $CF_3$ | $CH_2C\equiv CH$ |
| H.245 | Cl | $CHF_2$ | $CH_2C\equiv CH$ |
| H.246 | Cl | $CH_2F$ | $CH_2C\equiv CH$ |
| H.247 | Cl | Cl | $CH_2C\equiv CH$ |
| H.248 | Cl | $OCH_3$ | $CH_2C\equiv CH$ |
| H.249 | Cl | $OCH_2CH_3$ | $CH_2C\equiv CH$ |
| H.250 | Cl | CN | $CH_2C\equiv CH$ |
| H.251 | $CH_3$ | H | $CH_2C\equiv CH$ |
| H.252 | $CH_3$ | $CH_3$ | $CH_2C\equiv CH$ |
| H.253 | $CH_3$ | $CH_2CH_3$ | $CH_2C\equiv CH$ |
| H.254 | $CH_3$ | $CF_3$ | $CH_2C\equiv CH$ |
| H.255 | $CH_3$ | $CHF_2$ | $CH_2C\equiv CH$ |
| H.256 | $CH_3$ | $CH_2F$ | $CH_2C\equiv CH$ |
| H.257 | $CH_3$ | Cl | $CH_2C\equiv CH$ |
| H.258 | $CH_3$ | $OCH_3$ | $CH_2C\equiv CH$ |
| H.259 | $CH_3$ | $OCH_2CH_3$ | $CH_2C\equiv CH$ |
| H.260 | $CH_3$ | CN | $CH_2C\equiv CH$ |
| H.261 | $CF_3$ | H | $CH_2C\equiv CH$ |
| H.262 | $CF_3$ | $CH_3$ | $CH_2C\equiv CH$ |
| H.263 | $CF_3$ | $CH_2CH_3$ | $CH_2C\equiv CH$ |
| H.264 | $CF_3$ | $CF_3$ | $CH_2C\equiv CH$ |
| H.265 | $CF_3$ | $CHF_2$ | $CH_2C\equiv CH$ |
| H.266 | $CF_3$ | $CH_2F$ | $CH_2C\equiv CH$ |
| H.267 | $CF_3$ | Cl | $CH_2C\equiv CH$ |
| H.268 | $CF_3$ | $OCH_3$ | $CH_2C\equiv CH$ |
| H.269 | $CF_3$ | $OCH_2CH_3$ | $CH_2C\equiv CH$ |
| H.270 | $CF_3$ | CN | $CH_2C\equiv CH$ |
| H.271 | Cl | H | $CH_2C\equiv CCH_3$ |
| H.272 | Cl | $CH_3$ | $CH_2C\equiv CCH_3$ |
| H.273 | Cl | $CH_2CH_3$ | $CH_2C\equiv CCH_3$ |
| H.274 | Cl | $CF_3$ | $CH_2C\equiv CCH_3$ |
| H.275 | Cl | $CHF_2$ | $CH_2C\equiv CCH_3$ |
| H.276 | Cl | $CH_2F$ | $CH_2C\equiv CCH_3$ |
| H.277 | Cl | Cl | $CH_2C\equiv CCH_3$ |
| H.278 | Cl | $OCH_3$ | $CH_2C\equiv CCH_3$ |
| H.279 | Cl | $OCH_2CH_3$ | $CH_2C\equiv CCH_3$ |
| H.280 | Cl | CN | $CH_2C\equiv CCH_3$ |
| H.281 | $CH_3$ | H | $CH_2C\equiv CCH_3$ |
| H.282 | $CH_3$ | $CH_3$ | $CH_2C\equiv CCH_3$ |
| H.283 | $CH_3$ | $CH_2CH_3$ | $CH_2C\equiv CCH_3$ |
| H.284 | $CH_3$ | $CF_3$ | $CH_2C\equiv CCH_3$ |
| H.285 | $CH_3$ | $CHF_2$ | $CH_2C\equiv CCH_3$ |
| H.286 | $CH_3$ | $CH_2F$ | $CH_2C\equiv CCH_3$ |
| H.287 | $CH_3$ | Cl | $CH_2C\equiv CCH_3$ |
| H.288 | $CH_3$ | $OCH_3$ | $CH_2C\equiv CCH_3$ |
| H.289 | $CH_3$ | $OCH_2CH_3$ | $CH_2C\equiv CCH_3$ |
| H.290 | $CH_3$ | CN | $CH_2C\equiv CCH_3$ |
| H.291 | $CF_3$ | H | $CH_2C\equiv CCH_3$ |
| H.292 | $CF_3$ | $CH_3$ | $CH_2C\equiv CCH_3$ |
| H.293 | $CF_3$ | $CH_2CH_3$ | $CH_2C\equiv CCH_3$ |
| H.294 | $CF_3$ | $CF_3$ | $CH_2C\equiv CCH_3$ |
| H.295 | $CF_3$ | $CHF_2$ | $CH_2C\equiv CCH_3$ |
| H.296 | $CF_3$ | $CH_2F$ | $CH_2C\equiv CCH_3$ |
| H.297 | $CF_3$ | Cl | $CH_2C\equiv CCH_3$ |
| H.298 | $CF_3$ | $OCH_3$ | $CH_2C\equiv CCH_3$ |
| H.299 | $CF_3$ | $OCH_2CH_3$ | $CH_2C\equiv CCH_3$ |
| H.300 | $CF_3$ | CN | $CH_2C\equiv CCH_3$ |
| H.301 | Cl | H | $CH_2C\equiv C-I$ |
| H.302 | Cl | $CH_3$ | $CH_2C\equiv C-I$ |
| H.303 | Cl | $CH_2CH_3$ | $CH_2C\equiv C-I$ |
| H.304 | Cl | $CF_3$ | $CH_2C\equiv C-I$ |
| H.305 | Cl | $CHF_2$ | $CH_2C\equiv C-I$ |
| H.306 | Cl | $CH_2F$ | $CH_2C\equiv C-I$ |
| H.307 | Cl | Cl | $CH_2C\equiv C-I$ |
| H.308 | Cl | $OCH_3$ | $CH_2C\equiv C-I$ |

TABLE H-continued

| No. | $R^b$ | $R^\alpha$ | $R^\beta$ |
|---|---|---|---|
| H.309 | Cl | OCH$_2$CH$_3$ | CH$_2$C≡C—I |
| H.310 | Cl | CN | CH$_2$C≡C—I |
| H.311 | CH$_3$ | H | CH$_2$C≡C—I |
| H.312 | CH$_3$ | CH$_3$ | CH$_2$C≡C—I |
| H.313 | CH$_3$ | CH$_2$CH$_3$ | CH$_2$C≡C—I |
| H.314 | CH$_3$ | CF$_3$ | CH$_2$C≡C—I |
| H.315 | CH$_3$ | CHF$_2$ | CH$_2$C≡C—I |
| H.316 | CH$_3$ | CH$_2$F | CH$_2$C≡C—I |
| H.317 | CH$_3$ | Cl | CH$_2$C≡C—I |
| H.318 | CH$_3$ | OCH$_3$ | CH$_2$C≡C—I |
| H.319 | CH$_3$ | OCH$_2$CH$_3$ | CH$_2$C≡C—I |
| H.320 | CH$_3$ | CN | CH$_2$C≡C—I |
| H.321 | CF$_3$ | H | CH$_2$C≡C—I |
| H.322 | CF$_3$ | CH$_3$ | CH$_2$C≡C—I |
| H.323 | CF$_3$ | CH$_2$CH$_3$ | CH$_2$C≡C—I |
| H.324 | CF$_3$ | CF$_3$ | CH$_2$C≡C—I |
| H.325 | CF$_3$ | CHF$_2$ | CH$_2$C≡C—I |
| H.326 | CF$_3$ | CH$_2$F | CH$_2$C≡C—I |
| H.327 | CF$_3$ | Cl | CH$_2$C≡C—I |
| H.328 | CF$_3$ | OCH$_3$ | CH$_2$C≡C—I |
| H.329 | CF$_3$ | OCH$_2$CH$_3$ | CH$_2$C≡C—I |
| H.330 | CF$_3$ | CN | CH$_2$C≡C—I |
| H.331 | Cl | H | CH(CH$_3$)C≡CH |
| H.332 | Cl | CH$_3$ | CH(CH$_3$)C≡CH |
| H.333 | Cl | CH$_2$CH$_3$ | CH(CH$_3$)C≡CH |
| H.334 | Cl | CF$_3$ | CH(CH$_3$)C≡CH |
| H.335 | Cl | CHF$_2$ | CH(CH$_3$)C≡CH |
| H.336 | Cl | CH$_2$F | CH(CH$_3$)C≡CH |
| H.337 | Cl | Cl | CH(CH$_3$)C≡CH |
| H.338 | Cl | OCH$_3$ | CH(CH$_3$)C≡CH |
| H.339 | Cl | OCH$_2$CH$_3$ | CH(CH$_3$)C≡CH |
| H.340 | Cl | CN | CH(CH$_3$)C≡CH |
| H.341 | CH$_3$ | H | CH(CH$_3$)C≡CH |
| H.342 | CH$_3$ | CH$_3$ | CH(CH$_3$)C≡CH |
| H.343 | CH$_3$ | CH$_2$CH$_3$ | CH(CH$_3$)C≡CH |
| H.344 | CH$_3$ | CF$_3$ | CH(CH$_3$)C≡CH |
| H.345 | CH$_3$ | CHF$_2$ | CH(CH$_3$)C≡CH |
| H.346 | CH$_3$ | CH$_2$F | CH(CH$_3$)C≡CH |
| H.347 | CH$_3$ | Cl | CH(CH$_3$)C≡CH |
| H.348 | CH$_3$ | OCH$_3$ | CH(CH$_3$)C≡CH |
| H.349 | CH$_3$ | OCH$_2$CH$_3$ | CH(CH$_3$)C≡CH |
| H.350 | CH$_3$ | CN | CH(CH$_3$)C≡CH |
| H.351 | CF$_3$ | H | CH(CH$_3$)C≡CH |
| H.352 | CF$_3$ | CH$_3$ | CH(CH$_3$)C≡CH |
| H.353 | CF$_3$ | CH$_2$CH$_3$ | CH(CH$_3$)C≡CH |
| H.354 | CF$_3$ | CF$_3$ | CH(CH$_3$)C≡CH |
| H.355 | CF$_3$ | CHF$_2$ | CH(CH$_3$)C≡CH |
| H.356 | CF$_3$ | CH$_2$F | CH(CH$_3$)C≡CH |
| H.357 | CF$_3$ | Cl | CH(CH$_3$)C≡CH |
| H.358 | CF$_3$ | OCH$_3$ | CH(CH$_3$)C≡CH |
| H.359 | CF$_3$ | OCH$_2$CH$_3$ | CH(CH$_3$)C≡CH |
| H.360 | CF$_3$ | CN | CH(CH$_3$)C≡CH |
| H.361 | Cl | H | CH$_2$CH$_2$—O—CH$_2$CH$_3$ |
| H.362 | Cl | CH$_3$ | CH$_2$CH$_2$—O—CH$_2$CH$_3$ |
| H.363 | Cl | CH$_2$CH$_3$ | CH$_2$CH$_2$—O—CH$_2$CH$_3$ |
| H.364 | Cl | CF$_3$ | CH$_2$CH$_2$—O—CH$_2$CH$_3$ |
| H.365 | Cl | CHF$_2$ | CH$_2$CH$_2$—O—CH$_2$CH$_3$ |
| H.366 | Cl | CH$_2$F | CH$_2$CH$_2$—O—CH$_2$CH$_3$ |
| H.367 | Cl | Cl | CH$_2$CH$_2$—O—CH$_2$CH$_3$ |
| H.368 | Cl | OCH$_3$ | CH$_2$CH$_2$—O—CH$_2$CH$_3$ |
| H.369 | Cl | OCH$_2$CH$_3$ | CH$_2$CH$_2$—O—CH$_2$CH$_3$ |
| H.370 | Cl | CN | CH$_2$CH$_2$—O—CH$_2$CH$_3$ |
| H.371 | CH$_3$ | H | CH$_2$CH$_2$—O—CH$_2$CH$_3$ |
| H.372 | CH$_3$ | CH$_3$ | CH$_2$CH$_2$—O—CH$_2$CH$_3$ |
| H.373 | CH$_3$ | CH$_2$CH$_3$ | CH$_2$CH$_2$—O—CH$_2$CH$_3$ |
| H.374 | CH$_3$ | CF$_3$ | CH$_2$CH$_2$—O—CH$_2$CH$_3$ |
| H.375 | CH$_3$ | CHF$_2$ | CH$_2$CH$_2$—O—CH$_2$CH$_3$ |
| H.376 | CH$_3$ | CH$_2$F | CH$_2$CH$_2$—O—CH$_2$CH$_3$ |
| H.377 | CH$_3$ | Cl | CH$_2$CH$_2$—O—CH$_2$CH$_3$ |
| H.378 | CH$_3$ | OCH$_3$ | CH$_2$CH$_2$—O—CH$_2$CH$_3$ |
| H.379 | CH$_3$ | OCH$_2$CH$_3$ | CH$_2$CH$_2$—O—CH$_2$CH$_3$ |
| H.380 | CH$_3$ | CN | CH$_2$CH$_2$—O—CH$_2$CH$_3$ |
| H.381 | CF$_3$ | H | CH$_2$CH$_2$—O—CH$_2$CH$_3$ |
| H.382 | CF$_3$ | CH$_3$ | CH$_2$CH$_2$—O—CH$_2$CH$_3$ |
| H.383 | CF$_3$ | CH$_2$CH$_3$ | CH$_2$CH$_2$—O—CH$_2$CH$_3$ |
| H.384 | CF$_3$ | CF$_3$ | CH$_2$CH$_2$—O—CH$_2$CH$_3$ |
| H.385 | CF$_3$ | CHF$_2$ | CH$_2$CH$_2$—O—CH$_2$CH$_3$ |
| H.386 | CF$_3$ | CH$_2$F | CH$_2$CH$_2$—O—CH$_2$CH$_3$ |
| H.387 | CF$_3$ | Cl | CH$_2$CH$_2$—O—CH$_2$CH$_3$ |
| H.388 | CF$_3$ | OCH$_3$ | CH$_2$CH$_2$—O—CH$_2$CH$_3$ |
| H.389 | CF$_3$ | OCH$_2$CH$_3$ | CH$_2$CH$_2$—O—CH$_2$CH$_3$ |
| H.390 | CF$_3$ | CN | CH$_2$CH$_2$—O—CH$_2$CH$_3$ |
| H.391 | Cl | H | CH$_2$—C$_6$H$_5$ |
| H.392 | Cl | CH$_3$ | CH$_2$—C$_6$H$_5$ |
| H.393 | Cl | CH$_2$CH$_3$ | CH$_2$—C$_6$H$_5$ |
| H.394 | Cl | CF$_3$ | CH$_2$—C$_6$H$_5$ |
| H.395 | Cl | CHF$_2$ | CH$_2$—C$_6$H$_5$ |
| H.396 | Cl | CH$_2$F | CH$_2$—C$_6$H$_5$ |
| H.397 | Cl | Cl | CH$_2$—C$_6$H$_5$ |
| H.398 | Cl | OCH$_3$ | CH$_2$—C$_6$H$_5$ |
| H.399 | Cl | OCH$_2$CH$_3$ | CH$_2$—C$_6$H$_5$ |
| H.400 | Cl | CN | CH$_2$—C$_6$H$_5$ |
| H.401 | CH$_3$ | H | CH$_2$—C$_6$H$_5$ |
| H.402 | CH$_3$ | CH$_3$ | CH$_2$—C$_6$H$_5$ |
| H.403 | CH$_3$ | CH$_2$CH$_3$ | CH$_2$—C$_6$H$_5$ |
| H.404 | CH$_3$ | CF$_3$ | CH$_2$—C$_6$H$_5$ |
| H.405 | CH$_3$ | CHF$_2$ | CH$_2$—C$_6$H$_5$ |
| H.406 | CH$_3$ | CH$_2$F | CH$_2$—C$_6$H$_5$ |
| H.407 | CH$_3$ | Cl | CH$_2$—C$_6$H$_5$ |
| H.408 | CH$_3$ | OCH$_3$ | CH$_2$—C$_6$H$_5$ |
| H.409 | CH$_3$ | OCH$_2$CH$_3$ | CH$_2$—C$_6$H$_5$ |
| H.410 | CH$_3$ | CN | CH$_2$—C$_6$H$_5$ |
| H.411 | CF$_3$ | H | CH$_2$—C$_6$H$_5$ |
| H.412 | CF$_3$ | CH$_3$ | CH$_2$—C$_6$H$_5$ |
| H.413 | CF$_3$ | CH$_2$CH$_3$ | CH$_2$—C$_6$H$_5$ |
| H.414 | CF$_3$ | CF$_3$ | CH$_2$—C$_6$H$_5$ |
| H.415 | CF$_3$ | CHF$_2$ | CH$_2$—C$_6$H$_5$ |
| H.416 | CF$_3$ | CH$_2$F | CH$_2$—C$_6$H$_5$ |
| H.417 | CF$_3$ | Cl | CH$_2$—C$_6$H$_5$ |
| H.418 | CF$_3$ | OCH$_3$ | CH$_2$—C$_6$H$_5$ |
| H.419 | CF$_3$ | OCH$_2$CH$_3$ | CH$_2$—C$_6$H$_5$ |
| H.420 | CF$_3$ | CN | CH$_2$—C$_6$H$_5$ |
| H.421 | Cl | H | cyclopropyl |
| H.422 | Cl | CH$_3$ | cyclopropyl |
| H.423 | Cl | CH$_2$CH$_3$ | cyclopropyl |
| H.424 | Cl | CF$_3$ | cyclopropyl |
| H.425 | Cl | CHF$_2$ | cyclopropyl |
| H.426 | Cl | CH$_2$F | cyclopropyl |
| H.427 | Cl | Cl | cyclopropyl |
| H.428 | Cl | OCH$_3$ | cyclopropyl |
| H.429 | Cl | OCH$_2$CH$_3$ | cyclopropyl |
| H.430 | Cl | CN | cyclopropyl |
| H.431 | Cl | H | cyclopropyl |
| H.432 | CH$_3$ | CH$_3$ | cyclopropyl |
| H.433 | CH$_3$ | CH$_2$CH$_3$ | cyclopropyl |
| H.434 | CH$_3$ | CF$_3$ | cyclopropyl |
| H.435 | CH$_3$ | CHF$_2$ | cyclopropyl |
| H.436 | CH$_3$ | CH$_2$F | cyclopropyl |
| H.437 | CH$_3$ | Cl | cyclopropyl |
| H.438 | CH$_3$ | OCH$_3$ | cyclopropyl |
| H.439 | CH$_3$ | OCH$_2$CH$_3$ | cyclopropyl |
| H.440 | CH$_3$ | CN | cyclopropyl |
| H.441 | CF$_3$ | H | cyclopropyl |
| H.442 | CF$_3$ | CH$_3$ | cyclopropyl |
| H.443 | CF$_3$ | CH$_2$CH$_3$ | cyclopropyl |
| H.444 | CF$_3$ | CF$_3$ | cyclopropyl |
| H.445 | CF$_3$ | CHF$_2$ | cyclopropyl |
| H.446 | CF$_3$ | CH$_2$F | cyclopropyl |
| H.447 | CF$_3$ | Cl | cyclopropyl |
| H.448 | CF$_3$ | OCH$_3$ | cyclopropyl |
| H.449 | CF$_3$ | OCH$_2$CH$_3$ | cyclopropyl |
| H.450 | CF$_3$ | CN | cyclopropyl |
| H.451 | Cl | H | CH$_2$-(2,2-Cl$_2$-cyclopropyl) |
| H.452 | Cl | CH$_3$ | CH$_2$-(2,2-Cl$_2$-cyclopropyl) |
| H.453 | Cl | CH$_2$CH$_3$ | CH$_2$-(2,2-Cl$_2$-cyclopropyl) |
| H.454 | Cl | CF$_3$ | CH$_2$-(2,2-Cl$_2$-cyclopropyl) |
| H.455 | Cl | CHF$_2$ | CH$_2$-(2,2-Cl$_2$-cyclopropyl) |
| H.456 | Cl | CH$_2$F | CH$_2$-(2,2-Cl$_2$-cyclopropyl) |
| H.457 | Cl | Cl | CH$_2$-(2,2-Cl$_2$-cyclopropyl) |
| H.458 | Cl | OCH$_3$ | CH$_2$-(2,2-Cl$_2$-cyclopropyl) |
| H.459 | Cl | OCH$_2$CH$_3$ | CH$_2$-(2,2-Cl$_2$-cyclopropyl) |
| H.460 | Cl | CN | CH$_2$-(2,2-Cl$_2$-cyclopropyl) |
| H.461 | CH$_3$ | H | CH$_2$-(2,2-Cl$_2$-cyclopropyl) |
| H.462 | CH$_3$ | CH$_3$ | CH$_2$-(2,2-Cl$_2$-cyclopropyl) |

TABLE H-continued

| No. | $R^b$ | $R^\alpha$ | $R^\beta$ |
|---|---|---|---|
| H.463 | $CH_3$ | $CH_2CH_3$ | $CH_2$-(2,2-$Cl_2$-cyclopropyl) |
| H.464 | $CH_3$ | $CF_3$ | $CH_2$-(2,2-$Cl_2$-cyclopropyl) |
| H.465 | $CH_3$ | $CHF_2$ | $CH_2$-(2,2-$Cl_2$-cyclopropyl) |
| H.466 | $CH_3$ | $CH_2F$ | $CH_2$-(2,2-$Cl_2$-cyclopropyl) |
| H.467 | $CH_3$ | Cl | $CH_2$-(2,2-$Cl_2$-cyclopropyl) |
| H.468 | $CH_3$ | $OCH_3$ | $CH_2$-(2,2-$Cl_2$-cyclopropyl) |
| H.469 | $CH_3$ | $OCH_2CH_3$ | $CH_2$-(2,2-$Cl_2$-cyclopropyl) |
| H.470 | $CH_3$ | CN | $CH_2$-(2,2-$Cl_2$-cyclopropyl) |
| H.471 | $CF_3$ | H | $CH_2$-(2,2-$Cl_2$-cyclopropyl) |
| H.472 | $CF_3$ | $CH_3$ | $CH_2$-(2,2-$Cl_2$-cyclopropyl) |
| H.473 | $CF_3$ | $CH_2CH_3$ | $CH_2$-(2,2-$Cl_2$-cyclopropyl) |
| H.474 | $CF_3$ | $CF_3$ | $CH_2$-(2,2-$Cl_2$-cyclopropyl) |
| H.475 | $CF_3$ | $CHF_2$ | $CH_2$-(2,2-$Cl_2$-cyclopropyl) |
| H.476 | $CF_3$ | $CH_2F$ | $CH_2$-(2,2-$Cl_2$-cyclopropyl) |
| H.477 | $CF_3$ | Cl | $CH_2$-(2,2-$Cl_2$-cyclopropyl) |
| H.478 | $CF_3$ | $OCH_3$ | $CH_2$-(2,2-$Cl_2$-cyclopropyl) |
| H.479 | $CF_3$ | $OCH_2CH_3$ | $CH_2$-(2,2-$Cl_2$-cyclopropyl) |
| H.480 | $CF_3$ | CN | $CH_2$-(2,2-$Cl_2$-cyclopropyl) |
| H.481 | H | $CH_3$ | H |
| H.482 | H | $CH_2CH_3$ | H |
| H.483 | H | $CF_3$ | H |
| H.484 | H | Cl | H |
| H.485 | H | $OCH_3$ | H |
| H.486 | $CH_2CH_3$ | $CH_3$ | H |
| H.487 | $CH_2CH_3$ | $CH_2CH_3$ | H |
| H.488 | $CH_2CH_3$ | $CF_3$ | H |
| H.489 | $CH_2CH_3$ | Cl | H |
| H.490 | $CH_2CH_3$ | $OCH_3$ | H |
| H.491 | $CHF_2$ | $CH_3$ | H |
| H.492 | $CHF_2$ | $CH_2CH_3$ | H |
| H.493 | $CHF_2$ | $CF_3$ | H |
| H.494 | $CHF_2$ | Cl | H |
| H.495 | $CHF_2$ | $OCH_3$ | H |
| H.496 | $CH_2F$ | $CH_3$ | H |
| H.497 | $CH_2F$ | $CH_2CH_3$ | H |
| H.498 | $CH_2F$ | $CF_3$ | H |
| H.499 | $CH_2F$ | Cl | H |
| H.500 | $CH_2F$ | $OCH_3$ | H |
| H.501 | $OCH_3$ | $CH_3$ | H |
| H.502 | $OCH_3$ | $CH_2CH_3$ | H |
| H.503 | $OCH_3$ | $CF_3$ | H |
| H.504 | $OCH_3$ | Cl | H |
| H.505 | $OCH_3$ | $OCH_3$ | H |
| H.506 | $OCH_2CH_3$ | $CH_3$ | H |
| H.507 | $OCH_2CH_3$ | $CH_2CH_3$ | H |
| H.508 | $OCH_2CH_3$ | $CF_3$ | H |
| H.509 | $OCH_2CH_3$ | Cl | H |
| H.510 | $OCH_2CH_3$ | $OCH_3$ | H |
| H.511 | CN | $CH_3$ | H |
| H.512 | CN | $CH_2CH_3$ | H |
| H.513 | CN | $CF_3$ | H |
| H.514 | CN | Cl | H |
| H.1029 | CN | $OCH_3$ | H |
| H.1030 | H | $CH_3$ | $CH_3$ |
| H.1031 | H | $CH_2CH_3$ | $CH_3$ |
| H.1032 | H | $CF_3$ | $CH_3$ |
| H.1033 | H | Cl | $CH_3$ |
| H.1034 | H | $OCH_3$ | $CH_3$ |
| H.1035 | $CH_2CH_3$ | $CH_3$ | $CH_3$ |
| H.1036 | $CH_2CH_3$ | $CH_2CH_3$ | $CH_3$ |
| H.1037 | $CH_2CH_3$ | $CF_3$ | $CH_3$ |
| H.1038 | $CH_2CH_3$ | Cl | $CH_3$ |
| H.1039 | $CH_2CH_3$ | $OCH_3$ | $CH_3$ |
| H.1040 | $CHF_2$ | $CH_3$ | $CH_3$ |
| H.1041 | $CHF_2$ | $CH_2CH_3$ | $CH_3$ |
| H.1042 | $CHF_2$ | $CF_3$ | $CH_3$ |
| H.1043 | $CHF_2$ | Cl | $CH_3$ |
| H.1044 | $CHF_2$ | $OCH_3$ | $CH_3$ |
| H.1045 | $CH_2F$ | $CH_3$ | $CH_3$ |
| H.1046 | $CH_2F$ | $CH_2CH_3$ | $CH_3$ |
| H.1047 | $CH_2F$ | $CF_3$ | $CH_3$ |
| H.1048 | $CH_2F$ | Cl | $CH_3$ |
| H.1049 | $CH_2F$ | $OCH_3$ | $CH_3$ |
| H.1050 | $OCH_3$ | $CH_3$ | $CH_3$ |
| H.1051 | $OCH_3$ | $CH_2CH_3$ | $CH_3$ |
| H.1052 | $OCH_3$ | $CF_3$ | $CH_3$ |
| H.1053 | $OCH_3$ | Cl | $CH_3$ |
| H.1054 | $OCH_3$ | $OCH_3$ | $CH_3$ |
| H.1055 | $OCH_2CH_3$ | $CH_3$ | $CH_3$ |
| H.1056 | $OCH_2CH_3$ | $CH_2CH_3$ | $CH_3$ |
| H.1057 | $OCH_2CH_3$ | $CF_3$ | $CH_3$ |
| H.1058 | $OCH_2CH_3$ | Cl | $CH_3$ |
| H.1059 | $OCH_2CH_3$ | $OCH_3$ | $CH_3$ |
| H.1060 | CN | $CH_3$ | $CH_3$ |
| H.1061 | CN | $CH_2CH_3$ | $CH_3$ |
| H.1062 | CN | $CF_3$ | $CH_3$ |
| H.1063 | CN | Cl | $CH_3$ |
| H.1064 | CN | $OCH_3$ | $CH_3$ |
| H.1065 | H | $CH_3$ | $CH_2CH_3$ |
| H.1066 | H | $CH_2CH_3$ | $CH_2CH_3$ |
| H.1067 | H | $CF_3$ | $CH_2CH_3$ |
| H.1068 | H | Cl | $CH_2CH_3$ |
| H.1069 | H | $OCH_3$ | $CH_2CH_3$ |
| H.1070 | $CH_2CH_3$ | $CH_3$ | $CH_2CH_3$ |
| H.1071 | $CH_2CH_3$ | $CH_2CH_3$ | $CH_2CH_3$ |
| H.1072 | $CH_2CH_3$ | $CF_3$ | $CH_2CH_3$ |
| H.1073 | $CH_2CH_3$ | Cl | $CH_2CH_3$ |
| H.1074 | $CH_2CH_3$ | $OCH_3$ | $CH_2CH_3$ |
| H.1075 | $CHF_2$ | $CH_3$ | $CH_2CH_3$ |
| H.1076 | $CHF_2$ | $CH_2CH_3$ | $CH_2CH_3$ |
| H.1077 | $CHF_2$ | $CF_3$ | $CH_2CH_3$ |
| H.1078 | $CHF_2$ | Cl | $CH_2CH_3$ |
| H.1079 | $CHF_2$ | $OCH_3$ | $CH_2CH_3$ |
| H.1080 | $CH_2F$ | $CH_3$ | $CH_2CH_3$ |
| H.1081 | $CH_2F$ | $CH_2CH_3$ | $CH_2CH_3$ |
| H.1082 | $CH_2F$ | $CF_3$ | $CH_2CH_3$ |
| H.1083 | $CH_2F$ | Cl | $CH_2CH_3$ |
| H.1084 | $CH_2F$ | $OCH_3$ | $CH_2CH_3$ |
| H.1085 | $OCH_3$ | $CH_3$ | $CH_2CH_3$ |
| H.1086 | $OCH_3$ | $CH_2CH_3$ | $CH_2CH_3$ |
| H.1087 | $OCH_3$ | $CF_3$ | $CH_2CH_3$ |
| H.1088 | $OCH_3$ | Cl | $CH_2CH_3$ |
| H.1089 | $OCH_3$ | $OCH_3$ | $CH_2CH_3$ |
| H.1090 | $OCH_2CH_3$ | $CH_3$ | $CH_2CH_3$ |
| H.1091 | $OCH_2CH_3$ | $CH_2CH_3$ | $CH_2CH_3$ |
| H.1092 | $OCH_2CH_3$ | $CF_3$ | $CH_2CH_3$ |
| H.1093 | $OCH_2CH_3$ | Cl | $CH_2CH_3$ |
| H.1094 | $OCH_2CH_3$ | $OCH_3$ | $CH_2CH_3$ |
| H.1095 | CN | $CH_3$ | $CH_2CH_3$ |
| H.1096 | CN | $CH_2CH_3$ | $CH_2CH_3$ |
| H.1097 | CN | $CF_3$ | $CH_2CH_3$ |
| H.1098 | CN | Cl | $CH_2CH_3$ |
| H.1099 | CN | $OCH_3$ | $CH_2CH_3$ |
| H.1100 | H | $CH_3$ | $CH_2CH_2CH_3$ |
| H.1101 | H | $CH_2CH_3$ | $CH_2CH_2CH_3$ |
| H.1102 | H | $CF_3$ | $CH_2CH_2CH_3$ |
| H.1103 | H | Cl | $CH_2CH_2CH_3$ |
| H.1104 | H | $OCH_3$ | $CH_2CH_2CH_3$ |
| H.1105 | $CH_2CH_3$ | $CH_3$ | $CH_2CH_2CH_3$ |
| H.1106 | $CH_2CH_3$ | $CH_2CH_3$ | $CH_2CH_2CH_3$ |
| H.1107 | $CH_2CH_3$ | $CF_3$ | $CH_2CH_2CH_3$ |
| H.1108 | $CH_2CH_3$ | Cl | $CH_2CH_2CH_3$ |
| H.1109 | $CH_2CH_3$ | $OCH_3$ | $CH_2CH_2CH_3$ |
| H.1110 | $CHF_2$ | $CH_3$ | $CH_2CH_2CH_3$ |
| H.1111 | $CHF_2$ | $CH_2CH_3$ | $CH_2CH_2CH_3$ |
| H.1112 | $CHF_2$ | $CF_3$ | $CH_2CH_2CH_3$ |
| H.1113 | $CHF_2$ | Cl | $CH_2CH_2CH_3$ |
| H.1114 | $CHF_2$ | $OCH_3$ | $CH_2CH_2CH_3$ |
| H.1115 | $CH_2F$ | $CH_3$ | $CH_2CH_2CH_3$ |
| H.1116 | $CH_2F$ | $CH_2CH_3$ | $CH_2CH_2CH_3$ |
| H.1117 | $CH_2F$ | $CF_3$ | $CH_2CH_2CH_3$ |
| H.1118 | $CH_2F$ | Cl | $CH_2CH_2CH_3$ |
| H.1119 | $CH_2F$ | $OCH_3$ | $CH_2CH_2CH_3$ |
| H.1120 | $OCH_3$ | $CH_3$ | $CH_2CH_2CH_3$ |
| H.1121 | $OCH_3$ | $CH_2CH_3$ | $CH_2CH_2CH_3$ |
| H.1122 | $OCH_3$ | $CF_3$ | $CH_2CH_2CH_3$ |
| H.1123 | $OCH_3$ | Cl | $CH_2CH_2CH_3$ |
| H.1124 | $OCH_3$ | $OCH_3$ | $CH_2CH_2CH_3$ |
| H.1125 | $OCH_2CH_3$ | $CH_3$ | $CH_2CH_2CH_3$ |
| H.1126 | $OCH_2CH_3$ | $CH_2CH_3$ | $CH_2CH_2CH_3$ |
| H.1127 | $OCH_2CH_3$ | $CF_3$ | $CH_2CH_2CH_3$ |
| H.1128 | $OCH_2CH_3$ | Cl | $CH_2CH_2CH_3$ |
| H.1129 | $OCH_2CH_3$ | $OCH_3$ | $CH_2CH_2CH_3$ |
| H.1130 | CN | $CH_3$ | $CH_2CH_2CH_3$ |

TABLE H-continued

| No. | R^b | R^α | R^β |
|---|---|---|---|
| H.1131 | CN | $CH_2CH_3$ | $CH_2CH_2CH_3$ |
| H.1132 | CN | $CF_3$ | $CH_2CH_2CH_3$ |
| H.1133 | CN | Cl | $CH_2CH_2CH_3$ |
| H.1134 | CN | $OCH_3$ | $CH_2CH_2CH_3$ |
| H.1135 | H | $CH_3$ | $CH(CH_3)_2$ |
| H.1136 | H | $CH_2CH_3$ | $CH(CH_3)_2$ |
| H.1137 | H | $CF_3$ | $CH(CH_3)_2$ |
| H.1138 | H | Cl | $CH(CH_3)_2$ |
| H.1139 | H | $OCH_3$ | $CH(CH_3)_2$ |
| H.1140 | $CH_2CH_3$ | $CH_3$ | $CH(CH_3)_2$ |
| H.1141 | $CH_2CH_3$ | $CH_2CH_3$ | $CH(CH_3)_2$ |
| H.1142 | $CH_2CH_3$ | $CF_3$ | $CH(CH_3)_2$ |
| H.1143 | $CH_2CH_3$ | Cl | $CH(CH_3)_2$ |
| H.1144 | $CH_2CH_3$ | $OCH_3$ | $CH(CH_3)_2$ |
| H.1145 | $CHF_2$ | $CH_3$ | $CH(CH_3)_2$ |
| H.1146 | $CHF_2$ | $CH_2CH_3$ | $CH(CH_3)_2$ |
| H.1147 | $CHF_2$ | $CF_3$ | $CH(CH_3)_2$ |
| H.1148 | $CHF_2$ | Cl | $CH(CH_3)_2$ |
| H.1149 | $CHF_2$ | $OCH_3$ | $CH(CH_3)_2$ |
| H.1150 | $CH_2F$ | $CH_3$ | $CH(CH_3)_2$ |
| H.1151 | $CH_2F$ | $CH_2CH_3$ | $CH(CH_3)_2$ |
| H.1152 | $CH_2F$ | $CF_3$ | $CH(CH_3)_2$ |
| H.1153 | $CH_2F$ | Cl | $CH(CH_3)_2$ |
| H.1154 | $CH_2F$ | $OCH_3$ | $CH(CH_3)_2$ |
| H.1155 | $OCH_3$ | $CH_3$ | $CH(CH_3)_2$ |
| H.1156 | $OCH_3$ | $CH_2CH_3$ | $CH(CH_3)_2$ |
| H.1157 | $OCH_3$ | $CF_3$ | $CH(CH_3)_2$ |
| H.1158 | $OCH_3$ | Cl | $CH(CH_3)_2$ |
| H.1159 | $OCH_3$ | $OCH_3$ | $CH(CH_3)_2$ |
| H.1160 | $OCH_2CH_3$ | $CH_3$ | $CH(CH_3)_2$ |
| H.1161 | $OCH_2CH_3$ | $CH_2CH_3$ | $CH(CH_3)_2$ |
| H.1162 | $OCH_2CH_3$ | $CF_3$ | $CH(CH_3)_2$ |
| H.1163 | $OCH_2CH_3$ | Cl | $CH(CH_3)_2$ |
| H.1164 | $OCH_2CH_3$ | $OCH_3$ | $CH(CH_3)_2$ |
| H.1165 | CN | $CH_3$ | $CH(CH_3)_2$ |
| H.1166 | CN | $CH_2CH_3$ | $CH(CH_3)_2$ |
| H.1167 | CN | $CF_3$ | $CH(CH_3)_2$ |
| H.1168 | CN | Cl | $CH(CH_3)_2$ |
| H.1169 | CN | $OCH_3$ | $CH(CH_3)_2$ |
| H.1170 | H | $CH_3$ | $CH_2CH=CH_2$ |
| H.1171 | H | $CH_2CH_3$ | $CH_2CH=CH_2$ |
| H.1172 | H | $CF_3$ | $CH_2CH=CH_2$ |
| H.1173 | H | Cl | $CH_2CH=CH_2$ |
| H.1174 | H | $OCH_3$ | $CH_2CH=CH_2$ |
| H.1175 | $CH_2CH_3$ | $CH_3$ | $CH_2CH=CH_2$ |
| H.1176 | $CH_2CH_3$ | $CH_2CH_3$ | $CH_2CH=CH_2$ |
| H.1177 | $CH_2CH_3$ | $CF_3$ | $CH_2CH=CH_2$ |
| H.1178 | $CH_2CH_3$ | Cl | $CH_2CH=CH_2$ |
| H.1179 | $CH_2CH_3$ | $OCH_3$ | $CH_2CH=CH_2$ |
| H.1180 | $CHF_2$ | $CH_3$ | $CH_2CH=CH_2$ |
| H.1181 | $CHF_2$ | $CH_2CH_3$ | $CH_2CH=CH_2$ |
| H.1182 | $CHF_2$ | $CF_3$ | $CH_2CH=CH_2$ |
| H.1183 | $CHF_2$ | Cl | $CH_2CH=CH_2$ |
| H.1184 | $CHF_2$ | $OCH_3$ | $CH_2CH=CH_2$ |
| H.1185 | $CH_2F$ | $CH_3$ | $CH_2CH=CH_2$ |
| H.1186 | $CH_2F$ | $CH_2CH_3$ | $CH_2CH=CH_2$ |
| H.1187 | $CH_2F$ | $CF_3$ | $CH_2CH=CH_2$ |
| H.1188 | $CH_2F$ | Cl | $CH_2CH=CH_2$ |
| H.1189 | $CH_2F$ | $OCH_3$ | $CH_2CH=CH_2$ |
| H.1190 | $OCH_3$ | $CH_3$ | $CH_2CH=CH_2$ |
| H.1191 | $OCH_3$ | $CH_2CH_3$ | $CH_2CH=CH_2$ |
| H.1192 | $OCH_3$ | $CF_3$ | $CH_2CH=CH_2$ |
| H.1193 | $OCH_3$ | Cl | $CH_2CH=CH_2$ |
| H.1194 | $OCH_3$ | $OCH_3$ | $CH_2CH=CH_2$ |
| H.1195 | $OCH_2CH_3$ | $CH_3$ | $CH_2CH=CH_2$ |
| H.1196 | $OCH_2CH_3$ | $CH_2CH_3$ | $CH_2CH=CH_2$ |
| H.1197 | $OCH_2CH_3$ | $CF_3$ | $CH_2CH=CH_2$ |
| H.1198 | $OCH_2CH_3$ | Cl | $CH_2CH=CH_2$ |
| H.1199 | $OCH_2CH_3$ | $OCH_3$ | $CH_2CH=CH_2$ |
| H.1200 | CN | $CH_3$ | $CH_2CH=CH_2$ |
| H.1201 | CN | $CH_2CH_3$ | $CH_2CH=CH_2$ |
| H.1202 | CN | $CF_3$ | $CH_2CH=CH_2$ |
| H.1203 | CN | Cl | $CH_2CH=CH_2$ |
| H.1204 | CN | $OCH_3$ | $CH_2CH=CH_2$ |
| H.1205 | H | $CH_3$ | $CH_2CH=CH-Cl$ (trans) |
| H.1206 | H | $CH_2CH_3$ | $CH_2CH=CH-Cl$ (trans) |
| H.1207 | H | $CF_3$ | $CH_2CH=CH-Cl$ (trans) |
| H.1208 | H | Cl | $CH_2CH=CH-Cl$ (trans) |
| H.1209 | H | $OCH_3$ | $CH_2CH=CH-Cl$ (trans) |
| H.1210 | $CH_2CH_3$ | $CH_3$ | $CH_2CH=CH-Cl$ (trans) |
| H.1211 | $CH_2CH_3$ | $CH_2CH_3$ | $CH_2CH=CH-Cl$ (trans) |
| H.1212 | $CH_2CH_3$ | $CF_3$ | $CH_2CH=CH-Cl$ (trans) |
| H.1213 | $CH_2CH_3$ | Cl | $CH_2CH=CH-Cl$ (trans) |
| H.1214 | $CH_2CH_3$ | $OCH_3$ | $CH_2CH=CH-Cl$ (trans) |
| H.1215 | $CHF_2$ | $CH_3$ | $CH_2CH=CH-Cl$ (trans) |
| H.1216 | $CHF_2$ | $CH_2CH_3$ | $CH_2CH=CH-Cl$ (trans) |
| H.1217 | $CHF_2$ | $CF_3$ | $CH_2CH=CH-Cl$ (trans) |
| H.1218 | $CHF_2$ | Cl | $CH_2CH=CH-Cl$ (trans) |
| H.1219 | $CHF_2$ | $OCH_3$ | $CH_2CH=CH-Cl$ (trans) |
| H.1220 | $CH_2F$ | $CH_3$ | $CH_2CH=CH-Cl$ (trans) |
| H.1221 | $CH_2F$ | $CH_2CH_3$ | $CH_2CH=CH-Cl$ (trans) |
| H.1222 | $CH_2F$ | $CF_3$ | $CH_2CH=CH-Cl$ (trans) |
| H.1223 | $CH_2F$ | Cl | $CH_2CH=CH-Cl$ (trans) |
| H.1224 | $CH_2F$ | $OCH_3$ | $CH_2CH=CH-Cl$ (trans) |
| H.1225 | $OCH_3$ | $CH_3$ | $CH_2CH=CH-Cl$ (trans) |
| H.1226 | $OCH_3$ | $CH_2CH_3$ | $CH_2CH=CH-Cl$ (trans) |
| H.1227 | $OCH_3$ | $CF_3$ | $CH_2CH=CH-Cl$ (trans) |
| H.1228 | $OCH_3$ | Cl | $CH_2CH=CH-Cl$ (trans) |
| H.1229 | $OCH_3$ | $OCH_3$ | $CH_2CH=CH-Cl$ (trans) |
| H.1230 | $OCH_2CH_3$ | $CH_3$ | $CH_2CH=CH-Cl$ (trans) |
| H.1231 | $OCH_2CH_3$ | $CH_2CH_3$ | $CH_2CH=CH-Cl$ (trans) |
| H.1232 | $OCH_2CH_3$ | $CF_3$ | $CH_2CH=CH-Cl$ (trans) |
| H.1233 | $OCH_2CH_3$ | Cl | $CH_2CH=CH-Cl$ (trans) |
| H.1234 | $OCH_2CH_3$ | $OCH_3$ | $CH_2CH=CH-Cl$ (trans) |
| H.1235 | CN | $CH_3$ | $CH_2CH=CH-Cl$ (trans) |
| H.1236 | CN | $CH_2CH_3$ | $CH_2CH=CH-Cl$ (trans) |
| H.1237 | CN | $CF_3$ | $CH_2CH=CH-Cl$ (trans) |
| H.1238 | CN | Cl | $CH_2CH=CH-Cl$ (trans) |
| H.1239 | CN | $OCH_3$ | $CH_2CH=CH-Cl$ (trans) |
| H.1240 | H | $CH_3$ | $CH_2CCl=CH_2$ |
| H.1241 | H | $CH_2CH_3$ | $CH_2CCl=CH_2$ |
| H.1242 | H | $CF_3$ | $CH_2CCl=CH_2$ |
| H.1243 | H | Cl | $CH_2CCl=CH_2$ |
| H.1244 | H | $OCH_3$ | $CH_2CCl=CH_2$ |
| H.1245 | $CH_2CH_3$ | $CH_3$ | $CH_2CCl=CH_2$ |
| H.1246 | $CH_2CH_3$ | $CH_2CH_3$ | $CH_2CCl=CH_2$ |
| H.1247 | $CH_2CH_3$ | $CF_3$ | $CH_2CCl=CH_2$ |
| H.1248 | $CH_2CH_3$ | Cl | $CH_2CCl=CH_2$ |
| H.1249 | $CH_2CH_3$ | $OCH_3$ | $CH_2CCl=CH_2$ |
| H.1250 | $CHF_2$ | $CH_3$ | $CH_2CCl=CH_2$ |
| H.1251 | $CHF_2$ | $CH_2CH_3$ | $CH_2CCl=CH_2$ |
| H.1252 | $CHF_2$ | $CF_3$ | $CH_2CCl=CH_2$ |
| H.1253 | $CHF_2$ | Cl | $CH_2CCl=CH_2$ |
| H.1254 | $CHF_2$ | $OCH_3$ | $CH_2CCl=CH_2$ |
| H.1255 | $CH_2F$ | $CH_3$ | $CH_2CCl=CH_2$ |
| H.1256 | $CH_2F$ | $CH_2CH_3$ | $CH_2CCl=CH_2$ |
| H.1257 | $CH_2F$ | $CF_3$ | $CH_2CCl=CH_2$ |
| H.1258 | $CH_2F$ | Cl | $CH_2CCl=CH_2$ |
| H.1259 | $CH_2F$ | $OCH_3$ | $CH_2CCl=CH_2$ |
| H.1260 | $OCH_3$ | $CH_3$ | $CH_2CCl=CH_2$ |
| H.1261 | $OCH_3$ | $CH_2CH_3$ | $CH_2CCl=CH_2$ |
| H.1262 | $OCH_3$ | $CF_3$ | $CH_2CCl=CH_2$ |
| H.1263 | $OCH_3$ | Cl | $CH_2CCl=CH_2$ |
| H.1264 | $OCH_3$ | $OCH_3$ | $CH_2CCl=CH_2$ |
| H.1265 | $OCH_2CH_3$ | $CH_3$ | $CH_2CCl=CH_2$ |
| H.1266 | $OCH_2CH_3$ | $CH_2CH_3$ | $CH_2CCl=CH_2$ |
| H.1267 | $OCH_2CH_3$ | $CF_3$ | $CH_2CCl=CH_2$ |
| H.1268 | $OCH_2CH_3$ | Cl | $CH_2CCl=CH_2$ |
| H.1269 | $OCH_2CH_3$ | $OCH_3$ | $CH_2CCl=CH_2$ |
| H.1270 | CN | $CH_3$ | $CH_2CCl=CH_2$ |
| H.1271 | CN | $CH_2CH_3$ | $CH_2CCl=CH_2$ |
| H.1272 | CN | $CF_3$ | $CH_2CCl=CH_2$ |
| H.1273 | CN | Cl | $CH_2CCl=CH_2$ |
| H.1274 | CN | $OCH_3$ | $CH_2CCl=CH_2$ |
| H.1275 | H | $CH_3$ | $CH_2C\equiv CH$ |
| H.1276 | H | $CH_2CH_3$ | $CH_2C\equiv CH$ |
| H.1277 | H | $CF_3$ | $CH_2C\equiv CH$ |
| H.1278 | H | Cl | $CH_2C\equiv CH$ |
| H.1279 | H | $OCH_3$ | $CH_2C\equiv CH$ |
| H.1280 | $CH_2CH_3$ | $CH_3$ | $CH_2C\equiv CH$ |
| H.1281 | $CH_2CH_3$ | $CH_2CH_3$ | $CH_2C\equiv CH$ |
| H.1282 | $CH_2CH_3$ | $CF_3$ | $CH_2C\equiv CH$ |
| H.1283 | $CH_2CH_3$ | Cl | $CH_2C\equiv CH$ |
| H.1284 | $CH_2CH_3$ | $OCH_3$ | $CH_2C\equiv CH$ |

TABLE H-continued

| No. | R$^b$ | R$^\alpha$ | R$^\beta$ |
|---|---|---|---|
| H.1285 | CHF$_2$ | CH$_3$ | CH$_2$C≡CH |
| H.1286 | CHF$_2$ | CH$_2$CH$_3$ | CH$_2$C≡CH |
| H.1287 | CHF$_2$ | CF$_3$ | CH$_2$C≡CH |
| H.1288 | CHF$_2$ | Cl | CH$_2$C≡CH |
| H.1289 | CHF$_2$ | OCH$_3$ | CH$_2$C≡CH |
| H.1290 | CH$_2$F | CH$_3$ | CH$_2$C≡CH |
| H.1291 | CH$_2$F | CH$_2$CH$_3$ | CH$_2$C≡CH |
| H.1292 | CH$_2$F | CF$_3$ | CH$_2$C≡CH |
| H.1293 | CH$_2$F | Cl | CH$_2$C≡CH |
| H.1294 | CH$_2$F | OCH$_3$ | CH$_2$C≡CH |
| H.1295 | OCH$_3$ | CH$_3$ | CH$_2$C≡CH |
| H.1296 | OCH$_3$ | CH$_2$CH$_3$ | CH$_2$C≡CH |
| H.1297 | OCH$_3$ | CF$_3$ | CH$_2$C≡CH |
| H.1298 | OCH$_3$ | Cl | CH$_2$C≡CH |
| H.1299 | OCH$_3$ | OCH$_3$ | CH$_2$C≡CH |
| H.1300 | OCH$_2$CH$_3$ | CH$_3$ | CH$_2$C≡CH |
| H.1301 | OCH$_2$CH$_3$ | CH$_2$CH$_3$ | CH$_2$C≡CH |
| H.1302 | OCH$_2$CH$_3$ | CF$_3$ | CH$_2$C≡CH |
| H.1303 | OCH$_2$CH$_3$ | Cl | CH$_2$C≡CH |
| H.1304 | OCH$_2$CH$_3$ | OCH$_3$ | CH$_2$C≡CH |
| H.1305 | CN | CH$_3$ | CH$_2$C≡CH |
| H.1306 | CN | CH$_2$CH$_3$ | CH$_2$C≡CH |
| H.1307 | CN | CF$_3$ | CH$_2$C≡CH |
| H.1308 | CN | Cl | CH$_2$C≡CH |
| H.1309 | CN | OCH$_3$ | CH$_2$C≡CH |
| H.1310 | H | CH$_3$ | CH$_2$C≡CCH$_3$ |
| H.1311 | H | CH$_2$CH$_3$ | CH$_2$C≡CCH$_3$ |
| H.1312 | H | CF$_3$ | CH$_2$C≡CCH$_3$ |
| H.1313 | H | Cl | CH$_2$C≡CCH$_3$ |
| H.1314 | H | OCH$_3$ | CH$_2$C≡CCH$_3$ |
| H.1315 | CH$_2$CH$_3$ | CH$_3$ | CH$_2$C≡CCH$_3$ |
| H.1316 | CH$_2$CH$_3$ | CH$_2$CH$_3$ | CH$_2$C≡CCH$_3$ |
| H.1317 | CH$_2$CH$_3$ | CF$_3$ | CH$_2$C≡CCH$_3$ |
| H.1318 | CH$_2$CH$_3$ | Cl | CH$_2$C≡CCH$_3$ |
| H.1319 | CH$_2$CH$_3$ | OCH$_3$ | CH$_2$C≡CCH$_3$ |
| H.1320 | CHF$_2$ | CH$_3$ | CH$_2$C≡CCH$_3$ |
| H.1321 | CHF$_2$ | CH$_2$CH$_3$ | CH$_2$C≡CCH$_3$ |
| H.1322 | CHF$_2$ | CF$_3$ | CH$_2$C≡CCH$_3$ |
| H.1323 | CHF$_2$ | Cl | CH$_2$C≡CCH$_3$ |
| H.1324 | CHF$_2$ | OCH$_3$ | CH$_2$C≡CCH$_3$ |
| H.1325 | CH$_2$F | CH$_3$ | CH$_2$C≡CCH$_3$ |
| H.1326 | CH$_2$F | CH$_2$CH$_3$ | CH$_2$C≡CCH$_3$ |
| H.1327 | CH$_2$F | CF$_3$ | CH$_2$C≡CCH$_3$ |
| H.1328 | CH$_2$F | Cl | CH$_2$C≡CCH$_3$ |
| H.1329 | CH$_2$F | OCH$_3$ | CH$_2$C≡CCH$_3$ |
| H.1330 | OCH$_3$ | CH$_3$ | CH$_2$C≡CCH$_3$ |
| H.1331 | OCH$_3$ | CH$_2$CH$_3$ | CH$_2$C≡CCH$_3$ |
| H.1332 | OCH$_3$ | CF$_3$ | CH$_2$C≡CCH$_3$ |
| H.1333 | OCH$_3$ | Cl | CH$_2$C≡CCH$_3$ |
| H.1334 | OCH$_3$ | OCH$_3$ | CH$_2$C≡CCH$_3$ |
| H.1335 | OCH$_2$CH$_3$ | CH$_3$ | CH$_2$C≡CCH$_3$ |
| H.1336 | OCH$_2$CH$_3$ | CH$_2$CH$_3$ | CH$_2$C≡CCH$_3$ |
| H.1337 | OCH$_2$CH$_3$ | CF$_3$ | CH$_2$C≡CCH$_3$ |
| H.1338 | OCH$_2$CH$_3$ | Cl | CH$_2$C≡CCH$_3$ |
| H.1339 | OCH$_2$CH$_3$ | OCH$_3$ | CH$_2$C≡CCH$_3$ |
| H.1340 | CN | CH$_3$ | CH$_2$C≡CCH$_3$ |
| H.1341 | CN | CH$_2$CH$_3$ | CH$_2$C≡CCH$_3$ |
| H.1342 | CN | CF$_3$ | CH$_2$C≡CCH$_3$ |
| H.1343 | CN | Cl | CH$_2$C≡CCH$_3$ |
| H.1344 | CN | OCH$_3$ | CH$_2$C≡CCH$_3$ |
| H.1345 | H | CH$_3$ | CH$_2$C≡C—I |
| H.1346 | H | CH$_2$CH$_3$ | CH$_2$C≡C—I |
| H.1347 | H | CF$_3$ | CH$_2$C≡C—I |
| H.1348 | H | Cl | CH$_2$C≡C—I |
| H.1349 | H | OCH$_3$ | CH$_2$C≡C—I |
| H.1350 | CH$_2$CH$_3$ | CH$_3$ | CH$_2$C≡C—I |
| H.1351 | CH$_2$CH$_3$ | CH$_2$CH$_3$ | CH$_2$C≡C—I |
| H.1352 | CH$_2$CH$_3$ | CF$_3$ | CH$_2$C≡C—I |
| H.1353 | CH$_2$CH$_3$ | Cl | CH$_2$C≡C—I |
| H.1354 | CH$_2$CH$_3$ | OCH$_3$ | CH$_2$C≡C—I |
| H.1355 | CHF$_2$ | CH$_3$ | CH$_2$C≡C—I |
| H.1356 | CHF$_2$ | CH$_2$CH$_3$ | CH$_2$C≡C—I |
| H.1357 | CHF$_2$ | CF$_3$ | CH$_2$C≡C—I |
| H.1358 | CHF$_2$ | Cl | CH$_2$C≡C—I |
| H.1359 | CHF$_2$ | OCH$_3$ | CH$_2$C≡C—I |
| H.1360 | CH$_2$F | CH$_3$ | CH$_2$C≡C—I |
| H.1361 | CH$_2$F | CH$_2$CH$_3$ | CH$_2$C≡C—I |
| H.1362 | CH$_2$F | CF$_3$ | CH$_2$C≡C—I |
| H.1363 | CH$_2$F | Cl | CH$_2$C≡C—I |
| H.1364 | CH$_2$F | OCH$_3$ | CH$_2$C≡C—I |
| H.1365 | OCH$_3$ | CH$_3$ | CH$_2$C≡C—I |
| H.1366 | OCH$_3$ | CH$_2$CH$_3$ | CH$_2$C≡C—I |
| H.1367 | OCH$_3$ | CF$_3$ | CH$_2$C≡C—I |
| H.1368 | OCH$_3$ | Cl | CH$_2$C≡C—I |
| H.1369 | OCH$_3$ | OCH$_3$ | CH$_2$C≡C—I |
| H.1370 | OCH$_2$CH$_3$ | CH$_3$ | CH$_2$C≡C—I |
| H.1371 | OCH$_2$CH$_3$ | CH$_2$CH$_3$ | CH$_2$C≡C—I |
| H.1372 | OCH$_2$CH$_3$ | CF$_3$ | CH$_2$C≡C—I |
| H.1373 | OCH$_2$CH$_3$ | Cl | CH$_2$C≡C—I |
| H.1374 | OCH$_2$CH$_3$ | OCH$_3$ | CH$_2$C≡C—I |
| H.1375 | CN | CH$_3$ | CH$_2$C≡C—I |
| H.1376 | CN | CH$_2$CH$_3$ | CH$_2$C≡C—I |
| H.1377 | CN | CF$_3$ | CH$_2$C≡C—I |
| H.1378 | CN | Cl | CH$_2$C≡C—I |
| H.1379 | CN | OCH$_3$ | CH$_2$C≡C—I |
| H.1380 | H | CH$_3$ | CH(CH$_3$)C≡CH |
| H.1381 | H | CH$_2$CH$_3$ | CH(CH$_3$)C≡CH |
| H.1382 | H | CF$_3$ | CH(CH$_3$)C≡CH |
| H.1383 | H | Cl | CH(CH$_3$)C≡CH |
| H.1384 | H | OCH$_3$ | CH(CH$_3$)C≡CH |
| H.1385 | CH$_2$CH$_3$ | CH$_3$ | CH(CH$_3$)C≡CH |
| H.1386 | CH$_2$CH$_3$ | CH$_2$CH$_3$ | CH(CH$_3$)C≡CH |
| H.1387 | CH$_2$CH$_3$ | CF$_3$ | CH(CH$_3$)C≡CH |
| H.1388 | CH$_2$CH$_3$ | Cl | CH(CH$_3$)C≡CH |
| H.1389 | CH$_2$CH$_3$ | OCH$_3$ | CH(CH$_3$)C≡CH |
| H.1390 | CHF$_2$ | CH$_3$ | CH(CH$_3$)C≡CH |
| H.1391 | CHF$_2$ | CH$_2$CH$_3$ | CH(CH$_3$)C≡CH |
| H.1392 | CHF$_2$ | CF$_3$ | CH(CH$_3$)C≡CH |
| H.1393 | CHF$_2$ | Cl | CH(CH$_3$)C≡CH |
| H.1394 | CHF$_2$ | OCH$_3$ | CH(CH$_3$)C≡CH |
| H.1395 | CH$_2$F | CH$_3$ | CH(CH$_3$)C≡CH |
| H.1396 | CH$_2$F | CH$_2$CH$_3$ | CH(CH$_3$)C≡CH |
| H.1397 | CH$_2$F | CF$_3$ | CH(CH$_3$)C≡CH |
| H.1398 | CH$_2$F | Cl | CH(CH$_3$)C≡CH |
| H.1399 | CH$_2$F | OCH$_3$ | CH(CH$_3$)C≡CH |
| H.1400 | OCH$_3$ | CH$_3$ | CH(CH$_3$)C≡CH |
| H.1401 | OCH$_3$ | CH$_2$CH$_3$ | CH(CH$_3$)C≡CH |
| H.1402 | OCH$_3$ | CF$_3$ | CH(CH$_3$)C≡CH |
| H.1403 | OCH$_3$ | Cl | CH(CH$_3$)C≡CH |
| H.1404 | OCH$_3$ | OCH$_3$ | CH(CH$_3$)C≡CH |
| H.1405 | OCH$_2$CH$_3$ | CH$_3$ | CH(CH$_3$)C≡CH |
| H.1406 | OCH$_2$CH$_3$ | CH$_2$CH$_3$ | CH(CH$_3$)C≡CH |
| H.1407 | OCH$_2$CH$_3$ | CF$_3$ | CH(CH$_3$)C≡CH |
| H.1408 | OCH$_2$CH$_3$ | Cl | CH(CH$_3$)C≡CH |
| H.1409 | OCH$_2$CH$_3$ | OCH$_3$ | CH(CH$_3$)C≡CH |
| H.1410 | CN | CH$_3$ | CH(CH$_3$)C≡CH |
| H.1411 | CN | CH$_2$CH$_3$ | CH(CH$_3$)C≡CH |
| H.1412 | CN | CF$_3$ | CH(CH$_3$)C≡CH |
| H.1413 | CN | Cl | CH(CH$_3$)C≡CH |
| H.1414 | CN | OCH$_3$ | CH(CH$_3$)C≡CH |
| H.1415 | H | CH$_3$ | CH$_2$CH$_2$—O—CH$_2$CH$_3$ |
| H.1416 | H | CH$_2$CH$_3$ | CH$_2$CH$_2$—O—CH$_2$CH$_3$ |
| H.1417 | H | CF$_3$ | CH$_2$CH$_2$—O—CH$_2$CH$_3$ |
| H.1418 | H | Cl | CH$_2$CH$_2$—O—CH$_2$CH$_3$ |
| H.1419 | H | OCH$_3$ | CH$_2$CH$_2$—O—CH$_2$CH$_3$ |
| H.1420 | CH$_2$CH$_3$ | CH$_3$ | CH$_2$CH$_2$—O—CH$_2$CH$_3$ |
| H.1421 | CH$_2$CH$_3$ | CH$_2$CH$_3$ | CH$_2$CH$_2$—O—CH$_2$CH$_3$ |
| H.1422 | CH$_2$CH$_3$ | CF$_3$ | CH$_2$CH$_2$—O—CH$_2$CH$_3$ |
| H.1423 | CH$_2$CH$_3$ | Cl | CH$_2$CH$_2$—O—CH$_2$CH$_3$ |
| H.1424 | CH$_2$CH$_3$ | OCH$_3$ | CH$_2$CH$_2$—O—CH$_2$CH$_3$ |
| H.1425 | CHF$_2$ | CH$_3$ | CH$_2$CH$_2$—O—CH$_2$CH$_3$ |
| H.1426 | CHF$_2$ | CH$_2$CH$_3$ | CH$_2$CH$_2$—O—CH$_2$CH$_3$ |
| H.1427 | CHF$_2$ | CF$_3$ | CH$_2$CH$_2$—O—CH$_2$CH$_3$ |
| H.1428 | CHF$_2$ | Cl | CH$_2$CH$_2$—O—CH$_2$CH$_3$ |
| H.1429 | CHF$_2$ | OCH$_3$ | CH$_2$CH$_2$—O—CH$_2$CH$_3$ |
| H.1430 | CH$_2$F | CH$_3$ | CH$_2$CH$_2$—O—CH$_2$CH$_3$ |
| H.1431 | CH$_2$F | CH$_2$CH$_3$ | CH$_2$CH$_2$—O—CH$_2$CH$_3$ |
| H.1432 | CH$_2$F | CF$_3$ | CH$_2$CH$_2$—O—CH$_2$CH$_3$ |
| H.1433 | CH$_2$F | Cl | CH$_2$CH$_2$—O—CH$_2$CH$_3$ |
| H.1434 | CH$_2$F | OCH$_3$ | CH$_2$CH$_2$—O—CH$_2$CH$_3$ |
| H.1435 | OCH$_3$ | CH$_3$ | CH$_2$CH$_2$—O—CH$_2$CH$_3$ |
| H.1436 | OCH$_3$ | CH$_2$CH$_3$ | CH$_2$CH$_2$—O—CH$_2$CH$_3$ |
| H.1437 | OCH$_3$ | CF$_3$ | CH$_2$CH$_2$—O—CH$_2$CH$_3$ |
| H.1438 | OCH$_3$ | Cl | CH$_2$CH$_2$—O—CH$_2$CH$_3$ |

TABLE H-continued

| No. | $R^b$ | $R^\alpha$ | $R^\beta$ |
|---|---|---|---|
| H.1439 | $OCH_3$ | $OCH_3$ | $CH_2CH_2-O-CH_2CH_3$ |
| H.1440 | $OCH_2CH_3$ | $CH_3$ | $CH_2CH_2-O-CH_2CH_3$ |
| H.1441 | $OCH_2CH_3$ | $CH_2CH_3$ | $CH_2CH_2-O-CH_2CH_3$ |
| H.1442 | $OCH_2CH_3$ | $CF_3$ | $CH_2CH_2-O-CH_2CH_3$ |
| H.1443 | $OCH_2CH_3$ | $Cl$ | $CH_2CH_2-O-CH_2CH_3$ |
| H.1444 | $OCH_2CH_3$ | $OCH_3$ | $CH_2CH_2-O-CH_2CH_3$ |
| H.1445 | $CN$ | $CH_3$ | $CH_2CH_2-O-CH_2CH_3$ |
| H.1446 | $CN$ | $CH_2CH_3$ | $CH_2CH_2-O-CH_2CH_3$ |
| H.1447 | $CN$ | $CF_3$ | $CH_2CH_2-O-CH_2CH_3$ |
| H.1448 | $CN$ | $Cl$ | $CH_2CH_2-O-CH_2CH_3$ |
| H.1449 | $CN$ | $OCH_3$ | $CH_2CH_2-O-CH_2CH_3$ |
| H.1450 | $H$ | $CH_3$ | $CH_2-C_6H_5$ |
| H.1451 | $H$ | $CH_2CH_3$ | $CH_2-C_6H_5$ |
| H.1452 | $H$ | $CF_3$ | $CH_2-C_6H_5$ |
| H.1453 | $H$ | $Cl$ | $CH_2-C_6H_5$ |
| H.1454 | $H$ | $OCH_3$ | $CH_2-C_6H_5$ |
| H.1455 | $CH_2CH_3$ | $CH_3$ | $CH_2-C_6H_5$ |
| H.1456 | $CH_2CH_3$ | $CH_2CH_3$ | $CH_2-C_6H_5$ |
| H.1457 | $CH_2CH_3$ | $CF_3$ | $CH_2-C_6H_5$ |
| H.1458 | $CH_2CH_3$ | $Cl$ | $CH_2-C_6H_5$ |
| H.1459 | $CH_2CH_3$ | $OCH_3$ | $CH_2-C_6H_5$ |
| H.1460 | $CHF_2$ | $CH_3$ | $CH_2-C_6H_5$ |
| H.1461 | $CHF_2$ | $CH_2CH_3$ | $CH_2-C_6H_5$ |
| H.1462 | $CHF_2$ | $CF_3$ | $CH_2-C_6H_5$ |
| H.1463 | $CHF_2$ | $Cl$ | $CH_2-C_6H_5$ |
| H.1464 | $CHF_2$ | $OCH_3$ | $CH_2-C_6H_5$ |
| H.1465 | $CH_2F$ | $CH_3$ | $CH_2-C_6H_5$ |
| H.1466 | $CH_2F$ | $CH_2CH_3$ | $CH_2-C_6H_5$ |
| H.1467 | $CH_2F$ | $CF_3$ | $CH_2-C_6H_5$ |
| H.1468 | $CH_2F$ | $Cl$ | $CH_2-C_6H_5$ |
| H.1469 | $CH_2F$ | $OCH_3$ | $CH_2-C_6H_5$ |
| H.1470 | $OCH_3$ | $CH_3$ | $CH_2-C_6H_5$ |
| H.1471 | $OCH_3$ | $CH_2CH_3$ | $CH_2-C_6H_5$ |
| H.1472 | $OCH_3$ | $CF_3$ | $CH_2-C_6H_5$ |
| H.1473 | $OCH_3$ | $Cl$ | $CH_2-C_6H_5$ |
| H.1474 | $OCH_3$ | $OCH_3$ | $CH_2-C_6H_5$ |
| H.1475 | $OCH_2CH_3$ | $CH_3$ | $CH_2-C_6H_5$ |
| H.1476 | $OCH_2CH_3$ | $CH_2CH_3$ | $CH_2-C_6H_5$ |
| H.1477 | $OCH_2CH_3$ | $CF_3$ | $CH_2-C_6H_5$ |
| H.1478 | $OCH_2CH_3$ | $Cl$ | $CH_2-C_6H_5$ |
| H.1479 | $OCH_2CH_3$ | $OCH_3$ | $CH_2-C_6H_5$ |
| H.1480 | $CN$ | $CH_3$ | $CH_2-C_6H_5$ |
| H.1481 | $CN$ | $CH_2CH_3$ | $CH_2-C_6H_5$ |
| H.1482 | $CN$ | $CF_3$ | $CH_2-C_6H_5$ |
| H.1483 | $CN$ | $Cl$ | $CH_2-C_6H_5$ |
| H.1484 | $CN$ | $OCH_3$ | $CH_2-C_6H_5$ |
| H.1485 | $H$ | $CH_3$ | cyclopropyl |
| H.1486 | $H$ | $CH_2CH_3$ | cyclopropyl |
| H.1487 | $H$ | $CF_3$ | cyclopropyl |
| H.1488 | $H$ | $Cl$ | cyclopropyl |
| H.1489 | $H$ | $OCH_3$ | cyclopropyl |
| H.1490 | $CH_2CH_3$ | $CH_3$ | cyclopropyl |
| H.1491 | $CH_2CH_3$ | $CH_2CH_3$ | cyclopropyl |
| H.1492 | $CH_2CH_3$ | $CF_3$ | cyclopropyl |
| H.1493 | $CH_2CH_3$ | $Cl$ | cyclopropyl |
| H.1494 | $CH_2CH_3$ | $OCH_3$ | cyclopropyl |
| H.1495 | $CHF_2$ | $CH_3$ | cyclopropyl |
| H.1496 | $CHF_2$ | $CH_2CH_3$ | cyclopropyl |
| H.1497 | $CHF_2$ | $CF_3$ | cyclopropyl |
| H.1498 | $CHF_2$ | $Cl$ | cyclopropyl |
| H.1499 | $CHF_2$ | $OCH_3$ | cyclopropyl |
| H.1500 | $CH_2F$ | $CH_3$ | cyclopropyl |
| H.1501 | $CH_2F$ | $CH_2CH_3$ | cyclopropyl |
| H.1502 | $CH_2F$ | $CF_3$ | cyclopropyl |
| H.1503 | $CH_2F$ | $Cl$ | cyclopropyl |
| H.1504 | $CH_2F$ | $OCH_3$ | cyclopropyl |
| H.1505 | $OCH_3$ | $CH_3$ | cyclopropyl |
| H.1506 | $OCH_3$ | $CH_2CH_3$ | cyclopropyl |
| H.1507 | $OCH_3$ | $CF_3$ | cyclopropyl |
| H.1508 | $OCH_3$ | $Cl$ | cyclopropyl |
| H.1509 | $OCH_3$ | $OCH_3$ | cyclopropyl |
| H.1510 | $OCH_2CH_3$ | $CH_3$ | cyclopropyl |
| H.1511 | $OCH_2CH_3$ | $CH_2CH_3$ | cyclopropyl |
| H.1512 | $OCH_2CH_3$ | $CF_3$ | cyclopropyl |
| H.1513 | $OCH_2CH_3$ | $Cl$ | cyclopropyl |
| H.1514 | $OCH_2CH_3$ | $OCH_3$ | cyclopropyl |
| H.1515 | $CN$ | $CH_3$ | cyclopropyl |
| H.1516 | $CN$ | $CH_2CH_3$ | cyclopropyl |
| H.1517 | $CN$ | $CF_3$ | cyclopropyl |
| H.1518 | $CN$ | $Cl$ | cyclopropyl |
| H.1519 | $CN$ | $OCH_3$ | cyclopropyl |
| H.1520 | $H$ | $CH_3$ | $CH_2$-(2,2-$Cl_2$-cyclopropyl) |
| H.1521 | $H$ | $CH_2CH_3$ | $CH_2$-(2,2-$Cl_2$-cyclopropyl) |
| H.1522 | $H$ | $CF_3$ | $CH_2$-(2,2-$Cl_2$-cyclopropyl) |
| H.1523 | $H$ | $Cl$ | $CH_2$-(2,2-$Cl_2$-cyclopropyl) |
| H.1524 | $H$ | $OCH_3$ | $CH_2$-(2,2-$Cl_2$-cyclopropyl) |
| H.1525 | $CH_2CH_3$ | $CH_3$ | $CH_2$-(2,2-$Cl_2$-cyclopropyl) |
| H.1526 | $CH_2CH_3$ | $CH_2CH_3$ | $CH_2$-(2,2-$Cl_2$-cyclopropyl) |
| H.1527 | $CH_2CH_3$ | $CF_3$ | $CH_2$-(2,2-$Cl_2$-cyclopropyl) |
| H.1528 | $CH_2CH_3$ | $Cl$ | $CH_2$-(2,2-$Cl_2$-cyclopropyl) |
| H.1529 | $CH_2CH_3$ | $OCH_3$ | $CH_2$-(2,2-$Cl_2$-cyclopropyl) |
| H.1530 | $CHF_2$ | $CH_3$ | $CH_2$-(2,2-$Cl_2$-cyclopropyl) |
| H.1531 | $CHF_2$ | $CH_2CH_3$ | $CH_2$-(2,2-$Cl_2$-cyclopropyl) |
| H.1532 | $CHF_2$ | $CF_3$ | $CH_2$-(2,2-$Cl_2$-cyclopropyl) |
| H.1533 | $CHF_2$ | $Cl$ | $CH_2$-(2,2-$Cl_2$-cyclopropyl) |
| H.1534 | $CHF_2$ | $OCH_3$ | $CH_2$-(2,2-$Cl_2$-cyclopropyl) |
| H.1535 | $CH_2F$ | $CH_3$ | $CH_2$-(2,2-$Cl_2$-cyclopropyl) |
| H.1536 | $CH_2F$ | $CH_2CH_3$ | $CH_2$-(2,2-$Cl_2$-cyclopropyl) |
| H.1537 | $CH_2F$ | $CF_3$ | $CH_2$-(2,2-$Cl_2$-cyclopropyl) |
| H.1538 | $CH_2F$ | $Cl$ | $CH_2$-(2,2-$Cl_2$-cyclopropyl) |
| H.1539 | $CH_2F$ | $OCH_3$ | $CH_2$-(2,2-$Cl_2$-cyclopropyl) |
| H.1540 | $OCH_3$ | $CH_3$ | $CH_2$-(2,2-$Cl_2$-cyclopropyl) |
| H.1541 | $OCH_3$ | $CH_2CH_3$ | $CH_2$-(2,2-$Cl_2$-cyclopropyl) |
| H.1542 | $OCH_3$ | $CF_3$ | $CH_2$-(2,2-$Cl_2$-cyclopropyl) |
| H.1543 | $OCH_3$ | $Cl$ | $CH_2$-(2,2-$Cl_2$-cyclopropyl) |
| H.1544 | $OCH_3$ | $OCH_3$ | $CH_2$-(2,2-$Cl_2$-cyclopropyl) |
| H.1545 | $OCH_2CH_3$ | $CH_3$ | $CH_2$-(2,2-$Cl_2$-cyclopropyl) |
| H.1546 | $OCH_2CH_3$ | $CH_2CH_3$ | $CH_2$-(2,2-$Cl_2$-cyclopropyl) |
| H.1547 | $OCH_2CH_3$ | $CF_3$ | $CH_2$-(2,2-$Cl_2$-cyclopropyl) |
| H.1548 | $OCH_2CH_3$ | $Cl$ | $CH_2$-(2,2-$Cl_2$-cyclopropyl) |
| H.1549 | $OCH_2CH_3$ | $OCH_3$ | $CH_2$-(2,2-$Cl_2$-cyclopropyl) |
| H.1550 | $CN$ | $CH_3$ | $CH_2$-(2,2-$Cl_2$-cyclopropyl) |
| H.1551 | $CN$ | $CH_2CH_3$ | $CH_2$-(2,2-$Cl_2$-cyclopropyl) |
| H.1552 | $CN$ | $CF_3$ | $CH_2$-(2,2-$Cl_2$-cyclopropyl) |
| H.1553 | $CN$ | $Cl$ | $CH_2$-(2,2-$Cl_2$-cyclopropyl) |
| H.1554 | $CN$ | $OCH_3$ | $CH_2$-(2,2-$Cl_2$-cyclopropyl) |

The compounds I are suitable as fungicides.

The compounds I are distinguished by an outstanding activity against a broad spectrum of phytopathogenic fungi, in particular from the classes of the Ascomycetes, Deuteromycetes, Phycomycetes and Basidiomycetes. Some of them act systemically and can be employed in crop protection as foliar- and soil-acting fungicides.

They are particularly important for controlling a large number of fungi which infect a variety of crop plants, such as wheat, rye, barley, oats, bananas, rice, corn, grass, cotton, soybean, coffee, sugar cane, grapevines, fruit species, ornamentals and vegetable species, such as cucumbers, beans, tomatoes, potatoes and cucurbits, as well as the seeds of these plants.

Specifically, they are suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinerea* (gray mold) in strawberries, vegetable and ornamental species, grapevines, *Cercospora arachidicola* in peanuts, *Pseudocercosporella herpotrichoides* in wheat, barley, *Pyricularia oryzae* in rice, *Phytophthora infestans* in potatoes and tomatoes, *Fusarium* and *Verticillium* species in a variety of plants, *Plasmopara viticola* in grapevines, *Pseudocercosporella* species in hops and cucumbers, *Alternaria* species in vegetables and fruit, and *Mycosphaerella* species in bananas.

Furthermore, the compounds I are suitable for controlling harmful fungi in the protection of materials (eg. wood, paper, paint dispersions, fibers or fabrics) and in the protection of stored products.

The compounds I are used by treating the fungi, or the plants, seeds or materials to be protected against fungal infection, or the soil, with a fungicidally effective amount of the active ingredients. Application is effected before or after infection of the materials, plants or seeds by the fungi.

They can be converted into the customary formulations, such as solutions, emulsions, suspensions, dusts, powders, pastes and granules. The use form depends on the specific purpose; in any case, it should guarantee fine and uniform distribution of the compound according to the invention. The formulations are prepared in a known manner; eg. by extending the active ingredient with solvents and/or carriers, if desired using emulsifiers and dispersants, it also being possible to use other organic solvents as auxiliary solvents if water is used as the diluent. Suitable auxiliaries are essentially the following: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin sulfite waste liquors and methylcellulose.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the desired effect.

In the treatment of seed, amounts of from 0.001 to 0.1 g, preferably 0.01 to 0.05 g, of active ingredient are generally required for kilogram of seed.

When used in the protection of materials or stored products, the rate of application of active ingredient depends on the field of application and on the desired effect. Usual rates of application in the protection of materials are, for example, from 0.001 g to 2 kg, preferably 0.005 g to 1 kg, of active ingredient per cubic meter of material treated.

In the use form as fungicides, the compositions according to the invention may also be present together with other active ingredients, eg. with herbicides, insecticides, growth regulators, fungicides or else fertilizers.

Mixtures with fungicides frequently result in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachlorethylthio)tetrahydrophthalimide, N-trichlormethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formylmorpholine 2,2,2-trichlorethyl acetal, piperazine-1,4-diylbis(2,2,2-trichloroethyl)formamide, 1-(3,4-dichloroanilino)-1-formylamino-2,2,2-trichlorethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)

pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoximino-[α-(2-phenoxyphenyl)]acetamide, N-methyl-E-methoximino-[α-(2,5-dimethylphenoxy)-o-tolyl]acetamide;

anilinopyrimidins such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline;

phenylpyrrols such as 4-(2,2-difluoro-1,3-benzodioxol-4-yl)pyrrole-3-carbonitrile;

cinnamamides such as 3-(4-chlorophenyl)-3-(3,4-dimethoxyphenyl)-acryloylmorpholine;

(2RS,3SR)-1-[3-(2-chlorophenyl)-2-[4-fluorophenyl]oxiran-2-yl-methyl]-1H-1,2,4-triazole.

The compounds of the formula I are furthermore suitable for effectively controlling pests from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example root knot nematodes, eg. *Meloidogyne hapla, Meloidogyne incognita, Meloidogyne javanica*, cyst nematodes, eg. *Globodera rostochiensis, Heterodera avenae, Heterodera glycines, Heterodera schachtii, Heterodera trifolii*, stem eelworms and foliar nematodes , eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be applied as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations comprising over 95% by weight of active ingredient, or even the active ingredient without additives.

The rate of application of active ingredient for controlling pests is from 0.1 to 2.0, preferably 0.2 to 1.0, kg/ha under field conditions.

Substances which are suitable for preparing directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalane, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates which are composed of active substance, wetting agent, tackifier, dispersant or emulsifier and, if desired, solvent or oil, and which are suitable for dilution with water.

Suitable surfactants are alkali metal salts, alkaline earth metal salts and ammonium salts of lignosulfonic acid, naphthalenesulfonic acid, phenolsulfonic acid, dibutylnaphthalenesulfonic acid; alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenol polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methylcellulose.

Powders, materials for spreading and dusts can be prepared by mixing or concomitantly grinding the active substances together with a solid carrier.

In general, the formulations comprise from 0.01 to 95%, preferably from 0.1 to 90% by weight, of the active ingredient. The active ingredients are employed in a purity of from 90% to 100%, preferably 95% to 100% (according to NMR spectrum). Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a preparation of the active ingredient with good adherence properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, parts by weight of isobutanol, 20 parts by weight of the adduct of 7 mol of ethylene oxide and 1 mol of isooctylphenol and parts by weight of the adduct of 40 mol of ethylene and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules, homogeneous granules, can be prepared by binding the active ingredients onto solid carriers. Examples of solid carriers are mineral earths such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders, and other solid carriers.

Various types of oils, or herbicides, fungicides, other pesticides, or bactericides, may be added to the active ingredients, if desired only just prior to use (tank mix). These agents can be admixed with the agents according to the invention in a weight ratio of 1:10 to 10:1.

SYNTHESIS EXAMPLES

The protocols given in the synthesis examples which follow were used for obtaining other compounds I by modifying the starting compounds as required. The resulting compounds are listed in the tables which follow together with physical data.

1. Preparation of methyl N-Hydroxy-N-(2-phenoxypyridin-3-yl)carbamate

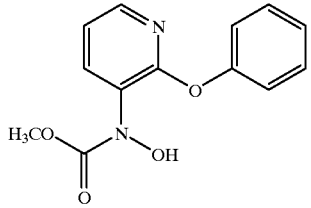

1.a) 3-Nitro-2-phenoxypyridine 3.6 g (150 mmol) of sodium hydride were added, a little at a time, to a mixture of 12 g (128 mmol) of phenol and 100 ml of dimethylformamide. After the evolution of gas had ceased, the resulting mixture was treated with 18 g (114 mmol) of 2-chloro-3-nitropyridine. After the reaction mixture had been stirred at room temperature (approximately 25° C.) for 3 hours, it was treated with water. Following extraction with tert-butyl methyl ether, washing and drying the organic phase and removal of the solvent under reduced pressure, the product crystallized out. It was purified further by stirring with tert-butyl methyl ether/n-pentane. This gave 6.6 g (27%) of the title compound. A further 3.0 g (12%) of the title compound were obtained from the mother liquor.

$^1$H NMR (CDCl$_3$; δ in ppm): 7.1 (m,3H, phenyl) ; 7.2 (t,1H) ; 7.4 (t, br, 2H); 8.3 (m,2H, pyridyl).

1.b) N-(2-Phenoxypyridin-3-yl)hydroxylamine

A mixture of 9.2 g (43 mmol) of 3-nitro-2-phenoxypyridine (Example 1.a) and 100 ml of N-methylmorpholine was hydrogenated at room temperature (approximately 25° C.) and an H$_2$ pressure of approximately 1.1 bar in the presence of 1 g of 5% platinum/charcoal (51% water; manufactured by Degussa). The hydrogen uptake ceased after approximately 2 hours. The catalyst was removed by filtration through active charcoal. The resulting solution was freed from solvent under reduced pressure ("high vacuum"). This gave 7.8 g (90%) of the title compound as a white solid.

$^1$H NMR (d$_6$-DMSO; δ in ppm): 7.1 (m,4H, phenyl); 7.4 (m,4H, 3×pyridyl, 1×phenyl); 8.5; 8.6 (in each case: s,1H, NH, OH).

1.c) Methyl N-hydroxy-N-(2-phenoxypyridin-3-yl)carbamate 3 g (mmol) of methyl chloroformate were added dropwise at 0° C. to a mixture of 7.8 g (39 mmol) of N-(2-phenoxypyridin-3-yl)hydroxylamine (Example 1.b), 4 g (50 mmol) of NaHCO$_3$ (solid) and 10 ml of methylene chloride. After 1 hour at room temperature (approximately 25° C.), the reaction mixture was treated with a further 2 g of methyl chloroformate and stirred for a further 2 hours at room temperature. The reaction mixture was subsequently treated with a further 2 g of methyl chloroformate and left for approximately 12 hours at 5° C. The resulting mixture was treated with water and extracted repeatedly using tert-butyl methyl ether. The organic phases were combined, washed and dried, and the solvent was removed under reduced pressure. The residue obtained was purified by column chromatography (cyclohexane/ethyl acetate). This gave 2.5 g of the title compound as a solid (m.p.: 140° C.

$^1$H NMR (CDCl$_3$; δ in ppm): 3.8 (s,3H,OCH$_3$); 7.1 (m,1H, phenyl); 7.1 (d,br,2H, phenyl); 7.2 (t,br,1H, phenyl); 7.4 (t,br,2H, 1×pyridyl, 1×phenyl); 7.8 (d,br,1H, pyridyl; s, very br,1H, OH); 8.1 (d,1H, pyridyl)

2. Preparation of methyl N-methoxy-N-(2-phenoxypyridin-3-yl)carbamate

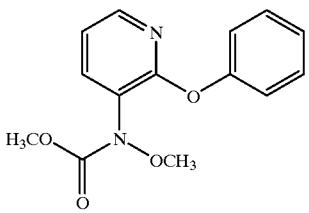

A mixture of 2 g (7.6 mmol) of methyl N-hydroxy-N-(2-phenoxypyridin-3-yl)carbamate (Example 1.c), 1.6 g (11 mmol) of K$_2$CO$_3$, 1 g (13 mmol) of dimethyl sulfate and 10 ml of acetone was stirred for approximately 12 hours at room temperature (approximately 25° C.). The mixture was subsequently diluted with water and 10% strength NH$_3$ solution and extracted repeatedly using tert-butyl methyl ether. The organic phases were combined, washed and dried, and the solvent was removed under reduced pressure. The resulting residue was purified by column chromatography (tert-butyl methyl ether). This gave 1.1 g of the title compound as a pale oil.

$^1$H NMR (CDCl$_3$; δ in ppm): 3.8 (s,3H, OCH$_3$); 3.9 (s,3H, OCH$_3$); 7.05 (m,1H, phenyl); 7.1 (d,2H, phenyl); 7.2 (m,1H, phenyl); 7.4 (t,br,2H, 1×pyridyl, 1×phenyl); 7.75 (d,br,1H, pyridyl); 8.15 (d,1H, pyridyl).

3. Preparation of methyl N-hydroxy-N-[2-(2-methylphenoxymethyl)pyridin-3-yl]carbamate

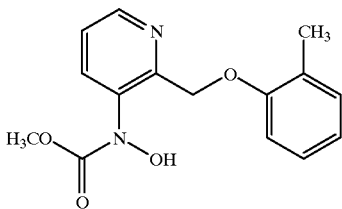

3.a) Diethyl(3-nitropyridin-2-yl)malonate 50 g (0.31 mol) of diethyl malonate were added, a little at a time, at not more than 50° C. to a mixture of 7.5 g (0.31 mol) of sodium hydride and 50 ml of dimethylformamide, with ice-cooling. After the mixture had cooled to room temperature (approximately 25° C.), it was treated with g (0.173 mol) of 2-chloro-3-nitropyridine. After approximately 15 hours, the reaction mixture was diluted with water, acidified using acetic acid and extracted using ethyl acetate. The organic phases were combined, washed and dried, and the solvent was removed under reduced pressure. The excess malonic ester was distilled off at elevated temperature and reduced pressure ("high vacuum"). This gave 43 g (66%) of the title compound as a yellow oil (purity approximately 75%).

$^1$H NMR (CDCl$_3$; δ in ppm): 1.3 (t,6H, 2×CH$_3$); 4.3 (q,4H, 2×CH$_2$); 5.5 (s,1H, CH); 7.55 (dd,1H, pyridyl); 8.5 (d,br,1H, pyridyl); 8.8 (d,1H, pyridyl).

3.b) 2-Methyl-3-nitropyridine

A mixture of 43 g (115 mmol) of diethyl(3-nitropyridin-2-yl)malonate (purity approximately 75%; Example 3.a) and 150 ml of 18% strength hydrochloric acid was stirred for 3 hours at 100 ° C. After the mixture had cooled to room temperature (approximately 25° C.), it was diluted with water and extracted using tert-butyl methyl ether. The aqueous phase was evaporated under reduced pressure, and the resulting crystalline residue was taken up in (aqueous) Na$_2$CO$_3$ solution. The Na$_2$CO$_3$ solution was extracted repeatedly using methylene chloride. The organic phases were combined, washed and dried, and the solvent was removed under reduced pressure. This gave 10 g (79%) of the title compound as a yellow oil.

$^1$H NMR (CDCl$_3$; δ in ppm): 2.85 (s,3H, CH$_3$); 7.4 (dd,1H, pyridyl); 8.3 (d,br,1H, pyridyl); 8.75 (d,1H, pyridyl).

3.c) 2-Bromomethyl-3-nitropyridine 51 g (290 mmol) of N-bromosuccinimide and 0.5 g of benzoyl peroxide were added, a little at a time, to a mixture of 40 g (290 mmol) of 2-methyl-3-nitropyridine (Example 3.b) and 400 ml of chlorobenzene, at the boiling point (liberation of bromine). After approximately 2 hours, the reaction mixture was cooled to room temperature (approximately 25° C.) and filtered, and the resulting solution was freed from solvent under reduced pressure. The resulting residue was chromatographed twice (cyclohexane/methylene chloride; cyclohexane/ethyl acetate). This gave 10.4 g (17%) of the title compound as a yellow oil.

$^1$H NMR (CDCl$_3$; δ in ppm): 5.0 (s,2H, CH$_2$Br); 7.55 (dd,1H, pyridyl); 8.4 (d,br,1H, pyridyl); 8.85 (d,1H, pyridyl).

3.d) 2-(2-Methylphenoxymethyl)-3-nitropyridine

A mixture of 10.4 g (48 mmol) of 2-bromomethyl-3-nitropyridine (Example 3.c), 4.8 g (44 mmol) of o-cresol, 10 g (72 mmol) of K$_2$CO$_3$ and 50 ml of dimethylformamide were stirred for 3 days at room temperature (approximately 25° C.). The mixture was subsequently diluted with water and extracted repeatedly using tert-butyl methyl ether. The organic phases were combined, washed and dried, and the solvent was removed under reduced pressure. The residue obtained was purified by column chromatography (cyclohexane/ethyl acetate). This gave 5 g (47%) of the title compound as a yellow oil.

$^1$H NMR (CDCl$_3$; δ in ppm): 2.2 (s,3H, CH$_3$); 5.55 (s,2H, OCH$_2$); 6.9 (t, 2H, phenyl); 7.1 (m,2H, phenyl); 7.45 (dd, 1H, pyridyl); 8.25 (d,br,1H, pyridyl); 8.8 (d,br,1H, pyridyl).

3.e) N-[2-(2-Methylphenoxymethyl)pyridin-3-yl]hydroxylamine

A mixture of 5.0 g (21 mmol) of 2-(2-methylphenoxymethyl)-3-nitropyridine (Example 3.d) and 100 ml of N-methylmorpholine was hydrogenated at room temperature (approximately 25° C.) and an H$_2$ pressure of approximately 1.1 bar in the presence of 1 g of 5% platinum/charcoal (51% water; manufactured by Degussa). The hydrogen uptake ceased after approximately 90 minutes. The catalyst was removed by filtration through active charcoal. The resulting solution was freed from solvent under reduced pressure, and the residue obtained was treated with approximately 50 ml of petroleum ether. This gave 7.8 g (90%) of the title compound as a white solid. The solvent was removed under reduced pressure ("high vacuum"), and the residue obtained was washed using hexane. This gave 4.5 g (94%) of the title compound as a white solid.

$^1$H NMR (CDCl$_3$; δ in ppm): 2.15 (s,3H, CH$_3$); 5.15 (s,2H, OCH$_2$); 6.85 (t,1H, phenyl); 7.0 (d,1H, phenyl); 7.1 (t,2H, phenyl); 7.3 (dd,2H, pyridyl); 7.5 (d,br,1H, pyridyl); 8.0 (d,br,1H, pyridyl); 8.35 (s,1H); 8.7 (s,br,1H).

3.f) methyl N-hydroxy-N-[2-(2-methylphenoxymethyl)pyridin-3-yl]carbamate 2.1 g (22 mmol) of methyl chloroformate were added dropwise at −10° C. to a mixture of 4.3 g ( mmol) of N-[2-(2-methylphenoxymethyl)pyridin-3-yl]hydroxylamine (Example 3.e), 3.3 g (39 mmol) of NaHCO$_3$ (solid) and 50 ml of methylene chloride. After the reaction mixture had been stirred for 4 hours at room temperature (approximately 25° C.), it was washed with water, dried and freed from solvent under reduced pressure. The residue was purified by column chromatography (cyclohexane/ethyl acetate). This gave 0.6 g (10%) of the title compound as a yellow oil.

$^1$H NMR (CDCl$_3$; δ in ppm): 2.2 (s,3H, CH$_3$); 3.65 (s,3H, OCH$_3$); 5.25 (s,2H, OCH$_2$); 6.85 (m,2H, phenyl); 7.1 (m,2H, phenyl); 7.3 (dd,2H, pyridyl); 7.7 (d,br,1H, pyridyl); 8.5 (d,br,1H, pyridyl); 9.0 (s,br,1H, OH).

4. Preparation of methyl N-methoxy-N-[2-(2-methylphenoxymethyl)pyridin-3-yl]carbamate

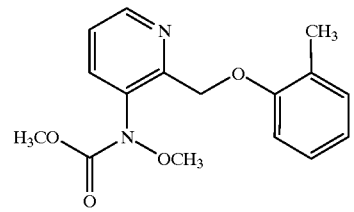

A mixture of 0.6 g (2.1 mmol) of methyl N-hydroxy-N-[2-(2-methyl-phenoxymethyl)pyridin-3-yl]carbamate (Example 3), 0.5 g (3.6 mmol) of K$_2$CO$_3$, 0.3 g (2.3 mmol) of dimethyl sulfate and 5 ml of acetone was stirred for approximately 12 hours at room temperature (approximately 25° C.). The mixture was subsequently diluted with water and 10% strength NH$_3$ solution and extracted repeatedly using methylene chloride. The organic phases were combined, washed and dried, and the solvent was removed under reduced pressure. The resulting residue was purified by column chromatography (cyclohexane/ethyl acetate). This gave 0.2 g of the title compound as a yellow oil.

¹H NMR (CDCl₃; δ in ppm): 2.2 (s,3H, CH₃); 3.65 (s,3H, OCH₃); 3.8 (s,3H, OCH₃); 5.25 (s,2H, OCH₂); 6.9 (m,2H, phenyl); 7.1 (t,2H, phenyl); 7.35 (dd,2H, pyridyl); 7.75 (d,br,1H, pyridyl); 8.65 (d,br,1H, pyridyl).

5. Preparation of methyl N-methoxy-N-(2-(3-trifluoromethylacetophenoneamineoxymethyl)pyridin-3-yl) carbamate

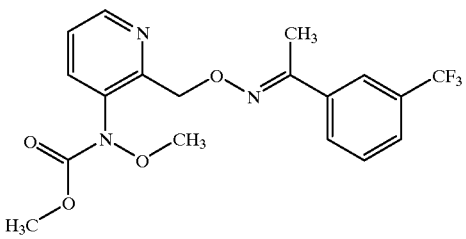

5a) N-(2-methylpyridin-3-yl)hydroxylamine

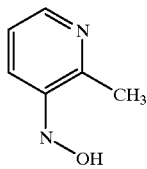

A mixture of 19.6 g (14.2 mmol) of 2-methyl-3-nitropyridine (Synth. Commun. 1990, 20, 2965) in 200 ml of N-methylmorpholine is hydrogenated in the presence of 1 g of 5% platinum/charcoal. During this process, the temperature of the reaction mixture rises to approximately 35° C. After approximately 4.5 hours, the uptake of hydrogen has ceased, and the reaction mixture is filtered with suction through kieselguhr. The filter residue is washed with N-methylmorpholine, and the combined organic phases are concentrated in vacuo (T<45° C.).

The residue is taken up in 100 ml of Solvesso 150 (b.p.=185–205° C.) and the resulting mixture is concentrated under a high vacuum (T<80° C.). The residue crystallizes and is digested in hexane. This gives 17.2 g (98%) of the title compound as a pale beige solid.

¹H NMR (CDCl₃; δ in ppm): 8.35 (d,1H,NH); 8.15 (s,broad,1H,OH); 7.85 (dd,1H, pyridyl); 7.25 (d,broad,1H, pyridyl); 7.05 (dd,1H, pyridyl); 2.2 (s,3H, CH₃).

5b) 3-(N,O-bismethoxycarbonyl)hydroxylamino-2-methylpyridine-N-(2-methylpyridin-3-yl)hydroxylamine

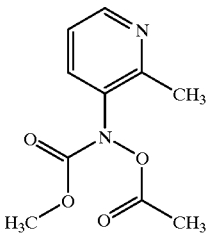

A mixture of 12.5 g (100 mmol) of N-(2-methylpyridin-3-yl)hydroxylamine in 200 ml of tetrahydrofuran is treated with 30.5 g (250 mmol) of p-dimethylaminopyridine and 28 g (300 mmol) of methyl chloroformate. The mixture is stirred overnight at room temperature. Then, such an amount of water is added that a clear two-phase mixture is present. The organic phase is separated off and the aqueous phase is extracted with ethyl acetate. The combined organic phases are filtered with suction through silica gel, dried and concentrated. The residue is purified by column chromatography using cyclohexane/ethyl acetate mixtures. 16.4 g (69%) of the title compound are obtained as a yellow oil.

¹H NMR (CDCl₃; δ in ppm): 8.5 (d,broad,1H, pyridyl); 7.75 (d,broad,1H, pyridyl); 7.2 (dd,1H, pyridyl); 3.9 (s,3H, OCH₃); 3.8 (s,3H,OCH₃); 2.55 (s,3H,CH₃).

5c) Methyl N-hydroxy-N-(2-methylpyridin-3-yl) carbamate

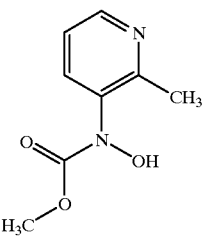

A mixture of 16 g (66 mmol) of the compound of Example 5b) and 6.5 g (82 mmol) pyridine in 300 ml of methanol is refluxed for 4 hours. The reaction mixture is subsequently concentrated, part of the title compound crystallizing out. The residue is taken up in ethyl acetate and filtered, giving 2.5 g of the title compound. The mother liquor is concentrated and the residue is purified by column chromatography using cyclohexane/ethyl acetate mixtures. This gives 3.8 g of the title compound (total yield 52%) as a pale beige solid (m.p.=132–133° C.).

¹H NMR (CDCl₃; δ in ppm): 10.5 (s,broad,1H,OH); 8.4 (d,broad,1H, pyridyl); 7.7 (broad,1H, pyridyl); 7.3 (dd,1H, pyridyl); 3.7 (s,3H,OCH₃); 2.4 (s,3H,CH₃).

5d) Methyl N-methoxy-N-(2-methylpyridin-3-yl) carbamate

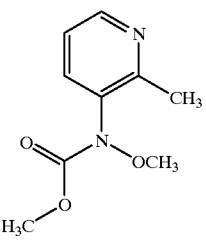

A mixture of 3.8 g (20.8 mmol) of methyl N-hydroxy-N-(2-methylpyridin-3-yl)carbamate (Example 5c), 5.6 g ( mmol) of potassium carbonate and 3.4 g (24 mmol) of methyl iodide in 40 ml of acetone is stirred for hours at room temperature. The reaction mixture is subsequently evaporated in vacuo. The residue is taken up in methyl t-butyl ether and filtered with suction through silica gel. The solvent is distilled off and the residue (3.8 g) together with approximately 1.1 g of crude product from the previous reaction batches, is purified by column chromatography using cyclohexane/ethyl acetate mixtures. Approximately 4.9 g (93%) of the title compound are obtained as a yellow oil.

¹H NMR (CDCl₃; δ in ppm): 8.5 (d,broad, pyridyl); 7.6 (d,broad,1H, pyridyl); 7.2 (dd,1H, pyridyl); 3.8 (s,3H, OCH₃); 3.75 (s,3H,OCH₃); 2.5 (s,3H,CH₃).

5e) Methyl N-methoxy-N-(2-bromomethylpyridin-3-yl)carbamate

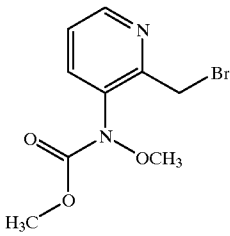

A mixture of 4.3 g (22 mmol) of methyl N-methoxy-N-(2-methylpyridin-3-yl)carbamate (Example 5d), 3.9 g (22 mmol) of N-bromo-succinimide and 1 spatula-tipful of azoisobutyronitrile in 50 ml of carbon tetrachloride is irradiated with a 300 W UV lamp, during which process the temperature of the reaction mixture comes to reflux point. After 3 hours, a further 0.5 g (2.8 mmol) of N-bromosuccinimide is added, and irradiation is carried out for approximately 2 more hours. The liquid phase is subsequently decanted off, and the solid which remains is extracted repeatedly with ethyl acetate. The combined organic phases are filtered with suction through silica gel and concentrated. The residue is purified by column chromatography using cyclohexane/ethyl acetate mixtures. 1.8 g (30%) of the title compound are obtained as a yellow oil.

$^1$H NMR (CDCl$_3$; δ in ppm): 8.5 (d,broad, pyridyl); 7.7 (d,broad,1H, pyridyl); 7.35 (dd,1H, pyridyl); 4.6 (s,2H, CH$_2$Br); 3.85 (2s, in each case 3H,2×OCH$_3$).

5f) Methyl N-methoxy-N-(2-(3-trifluoromethylacetophenoneamineoxymethyl)pyridin-3-yl)carbamate

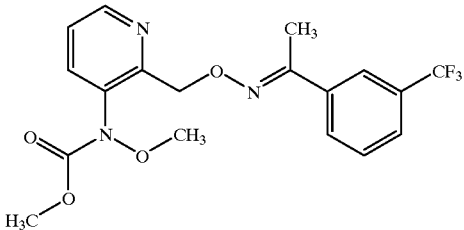

At 0° C., 0.8 g (4 mmol) of 3-trifluoromethylacetophenone oxime in 20 ml of dimethylformamide is treated with 0.1 g (4.2 mmol) of sodium hydride. 1 g (3.6 mmol) of methyl N-methoxy-N-(2-bromomethylpyridin-3-yl)carbamate, dissolved in dimethylformamide, is added, and the mixture is stirred for approximately 1 hour at room temperature. The reaction mixture is subsequently diluted with water and the aqueous phase is extracted with methyl t-butyl ether. The combined organic phases are extracted with water, dried and concentrated. The residue is purified by column chromatography using cyclohexane/ethyl acetate mixtures. 0.5 g (35%) of the title compound is obtained as a yellow oil.

$^1$H NMR (CDCl$_3$; δ in ppm): 8.65 (d,broad, pyridyl); 7.85 (s,broad,1H, phenyl); 7.75 (m,2H, phenyl, pyridyl); 7.6 (d,broad,1H, phenyl); 7.45 (t,1H, phenyl); 7.45 (dd,1H, pyridyl); 5.35 (s,2H,OCH$_2$); 3.8 (2s, in each case 3H,2× OCH$_3$); 2.3 (s,3H;CH$_3$).

6. Preparation of methyl N-methoxy-N-[2-(2-methoxyimino-1-methylpropylideneaminooxy)pyridin-3-yl]carbamate

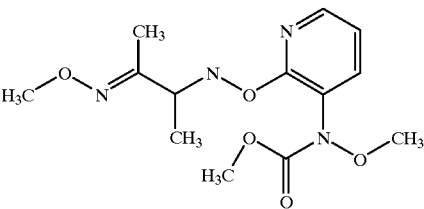

a) 3-Hydroxylamino-2-chloropyridine

A mixture of 18.3 g (115 mmol) of 2-chloro-3-nitropyridine and 300 ml of N-methylmorpholine was hydrogenated at room temperature and a hydrogen pressure of approximately 1.1 bar in the presence of 3 g of 5% platinum/charcoal (55.5% of water [Degussa]). After approximately 1.5 hours, the hydrogen uptake had ceased. The catalyst was removed by filtration through kieselguhr. The filtrate obtained was freed from solvent at approximately 45° C. under reduced pressure. Any remaining N-methylmorpholine was distilled off with 200 ml of Solvesso (Esso) under reduced pressure using a 20 cm column. The crystallizate which remained was taken up in 200 ml of n-hexane, filtered off with suction and washed with n-hexane. 15.9 g (96%) of the title compound were obtained as brown crystals.

$^1$H NMR (d$_6$-DMSO; δ in ppm): 7.3 (m, 1H, pyridyl); 7.5 (d, 1H, pyridyl); 7.8 (d, 1H, pyridyl); 8.5; 8.8 (in each case: s, 1H, NH, OH).

M.p.: decomposition b) 3-(N,O-bismethoxycarbonyl)hydroxylamino-2-chloropyridine

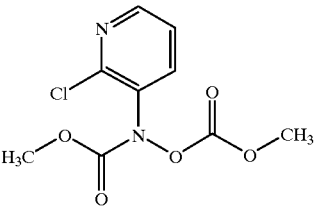

10.5 g (110 mmol) of methyl chloroformate were added dropwise at 0° C. to a mixture of 8 g (55 mmol) of 3-hydroxylamino-2-chloropyridine, 12.2 g (121 mmol) of triethylamine, catalytic amounts of 4-dimethylaminopyridine and 10 ml of tetrahydrofuran. After 1 hour at room temperature, the reaction mixture was treated with a further 5.6 g (55 mmol) of triethylamine and 2.6 g (27 mmol) of methyl chloroformate and again stirred for hours at room temperature. The reaction mixture was treated with 50 ml of water, the pH was brought to 3 using 2 N HCl, and the mixture was extracted with ethyl acetate. The organic phases were combined, washed with saturated NaCl solution and dried, and the solvent was removed under reduced pressure. The resulting residue was purified by column chromatography over silica gel using cyclohexane/ethyl acetate (3:1). 12 g (84%) of the title compound were obtained as a brown solid.

$^1$H NMR (CDCl$_3$; δ in ppm): 3.86 (s, 3H, OCH$_3$); 3.92 (s, 3H, OCH$_3$); 7.36 (m, 1H, pyridyl); 7.98 (d, 1H, pyridyl); 8.44 (d, 1H, pyridyl).

M.p.: 72–73° C.

c) Methyl N-hydroxy-N-(2-chloropyridin-3-yl)carbamate

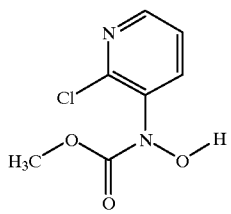

A mixture of 4.0 g (15 mmol) of 3-(N,O-bismethoxycarbonyl)hydroxylamino-2-chloropyridine, 1.2 g (15 mmol) of pyridine and 60 ml of methanol was refluxed for 8 hours. The solvents were removed under reduced pressure, and the resulting residue was purified by column chromatography over silica gel using cyclohexane/ethyl acetate (1:1). This gave 2.1 g (68%) of the title compound as a brown solid.

$^1$H NMR (CDCl$_3$; δ in ppm): 3.8 (s, 3H, OCH$_3$); 7.4 (m, 1H, pyridyl); 7.9 (d, 1H, pyridyl); 8.4 (d, 1H, pyridyl); 9.1 (br, s, 1H, OH).

M.p.: 85–87° C.

d) Methyl N-methoxy-N-(2-chloropyridin-3-yl)carbamate

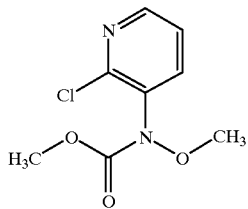

A mixture of 5.8 g (28 mmol) of methyl N-hydroxy-N-(2-chloropyridin-3-yl)carbamate, 3.9 g (28 mmol) of potassium carbonate and 60 ml of acetone was treated with 4 g (28 mmol) of methyl iodide at room temperature. After hours at room temperature, the potassium carbonate which remained was separated off, and the resulting solution was freed from solvent under reduced pressure. The residue was taken up in ethyl acetate and washed with water, the organic phases were dried, and the solvent was removed under reduced pressure. The resulting residue was purified by column chromatography over silica gel using cyclohexane/ethyl acetate (4:1). 3.5 g (57%) of the title compound were obtained as a brown oil.

$^1$H NMR (CDCl$_3$; δ in ppm): 3.82 (s, 6H, 2×OCH$_3$); 7.35 (m, 1H, pyridyl); 7.78 (d, 1H, pyridyl); 8.4 (d, 1H, pyridyl). IR (cm$^{-1}$): 3000, 2940, 2920, 1749, 1567, 1442, 1409, 1339, 1273, 1248, 1100, 801, 748.

e) Methyl N-methoxy-N-[2-(2-methoxyimino-1-methylpropylideneaminooxy)pyridin-3-yl]carbamate At 70° C., a mixture of 1.2 g (9.2 mmol) of 2-methoxyimino-3-hydroxyiminobutane and 25 ml of tert-butanol was treated with 1.03 g (9.2 mmol) of potassium tert-butylate, and the mixture was stirred for 1 hour. The reaction mixture was freed from solvent under reduced pressure at approximately 40° C. The residue was introduced into 15 ml of dimethyl sulfoxide, and 2 g (9.2 mmol) of methyl N-methoxy-N-(2-chloropyridin-3-yl)carbamate, dissolved in 3 ml of dimethyl sulfoxide, were added at 50° C. The mixture was stirred for 2 hours at 100° C., and the reaction mixture was transferred to approximately 150 g of ice and extracted with tert-butyl methyl ether. The organic phases were combined, washed with water, dried, and the solvent was removed, under reduced pressure. The resulting residue was purified by column chromatography over silica gel using cyclohexane/ethyl acetate (2:1). This gave 470 mg (17%) of the title compound as a brown solid.

$^1$H NMR (CDCl$_3$; δ in ppm) : 2.15 (s, 3H, CH$_3$); 2.25 (s, 3H, CH$_3$); 3.8 (br. s, 6H, 2×OCH$_3$); 4.0 (s, 3H, OCH$_3$); 7.1 (m, 1H, pyridyl); 7.7 (d, 1H, pyridyl); 8.3 (d, 1H, pyridyl).

M.p.: 86–88° C.

TABLE I.1

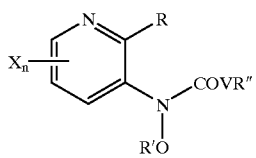

I.1

| No. | X$_n$ | R$^9$ | VR" | R | Physical data |
|---|---|---|---|---|---|
| I.1-1 | H | H | OCH$_3$ | OC$_6$H$_5$ | m.p.: 140° C. |
| I.1-2 | H | CH$_3$ | OCH$_3$ | OC$_6$H$_5$ | oil |
| I.1-3 | H | H | OCH$_3$ | CH$_2$O-(2-CH$_3$—C$_6$H$_4$) | oil |
| I.1-4 | H | CH$_3$ | OCH$_3$ | CH$_2$O-(2-CH$_3$—C$_6$H$_4$) | oil |
| I.1-5 | H | CO$_2$CH$_3$ | OCH$_3$ | CH$_3$ | 1797, 1747. 1450, 1340, 1249, 1194, 1114, 928, 781, 735 |
| I.1-6 | H | H | OCH$_3$ | CH$_3$ | 132–133 |
| I.1-7 | H | CH$_3$ | OCH$_3$ | CH$_3$ | 132–133 |
| I.1-8 | H | CH$_3$ | OCH$_3$ | CH$_2$O-(2,5-(CH$_3$)$_2$—C$_6$H$_3$) | 1744, 1509, 1455, 1439, 1336, 1263, 1155, 1130, 1103, 1034 |
| I.1-9 | H | CH$_3$ | OCH$_3$ | CH$_2$O-(2-CH$_3$-4-CH$_3$C=NOCH$_3$—C$_6$H$_3$) | 1744, 1506, 1456, 1440, 1322, 1278, 1253, 1238, 1144, 1051 |
| I.1-10 | H | CH$_3$ | OCH$_3$ | CH$_2$ON=C(CH$_3$)-(4-Cl—C$_6$H$_4$) | 1742, 1491, 1448, 1366, 1339, 1318, 1096, 1032, |

TABLE I.1-continued

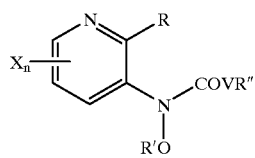

I.1

| No. | $X_n$ | $R^9$ | VR" | R | Physical data |
|---|---|---|---|---|---|
| I.1-11 | H | $CH_3$ | $OCH_3$ | $CH_2ON=C(CH_3)-(3-CF_3-C_6H_4)$ | 1013, 830<br>1742, 1442, 1341, 1300,<br>1276, 1167, 1126, 1072,<br>1033, 698 |
| I.1-12 | H | $CH_3$ | $OCH_3$ | $CH_2ON=C(CH_3)-(3,5-Cl_2-C_6H_3)$ | 1743, 1584, 1558, 1441,<br>1388, 1306, 1106, 1032,<br>833, 801 |
| I.1-13 | H | $CH_3$ | $OCH_3$ | $CH_2ON=C(CH_3)-C(4-F-C_6H_4)=NOCH_3$ | 1744, 1509, 1457, 1442,<br>1346, 1223, 1067, 1022,<br>982, 872 |
| I.1-14 | H | $CH_3$ | $OCH_3$ | $CH_2ON=C(CH_3)-C(4-Cl-C_6H_4)=NOCH_3$ | 75–80 |
| I.1-15 | H | H | $OCH_3$ | $CH_2O-(2-CH_3-4-CH_3C=NOCH_3-C_6H_3)$ | 1737, 1506, 1457, 1441,<br>1367, 1322, 1279, 1255,<br>1239, 1051 |
| I.1-16 | H | H | $OCH_3$ | $CH_2ON=C(CH_3)-(3,5-Cl_2-C_6H_3)$ | 126–128 |
| I.1-17 | H | H | $OCH_3$ | $CH_2ON=C(CH_3)-C(4-Cl-C_6H_4=NOCH_3$ | 145–146 |
| I.1-18 | H | $CO_2CH_3$ | $OCH_3$ | $CH_2O-(2-CH_3-4-CH_3C=NOCH_2-C_6H_3)$ | 107–109 |
| I.1-19 | H | $CO_2CH_3$ | $OCH_3$ | $CH_2ON=C(CH_3)-(3,5-Cl_2-C_6H_3)$ | 1797, 1748, 1558, 1442,<br>1368, 1306, 1246, 1119,<br>1039, 801 |
| I.1-20 | H | $CO_2CH_3$ | $OCH_3$ | $CH_2ON=C(CH_3)-C(4-F-C_6H_4)=NOCH_3$ | 1798, 1750, 1509, 1442,<br>1367, 1247, 1196, 1068,<br>1014, 983 |
| I.1-21 | H | $CO_2CH_3$ | $OCH_3$ | $CH_2ON=C(CH_3)-C(4-Cl-C_6H_4)=NOCH_3$ | 1798, 1750, 1442, 1246,<br>1120, 1090, 1068, 1023,<br>1013, 982 |
| I.1-22 | H | H | $OCH_3$ | $CH_2ON=C(CH_3)-C(4-F-C_6H_4)=NOCH_3$ | 142–144 |
| I.1-23 | H | $CH_3$ | $OCH_3$ | $CH_2-Br$ | 8,6(d, broad, 1H); 7.7(d, broad,<br>1H); 7.35(dd, 1H); 4.6(s, 2H);<br>3.85(2s, each 3H) |
| I.1-24 | H | $CH_3$ | $OCH_3$ | CHO | 10.1(s, 1H); 8.7(d, broad,<br>1H); 7.9(d, broad, 1H); 7.6(dd,<br>1H); 3.8(2s, each 3H) |
| I.1-25 | H | $CH_3$ | $OCH_3$ | $CH_2P^+(C_6H_5)_3Br$ | 5.65(d, broad, 2H) |
| I.1-26 | H | $CH_3$ | $NH-CH_3$ | $CH_2O-(2-CH_3-4-CH_3C=NOCH_3-C_6H_3)$ | 8.55(d, broad, 1H); 7.7(d, broad,<br>1H), 7.45(s, 1H); 7.3(m, 2H);<br>6.9(d, 1H); 6.0(s, 3H); 5.25(s,<br>2H); 3.95(s, 3H); 3.65(s, 3H); 2.9<br>(d, 3H); 2.2(s, 3H); 2.15(s, 3H) |

Physical data: m.p. [°C.], IR [cm$^{-1}$] or $^1$H NMR [ppm].

Examples of the Activity Against Harmful Fungi

The fungicidal activity of the compounds of the general formula I as demonstrated by the following experiments:

The active ingredients were formulated as a 20% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration.

Activity Against Wheat Mildew

Leaves of wheat seedlings cv. "Frühgold", in pots, were sprayed to runoff point with aqueous spray mixture which had been made with a stock solution of 10% of active ingredient, 63% of cyclohexanone and 27% of emulsifier, and, 24 hours after the spray coating had dried on, dusted with spores of powdery mildew of wheat (*Erysiphe graminis* var. *tritici*). The test plants were subsequently placed in a greenhouse at from 20 to 22° C. and a relative atmospheric humidity of 75 to 80%. After 7 days, the extent of the mildew development was determined visually in % diseased leaf area of the entire leaf area.

In this text, a disease level of not more than 15% was shown by the plants which had been treated with 250 ppm of the compounds No. I.1-4, I.1-8, I.1-9, I.1-11 and I.1-19, while the disease level of the untreated plants was 75%.

Activity Against *Plasmopara viticola*

Leaves of grapevines cv. "Müller-Thurgau" in pots, were sprayed to runoff point with aqueous spray mixture which had been made with a stock solution of 10% active ingredient, 63% of cyclohexanone and 27% of emulsifier. In order to be able to assess the long-term action of the substances, the plants were placed in a greenhouse for 7 days after the spray coating had dried on. Only then were the leaves innoculated with an aqueous zoo spore suspension of *Plasmopara viticola*. Then, the vines were first placed for 48 hours into a water-vapor-saturated chamber at 24° C. and then for 5 days in a greenhouse at from 20 to 30° C. After this time, the plants were returned for 16 hours into a humid chamber to accelerate the eruption of sporangiophores. Then, the extent of the disease development on the underside of the leaves was determined visually.

In this test, a maximum disease level of 15% was shown by the plants which had been treated with 250 ppm of the compounds No. I.1-4, I.1-12, I.1-13 and I.1-14, while the disease level of the untreated plants was 70%.

Activity Against *Pyricularia oryzae*

Leaves of rice seedlings cv. "Tai-Nong 67", in pots, were sprayed to runoff point with aqueous spray mixture which had been made with a stock solution of 10% of active ingredient, 63% of cyclohexanone and 27% of emulsifier. The following day, the plants were innoculated with an aqueous spore suspension of *Pyricularia oryzae*. The test plants were subsequently placed for 6 days into controlled-environment cabinets at 22–24° C. and a relative atmospheric humidity of 95–99%. Then, the extent of the disease development on the leaves was determined visually.

In this test, a maximum disease level of 15% was shown by the plants which had been treated with 250 ppm of the compounds No. I.1-4, I.1-9, I.1-14 and I.1-21, while the disease level of the untreated plants was 70%.

Examples of the Activity Against Animal Pests

The activity of the compounds of the general formula I against animal pests was demonstrated by the following experiments:

The active ingredients were formulated
a. as a 0.1% strength solution in acetone or
b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted to give the desired concentration, using acetone in the case of a. or water in the case of b.

After the experiments had ended, in each case the lowest concentration at which the compounds still caused an 80 to 100% inhibition or mortality (activity limit or minimal concentration) in comparison with untreated control experiments was determined.

We claim:

1. A pyridylcarbamate compound of the formula I

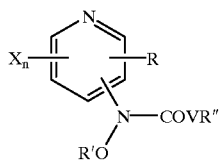

where the index and the substituents have the following meanings:

R' is hydrogen,
  unsubstituted or substituted alkyl, alkenyl, alkynyl, cycloalkyl, cycloalkenyl, alkylcarbonyl and alkoxycarbonyl;
R" is unsubstituted or substituted alkyl, alkenyl, alkynyl, cycloalkyl and cycloalkenyl, or
  when V is an amino group, R" is additionally hydrogen;
V is oxygen (—O—), sulfur (—S—) or an amino group which can have attached to it one of the following radicals: alkyl, alkenyl, alkynyl or cycloalkyl;
X is cyano, nitro, halogen,
  unsubstituted or substituted alkyl, alkenyl, alkynyl, alkoxy, alkenyloxy, alkynyloxy, or
  in the event that n>1, an unsubstituted or substituted bridge which is bonded to two adjacent C atoms of the pyridyl ring and which contains 3 to 4 members from amongst the group consisting of 3 or 4 carbon atoms, 2 or 3 carbon atoms and one or two nitrogen, oxygen and/or sulfur atoms, it being possible for this bridge together with the ring to which it is bonded to form a partially unsaturated or aromatic radical;
n is 0, 1, 2 or 3, it being possible for the radicals X to differ when n>1;
R is halogen, hydroxyl, mercapto, amino, formyl, carboxyl, carbonylamino or
  unsubstituted or substituted alkyl, alkenyl, alkynyl, cycloalkyl, heterocyclyl, aryl or hetaryl, each of which is bonded directly or via an oxy, mercapto, amino, carboxyl or carbonylamino group, or
  together with a group X and the pyridyl ring to which they are bonded an unsubstituted or substituted bicyclic, partially or fully unsaturated system which, in addition to carbon ring members, can contain hetero atoms from amongst the group consisting of oxygen, sulfur and nitrogen.

2. A process for the preparation of a compound I as defined in claim 1 where R' is hydrogen, which comprises reducing a nitropyridine of the formula II

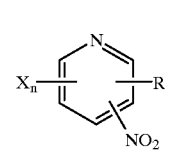

to give the corresponding N-hydroxyamino-pyridine of the formula III

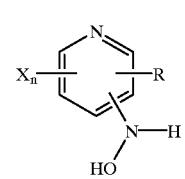

and subsequently reacting III with a carbonyl compound of the formula IV

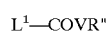

where $L^1$ is a nucleophilically exchangeable group to give I.

3. A process for the preparation of a compound I as defined in claim 1 where R' is not hydrogen, which comprises reacting a compound of the formula I where R' is hydrogen with a reagent of the formula V

where $L^2$ is a nucleophilically exchangeable group.

4. A compound of the formula XX

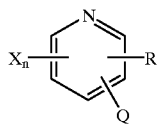

XX where

Q is N(OR')—CO₂—Ar, Ar being an unsubstituted or substituted aromatic radical;

X is cyano, nitro, halogen,
  unsubstituted or substituted alkyl, alkenyl, alkynyl, alkoxy, alkenyloxy, alkynyloxy, or
  in the event that n>1, an unsubstituted or substituted bridge which is bonded to two adjacent C atoms of the pyridyl ring and which contains 3 to 4 members from amongst the group consisting of 3 or 4 carbon atoms, 2 or 3 carbon atoms and one or two nitrogen, oxygen and/or sulfur atoms, it being possible for this bridge together with the ring to which it is bonded to form a partially unsaturated or aromatic radical;

n is 0, 1, 2 or 3, it being possible for the radicals X to differ when n>1;

R is halogen, hydroxyl, mercapto, amino, formyl, carboxyl, carbonylamino or
  unsubstituted or substituted alkyl, alkenyl, alkynyl, cycloalkyl, heterocyclyl, aryl or hetaryl, each of which is bonded directly or via an oxy, mercapto, amino, carboxyl or carbonylamino group, or
  together with a group X and the pyridyl ring to which they are bonded an unsubstituted or substituted bicyclic, partially or fully unsaturated system which, in addition to carbon ring members, can contain hetero atoms from amongst the group consisting of oxygen, sulfur and nitrogen.

5. A compound of the formula XY

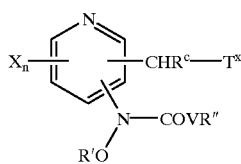

XY where $R^c$ is hydrogen or an alkyl group;

$T^x$ is hydrogen, hydroxyl, oxyamino, halogen, alkoxy, alkylcarbonyloxy, aryloxy, triaryloxyphosphonium halide or alkyl- or arylphosphonate;

R' is hydrogen,
  unsubstituted or substituted alkyl, alkenyl, alkynyl, cycloalkyl, cycloalkenyl, alkylcarbonyl and alkoxycarbonyl;

R" is unsubstituted or substituted alkyl, alkenyl, alkynyl, cycloalkyl and cycloalkenyl, or
  when V is an amino group, R" is additionally hydrogen;

V is oxygen (—O—), sulfur (—S—) or an amino group which can have attached to it one of the following radicals: alkyl, alkenyl, alkynyl or cycloalkyl;

X is cyano, nitro, halogen,
  unsubstituted or substituted alkyl, alkenyl, alkynyl, alkoxy, alkenyloxy, alkynyloxy, or
  in the event that n>1, an unsubstituted or substituted bridge which is bonded to two adjacent C atoms of the pyridyl ring and which contains 3 to 4 members from amongst the group consisting of 3 or 4 carbon atoms, 2 or 3 carbon atoms and one or two nitrogen, oxygen and/or sulfur atoms, it being possible for this bridge together with the ring to which it is bonded to form a partially unsaturated or aromatic radical;

n is 0, 1, 2 or 3, it being possible for the radicals X to differ when n>1.

6. A compound of the formula XZ

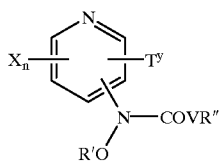

XZ where $T^y$ is cyano, nitro, hydroxyl, amino, formyl, halogen, alkylcarbonyl, alkylsulfonyl, alkylsulfonyloxy, arylsulfonyl or arylsulfonyloxy;

R' is hydrogen,
  unsubstituted or substituted alkyl, alkenyl, alkynyl, cycloalkyl, cycloalkenyl, alkylcarbonyl and alkoxycarbonyl;

R" is unsubstituted or substituted alkyl, alkenyl, alkynyl, cycloalkyl and cycloalkenyl, or
  when V is an amino group, R" is additionally hydrogen;

V is oxygen (—O—), sulfur (—S—) or an amino group which can have attached to it one of the following radicals: alkyl, alkenyl, alkynyl or cycloalkyl;

X is cyano, nitro, halogen,
  unsubstituted or substituted alkyl, alkenyl, alkynyl, alkoxy, alkenyloxy, alkynyloxy, or
  in the event that n>1, an unsubstituted or substituted bridge which is bonded to two adjacent C atoms of the pyridyl ring and which contains 3 to 4 members from amongst the group consisting of 3 or 4 carbon atoms, 2 or 3 carbon atoms and one or two nitrogen, oxygen and/or sulfur atoms, it being possible for this bridge together with the ring to which it is bonded to form a partially unsaturated or aromatic radical;

n is 0, 1, 2 or 3, it being possible for the radicals X to differ when n>1.

7. A composition which is suitable for controlling animal pests or harmful fungi, comprising a solid or liquid carrier and a compound of the formula I as defined in claim 1.

8. A method of controlling harmful fungi, which comprises treating the fungi, or the materials, plants, the soil or seeds to be protected against fungal infection, with an effective amount of a compound of the formula I as defined in claim 1.

9. A method of controlling animal pests, which comprises treating the pests, or the materials, plants, the soil or seeds to be protected against them, with an effective amount of a compound of the formula I as defined in claim 1.

10. A process for the preparation of a compound I as defined in claim 1 where R' is hydrogen, which comprises acylating an N-hydroxyaminopyridine of the formula III

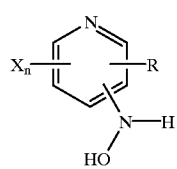 III
with at least 2 equivalents of a carbonyl compound of the formula IV
L¹—COVR''  IV
where $L^1$ is a nucleophilically exchangeable group to give a compound IIIa
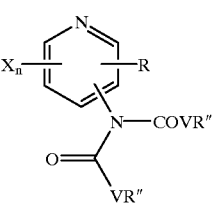 IIIa
and subsequently reacting IIIa in the presence of a base and an alcohol to give the compound I.
* * * * *